US011534452B2

(12) United States Patent
Javanbakht et al.

(10) Patent No.: US 11,534,452 B2
(45) Date of Patent: Dec. 27, 2022

(54) NUCLEIC ACID MOLECULES FOR REDUCTION OF PAPD5 OR PAPD7 MRNA FOR TREATING HEPATITIS B INFECTION

(71) Applicant: HOFFMANN-LA ROCHE INC., Little Falls, NJ (US)

(72) Inventors: Hassan Javanbakht, San Francisco, CA (US); Søren Ottosen, Glostrup (DK); Lykke Pedersen, Copenhagen NV (DK); Henrik Mueller, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 16/310,789

(22) PCT Filed: Jun. 19, 2017

(86) PCT No.: PCT/EP2017/064980
§ 371 (c)(1),
(2) Date: Dec. 17, 2018

(87) PCT Pub. No.: WO2017/216390
PCT Pub. Date: Dec. 21, 2017

(65) Prior Publication Data

US 2019/0216846 A1 Jul. 18, 2019

(30) Foreign Application Priority Data

Jun. 17, 2016 (EP) .................................... 16175045

(51) Int. Cl.

| | |
|---|---|
| ***A61K 31/7125*** | (2006.01) |
| ***C12N 15/113*** | (2010.01) |
| ***C12Q 1/6883*** | (2018.01) |
| ***C12Q 1/70*** | (2006.01) |
| ***A61P 31/14*** | (2006.01) |
| ***A61K 31/4745*** | (2006.01) |
| ***A61K 31/519*** | (2006.01) |
| ***C07K 16/40*** | (2006.01) |
| ***A61P 31/20*** | (2006.01) |

(52) U.S. Cl.
CPC ...... *A61K 31/7125* (2013.01); *A61K 31/4745* (2013.01); *A61K 31/519* (2013.01); *A61P 31/14* (2018.01); *A61P 31/20* (2018.01); *C07K 16/40* (2013.01); *C12N 15/113* (2013.01); *C12N 15/1137* (2013.01); *C12Q 1/6883* (2013.01); *C12Q 1/706* (2013.01); *C07K 2317/732* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 4,711,955 | A | 12/1987 | Ward et al. | |
| 5,525,711 | A | 6/1996 | Hawkins et al. | |
| 5,792,608 | A | 8/1998 | Swaminathan et al. | |
| 5,885,968 | A | 3/1999 | Biessen et al. | |
| 8,090,542 | B2 | 1/2012 | Khvorova et al. | |
| 8,349,809 | B2 | 1/2013 | Brown | |
| 8,513,207 | B2 | 8/2013 | Brown | |
| 9,458,153 | B2 | 10/2016 | Han | |
| 10,093,671 | B2 | 10/2018 | Han et al. | |
| 10,953,034 | B2 * | 3/2021 | Kammler | C12N 15/1137 |
| 2004/0157780 | A1 | 8/2004 | Grey | |
| 2005/0272080 | A1 | 12/2005 | Palma et al. | |
| 2006/0257851 | A1 | 11/2006 | Bentwich | |
| 2010/0173974 | A1 | 7/2010 | Brown | |
| 2010/0249219 | A1 | 9/2010 | Hedtjarn et al. | |
| 2011/0118337 | A1 * | 5/2011 | Chau | C12N 15/113 514/44 A |
| 2012/0040460 | A1 | 2/2012 | Rigoutsos et al. | |
| 2017/0023568 | A1 | 1/2017 | Brophy et al. | |
| 2017/0235368 | A1 | 8/2017 | El-Ouardi et al. | |
| 2019/0111073 | A1 | 4/2019 | Kammler et al. | |
| 2019/0194768 | A1 | 6/2019 | Han et al. | |
| 2019/0211339 | A1 * | 7/2019 | Agarwal | A61K 2300/00 |
| 2019/0216846 | A1 | 7/2019 | Javanbakht | |

(Continued)

FOREIGN PATENT DOCUMENTS

| | | |
|---|---|---|
| CL | 201803561 | 12/2018 |
| CL | 201900945 | 4/2020 |
| CL | 202001638 | 8/2020 |

(Continued)

OTHER PUBLICATIONS

Ogami et al. Biochemical and Biophysical Research Communications 432, 135-140 (Year: 2013).*
Hagedorn et al. Nucleic Acid Research vol. 45, pp. 2262-2282 (Year: 2017).*
Fakhr et al. Cancer Gene Therapy 23, 73-82, (Year: 2016).*
Ansel, HC et al., “Pharmaceutical Dosage Forms and Drug Delivery Systems,” 1995, Williams & Wilkins, ppxi-xii, 105-116, 194-200, 497-514, cover pages, 41 pages.

(Continued)

*Primary Examiner* — Brian Whiteman
(74) *Attorney, Agent, or Firm* — Holland & Hart LLP

(57) ABSTRACT

A method for identifying a compound that prevents, ameliorates and/or inhibits a hepatitis B virus (HBV) infection is provided, wherein a compound that reduces the expression and/or activity of PAP associated domain containing 5 (PAPD5) and/or PAP associated domain containing 7 (PAPD7) is identified as a compound that prevents, ameliorates and/or inhibits a HBV infection. Inhibitors of PAPD5 or PAPD7 are provided for use in treating and/or preventing a HBV infection; as well as a combined preparation comprising an inhibitor of PAPD5 and an inhibitor of PAPD7 for simultaneous or sequential use in the treatment or prevention of a HBV infection.

18 Claims, 10 Drawing Sheets

Specification includes a Sequence Listing.

(56) References Cited

U.S. PATENT DOCUMENTS

2020/0147123 A1 5/2020 Kammler et al.

FOREIGN PATENT DOCUMENTS

| | | | |
|---|---|---|---|
| CL | 2020003329 A1 | 6/2021 | |
| CL | 2020003330 A1 | 6/2021 | |
| CN | 101541977 A | 9/2009 | |
| CN | 104080481 A | 10/2014 | |
| CN | 107108610 A1 | 8/2017 | |
| CN | 109328237 A | 2/2019 | |
| EP | 0302175 A2 | 2/1982 | |
| EP | 1013661 A1 | 6/2000 | |
| EP | 1152009 A1 | 7/2001 | |
| EP | 221373 | 6/2004 | |
| EP | 1752536 A1 | 12/2005 | |
| EP | 2213738 A2 | 8/2010 | |
| EP | 2890789 A1 | 7/2015 | |
| EP | 3472362 A1 | 4/2019 | |
| JP | 2005-116204 A | 4/2005 | |
| JP | 2017515862 | 6/2017 | |
| JP | 6462155 B2 | 1/2019 | |
| JP | 2017557384 | 1/2019 | |
| JP | 2019523649 A | 8/2019 | |
| RU | 2146706 C1 | 3/2000 | |
| WO | 9307883 A1 | 4/1993 | |
| WO | 95/27072 A1 | 10/1995 | |
| WO | 9839352 A1 | 9/1998 | |
| WO | 9914226 A2 | 3/1999 | |
| WO | 0047599 A1 | 8/2000 | |
| WO | 0066604 A2 | 11/2000 | |
| WO | 0123613 A1 | 4/2001 | |
| WO | 03022987 A2 | 3/2003 | |
| WO | 2004046160 A2 | 6/2004 | |
| WO | 2005014806 A2 | 2/2005 | |
| WO | 2005116204 A1 | 8/2005 | |
| WO | 2007031091 A2 | 3/2007 | |
| WO | 2007090071 A2 | 8/2007 | |
| WO | 20070106407 A2 | 9/2007 | |
| WO | 2007134181 A2 | 11/2007 | |
| WO | 2007146511 A2 | 12/2007 | |
| WO | 2008049085 A1 | 4/2008 | |
| WO | 2008082730 A2 | 7/2008 | |
| WO | 2008113832 A2 | 9/2008 | |
| WO | 2008150729 A2 | 12/2008 | |
| WO | 2008154401 A2 | 12/2008 | |
| WO | 2009006478 A2 | 1/2009 | |
| WO | 2009067647 | 5/2009 | |
| WO | 2009067647 A1 | 5/2009 | |
| WO | 2009090182 A1 | 7/2009 | |
| WO | 2009124238 A1 | 10/2009 | |
| WO | 2010036698 A1 | 4/2010 | |
| WO | 2010040571 A2 | 4/2010 | |
| WO | 2010077578 A1 | 7/2010 | |
| WO | 2010093788 A2 | 8/2010 | |
| WO | 2011017521 A2 | 2/2011 | |
| WO | 2011108699 | 9/2011 | |
| WO | 2011108699 A1 | 9/2011 | |
| WO | 2011156202 A1 | 12/2011 | |
| WO | 2012024170 A2 | 2/2012 | |
| WO | 2012055362 A1 | 5/2012 | |
| WO | 2012109395 A1 | 8/2012 | |
| WO | 2012145697 A1 | 10/2012 | |
| WO | 2013003520 A1 | 1/2013 | |
| WO | 2013022984 A1 | 2/2013 | |
| WO | 2013033230 A1 | 3/2013 | |
| WO | 2013036868 A1 | 3/2013 | |
| WO | 2013113501 A1 | 8/2013 | |
| WO | 2013154798 A1 | 10/2013 | |
| WO | 2013159109 A1 | 10/2013 | |
| WO | 2013166264 A2 | 11/2013 | |
| WO | 2014012081 A2 | 1/2014 | |
| WO | 2014036429 A1 | 3/2014 | |
| WO | 2014076195 A1 | 5/2014 | |
| WO | 2014076196 A1 | 5/2014 | |
| WO | 2014179620 A1 | 11/2014 | |
| WO | 2014179629 A2 | 11/2014 | |
| WO | 2014207232 A1 | 12/2014 | |
| WO | 2015031694 A2 | 3/2015 | |
| WO | 2015113922 A1 | 8/2015 | |
| WO | 2015113990 A1 | 8/2015 | |
| WO | 2015173164 A1 | 11/2015 | |
| WO | 2015173208 A2 | 11/2015 | |
| WO | 2016051116 | 4/2016 | |
| WO | 2016055601 A1 | 4/2016 | |
| WO | 2016071215 A1 | 5/2016 | |
| WO | 2016079181 A1 | 5/2016 | |
| WO | 2016/096938 A1 | 6/2016 | |
| WO | 2016107832 A1 | 7/2016 | |
| WO | 2016127002 A1 | 8/2016 | |
| WO | 2016177655 A1 | 11/2016 | |
| WO | 2017015175 A1 | 1/2017 | |
| WO | 2017027350 A2 | 2/2017 | |
| WO | 2017066712 A2 | 4/2017 | |
| WO | WO-2017066712 A2 * | 4/2017 | ............ C07K 16/40 |
| WO | 2017178656 A1 | 10/2017 | |
| WO | 2017216390 A1 | 12/2017 | |
| WO | 2017216391 A1 | 12/2017 | |
| WO | 2018059718 A1 | 4/2018 | |
| WO | 2019/076842 A1 | 4/2019 | |
| WO | 2019145543 A1 | 8/2019 | |

OTHER PUBLICATIONS

Bastin, RJ et al., "Salt Selection and Optimisation Procedures for Pharmaceutical New Chemical Entities," Organic Process Research & Development, 2000, vol. 4, pp. 427-435, 9 pages.

Biessen, EAL et al., "Synthesis of Cluster Galactosides with High Affinity for the Hepatic Asialoglycoprotein Receptor," J. Med. Chem., 1995, vol. 38(9), pp. 1538-1546, 9 pages.

Biessen, EAL et al., "Receptor-Dependent Cell Specific Delivery of Antisense Oligonucleotides," Developments in Cardiovascular Medicine, 1999, 24, pp. 285-299, 15 pages.

Buster, EH et al., "Peginterferon alpha-2b is safe and effective in HBeAg-positive chronic hepatitis B patients with advanced fibrosis," Hepatology, 2007, vol. 46, No. 2, pp. 388-394, 7 pages.

Cahn, RS, et al., "Specification of Molecular Chirality," Angewandte Chemie International Edition, 1966, vol. 5, No. 4, pp. 385-415, 31 pages.

Caruthers, MH et al., "Chemical Synthesis of Deoxyoligonucleotides by the Phosphoramidite Method," Methods in Enzymology, 1987, vol. 154, pp. 287-313, 27 pages.

Chang, Mei-Hwei, "Hepatitis B virus infection," Elsevier, Seminars in Fetal Neonatal Medicine, 2007, vol. 12, pp. 160-167, 8 pages.

Deleavey, GF et al., "Designing Chemically Modified Oligonucleotides for Targeted Gene Silencing," Chemistry and Biology, 2012, vol. 19(8), pp. 937-954, 18 pages.

Duff, RJ et al., "Intrabody Tissue-Specific Delivery of Antisense Conjugates in Animals: Ligand-Linker-Antisense Oligomer Conjugates," Methods in Enzymolology, 2000, vol. 313(17), pp. 297-321, 25 pages.

Fluiter, K et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Molecular Biosystems, 2009, vol. 5, pp. 838-843, 6 pages.

Freier, SM et al., "The ups and downs of nucleic acid duplex stability: structure-stability studies on chemically-modified DNA:RNA duplexes," Nucleic Acids Research, 1997, vol. 25(22), pp. 4429-4443, 16 pages.

Hansen, LD et al., "Entropy Titration. A calorimetric method for the determination of ΔG°(K), ΔH° and ΔS°1," Chemical Communications, 1965, No. 3, pp. 36-38, 3 pages.

Hantz, O et al., "Persistence of the hepatitis B virus covalently closed circular DNA in HepaRG human hepatocyte-like cells," Journal of General Virology, 2009, vol. 90, Part 1, pp. 127-135, 9 pages.

Hirao, I et al., "Natural versus Aililicial Creation of Base Pairs in DNA: Origin of Nucleobases from the Perspectives of Unnatural Base Pair Studies," Accounts of Chemical Research, 2012, vol. 45, No. 12, pp. 2055-2065, 11 pages.

(56) References Cited

OTHER PUBLICATIONS

Ishida, Y et al., "Novel Robust in Vitro Hepatitis B Virus Infection Model Using Fresh Human Hepatocytes Isolated from Humanized Mice," American Journal of Pathology, 2015, vol. 185, No. 5, pp. 1275-1285, 11 pages.
Khorev, O et al., "Trivalent, Gal/GalNAc-containing ligands designed for the asialoglycoprotein receptor," Bioorganic & Medicinal Chemistry, 2008, vol. 16(9), pp. 5216-5231, 16 pages.
Knowles, BB et al., "Human Hepatocellular Carcinoma Cell Lines Secrete the Major Plasma Proteins and Hepatitis B Surface Antigen," Science, 1980, vol. 209(4455), pp. 497-499, 3 pages.
Langer, R, "New Methods of Drug Delivery," Science, 1990, vol. 249, issue 4976, pp. 1527-1533, 7 pages.
Mangos, MM et al., "Efficient RNase H-Directed Cleavage of RNA Promoted by Antisense DNA or 2'F-ANA Constructs Containing Acyclic Nucleotide Inserts," J. Am. Chem. Soc., 2003, vol. 125(3), pp. 654-661, 8 pages.
McTigue, PM et al., "Sequence-Dependent Thermodynamic Parameters for Locked Nucleic Acid (LNA)-DNA Duplex Formation," Biochemistry, 2004, vol. 43(18), pp. 5388-5405, 18 pages.
Mergny, JL et al., "Analysis of Thermal Melting Curves," Oligonucleotides, 2003, vol. 13(6), pp. 515-537, 23 pages.
Milich, DR, "Influence of T-helper cell subsets and crossregulation in hepatitis B virus infection," Journal of Viral Hepatitis, 1997, vol. 4 (suppl 2), pp. 48-59, 12 pages.
Mitsuoka, Y et al., "A bridged nucleic acid, 2',4'-BNACOC: synthesis of fully modified oligonucleotides bearing thymine, 5-methylcytosine, adenine and guanine 2',4'-BNACOC monomers and RNA-selective nucleic-acid recognition," Nucleic Acids Research, 2009, vol. 37, No. 4, pp. 1225-1238, 14 pages.
Morita, K. et al., "2'-O,4'-C-ethylene-bridged nucleic acids (ENA): highly nuclease-resistant and thermodynamically stable oligonucleotides for antisense drug," Bioorganic & Medicinal Chemistry Letters, 2002, vol. 12:1, pp. 73-76, 4 pages.
Nayersina, R et al, "HLA A2 restricted cytotoxic T lymphocyte responses to multiple hepatitis B surface antigen epitopes during hepatitis B virus infection," Journal of Immunology, 1993, vol. 150:10, pp. 4659-4671, 14 pages.
Rukov, JL et al., "Dissecting the target specificity of RNase H recruiting oligonucleotides using massively parallel reporter analysis of short RNA motifs," Nucleic Acids Research, 2015, vol. 43:17, pp. 8476-8487, 12 pages.
Santalucia, J Jr., "unified view of polymer, dumbbell, and oligonucleotide DNA nearest-neighbor thermodynamics," Proc. National Academy Science USA., 1998, vol. 95:4, pp. 1460-1465, 6 pages.
Sells, MA et al., "Production of hepatitis B virus particles in Hep G2 cells transfected with cloned hepatitis B virus DNA," Proceedings of National Academy Science USA, 1987, vol. 84:4, pp. 1005-1009, 5 pages.
Seth, PP et al.,"Synthesis and Biophysical Evaluation of 2',4'-Constrained 2'O-Methoxyethyl and 2',4'-Constrained 2'O-Ethyl Nucleic Acid Analogues," J. Org. Chem., 2010, vol. 75:5, pp. 1569-1581, 7 pages.
Shi, CC et al., "Hepatitis B virus suppresses the functional interaction between natural killer cells and plasmacytoid dendritic cells," Journal Viral Hepatitas, 2012, vol. 19:2, e26-e33, 8 pages.
Sugimoto, N et al., "Thermodynamic Parameters to Predict Stability of RNA/DNA Hybrid Duplexes," Biochemistry, 1995, vol. 34:35, pp. 11211-11216, 6 pages.
Uhlmann, E, "Recent advances in the medicinal chemistry of antisense olignonucleotides," Current Opinion in Drug Discovery & Development, 2000, vol. 3:2, pp. 203-213, 12 pages.
Vester, B et al., "Chemically modified oligonucleotides with efficient RNase H response," Bioorganic & Medicinal Chemistry Letters, 2008, vol. 18:7, pp. 2296-2300, 5 pages.
Walsh, R et al., "Targeting the hepatits B virus procore antigen with a novel IgNAR singel variable domain intrabody," Virology, 2011, vol. 411:1, pp. 132-141, 10 pages.
Wieland, SF et al., "Stealth and Cunning: Hepatitis B and Hepatitis C Viruses," J Virol, 2005, 79, pp. 9369-9680, 12 pages.
Woltman et al., Hepatitis B Virus Lacks Immune Activating Capacity, but Actively Inhibits Plasmacytoid Dendritic Cell Function; PLoS One, 2011, 6, e15324, 14 pages.
Wooddell, CI et al., "RNAi-based treatment of chronically infected patients and chimpanzees reveals that integrated hepatitis B virus DNA is a source of HBsAg," Science Translational Medicine, 2017, vol. 9, No. 409, eaan0241, 12 pages.
Yan et al., "Molecular Determinants of Hepatitis B and D Virus Entry Restriction in Mouse Sodium Taurocholate Cotransporting Polypeptide," J Virol, 87, 2013, pp. 7977-7991, 8 pages.
Yang, D et al., "A mouse model for HBV immunotolerance and immunotherapy," Cellular & Molecular Immunology, 2014, vol. 11, pp. 71-78, 8 pages.
PCT International Search Report for PCT International Patent Application No. PCT/EP2017/064981, dated Oct. 2, 2017, 5 pages.
Wang, et al., "Identification of acetyltransferase genes (HAT1 and KAT8) regulating HBV replication by RNAi screening," Cell Biosci (2015) 5:66.
PCT International Search Report for PCT International Patent Application No. PCT/EP2017/064980, dated Oct. 2, 2017.
N.N: database entry: ATJ17241, Sep. 20, 2007 (Sep. 20, 2007), pp. 1-1, XP055404262, Retrieved from the Internet: URL:file:///C:/Users/TL23249/Documents/Downloads/GSN_ATJ17241.pdf [retrieved on Sep. 6, 2017], 1 page.
Database EMBL, Aug. 18, 2010, (Aug. 18, 2010) Sequence 593709 from Patent EP2213738., XP002787331, retrieved from EBI accession No. EM PAT:HD716993 Database accession No. HD716993 sequence, 1 page.
Database EMBL, Apr. 19, 2011, (Apr. 19, 2011) WO 2005116204-A/507823: Double strand polynucleotides generating RNA interference., XP002787332, retrieved from EBI accession No. EM PAT:FZ101298 Database accession No. FZ101298 sequence, 1 page.
Database EMBL, Aug. 18, 2011, (Aug. 18, 2011) 11 Sequence 447635 from Patent EP2213738. II XP002787330, retrieved from EBI accession No. EM PAT:HD570919 Database accession No. HD570919 sequence, 1 page.
N.N: database entry: GZ986077, Jun. 4, 2013 (Jun. 4, 2013), pp. 1-1, XP055404295, Retrieved from the Internet URL:file:///C:/Users/TL23249/Documents/Downloads/EM_PAT_GZ986077.pdf [retrieved on Sep. 6, 2017], 1 page.
N.N: database entry: miRTarBase—targets for hsa-mir-192-5p, Jun. 3, 2014 (Jun. 3, 2014), XP055404326, Retrieved from the Internet: URL:file:///C:/Users/TL23249/Documents/Downloads/miRNA-Target Interaction Search Results.pdf [retrieved on Sep. 6, 2017], 6 pages.
N.N: database entry GS _ NUC ALERT:W02015031694.237191, Mar. 5, 2015 (Mar. 5, 2015), pp. 1-1, XP055404257, Retrieved from the Internet: URL:www C:/Users/TL23249/Documents/Downloads/GS_NUC_ALERT_WO2015031694.pdf [retrieved on Sep. 6, 2017], 1 page.
Block, Timothy M. et al., "Chronic hepatitis B: A wave of new therapies on the horizon," Antiviral Research, Elsevier BV, NL, vol. 121, 2015, pp. 69-81, 14 pages.
Buster et al., "Withdrawal Flares After Treatment with Peginterferon Alpha-2b alone or in Combination with Lamivudine in HBeAg-Positive Chronic Hepatitis B," Hepatology, 2007, 46, 1 page.
Chen et al., "Immune Tolerance Split between Hepatitis B Virus Precore and Core Proteins," Journal of Virology, 2005, 79:5, pp. 3016-3027, 12 pages.
Fisicaro et al., "Antiviral Intrahepatic T-Cell Responses Can be Restored by Blocking Programmed Death-1 Pathway in Chronic Hepatitis B," Gastroenterology, 2010, 138, pp. 682-693, 16 pages.
Geng, Ca et al., "Small-molecule inhibitors for the treatment of hepatitis B virus documented in patents," Mini Reviews in Medicinal Chemistry, Bentham Science Publ, NL, vol. 13, No. 5, 2013, pp. 749-776, 28 pages.
Hadziyannis, Stephanos J., "Natural history of chronic hepatitis B in Euro-Mediterranean and African Countries," Journal of Hepatology, 2011, vol. 55, 183-191, 1 page.
Janssen et al., "Pegylated interferon alfa-2b alone or in combination with lamivudine for HBeAg-positive chronic hepatitis B: a randomised trial," Lancet, 2005, 365, pp. 123-129, 7 pages.

(56) References Cited

OTHER PUBLICATIONS

Kondo et al., "Recovery of Functional Cytotoxic T LymphocytesDuring Lamivudine Therapy by AcquiringMulti-Specificity," Journal of Medical Virology, 2004, vol. 74, pp. 425-433, 9 pages.
Kondo et al., "Hepatitis B Surface Antigen Could Contribute to the Immunopathogenesis of Hepatitis B Virus Infection," ISRN Gasteroenterology, 2013, Article ID 935295, 9 pages.
Kumar et al., "Hepatitis B Virus Regulatory HBx Protein Binds to Adaptor Protein IPS-1 and Inhibits the Activation of Beta Interferon," J Virol, 2011, 85:2, pp. 987-995, 9 pages.
Liaw et al., "Hepatitis B virus infection," Lancet, 2009, 373, pp. 582-592, 11 pages.
Liaw et al., "Hepatitis B e Antigen Seroconversion: A Critical Event in Chronic Hepatitis B Virus Infection," Dig. Dis. Sci., 2010, 55, pp. 2727-2734, 8 pages.
Marcellin et al., "Peginterferon Alfa-2a Alone, Lamivudine Alone, and the Two in Combination in Patients with HBeAg-Negative Chronic Hepatitis B," N. Engl. J. Med., 2004, vol. 351:12, pp. 1206-1217, 12 pages.
Milich et al., "The Secreted Hepatitis B Precore Antigen Can Modulate the Immune Response to the Nucleocapsid: A Mechanism for Persistence," 1998, J. Immunol. 160, pp. 2013-2021, 10 pages.
Mueller et al., "PAPD5/7 are novel host factors that are required for Hepatitis B virus RNA stabilization," Hepatology, 2018, XP-002787333, pp. 1527-3350.
Op Den Brouw et al., "Hepatitis B virus surface antigen impairs myeloid dendritic cellfunction: a possible immune escape mechanism of hepatitis B virus," Immunology, 2009b, 126, pp. 280-289, 10 pages.
Ra Palma et al., Database entry: GC056445, Aug. 12, 2005 (Aug. 12, 2005), pp. 1-1, XP055404289, Retrieved from the Internet: URL:file:///C:/Users/TL23249/Documents/Downloads/EM_PAT_GC056445.pdf [retrieved on Sep. 6, 2017], 1 page.
Schulze et al., "Detection of CD4+ T Cell Responses in Patients with acute HCV Infection Irrespective of Clinical Outcome," Hepatology, 463, 2007, 1 page.
Shin et al., "Prediction of response to entecavir therapy in patients withHBeAg-positive chronic hepatitis B based on ontreatmentHBsAg, HBeAg and HBV DNA levels," Journal of Viral Hepatitis, 2012, 19, pp. 724-731, 8 pages.
Tavis John E. et al., "The hepatitis B virus ribonuclease H as a drug target," Antiviral Research, vol. 118, 2015, pp. 132-138, 8 pages.
Altschul, SF et al., "Basic Local Alignment Search Tool," J Mol Biol, 1990, vol. 215, pp. 403-410, 8 pages.
Altschul, SF, "A Protein Alignment Scoring System Sensitive at All Evolutionary Distances," Journal Molecular Evolution, 1993, vol. 36, pp. 290-300; 11 pages.
Altschul, SF et al., "Gapped BLAST and PSI-BLAST: a new generation of protein database search programs," Nucleic Acids Research, 1997, vol. 25:17, pp. 3389-3402, 14 pages.
Bartel et al., "Cellular interactions in Development: A practical approach." Oxford University Press, pp. 153-179, 28 pages.
Bergstrom DE, "Unnatural Nucleosides with Unusual Base Pairing Properties," Current Protocols in Nucleic Acid Chemistry, 2001, Suppl. 5, pp. 1.4.1-1.4.13, 13 pages.
Brutlag et al., "Improved sensitivity of biological sequence database searches," 1990, vol. 6:3, pp. 237-245, 9 pages.
Chidley, C. et al., "A yeast-based screen reveals that sulfasalazine inhibits tetrahydrobiopterin biosynthesis", Nature Chemical Biology, 2011, vol. 7, pp. 375-383, 9 pages.
Heidenreich, M et al., "Applications of CRISPR-Cas systems in neuroscience", Nat Rev Neurosci, 2016, vol. 17(1) pp. 36-44, 23 pages.
Holdgate, GA et al., "Measurements of binding thermodynamics in drug discovery," Drug Discovery Today, 2005, vol. 10, No. 22, pp. 1543-1550, 8 pages.
Lagos-Quintana, M et al. "New microRNAs from mouse and human," RNA, 2003, vol. 9, pp. 175-179, 5 pages.
Lewis BP et al., "Conserved Seed Pairing, Often Flanked by Adenosines, Indicates that Thousands of Human Genes are MicroRNA Targets," Cell, 2005, vol. 120, pp. 15-20, 6 pages.
Licitra, EJ et al., "A three-hybrid system for detecting small ligand-protein receptor interactions", Proc Natl Academy of Science USA, 1996, vol. 93, pp. 12817-12821, 5 pages.
Manoharan, M., "Oligonucleotide Conjugates in Antisense Technology," Antisense Drug Technology, Marcel Dekker, Inc., 2001, Ch. 16, pp. 391-469, 81 pages.
N.N: database entry: mRNA—"EM_EST:AW015126; SV 1; linear; mRNA; EST; HUM; 244 BP," Sep. 13, 1999; Retrieved from the Internet: URL:file:///ibis.internal.epo.org/exam/dbfetch.jsp?id=EM EST:AW015126 [retrieved on Jan. 15, 2020], 1 page.
Ogami, K et al., "Molecular cloning and characterization of a novel isoform of the non-canonical poly(A) polymerase PAPD7", Biochemical and Biophysical Research Communications, 2013, 432.1, pp. 135-140, 6 pages.
Rammelt, C et al., "PAPD5, a noncanonical poly(A) polymerase with an unusual RNA-binding motif", RNA, 2011, vol. 17, pp. 1737-1746, 10 pages.
Thompson, JD et al., "Clustal W: improving the sensitivity of progressive multiple sequence alignment through sequence weighting, position-specific gap penalties and weight matrix choice," Nucleic Acids Res., 1994, vol. 22(22), pp. 4673-4680, 8 pages.
Ward, ES et al., "Binding activities of a repertoire of single immunoglobulin variable domains secreted from *Escherichia coli*," Nature, 1989, vol. 341, pp. 544-546, 3 pages.
Winther, TH et al., "Circulating MicroRNAs in Plasma of Hepatitis B e Antigent Positive Children Reveal Liver-Specifc Target Genes", International Journal of Hepatology, 2014, article ID791045, pp. 1-10, 10 pages.
Wu Q et al., "EM_EST:EH352838; Sv 1; linear; mRNA; EST; HUM; 105 BP," Mar. 2, 2007; Retrieved from the Internet: URL:file:///ibis.internal.epo.org/exam/dbfetch.jsp?id=EM_EST:EH352838 [retrieved on Jan. 15, 2020], 1 page.
Zhou, T et al., "HBsAg mRNA degradation induced by a dihydroquinolizinone compound depends on the HBV posttranscription regulatory element," Antiviral Research, 2018, vol. 149, pp. 191-201, 11 pages.
Schulze A. et al., Hepatitis B virus infection initiates with a large surface protein-dependent binding to heparan sulfate proteoglycans, Hepatology, 2007, vol. 46(6), pp. 1759-1768.
U.S. Centers for Disease Control and Prevention ("CDC"), "Hepatitis B FAQs for the Public", retrieved Jan. 28, 2020, 7 pages.
World Health Organization ("WHO"), "Hepatitis B Fact sheet No. 204", Jul. 2014, retrieved Jan. 28, 2020, 4 pages.
MiRTasBase accession No. MIRT026642 [miRNA, hsa-miR-192-5p : PAPD5, target gene], downloaded Jun. 28, 2019, 4 pages.
MiRTasBase accession No. MIRT026248 [miRNA, hsa-miR-192-5p : PAPD7, target gene], downloaded Jun. 28, 2019, 4 pages.
Examination Report issued in EP Application No. 17732082.7 dated Aug. 5, 2020, 5 pages.
Notice of Allowance dated May 6, 2020, in related U.S. Appl. No. 16/162,279, 10 pages.
Non-Final Office Action dated Jun. 25, 2020, in related U.S. Appl. No. 16/310,765, 10 pages.
Chan: Antisense Oligonucleotides: from design to therapeutic application, Clinical and Experimental Pharmacology and Physiology, 2006, p. 533-540, 8 pgs.
Friend: High-yield Preparation of Isolated Rat Liver Parenchymal Cells: A Biochemical and Fine Structural Study, J. Cell Biol., 1969, 15 pgs.
Iobst: Selective Sugar Binding to the Carbohydrate Recognition Domains of the Rat Hepatic and Macrophage Asialoglycoprotein Receptors, 1996, 8 pgs.
Burroughs: Genome Research, vol. 20, pp. 1398-1419, 14 pgs.
Paterna: Antioxidant and Cytoprotective Properties of Tagatose in Cultured Murine Hepatocytes, 1998, Toxiol. Appl. Pharmacol., 1998, 9 pgs.
Russian Office Action issued in 2020115761/10(025899), 12 pgs.
Zenkova: Imperfectly matched nucleic acid complexes and their biochemical manifestation, Russian Chemical Reviews, 1993, pp. 414-435, 21 pgs.

(56) References Cited

OTHER PUBLICATIONS

International Search Report and Written Opinion issued in PCT/EP2017/064980 dated Sep. 15, 2017, 14 pgs.
International Preliminary Report on Patentability issued in PCT/EP2017/064980, dated Dec. 18, 2018, 9 pgs.
International Search Report and Written Opinion issued in PCT/EP2018/078136 dated Dec. 18, 2018, 13 pgs.
International Preliminary Report on Patentability issued in PCT/EP2018/078136 dated Apr. 21, 2020, 8 pgs.
Boele: PAPD5-mediated 3'adenylation and subsequent degradation of miR-21 is disrupted in proliferative disease, Proc National Academy of Science USA, Aug. 5, 2014, vol. 111, Issue 31, pp. 11467-11472, 6 pgs.
Inan: Hepatitis B Virus: Biology and Life Cycle, Viral Hepatitis Journal, 2015, vol. 1, pp. 1-7, 7 pgs.
Laishram: Poly(A) polymerase (PAP) diversity in gene expression—Star-PAP vs canonical PAP, FEBS Letters, 2014, vol. 588(14) pp. 2185-2197, 30 pgs.
Doudna: CRISPR-Cas: A Laboratory Manual, 2016, ISBN 978-1-621821-31-1, 1 pg.
Remington: The Science and Practice of Pharmacy, Philadelphia; Lippincott, Williams & Wilkins 2000, 1 pg.
Rowe: Handbook of Pharmaceutical Excipients, Chicago, Pharmaceutical Press, 2005, 1 pg.
Notice of Reasons for Refusal issued in JP 2018-565394, dated Jul. 30, 2021, 5 pgs.
Notice of Reasons for Refusal issued in JP 2018-565300, dated May 26, 2021, 5 pgs.
Ansel's Pharmaceutical Dosage Forms and Drug Delivery Systems, Lippicott Williams & Wilkins, 2004, 4 pgs.
Database EMBL, Aug. 18, 2011, (Aug. 18, 2011) 11 Sequence 447635 from Patent EP2213738. 11 XP002787330, retrieved from EBI accession No. EM PAT:HD570919 Database accession No. HD570919 sequence, 1 pg.
Hepatitis B Fact sheet N°204, http://www.who.int/medicalcentre/factsheets/fs204/en/, Jul. 2014, Retrieved Nov. 4, 2014, 4 pgs.
Centers for Disease Control and Prevention, Hepatitis B FAQs for the Public, http://www.cdc.gov/hepatitis/b/bfaq.htm, 7 pgs.
Georges: Coordinated Regulation of Cell Cycle Transcripts by p53-InduciblemicroRNAs, miR-192 and miR-215, Cancer Research vol. 68(24) pp. 10105-10112, 9 pgs.
Atschul: Gapped BLAST and PSI-BLAST—a new generation go protein database search programs, Nucliec Acids Research, 1997, 14 pgs.
Non-final Office Action issued in U.S. Appl. No. 16/310,765 dated Jun. 26, 2020, 10 pgs.
Afang: Abstract: Status and research progress in clinical medication of hepatitis drugs, Anti Infect Pharm, Dec. 31, 2019, vol. 16, issue 12 pp. 2034-2039, 6 pgs.
Database—237191 [N.N: database entry GS_NUC ALERT:W02015031694.237191, Mar. 5, 2015 (Mar. 5, 2015), pp. 1-1, XP055404257, Retrieved from the Internet: URL:www [retrieved on Sep. 6, 2017.], 1 pg.
Afang: The Current status and research progress of clinical treatment of hepatitis B drugs, Anti Infect Pharm, 2019, 6 pgs. Abstract only.
Bergstrom DE, "Unnatural nucleosides with unusual base pairing properties", Current Protocols in Nucleic Acid Chemistry, 2009, Suppl. 37 1.4.1, 32 pgs.
Examination Report issued in EP Application No. 17732082.7 dated Aug. 5, 2020, 6 pages.
Examination Report issued in EP Application No. 17732082.7 dated Jan. 22, 2020, 6 pages.
Examination Report issued in EP Application No. 17732082.7 dated Mar. 31, 2021, 6 pages.
Examination Report issued in EP Application No. 17732083.5 dated Sep. 2, 2020, 5 pages.
Examination Report issued in EP Application No. 17732083.5 dated Jan. 22, 2020, 6 pages.
Intention to Grant issued in EP Application No. 17732083.5 dated Dec. 17, 2021, 6 pages.
International Preliminary Report on Patentability received for PCT Patent Application No. PCT/EP2017/064981, dated Dec. 27, 2018, 9 pages.
Ko C et al., "Novel viral and host targets to cure hepatitis B," Current Opinion in Virology, Jun. 2017, vol. 24, pp. 38-45.
N.N: "database entry: miRTarBase—targets for hsa-mir-192-5p", Jun. 3, 2014 (Jun. 3, 2014), XP055404326, Retrieved from the Internet: URL:file:///C:/Users/TL23249/Documents/Downloads/miRNA-Target Interaction Search Results.pdf retrieved on Sep. 6, 2017].

* cited by examiner

| # | Prey ID | Protein | Results |
|---|---|---|---|
| A | PLA_RP6_hgx4240v1_pB409_A-15 | PAPD7 varX1 | validated |
| B | PLA_RP6_hgx4241v1_pB409_A-112 | PAPD5 var1 | Validated |
| C | PLA_RP6_hgx4240v1_pB409_A-24 | PAPD5 var2 | validated |

| # | Prey ID | Protein | Results |
|---|---|---|---|
| A | hgx4386v1_pP7 | PAPD5 var1 full length | validated |
| B | hgx4388v2_pP7 | PAPD7 varX1 full length | Validated |

A

B

NUCLEIC ACID MOLECULES FOR REDUCTION OF PAPD5 OR PAPD7 MRNA FOR TREATING HEPATITIS B INFECTION

The present application claims the benefit of priority from PCT/EP2017/064980, filed 19 Jun. 2017, and to EP 16175045.0, entitled "NUCLEIC ACID MOLECULES FOR REDUCTION OF PAPD5 AND PAPD7 mRNA FOR TREATING HEPATITIS B INFECTION," filed on 17 Jun. 2016, the contents of which is incorporated herein by reference.

FIELD OF THE INVENTION

The present invention relates to a method for identifying a compound that prevents, ameliorates and/or inhibits a hepatitis B virus (HBV) infection, wherein a compound that reduces the expression and/or activity of PAP associated domain containing 5 (PAPD5) or PAP associated domain containing 7 (PAPD7) is identified as a compound that prevents, ameliorates and/or inhibits a HBV infection. The invention also provides for inhibitors of PAPD5 or PAPD7 for use in treating and/or preventing a HBV infection. Specifically the present invention identifies nucleic acid molecules, such as antisense oligonucleotides or RNAi agents as inhibitors of PAPD5 or PAPD7 as well as a combined preparation of these comprising an inhibitor of PAPD5 and an inhibitor of PAPD7 for simultaneous or sequential use in the treatment or prevention of a HBV infection. Also comprised in the present invention is a pharmaceutical composition for use in the treatment and/or prevention of a HBV infection, and a method for monitoring the therapeutic success during the treatment of a HBV infection.

BACKGROUND

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, *Hepatology,* 46, (2007), 1759-68) and via the specific binding of HBV surface antigens (HBsAg) to the hepatocyte sodium-taurocholate cotransporting polypeptide (NTCP) receptor (Yan, *J Virol,* 87, (2013), 7977-91). The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the HBV infection remains a major health problem worldwide which concerns an estimated 350 million chronic carriers who have a higher risk of liver cirrhosis and hepatocellular carcinoma.

The secretion of antiviral cytokines in response to a HBV infection by the hepatocytes and/or the intra-hepatic immune cells plays a central role in the viral clearance of the infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) are thought to participate to the maintenance of the immunological tolerant state observed in chronically infected patients (CHB). The persistent exposure to HBsAg and other viral antigens can lead to HBV-specific T-cell deletion or to progressive functional impairment (Kondo, *Journal of Immunology* (1993), 150, 4659-4671; Kondo, *Journal of Medical Virology* (2004), 74, 425-433; Fisicaro, *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw, *Immunology*, (2009b), 126, 280-9; Woltman, *PLoS One*, (2011), 6, e15324; Shi, *J Viral Hepat*. (2012), 19, e26-33; Kondo, *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains one of the ultimate goals of therapy. Current therapy such as Nucleos(t)ide analogues are molecules that inhibit HBV DNA synthesis but are not directed at reducing HBsAg level. Nucleos(t)ide analogs, even with prolonged therapy, only show weak HBsAg clearance comparable to those observed naturally (between −1%-2%) (Janssen, *Lancet*, (2005), 365, 123-9; Marcellin, *N. Engl. J. Med.*, (2004), 351, 1206-17; Buster, *Hepatology*, (2007), 46, 388-94).

Hepatitis B e-antigen (also called HBV envelope antigen or HBeAg) is a viral protein that is secreted by hepatitis B infected cells. HBeAg is associated with chronic hepatitis B infections and is used as a marker of active viral disease and a patient's degree of infectiousness.

The function of the hepatitis B virus precore or HBeAg is not completely known. However HBeAg is well known to play a key role in viral persistence. HBeAg is thought to promote HBV chronicity by functioning as an immunoregulatory protein. In particular, the HBeAg is a secreted accessory protein, which appears to attenuate the host immune response to the intracellular nucleocapsid protein (Walsh, Virology, 2011, 411(1):132-141). The HBeAg acts as an immune tolerogen contributing to HBV persistence, and possibly functions in utero considering that soluble HBeAg traverses the placenta (Walsh, Virology, 2011, 411(1):132-141). Furthermore, HBeAg downregulates: i) cellular genes controlling intracellular signaling; and ii) the Toll-like receptor 2 (TLR-2) to dampen the innate immune response to viral infection (Walsh, Virology, 2011, 411(1):132-141). In the absence of HBeAg, HBV replication is associated with upregulation of the TLR2 pathway (Walsh, Virology, 2011, 411(1):132-141). Accordingly, HBeAg has a significant role in modulating virus/host interactions to influence the host immune response (Walsh, Virology, 2011, 411(1): 132-141). Thus, reducing HBeAg in HBeAg positive patient population may lead to reversal of HBV specific immune-dysfunction (Milich, 1997, J. Viral. Hep. 4: 48-59; Milich, 1998, J. Immunol. 160: 2013-2021). In addition, the secreted HBeAg is significantly more efficient than the intracellular hepatitis core antigen (HBcAg) at eliciting T-cell tolerance, and the split T-cell tolerance between the HBeAg and the HBcAg and the clonal heterogeneity of HBc/HBeAg-specific T-cell tolerance may have significant implications for natural HBV infection and especially for precore-negative chronic hepatitis (Chen, 2005, Journal of Virology, 79: 3016-3027).

Accordingly, reducing secretion of HBeAg in addition to secretion of HBsAg would lead to an improved inhibition of development of a chronic HBV infection as compared to the inhibition of secretion of HBsAg alone. In addition, the highest rates of transmission of an acute infection to chronic (>80%) have been reported in cases of matemo-fetal and neonatal HBV transmission from HBeAg-positive mothers (Liaw, Lancet, 2009, 373: 582-592; Liaw, Dig. Dis. Sci., 2010, 55: 2727-2734; and Hadziyannis, 2011, Joumal of hepatology, 55: 183-191). Therefore, reducing HBeAg in an expected mother may not only reduce the patient's degree of infectiousness, but may also inhibit the development of a chronic HBV infection of her child.

Therefore, in the therapy of HBV there is an unmet medical need to inhibit viral expression, particularly to inhibit secretion of HBsAg and HBeAg (Wieland, S. F. & F. V. Chisari. J Virol, (2005), 79, 9369-80; Kumar et al. J Virol, (2011), 85, 987-95; Woltman et al. PLoS One, (2011), 6, e15324; Op den Brouw et al. Immunology, (2009b), 126, 280-9).

WO 03/022987 discloses for example in Table 7A 1298 genes that are upregulated in hepatitis C-positive tissue. One of the mentioned genes is topoisomerase-related function protein 4 (TRF4, AF089897). AF089897 is also called TRF4-2, which is quite similar to position 880 to 2340 of SEQ ID NO: 4 herein. The observation that a fragment of PAPD5 is upregulated slightly in hepatitis C positive cells does not provide any indication that inhibiting PAPD5 represents an effective therapy. WO 03/022987A2 does not disclose any hint that fragments of PAPD5 plays any critical role during hepatitis C infection at all. In addition, HCV and HBV are two completely different viruses leading to two completely different diseases with different etiologies, different progression and different medication. This is in line with the observation of the present inventors that the PAPD5 and PAPD7 inhibitors DHQ and THP are inactive against hepatitis C virus (HCV) or other viruses beside HBV (data not shown).

In WO 2010/040571 PAPD5 has been suggested in a long list of other genes as having a potential role in cell proliferation in metabolic and tumorous disease without the provision of any actual evidence.

In WO 2013/166264 PAPD5 has been suggested in a long list of other genes as having a potential role in increasing viral replication without the provision of any actual evidence.

In WO 2017/066712 down regulation of PAPD5 in relation to the treatment and diagnosis of telomere diseases has been described. Five shRNA structures for this purpose have been described.

To our knowledge the expression of PAPD5 or PAPD7 has never been associated with HBV infection, nor has modified single stranded antisense oligonucleotides been made against these targets.

OBJECTIVE OF THE INVENTION

Thus, the technical problem underlying the present invention is the identification and provision of ameliorated means and methods for treating and/or preventing a HBV infection.

The technical problem is solved by the provision of the embodiments described herein and characterized in the claims.

SUMMARY OF THE INVENTION

Figure 1:
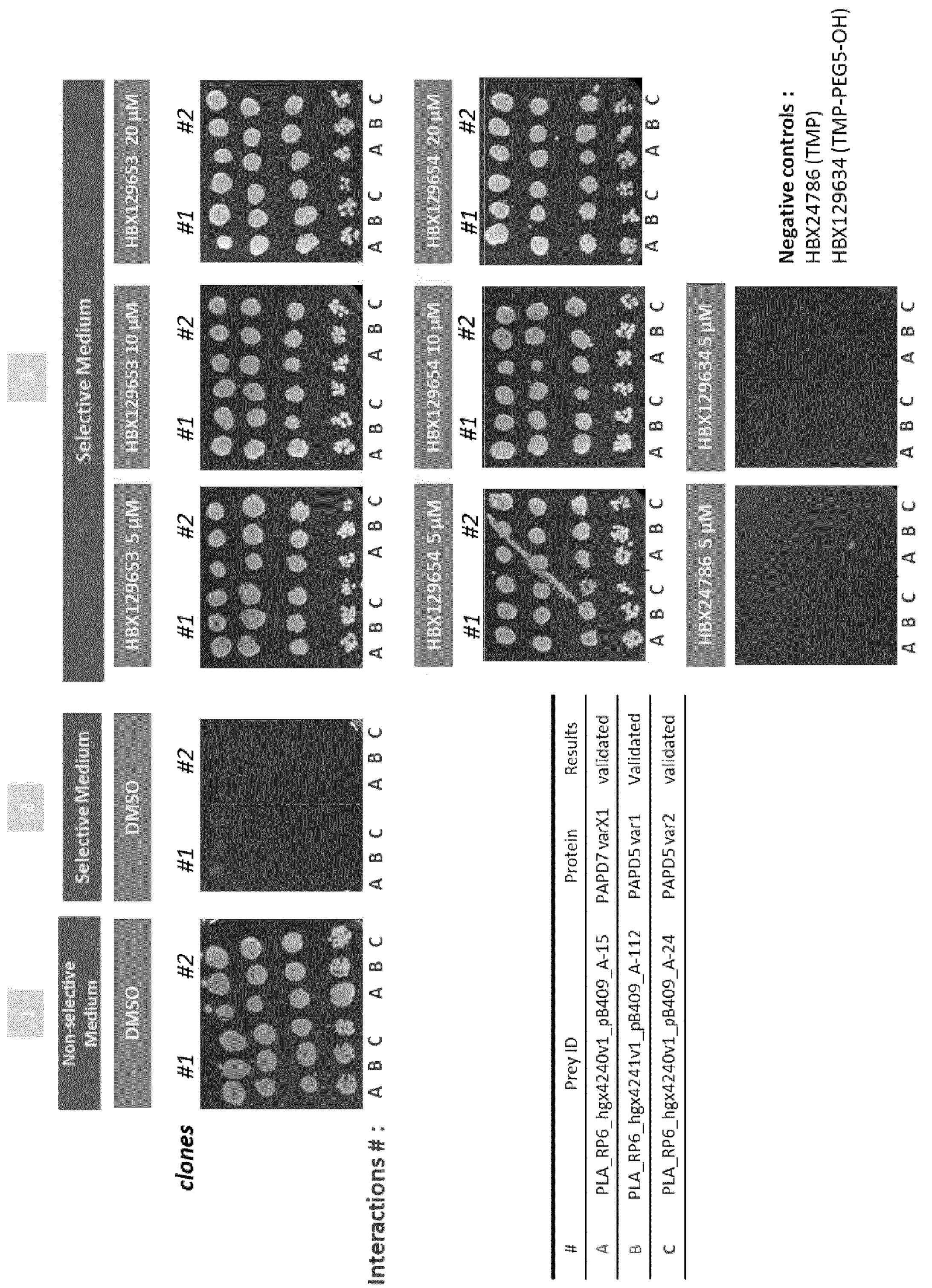
FIG. 1: Pictures from 1-by-1 experiment with HBX129653/HBX129654 chemical probes and the 3 prey fragments.

One aspect of the present invention relates to a composition comprising a nucleic acid molecule for use in the treatment and/or prevention of Hepatitis B virus infection, wherein said nucleic acid molecule inhibits expression and/or activity of PAPD5. In particular a composition comprising a combined preparation of a nucleic acid molecule inhibits expression and/or activity of PAPD5 and another nucleic acid molecule inhibits expression and/or activity of PAPD7 for use in the treatment and/or prevention of Hepatitis B virus infection.

A further aspect of the present invention relates to nucleic acid molecules that inhibit expression and/or activity of PAPD7. In particular single stranded antisense, siRNA and shRNA molecules.

A further aspect of the present invention relate to single stranded antisense oligonucleotides that inhibit expression and/or activity of PAPD5. In particular modified antisense oligonucleotides comprising 2'sugar modified oligonucleotide and phosphorothioate internucleoside linkages.

Further aspects of the invention are conjugates of nucleic acid molecules of the invention, combined preparations of nucleic acid molecules capable of inhibiting expression and/or activity of both PAPD5 and PAPD7 and pharmaceutical compositions comprising the molecules of the invention.

A further aspect of the invention is a method for identifying a compound or composition that prevents, ameliorates and/or inhibits a hepatitis B virus (HBV) infection, comprising:

a. contacting a test compound or composition with a cell expressing PAPD5 and/or PAPD7;
b. measuring the expression and/or activity of PAPD5 and/or PAPD7 in the presence and absence of said test compound or composition; and
c. identifying a compound or composition that reduces the expression and/or activity of PAPD5 and/or PAPD7 as a compound that prevents, ameliorates and/or inhibits a HBV infection.

DETAILED DESCRIPTION OF THE INVENTION

PAPD5 and PAPD7 are non-canonical poly(A)-polymerases that belong to the superfamily of polymerase β-like nucleotidyl transferases. In context of the present invention it has surprisingly been shown that a compound that is useful for the therapeutic intervention of a HBV infection can successfully be identified by analysing whether a test compound inhibits PAPD5 or PAPD7. Or, in other words, inhibition of PAPD5 or PAPD7, or the inhibition of both, was identified in the appended examples as being an indicator for the efficacy of a compound to inhibit a HBV infection. The appended examples demonstrate that a dihydroquinolizinone compound having the formula (III) shown in the Materials and Methods section, herein called DHQ, and a tetrahydropyridopyrimidine compound having the formula (IV) as shown in the Materials and Methods section, herein called THP, bind to PAPD5 and PAPD7 polypeptides (SEQ ID NO: 1 and 2 respectively). These compounds have the capacity to inhibit production of HBV surface antigen (HBsAg) and the expression of HBV RNA during HBV infection (WO 2015/113990 A1 and WO2016/177655). In addition, the appended examples show that inhibition of PAPD5 or PAPD7 or both by using pools of siRNA leads to an inhibition of viral expression, particularly of the secretion of HBsAg and HBeAg as well as of the production of intracellular HBV mRNA. These results directly indicate that by reducing the amount and/or activity (e.g. the amount) of PAPD5 and/or PAPD7 an HBV infection (e.g. a chronic HBV infection) can be prevented or treated (i.e. ameliorated and/or inhibited).

Screening Methods of the Invention

Thus, the present invention relates to a screening method, wherein a compound that reduces the expression and/or activity (e.g. the expression) of PAPD5 or PAPD7 (or combinations of compounds that reducePAPD5 and PAPD7) is identified as a compound that prevents and/or treats (i.e. ameliorates and/or inhibits) a HBV infection. In a preferred embodiment of the present invention the compound is a RNAi molecule, in particular a nucleic acid molecule, such as a siRNA, shRNA or antisense oligonucleotide. Using the screening method of the invention 240 LNA modified antisense oligonucleotides targeting either PAPD5 or PAPD7 mRNA have been screened for their ability to reduce the expression of PAPD5 or PAPD7, or both using combinations of compounds. Some of these have further been tested to confirm their ability to ameliorate and/or inhibits a HBV infection, either alone or in combination.

One aspect of the invention is a method for identifying a compound or composition that prevents, ameliorates and/or inhibits a hepatitis B virus (HBV) infection, comprising:

a) contacting a test compound with a cell expressing PAP associated domain containing 5 (PAPD5) and/or PAP associated domain containing 7 (PAPD7);
b) measuring the expression and/or activity of PAPD5 and/or PAPD7 in the presence and absence of said test compound or composition; and
c) identifying a compound that reduces the expression and/or activity of PAPD5 or PAPD7 as a compound or composition that prevents, ameliorates and/or inhibits a HBV infection; optionally
d) testing combinations of compounds to reduce the expression and/or activity of PAPD5 and PAPD7.

It has been found in context of the present invention that a compound (or composition) that reduces PAPD5 or PAPD7 or combinations of compounds that reduce PAPD5 and PAPD7 in combination leads to inhibition of HBV gene expression and replication; and thus, prevents, ameliorates and/or inhibits a HBV infection. Such a compound may lead to a reduction of the PAPD5 or PAPD7 expression and/or activity of 10-100%, preferably of 20-100%, more preferably of 30-100%, even more preferably of 40-100%, even more preferable of 50-100%, even more preferably of 60-100%, even more preferably of 70-100%, even more preferably of 80-100%, and most preferably of 90-100%.

In the herein provided screening method it is envisaged that the expression of PAPD5 and/or PAPD7 is measured (i.e. analyzed/determined) by using in step (a) a cell expressing PAPD5 and/or PAPD7, such as a HeLa or a HepaRG cell line. The expression and/or activity of PAPD5 and/or PAPD7 may be measured (i.e. analyzed/determined) by either (i) determining PAPD5 and/or PAPD7 polypeptide; or (ii) determining transcript levels in a cell expressing PAPD5 and/or PAPD7.

In one aspect of the invention, a compound that reduces the expression of PAPD5 or PAPD7 (e.g. of PAPD5, or preferably combinations of compounds that reduce both PAPD5 and PAPD7) is identified as a compound(s) that prevents, ameliorates and/or inhibits (i.e. treats) HBV infection. In another aspect of the invention a compound that reduces the activity of PAPD5 or PAPD7 polypeptide (e.g. of PAPD5, or preferably combinations of compounds that reduce both PAPD5 and PAPD7) is identified as a compound (s) that prevents, ameliorates and/or inhibits (i.e. treats) a HBV infection. It is prioritized that a compound that reduces the expression and/or activity of PAPD5 or combinations of compounds that reduce both molecules, PAPD5 and PAPD7, is identified as compounds that prevents, ameliorates and/or inhibits a HBV infection. Most preferably, a combination of compounds that reduces the expression and/or activity of both molecules, PAPD5 and PAPD7, is identified as a composition that prevents, ameliorates and/or inhibits a HBV infection.

The above described screening method lead to the identification of a compound or combination of compounds, that prevents, ameliorates and/or inhibits a HBV infection. It is prioritized that said compounds ameliorates and/or inhibits (i.e. treats) a HBV infection. Thus, the herein provided screening method is useful in the identification of a compound that treats a HBV infection.

In the context of the present invention, PAPD5 may be the PAPD5 polypeptide or the PAPD5 mRNA. It is prioritized in context of the screening methods provided herein that PAPD5 is the PAPD5 mRNA.

One aspect of the present invention relates to the herein provided screening method, wherein the cells expressing PAPD5 contain a PAPD5 target nucleic acid comprising or consisting of (i) a nucleotide sequence encoding the amino acid sequence of SEQ ID NO: 1 or 2;

(ii) a nucleotide sequence of SEQ ID NO: 4, 5 or 10 or natural variants thereof;

(iii) a nucleotide sequence encoding an amino acid sequence having at least 80%, preferably at least 90%, more preferably at least 95%, even more preferably at least 98%, and even more preferably at least 99% identity to SEQ ID NO: 1 or 2, wherein the polynucleotide encodes a polypeptide that has poly-A polymerase function;

(iv) a nucleotide sequence having at least 80% identity, preferably at least 90%, more preferably at least 95%, even more preferably at least 98%, and even more preferably at least 99% identity to the nucleotide sequence of (ii), wherein the polypeptide expressed from the nucleotide sequence has poly-A polymerase function;

(v) a nucleotide sequence encoding an enzymatically active fragment of SEQ ID NO: 1 or 2, such as a nucleotide sequence encoding SEQ ID NO: 7 or 8;

(vi) a nucleotide sequence encoding an amino acid sequence having at least 80%, preferably at least 90%, more preferably at least 95%, even more preferably at least 98%, and even more preferably at least 99% identity to an amino acid sequence of an enzymatically active fragment of SEQ ID NO: 1 or 2, such as SEQ ID NO: 7 or 8, wherein the polynucleotide encodes a polypeptide that has poly-A polymerase function; or (vii) a nucleotide sequence comprising or consisting of SEQ ID NO: 4, 5 or 10.

In preferred embodiments, the PAPD5 target nucleic acid is a mRNA, such as a pre-mRNA or mature mRNA. In further embodiments the PAPD5 target nucleic acid is a polynucleotide comprising or consisting of the nucleotide sequence of SEQ ID NO: 4, 5 or 10 or natural variants thereof. However, the PAPD5 mRNA may also be a polynucleotide comprising or consisting of a nucleotide sequence having at least 80%, preferably at least 90%, more preferably at least 95%, even more preferably at least 98%, and even more preferably at least 99% identity to SEQ ID NO: 4, 5 or 10, wherein the polynucleotide encodes a polypeptide that has poly-A polymerase function.

In context of the present invention PAPD7 may be the PAPD7 polypeptide or the PAPD7 mRNA. It is prioritized in context of the screening methods provided herein that PAPD7 is the PAPD7 mRNA.

One aspect of the present invention relates to the herein provided screening methods, wherein the cells expressing PAPD7 contain a PAPD7 target nucleic acid comprising or consisting of (i) a nucleotide sequence encoding the amino acid sequence of SEQ ID NO: 3;

(ii) a nucleotide sequence of SEQ ID NO: 6 or 11 or natural variants thereof;

(iii) a nucleotide sequence encoding an amino acid sequence having at least 80%, preferably at least 90%, more preferably at least 95%, even more preferably at least 98%, and even more preferably at least 99% identity to SEQ ID NO: 3, wherein the polynucleotide encodes a polypeptide that has poly-A polymerase function;

(iv) a nucleotide sequence having at least 80% identity, preferably at least 90%, more preferably at least 95%, even more preferably at least 98%, and even more preferably at least 99% identity to an nucleic acid sequence of (ii), wherein the polypeptide expressed from the nucleic acid sequence has poly-A polymerase function;

(v) a nucleotide sequence encoding an enzymatically active fragment of SEQ ID NO: 3, such as a nucleotide sequence encoding SEQ ID NO: 9; or (vi) a nucleotide sequence encoding an amino acid sequence having at least 80%, preferably at least 90%, more preferably at least 95%, even more preferably at least 98%, and even more preferably at least 99% identity to an amino acid sequence of an enzymatically active fragment of SEQ ID NO: 3, such as SEQ ID NO: 9, wherein the polynucleotide encodes a polypeptide that has poly-A polymerase function; or (vii) a nucleotide sequence comprising or consisting of SEQ ID NO: 6 or 11.

In preferred embodiments, the PAPD7 target nucleic acid is a mRNA, such as a pre-mRNA or mature mRNA. In further embodiments the PAPD7 target nucleic acid is a polynucleotide comprising or consisting of the nucleotide sequence of SEQ ID NO: 6 or 11, or natural variants thereof. However, the PAPD7 mRNA may also be a polynucleotide comprising or consisting of a nucleotide sequence having at least 80%, preferably at least 90%, more preferably at least 95%, even more preferably at least 98%, and even more preferably at least 99% identity to SEQ ID NO: 6 or 11, wherein the polynucleotide encodes a polypeptide that has poly-A polymerase function.

In context of the present invention the cell used for screening may be a eukaryotic cell. For example, said cell may be a yeast cell or a vertebrate cell. Vertebrate cells include fish, avian, reptilian, amphibian, marsupial, and mammalian cells. Preferably, the cell is a mammalian cell, most preferably, a human cell. Mammalian cells also include feline, canine, bovine, equine, caprine, ovine, porcine murine, such as mice and rat, and rabbit cells. In the herein provided screening methods, the "cell" may endogenously express PAPD5 and/or PAPD7 or overexpress PAPD5 and/or PAPD7. For overexpressing PAPD5 and/or PAPD7 the cell may comprise the nucleotide sequence encoding the PAPD5 polypeptide and/or the PAPD7 polypeptide within an expression vector. In preferred embodiments the cell comprises a nucleotide sequence encoding the PAPD5 polypeptide and a nucleotide sequence encoding the PAPD7 polypeptide. The cell of the herein provided screening methods may be comprised in a non-human animal, e.g. a mouse, rat, rabbit or ferret. The cells provided for the screening method described herein may also be termed target cells.

In the herein provided screening method wherein the activity of PAPD5 polypeptide and/or PAPD7 polypeptide is measured, said activity of PAPD5 and PAPD7 is preferably the poly-A polymerase function (i.e. the poly-A polymerase activity). The poly-A polymerase function/activity of a polypeptide (e.g. of PAPD5 or PAPD7) may be measured, e.g. by monitoring the in vitro polyadenylation of mRNA, e.g. as described in Rammelt, RNA, 2011, 17:1737-1746. This method can also be used to measure the poly-A polymerase function of PAPD5 and/or PAPD7 in the presence and absence of a test compound. In brief, a ribo-oligonucleotide $A_{15}$ may be incubated with recombinant PAPD5 protein expressed in *Escherichia coli* in the presence of ATP(A), CTP (C), GTP(G), UTP(U), or a mixture of all four dNTPs, respectively.

The expression of PAPD5 and/or PAPD7 in a cell in the presence and absence of the test compound may be measured, e.g. by using (q)PCR, western blot, or MassSpec.

A compound that inhibits the propagation of HBV may be a compound that reduces the expression of viral RNA, that reduces the production of viral DNA (HBV DNA) derived from viral RNA (HBV RNA), that reduces the production of new viral particles (HBV particles), and/or that produces production and/or secretion of HBsAg and/or HBeAg. Thus, one aspect of the present invention relates to the herein provided screening methods, wherein the compound that inhibits propagation of HBV inhibits secretion of HBsAg, inhibits secretion of HBeAg, and/or inhibits production of intracellular HBV mRNA or HBV DNA. Preferably, a compound that inhibits the propagation of HBV is a compound that inhibits secretion of HBsAg, secretion of HBeAg and production of intracellular HBV mRNA or HBV DNA.

For example, a compound that inhibits propagation of HBV may reduce the expression of viral RNA (HBV RNA), the production of viral DNA (HBV DNA) deriving from viral RNA, the production of new viral particles (HBV particles), the production and/or secretion of HBsAg and/or HBeAg by 10-100%, preferably by 20-100%, more preferably by 30-100%, even more preferably by 40-100%, even more preferable by 50-100%, even more preferably by 60-100%, even more preferably by 70-100%, even more preferably by 80-100%, and most preferably by 90-100%, when compared the untreated cells or animals or cell or animal treated with an appropriate control.

Inhibition of propagation of HBV may be measured, e.g., by measuring whether the test compound has the activity to inhibit secretion of HBsAg and/or of HBeAg, and/or to inhibit production of intracellular HBV mRNA or HBV DNA. Inhibition of secretion of HBsAg and/or HBeAg may be measured by ELISA, e.g. by using the CLIA ELISA Kit (Autobio Diagnostic) according to the manufacturers' instructions. Inhibition of production of intracellular HBV mRNA may be measured by real-time PCR, e.g. as described in the appended examples. Further methods for evaluating whether a test compound inhibits propagation of HBV are measuring secretion of HBV DNA by RT-qPCR e.g. as described in WO 2015/173208 or as described in the appended examples; Northern Blot; in-situ hybridization, or immuno-fluorescence.

The herein provided screening methods may additionally comprise the step of comparing the test compound to a control. Said control may be an inactive test compound, wherein said inactive test compound is a compound that does not reduce the expression and/or activity of PAPD5 or PAPD7.

This inactive test compound has no activity against HBV, e.g. it does not lead to inhibition of secretion of HBsAg and HBeAg and to inhibition of production of intracellular HBV mRNA. For example, the inactive test compound may have an $IC_{50}$ value in the inhibition of HBsAg of more than 6 μM. In the herein provided screening method, the inactive test compound may be a non-targeting antisense oligonucleotide, siRNA or shRNA. In the screening method wherein expression and/or activity of PAPD5 and/or PAPD7 is measured, the test compound as defined above in (i) may be used. An inactive compound can be designed from an active one, e.g., by chemical modification and/or functional interruption.

For performing the herein provided screening methods publicly or commercially available molecule libraries may be used. Thus, in context of the invention the said test compound may be a screening library of nucleic acid molecules selected from (i) single stranded antisense oligonucleotides, preferably comprising at least on 2' modified nucleoside; or (ii) siRNA molecules; or (iii) shRNA molecules.

The appended examples demonstrate that by inhibiting PAPD5 and/or PDPD7 polypeptide or mRNA, the secretion of HBsAg and HBeAg as well as production of intracellular HBV mRNA can effectively be inhibited. These data demonstrate that an inhibitor of PAPD5 and/or PAPD7 can be used to prevent and/or treat a HBV infection.

Several small molecule compounds that have a certain efficacy in the treatment of a HBV infection have been described in the art (see, e.g. WO 2015/113990 A1 and WO 2016/177655). The appended examples demonstrate for the first time a clear correlation between activity of the small molecule compound against a HBV infection and binding affinity towards PAPD5 and PAPD7. This realization opened for design of nucleic acid molecules targeting PAPD5 or PAPD7 mRNA leading to particularly high anti-HBV efficacy. The nucleic acid molecules can be targeted directly to the liver using conjugates capable of binding to the asialoglycoprotein receptor (ASGPr). Compared to systemically administered small molecules the nucleic acid molecules will have a different PK/PD profile and toxicity profile. Furthermore, the present invention shows for the first time that a compound(s) that inhibits PAPD5 or PAPD7, or particularly PAPD5 and PAPD7 has an extraordinary high activity in terms of inhibition of secretion of HBsAg and HBeAg as well as of production of intracellular HBV mRNA. Reduction of secretion of HBsAg and HBeAg inhibits development of chronic HBV infection more effectively as compared to the reduction of secretion of HBsAg alone. In addition, inhibition of secretion of HBsAg and HBeAg reduces the infectiousness of a HBV infected person. Furthermore, reducing HBeAg in an expected mother may also inhibit the development of a chronic HBV infection of her child. Thus, the present invention unexpectedly demonstrates that selectively using compounds that inhibit PAPD5 or PAPD7 target nucleic acids or combinations of compounds that inhibit both PAPD5 and PAPD7 target nucleic acids, leads to an improved therapeutic success in the treatment of a HBV infection in terms of a considerably more effective reduction of HBsAg and HBeAg.

Accordingly, an aspect of the present invention is using one or more inhibitors capable of reducing PAPD5 or PAPD7 target nucleic acids or combinations of compounds that inhibit expression of both PAPD5 and PAPD7 target nucleic acids, in the treatment of HBV infection, in particular a chronic HBV infection. In a further embodiment the invention relates to the use of at least two inhibitors capable of reducing PAPD5 and/or PAPD7 target nucleic acids, in reduction of the viral antigens HBsAg and HBeAg.

Thus, the present invention relates to an inhibitor or a combination of inhibitors of PAPD5 and/or PAPD7 for use in treating and/or preventing a HBV infection, wherein said inhibitor(s) are independently selected from the group consisting of:

(a) one or more RNA interference (RNAi) molecules against PAPD5 or PAPD7;

(b) a genome editing machinery, comprising:

(i) a site-specific DNA nuclease or a polynucleotide encoding a site-specific DNA nuclease; and (ii) a guide RNA or a polynucleotide encoding a guide RNA.

The RNAi molecules may independently be selected from the group consisting of:

a) a single stranded antisense oligonucleotide;

b) a siRNA molecule; and c) a shRNA molecule;

The inhibitor of the present invention may also be a PAPD5 or PAPD7 specific locked nucleic acid (LNA) molecule.

It is envisaged that the inhibitor of the invention is used for treating (e.g. ameliorating) a HBV infection.

The inhibitor may be a molecule that specifically inhibits PAPD7. Preferably, the inhibitor is a molecule that specifically inhibits PAPD5. More preferably, the inhibitors are combined such that they inhibit both, PAPD5 and PAPD7. Thus, it is prioritized that the inhibitors of the present invention either inhibits PAPD5 or are combined such that they inhibit both PAPD5 and PAPD7. Most preferably, the inhibitors of the present invention are combined such that they inhibit PAPD5 and PAPD7. In one aspect of the invention the inhibitors of the present invention are combined such that they inhibit both PAPD5 and PAPD7 and lead to a reduction of secretion of HBsAg and/or HBeAg of at least 50% as compared to the no drug control (i.e. compared to cells or subjects to which no drug has been administrated).

The inhibitor of the present invention may have an $IC_{50}$ value in the inhibition of HBsAg and HBeAg of below 6 μM, preferably of below 5 μM, preferably of below 4 μM, preferably of below 3 μM, preferably of below 2 μM, more preferably below 1 μM, more preferably below 0.5 μM, and most preferably below 0.1 μM.

Genome editing by using a site-specific DNA nuclease (such as Cas9 or Cpf1) and a guide RNA is commonly known in the art and described, e.g., in "CRISPR-Cas: A Laboratory Manual", 2016, edited by Jennifer Doudna, ISBN 978-1-621821-31-1.

For example, if said site-specific DNA nuclease is a Cas9 nuclease, then the genome editing machinery preferably further comprises:

(i) at least one guide RNA consisting of at least one target sequence specific CRISPR RNA (crRNA) molecule and at least one trans-activating crRNA (tracrRNA) molecule;

(ii) a polynucleotide encoding the RNA molecules of (i);

(iii) at least one guide RNA, which is a chimeric RNA molecule comprising at least one target sequence specific crRNA and at least one tracrRNA; or (iv) a polynucleotide encoding the chimeric RNA of (iii).

In an alternative example the site-specific DNA nuclease is a Cpf1 nuclease, and the genome editing machinery preferably further comprises:

(i) at least one guide RNA comprising a target sequence specific CRISPR RNA (crRNA) molecule; or (ii) a polynucleotide encoding the RNA molecules of (i).

The herein provided inhibitors of PAPD5 or PAPD7 may also be a genome editing machinery that comprises at least one pre-assembled Cas9 protein-guide RNA ribonucleoprotein complex (RNP).

Herein, the guide RNA is designed to target the genomic PAPD5 or PAPD7 DNA. Alternatively, several guide RNAs are used, so that the genomic DNA of PAPD5 and of PAPD7 can be targeted. Inhibition of PAPD5 and/or PAPD7 may be achieved by introducing frame-shift knockout mutations into the genomic PAPD5 and/or PAPD7 DNA through non-homologous end-joining (NHEJ), or by modifying the genomic PAPD5 and/or PAPD7 DNA through homology-directed repair (HDR). How these mechanisms can be induced is commonly known in the art and described, e.g., in Heidenreich, 2016, Nat Rev Neurosci 17 36-44.

The inhibitor of the present invention of the present invention is preferably a non-naturally occurring molecule. The inhibitor of the invention may be a nucleic acid molecule, selected from RNAi agents, including siRNA, shRNA, Crisper RNA and single stranded antisense oligonucleotides. Preferably the RNAi molecules comprise at least one non-naturally occurring nucleotide, such as a oligonucleotide thiophosphate, a substituted ribo-oligonucleotide, a 2' sugar modified nucleoside, a LNA nucleoside, a PNA nucleoside, a GNA (glycol nucleic acid) molecule, a TNA (threose nucleic acid) molecule, a morpholino nucleotide, or a nucleic acid with a modified backbone such as polysiloxane, 2'-O-(2-methoxy) ethyl-phosphorothioate, or a nucleic acid with a substituent, such as methyl-, thio-, sulphate, benzoyl-, phenyl-, amino-, propyl-, chloro-, and methanocarbanucleoside, or a reporter molecule to facilitate its detection. The inhibitor of the invention may also be naturally occurring or a non-naturally occurring small molecule or genome editing machinery.

In context of the present invention, the herein provided inhibitor inhibits expression and/or activity of PAPD5 or PAPD7.

For example, the inhibitor of the present invention may bind to PAPD5 target nucleic acid and inhibit activity of PAPD5 polypeptide. In another example, the inhibitor of the present invention binds to PAPD7 target nucleic acid and inhibits activity of PAPD7 polypeptide. It is prioritized herein that the inhibitors are combined to target both, PAPD5 and PAPD7 mRNA and inhibits the activity of both, PAPD5 and PAPD7 polypeptide. The inhibitor of the present invention may inhibit the expression of PAPD5 or PAPD7; or a combination of inhibitors may inhibit the expression of both, PAPD5 and PAPD7.

Compounds of the Invention

As described above, the inhibitor of the present invention may be a nucleic acid molecule.

In one aspect of the invention, the inhibitor of the present is a RNAi molecule against PAPD5 or PAPD7. Said RNAi molecule may be a siRNA or a shRNA.

For example, the inhibitor of the present invention may be a siRNA that is directed against PAPD5, wherein said siRNA is any one of or a combination of the following siRNAs:

PAPD5 siRNA Pool (L-010011-00-0010: ON-TARGETplus Human PAPD5):

```
siRNA-1-J-010011-05-Target Sequence:
                                        (SEQ ID NO: 252)
CAUCAAUGCUUUAUAUCGA

siRNA-2-J-010011-06-Target Sequence:
                                        (SEQ ID NO: 253)
GGACGACACUUCAAUUAUU

siRNA-3-J-010011-07-Target Sequence:
                                        (SEQ ID NO: 254)
GAUAAAGGAUGGUGGUUCA

siRNA-4-J-010011-08-Target Sequence:
                                        (SEQ ID NO: 255)
GAAUAGACCUGAGCCUUCA
```

The inhibitor of the present invention may also be a siRNA that is directed against PAPD7, wherein said siRNA is any one of or a combination of the following siRNAs:

PAPD7 siRNA Pool (L-009807-00-0005: ON-TARGETplus Human PAPD7):

```
siRNA-1-J-009807-05-Target Sequence:
                                        (SEQ ID NO: 256)
GGAGUGACGUUGAUUCAGA

siRNA-2-J-009807-06-Target Sequence:
                                        (SEQ ID NO: 257)
CGGAGUUCAUCAAGAAUUA

siRNA-3-J-009807-07-Target Sequence:
                                        (SEQ ID NO: 258)
CGGAGUUCAUCAAGAAUUA

siRNA-4-J-009807-08-Target Sequence:
                                        (SEQ ID NO: 259)
GCGAAUAGCCACAUGCAAU
```

Above, target sequences of suitable siRNAs are shown. The sequences of the corresponding siRNAs are directly complementary to these target sequences.

It is envisaged in context of the present invention that a combined preparation may comprise (a) siRNA(s) directed against PAPD5 is combined with (b) siRNA(s) directed against PAPD7, in order to inhibit expression of both, PAPD5 and PAPD7.

It is also envisaged in context of the present invention that a combined preparation may comprise (a) shRNA directed against PAPD5 is combined with (b) shRNA directed against PAPD7, in order to inhibit expression of both, PAPD5 and PAPD7. In this context the shRNA molecule in (a) may be one or more of the following shRNA molecules

```
                                        (SEQ ID NO: 260)
CCGGGCCACATATAGAGATTGGATACTCGAGTATCC

AATCTCTATATGTGGCTTTTTG

                                        (SEQ ID NO: 261)
CCGGCCAACAAATCTCAGCATGGATCTCGAGATCCA

TGCTGAGATTTGTTGGTTTTTG

                                        (SEQ ID NO: 262)
CCGGCGCCTGTAATCCCAGCACTTTCTCGAGAAAGT

GCTGGGATTACAGGCGTTTTTG
```

-continued

```
                                        (SEQ ID NO: 263)
CCGGGCCTGTAATCCCAGCACTTTACTCGAGTAAAG

TG CTG GGATTACAGGCTTTTTG

                                        (SEQ ID NO: 264)
CCGGCGATGTTGGAAGGAGTTCATACTCGAGTATGA

ACTCCTTCCAACATCGTTTTTG
```

In a further aspect the invention the RNAi molecule is an antisense oligonucleotide capable of inhibiting expression of PAPD5 or PAPD7. The modulation is achieved by hybridizing to a target nucleic acid encoding PAPD5 or PAPD7. The target nucleic acid may be a mammalian PAPD5, such as a sequence selected from the group consisting of SEQ ID NO: 4, 5 and 10, or natural variants thereof.

The target nucleic acid may be a mammalian PAPD7, such as a sequence selected from SEQ ID NO: 6 or 11 or natural variants thereof.

The oligonucleotide of the invention is an antisense oligonucleotide which targets PAPD5 or PAPD7.

In some embodiments the antisense oligonucleotide of the invention is capable of modulating the expression of the target by inhibiting or down-regulating it. Preferably, such modulation produces an inhibition of expression of at least 20% compared to the normal expression level of the target, more preferably at least 30%, 40%, 50%, 60%, 70%, 80%, or 90% inhibition compared to the normal expression level of the target. In some embodiments oligonucleotides of the invention may be capable of inhibiting expression levels of PAPD5 or PAPD7 mRNA by at least 60% or 70% in vitro using HeLa cells or HepaRG cells. In some embodiments compounds of the invention may be capable of inhibiting expression levels of PAPD5 or PAPD7 protein by at least 50% in vitro using HeLa cells or HepaRG cells. Suitable, assays which may be used to measure PAPD5 or PAPD7 RNA or protein inhibition are described under the screening methods above. The target modulation is triggered by the hybridization between a contiguous nucleotide sequence of the oligonucleotide and the target nucleic acid.

An aspect of the present invention relates to an antisense oligonucleotide which comprises a contiguous nucleotide sequence of 10 to 30 nucleotides in length wherein the contiguous nucleotide sequence is at least 90% complementarity to PAPD5. The antisense oligonucleotide is capable of reducing expression of PAPD5. Preferably the antisense oligonucleotide comprise at least one 2' sugar modified nucleoside.

Another aspect of the present invention relates to an antisense oligonucleotide which comprises a contiguous nucleotide sequence of 10 to 30 nucleotides in length wherein the contiguous nucleotide sequence is at least 90% complementarity to PAPD7. The antisense oligonucleotide is capable of reducing expression of PAPD7. Preferably the antisense oligonucleotide comprise at least one 2' sugar modified nucleoside.

In some embodiments, the oligonucleotide comprises a contiguous sequence which is at least 90% complementary, such as at least 91%, such as at least 92%, such as at least 93%, such as at least 94%, such as at least 95%, such as at least 96%, such as at least 97%, such as at least 98%, or 100% complementary with a region of the target nucleic acid or a target sequence.

In a preferred embodiment the oligonucleotide of the invention, or contiguous nucleotide sequence thereof is fully complementary (100% complementary) to a region of the target nucleic acid, or in some embodiments may comprise one or two mismatches between the oligonucleotide and the target nucleic acid.

In some embodiments the oligonucleotide comprises a contiguous nucleotide sequence of 10 to 30 nucleotides in length with at least 90% complementary, such as fully (or 100%) complementary, to a target nucleic acid region, such as a target sequence, present in SEQ ID NO: 4, 5 or 10. In some embodiments the oligonucleotide sequence is 100% complementary to a corresponding target nucleic acid region present in SEQ ID NO: 10. In some embodiments the oligonucleotide sequence is 100% complementary to a corresponding target nucleic acid region present SEQ ID NO: 4, 5 or 10.

In some embodiments the oligonucleotide comprises a contiguous nucleotide sequence of 10 to 30 nucleotides in length with at least 90% complementary, such as fully (or 100%) complementary, to a target nucleic acid region, such as a target sequence, present in SEQ ID NO: 6 or 11. In some embodiments the oligonucleotide sequence is 100% complementary to a corresponding target nucleic acid region present in SEQ ID NO: 11. In some embodiments the oligonucleotide sequence is 100% complementary to a corresponding target nucleic acid region present SEQ ID NO: 6 or 11.

In some embodiments, the oligonucleotide of the invention comprises or consists of 10 to 35 nucleotides in length, such as from 10 to 30, such as 11 to 22, such as from 12 to 20, such as from such as from 14 to 20, such as from 14 to 18 such as from 14 to 16, such as from 16 to 20 contiguous nucleotides in length.

In some embodiments, the oligonucleotide or contiguous nucleotide sequence thereof comprises or consists of 22 or less nucleotides, such as 20 or less nucleotides. It is to be understood that any range given herein includes the range endpoints. Accordingly, if an oligonucleotide is said to include from 10 to 30 nucleotides, both 10 and 30 nucleotides are included.

In some embodiments, the oligonucleotide or contiguous nucleotide sequence comprises or consists of a sequence selected from the group consisting of sequences listed in table 3, in the materials and method section.

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 12 to 131 (see motif sequences listed in table 3).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 15, 18, 23, 25, 26, 30, 32, 39, 54, 56, 58, 65, 80, 88, 92, 93, 111, 115, 116 and 118 (see motif sequences listed in table 3).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 23, 26, 54, 56, 80, 93 and 115.

In some embodiments, the oligonucleotide or contiguous nucleotide sequence comprises or consists of a sequence selected from the group consisting of sequences listed in table 4, in the materials and method section.

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 132 to 251 (see motif sequences listed in table 4).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 153, 155, 168, 171, 172, 174, 183, 184, 188, 190, 191, 194, 195, 197, 221, 224, 229, 232, 239, and 244 (see motif sequences listed in table 4).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 172, 188, 190, 229 and 239.

In a further aspect the invention relates to a combined preparation comprising a) a nucleic acid molecule which inhibits expression and/or activity of PAPD5; and b) a nucleic acid molecule which inhibits expression and/or activity of PAPD7. In particular embodiments the nucleic acid molecules are independently selected from siRNA, shRNA and antisense oligonucleotides described herein.

In some embodiments the combined preparation comprises a) one of more siRNA molecules targeting a PAPD5 target sequence selected from one or more of SEQ ID NO: 252, 253, 254 and 255; and b) one of more siRNA molecules targeting a PAPD7 target sequence selected from one or more of SEQ ID NO: 256, 257, 258 and 259.

In some embodiments the combined preparation comprises a) one of more siRNA molecules targeting a PAPD5 target sequence selected from one or more of SEQ ID NO: 252, 253, 254 and 255; and b) and b) one of more antisense oligonucleotides targeting a PAPD7 target sequence selected from the group consisting of SEQ ID NO: 153, 155, 168, 171, 172, 174, 183, 184, 188, 190, 191, 194, 195, 197, 221, 224, 229, 232, 239, and 244.

In some embodiments the combined preparation comprises a) one of more antisense oligonucleotide molecules targeting a PAPD5 target sequence selected from the group consisting of SEQ ID NO: 15, 18, 23, 25, 26, 30, 32, 39, 54, 56, 58, 65, 80, 88, 92, 93, 111, 115, 116 and 118; and b) one of more siRNA molecules targeting a PAPD7 target sequence selected from one or more of SEQ ID NO: 256, 257, 258 and 259.

In some embodiments the combined preparation comprises a) one of more shRNA molecules targeting a PAPD5 target sequence selected from one or more of SEQ ID NO: 260, 261, 262, 263 and 264; and b) one of more siRNA molecules targeting a PAPD7 target sequence selected from one or more of SEQ ID NO: 256, 257, 258 and 259.

In some embodiments the combined preparation comprises a) one of more shRNA molecules targeting a PAPD5 target sequence selected from one or more of SEQ ID NO: 260, 261, 262, 263 and 264; and b) one of more antisense oligonucleotides targeting a PAPD7 target sequence selected from the group consisting of SEQ ID NO: 153, 155, 168, 171, 172, 174, 183, 184, 188, 190, 191, 194, 195, 197, 221, 224, 229, 232, 239, and 244.

In some embodiments the combined preparation comprises a) an antisense oligonucleotide or contiguous nucleotide sequence comprises or consists of 10 to 30 nucleotides in length with at least 90% identity, preferably 100% identity, to a sequence selected from the group consisting of SEQ ID NO: 15, 18, 23, 25, 26, 30, 32, 39, 54, 56, 58, 65, 80, 88, 92, 93, 111, 115, 116 and 118 and b) an antisense oligonucleotide or contiguous nucleotide sequence comprises or consists of 10 to 30 nucleotides in length with at least 90% identity, preferably 100% identity, to a sequence selected from the group consisting of SEQ ID NO: 153, 155, 168, 171, 172, 174, 183, 184, 188, 190, 191, 194, 195, 197, 221, 224, 229, 232, 239, and 244.

In some embodiments the combined preparation comprises a) an antisense oligonucleotide or contiguous nucleotide sequence comprises or consists of 10 to 30 nucleotides in length with at least 90% identity, preferably 100% identity, to a sequence selected from the group consisting of SEQ ID NO: 18, 23, 25, 26, 32, 39, 54, 56, 80, 92, 93, 116 and 118 and b) an antisense oligonucleotide or contiguous nucleotide sequence comprises or consists of 10 to 30 nucleotides in length with at least 90% identity, preferably 100% identity, to a sequence selected from the group consisting of SEQ ID NO: 153, 155, 172, 174, 183, 188, 190, 195, 197, 221, 224, 229, 232 and 244.

In some embodiments the combined preparation comprises a) an antisense oligonucleotide or contiguous nucleotide sequence comprises or consists of 10 to 30 nucleotides in length with at least 90% identity, preferably 100% identity, to a sequence SEQ ID NO: 18 and b) an antisense oligonucleotide or contiguous nucleotide sequence comprises or consists of 10 to 30 nucleotides in length with at least 90% identity, preferably 100% identity, to a sequence of SEQ ID NO: 221.

In some embodiments the combined preparation comprises a) an antisense oligonucleotide or contiguous nucleotide sequence comprises or consists of 10 to 30 nucleotides in length with at least 90% identity, preferably 100% identity, to a sequence SEQ ID NO: 23 and b) an antisense oligonucleotide or contiguous nucleotide sequence comprises or consists of 10 to 30 nucleotides in length with at least 90% identity, preferably 100% identity, to a sequence of SEQ ID NO: 172 or 188.

In some embodiments the combined preparation comprises a) an antisense oligonucleotide or contiguous nucleotide sequence comprises or consists of 10 to 30 nucleotides in length with at least 90% identity, preferably 100% identity, to a sequence SEQ ID NO: 25 and b) an antisense oligonucleotide or contiguous nucleotide sequence comprises or consists of 10 to 30 nucleotides in length with at least 90% identity, preferably 100% identity, to a sequence of SEQ ID NO: 174 or 183.

In some embodiments the combined preparation comprises a) an antisense oligonucleotide or contiguous nucleotide sequence comprises or consists of 10 to 30 nucleotides in length with at least 90% identity, preferably 100% identity, to a sequence SEQ ID NO: 26 and b) an antisense oligonucleotide or contiguous nucleotide sequence comprises or consists of 10 to 30 nucleotides in length with at least 90% identity, preferably 100% identity, to a sequence of SEQ ID NO: 183.

In some embodiments the combined preparation comprises a) an antisense oligonucleotide or contiguous nucleotide sequence comprises or consists of 10 to 30 nucleotides in length with at least 90% identity, preferably 100% identity, to a sequence SEQ ID NO: 39 and b) an antisense oligonucleotide or contiguous nucleotide sequence comprises or consists of 10 to 30 nucleotides in length with at least 90% identity, preferably 100% identity, to a sequence of SEQ ID NO: 229.

In some embodiments the combined preparation comprises a) an antisense oligonucleotide or contiguous nucleotide sequence comprises or consists of 10 to 30 nucleotides in length with at least 90% identity, preferably 100% identity, to a sequence SEQ ID NO: 54 and b) an antisense oligonucleotide or contiguous nucleotide sequence comprises or consists of 10 to 30 nucleotides in length with at least 90% identity, preferably 100% identity, to a sequence of SEQ ID NO: 190 or 232.

In some embodiments the combined preparation comprises a) an antisense oligonucleotide or contiguous nucleotide sequence comprises or consists of 10 to 30 nucleotides in length with at least 90% identity, preferably 100% identity, to a sequence SEQ ID NO: 56 and b) an antisense oligonucleotide or contiguous nucleotide sequence comprises or consists of 10 to 30 nucleotides in length with at least 90% identity, preferably 100% identity, to a sequence of SEQ ID NO: 153 or 244.

In some embodiments the combined preparation comprises a) an antisense oligonucleotide or contiguous nucleotide sequence comprises or consists of 10 to 30 nucleotides in length with at least 90% identity, preferably 100% identity, to a sequence SEQ ID NO: 80 and b) an antisense oligonucleotide or contiguous nucleotide sequence comprises or consists of 10 to 30 nucleotides in length with at least 90% identity, preferably 100% identity, to a sequence of SEQ ID NO: 153 or 244.

In some embodiments the combined preparation comprises a) an antisense oligonucleotide or contiguous nucleotide sequence comprises or consists of 10 to 30 nucleotides in length with at least 90% identity, preferably 100% identity, to a sequence SEQ ID NO: 92 and b) an antisense oligonucleotide or contiguous nucleotide sequence comprises or consists of 10 to 30 nucleotides in length with at least 90% identity, preferably 100% identity, to a sequence of SEQ ID NO: 190 or 232.

In some embodiments the combined preparation comprises a) an antisense oligonucleotide or contiguous nucleotide sequence comprises or consists of 10 to 30 nucleotides in length with at least 90% identity, preferably 100% identity, to a sequence SEQ ID NO: 116 and b) an antisense oligonucleotide or contiguous nucleotide sequence comprises or consists of 10 to 30 nucleotides in length with at least 90% identity, preferably 100% identity, to a sequence of SEQ ID NO: 155 or 195.

Oligonucleotide Design

Oligonucleotide design refers to the pattern of nucleoside sugar modifications in the oligonucleotide sequence. The oligonucleotides of the invention comprise sugar-modified nucleosides and may also comprise DNA or RNA nucleosides. In some embodiments, the oligonucleotide comprises sugar-modified nucleosides and DNA nucleosides. Incorporation of modified nucleosides into the oligonucleotide of the invention may enhance the affinity of the oligonucleotide for the target nucleic acid. In that case, the modified nucleosides can be referred to as affinity enhancing modified nucleotides. The modified nucleosides may also be termed units.

In an embodiment, the oligonucleotide comprises at least 1 modified nucleoside, such as from 1 to 8 modified nucleosides, such as from 2 to 8 modified nucleosides, such as from 3 to 7 modified nucleosides, such as from 4 to 6 modified nucleosides.

In an embodiment, the oligonucleotide comprises one or more sugar modified nucleosides, such as 2' sugar modified nucleosides. Preferably the oligonucleotide of the invention comprise the one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. Even more preferably the one or more modified nucleoside is a locked nucleic acid (LNA).

In a further embodiment the oligonucleotide comprises at least one modified internucleoside linkage. In a preferred embodiment all the internucleoside linkages within the contiguous nucleotide sequence are phosphorothioate or boranophosphate internucleoside linkages. In some embodiments all the internucleotide linkages in the contiguous sequence of the oligonucleotide are phosphorothioate linkages.

In some embodiments, the oligonucleotide of the invention comprises at least one LNA nucleoside, such as from 1 to 8 LNA nucleosides, such as from 2 to 8 LNA nucleosides, such as from 3 to 7 LNA nucleosides, such as from 4 to 6 LNA nucleosides.

In some embodiments, the oligonucleotide of the invention comprises at least one LNA nucleoside and at least one 2' substituted modified nucleoside.

In an embodiment of the invention the oligonucleotide of the invention is capable of recruiting RNase H.

Gapmer Design

In a preferred embodiment the oligonucleotide of the invention has a gapmer design or structure also referred herein merely as "Gapmer". In a gapmer structure the oligonucleotide comprises at least three distinct structural regions a 5'-flank, a gap and a 3'-flank, F-G-F' in '5→3' orientation. In this design, flanking regions F and F' (also termed wing regions) comprise a contiguous stretch of modified nucleosides, which are complementary to the PAPD5 or PAPD7 target nucleic acid, while the gap region, G, comprises a contiguous stretch of nucleotides which are capable of recruiting a nuclease, preferably an endonuclease such as RNase, for example RNase H, when the oligonucleotide is in duplex with the target nucleic acid. In preferred embodiments the gap region consists of DNA nucleosides. Regions F and F', flanking the 5' and 3' ends of region G, preferably comprise non-nuclease recruiting nucleosides (nucleosides with a 3' endo structure), more preferably one or more affinity enhancing modified nucleosides. In some embodiments, the 3' flank comprises at least one LNA nucleoside, preferably at least 2 LNA nucleosides. In some embodiments, the 5' flank comprises at least one LNA nucleoside. In some embodiments both the 5' and 3' flanking regions comprise a LNA nucleoside. In some embodiments all the nucleosides in the flanking regions are LNA nucleosides. In other embodiments, the flanking regions may comprise both LNA nucleosides and other nucleosides (mixed flanks), such as DNA nucleosides and/or non-LNA modified nucleosides, such as 2' substituted nucleosides. In this case the gap is defined as a contiguous sequence of at least 5 RNase H recruiting nucleosides (nucleosides with a 2' endo structure, preferably DNA) flanked at the 5' and 3' end by an affinity enhancing modified nucleoside, preferably LNA, such as beta-D-oxy-LNA. Consequently, the nucleosides of the 5' flanking region and the 3' flanking region which are adjacent to the gap region are modified nucleosides, preferably non-nuclease recruiting nucleosides or high affinity nucleosides.

Region F

Region F (5' flank or 5' wing) is attached to the 5' end of region G and comprises, contains or consists of at least one modified nucleoside such as at least 2, at least 3, or at least 4 modified nucleosides. In an embodiment region F comprises or consists of from 1 to 4 modified nucleosides, such as from 2 to 4 modified nucleosides, such as from 1 to 3 modified nucleosides, such as 1, 2, 3 or 4 modified nucleosides. The F region is defined by having at least on modified nucleoside at the 5' end and at the 3' end of the region.

In some embodiments, the modified nucleosides in region F have a 3' endo structure.

In an embodiment, one or more of the modified nucleosides in region F are 2' modified nucleosides. In one embodiment all the nucleosides in Region F are 2' modified nucleosides.

In another embodiment region F comprises DNA and/or RNA nucleosides in addition to the 2' modified nucleosides. Flanks comprising DNA and/or RNA are characterized by having a 2' modified nucleoside in the 5' end and the 3'end (adjacent to the G region) of the F region. The DNA nucleosides in the flanks should preferably not be able to recruit RNase H. The length of the 5' flank (region F) in oligonucleotides with DNA and/or RNA nucleotides in the flanks may be longer, maintaining the number of 2' modified nucleotides at 1 to 4 as described above. In a further embodiment one or more of the 2' modified nucleosides in region F are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments the F region comprises both LNA and a 2' substituted modified nucleoside. These are often termed mixed wing or mixed flank oligonucleotides.

In one embodiment of the invention all the modified nucleosides in region F are LNA nucleosides. In a further embodiment all the nucleosides in region F are LNA nucleosides. In a further embodiment the LNA nucleosides in region F are independently selected from the group consisting of oxy-LNA, thio-LNA, amino-LNA, cET, and/or ENA, in either the beta-D or alpha-L configurations or combinations thereof. In a preferred embodiment region F comprises at least 1 beta-D-oxy LNA unit, at the 5' end of the contiguous sequence. In a further preferred embodiment region F consists of beta-D-oxy LNA nucleosides.

Region G

Region G (gap region) preferably comprise, contain or consist of from 4 to 18, or from 5 to 17, or from 6 to 16 or from 8 to 12 consecutive nucleotide units capable of recruiting RNase H nuclease.

The nucleoside units in region G, which are capable of recruiting nuclease are in an embodiment selected from the group consisting of DNA, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked "sugar" residue.

In some embodiments, region G consists of 100% DNA units.

In further embodiments the region G may consist of a mixture of DNA and other nucleosides capable of mediating RNase H cleavage.

In some embodiments, nucleosides in region G have a 2' endo structure.

Region F'

Region F' (3' flank or 3' wing) is attached to the 3' end of region G and comprises, contains or consists of at least one modified nucleoside such as at least 2, at least 3, or at least 4 modified nucleosides. In an embodiment region F' comprises or consists of from 1 to 4 modified nucleosides, such as from 2 to 4 modified nucleosides, such as from 1 to 3 modified nucleosides, such as 1, 2, 3 or 4 modified nucleosides. The F' region is defined by having at least on modified nucleoside at the 5' end and at the 3' end of the region.

In some embodiments, the modified nucleosides in region F' have a 3' endo structure.

In an embodiment, one or more of the modified nucleosides in region F' are 2' modified nucleosides. In one embodiment all the nucleosides in Region F' are 2' modified nucleosides.

In another embodiment region F' comprises DNA and/or RNA nucleosides in addition to the 2' modified nucleosides. Flanks comprising DNA and/or RNA are characterized by having a 2' modified nucleoside in the 5' end and the 3'end (adjacent to the G region) of the F' region. The DNA nucleosides in the flanks should preferably not be able to recruit RNase H. The length of the 3' flank (region F') in oligonucleotides with DNA and/or RNA nucleotides in the flanks may be longer, maintaining the number of 2' modified nucleotides at 1 to 4 as described above. In a further embodiment one or more of the 2' modified nucleosides in region F are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments the F' region comprises both LNA and a 2' substituted modified nucleoside. These are often termed mixed wing or mixed flank oligonucleotides.

In one embodiment of the invention all the modified nucleosides in region F' are LNA nucleosides. In a further embodiment all the nucleosides in region F' are LNA nucleosides. In a further embodiment the LNA nucleosides in region F' are independently selected from the group consisting of oxy-LNA, thio-LNA, amino-LNA, cET, and/or ENA, in either the beta-D or alpha-L configurations or combinations thereof. In a preferred embodiment region F' comprises at least two beta-D-oxy LNA unit, at the 3' end of the contiguous sequence. In a further preferred embodiment region F' consists of beta-D-oxy LNA nucleosides.

Region D' and D"

Region D' and D" can be attached to the 5' end of region F or the 3' end of region F', respectively.

Region D' or D" may independently comprise 1, 2, 3, 4 or 5 additional nucleotides, which may be complementary or non-complementary to the target nucleic acid. In this respect the oligonucleotide of the invention, may in some embodiments comprise a contiguous nucleotide sequence capable of modulating the target which is flanked at the 5' and/or 3' end by additional nucleotides. Such additional nucleotides may serve as a nuclease susceptible biocleavable linker (see definition of linkers). In some embodiments the additional 5' and/or 3' end nucleotides are linked with phosphodiester linkages, and may be DNA or RNA. In another embodiment, the additional 5' and/or 3' end nucleotides are modified nucleotides which may for example be included to enhance nuclease stability or for ease of synthesis. In one embodiment the oligonucleotide of the invention comprises a region D' and/or D" in addition to the contiguous nucleotide sequence.

The gapmer oligonucleotide of the present invention can be represented by the following formulae:

F-G-F'; in particular $F_{1-7}$-$G_{4-12}$-$F'_{1-7}$

D'-F-G-F', in particular $D'_{1-3}$-$F_{1-7}$-$G_{4-12}$-$F'_{1-7}$

F-G-F'-D", in particular $F_{1-7}$-$G_{4-12}$-$F'_{1-7}$-$D''_{1-3}$

D'-F-G-F'-D", in particular $D'_{1-3}$-$F_{1-7}$-$G_{4-12}$-$F'_{1-7}$-$D''_{1-3}$ The preferred number and types of nucleosides in regions F, G and F', D' and D" have been described above.

In some embodiments the oligonucleotide is a gapmer consisting of 14-20 nucleotides in length, wherein each of regions F and F' independently consists of 1, 2, 3 or 4 modified nucleoside units and region G consists of 6-17 nucleoside units, capable of recruiting nuclease when in duplex with the PAPD5 or PAPD7 target nucleic acid and wherein the oligonucleotide is complementary to the PAPD5 or PAPD7 target nucleic acid.

In all instances the F-G-F' design may further include region D' and/or D", which may have 1, 2 or 3 nucleoside units, such as DNA units. Preferably, the nucleosides in region F and F' are modified nucleosides, while nucleotides in region G are unmodified nucleosides.

In each design, the preferred modified nucleoside is LNA.

In another embodiment all the internucleoside linkages in the gap in a gapmer are phosphorothioate and/or boranophosphate linkages. In another embodiment all the internucleoside linkages in the flanks (F and F' region) in a gapmer are phosphorothioate and/or boranophosphate linkages. In another preferred embodiment all the internucleoside linkages in the D' and D" region in a gapmer are phosphodiester linkages.

For specific gapmers as disclosed herein, when the cytosine (C) residues are annotated as 5-methyl-cytosine, in various embodiments, one or more of the C's present in the oligonucleotide may be unmodified C residues.

For certain embodiments of the invention, the oligonucleotide is selected from the group of oligonucleotide compounds with CMP-ID-NO: 12_1 to 131_1 (see oligonucleotides listed in table 3).

For certain embodiments of the invention, the oligonucleotide is selected from the group of oligonucleotide compounds with CMP-ID-NO: 15_1, 18_1, 23_1, 25_1, 26_1, 30_, 32_1, 39_1, 54_1, 56_1, 58_1, 65_1, 80_1, 88_1, 92_1, 93_1, 111_1, 115_1, 116_1 and 118_1 (see oligonucleotides listed in table 3).

For certain embodiments of the invention, the oligonucleotide is selected from the group of oligonucleotide compounds with CMP-ID-NO: 23_1, 26_1, 54_1, 56_1, 80_1, 93_1 and 115_1.

For certain embodiments of the invention, the oligonucleotide is selected from the group of oligonucleotide compounds with CMP-ID-NO: 132_to 2511 (see oligonucleotides listed in table 4).

For certain embodiments of the invention, the oligonucleotide is selected from the group of oligonucleotide compounds with CMP-ID-NO: 153_1, 155_1, 168_1, 171_1, 172_1, 174_1, 183_1, 184_1, 188_1, 190_1, 191_1, 194_1, 195_1, 197_1, 221_1, 224_1, 229_1, 232_1, 239_1, and 244_1 (see oligonucleotides listed in table 4).

For certain embodiments of the invention, the oligonucleotide is selected from the group of oligonucleotide compounds with CMP-ID-NO: 172_1, 188_1, 190_1, 229_1 and 237_1.

An embodiment of the invention is a combined preparation comprising a) the oligonucleotide is selected from the group of oligonucleotide compounds with CMP ID NO: 18_1, 25_1, 26_1, 32_1, 39_1, 54_1, 56_1, 80_1, 92_1, 93_1, 116_1 and 118_1 and b) the oligonucleotide is selected from the group of oligonucleotide compounds with CMP ID NO: 153_1, 155_1, 168_1, 171_1, 172_1, 174_1, 183_1, 184_1, 188_1, 190_1, 191_1, 194_1, 195_1, 197_1, 221_1, 224_1, 229_1, 232_1, 23_19, and 244_1.

An embodiment of the invention is a combined preparation comprising a) the oligonucleotide compound with CMP ID NO: 18_1 and b) the oligonucleotide compound with CMP ID NO: 221_1.

An embodiment of the invention is a combined preparation comprising a) the oligonucleotide compound with CMP ID NO: 23_1 and b) the oligonucleotide compound with CMP ID NO: 172_1 or 188_1.

An embodiment of the invention is a combined preparation comprising a) the oligonucleotide compound with CMP ID NO: 25_1 and b) the oligonucleotide compound with CMP ID NO: 174_1 or 183_1.

An embodiment of the invention is a combined preparation comprising a) the oligonucleotide compound with CMP ID NO: 26_1 and b) the oligonucleotide compound with CMP ID NO: 183_1.

An embodiment of the invention is a combined preparation comprising a) the oligonucleotide compound with CMP ID NO: 39_1 and b) the oligonucleotide compound with CMP ID NO: 229_1.

An embodiment of the invention is a combined preparation comprising a) the oligonucleotide compound with CMP ID NO: 54_1 and b) the oligonucleotide compound with CMP ID NO: 190_1 or 232_1.

An embodiment of the invention is a combined preparation comprising a) the oligonucleotide compound with CMP ID NO: 56_1 and b) the oligonucleotide compound with CMP ID NO: 153_1 or 244_1.

An embodiment of the invention is a combined preparation comprising a) the oligonucleotide compound with CMP ID NO: 80_1 and b) the oligonucleotide compound with CMP ID NO: 153_1 or 244_1.

An embodiment of the invention is a combined preparation comprising a) the oligonucleotide compound with CMP ID NO: 116_1 and b) the oligonucleotide compound with CMP ID NO: 155_1 or 195_1.

Applications

In context of the present invention it has surprisingly been shown that the combined inhibition of PAPD5 and PAPD7 leads to a synergistic effect in the inhibition of HBV propagation. The appended examples show that reduction of the expression of PAPD5 alone leads to a reduction of the secretion of HBsAg and HBeAg of around 50%, likewise intracellular HBV mRNA was reduced using a PAPD5 inhibitor. Reduction of the expression of PAPD7 alone leads to a reduction of the secretion of HBsAg and HBeAg of not more than 15%. Simultaneous knock-down of PAPD5 and PAPD7 leads to a synergistic effect in the reduction of secretion of HBsAg and HBeAg that lies above the sum of the single knock-downs. Without being bound by theory, this synergistic effect may be due to a compensatory effect of PAPD5 and PAPD7 since both proteins have high sequence homology and same enzymatic functions. Due to the reduction of HBsAg secretion the inhibitor of the present invention inhibits development of chronic HBV infection. In particular, due to inhibition of HBeAg secretion, the inhibitor of the present invention more efficiently inhibits development of a chronic HBV infection as compared to a compound that only reduces secretion of HBsAg. In addition, reducing HBeAg in an expected mother may also inhibit the development of a chronic HBV infection of her child. Thus, due to the reduction of HBeAg secretion the inhibitor of the present invention inhibits development of a chronic HBV infection (such as development of a chronic HBV infection in the offspring of an HBV infected mother) and reduces the infectiousness of a HBV infected person. Accordingly, one aspect of the present invention related to the herein provided inhibitor, wherein the inhibitor reduces secretion of HBsAg and HBeAg. In line with this, a further aspect of the invention relates to the herein provided inhibitor, in particular a nucleic acid molecule or a combination of nucleic acid molecules, wherein the inhibitor inhibits development of chronic HBV infection and reduces the infectiousness of a HBV infected person. In a particular aspect of the invention, the herein provided inhibitor inhibits development of a chronic HBV infection in the offspring of a HBV infected mother. This mother is preferably HBeAg positive.

The subject to be treated with the inhibitor of the invention (or which prophylactically receives the inhibitor of the present invention) is preferably a human, more preferably a human patient who is HBsAg positive and/or HBeAg positive, even more preferably a human patient that is HBsAg positive and HBeAg positive. Said human patient may be an expected mother, e.g. an expected mother who is HBeAg positive and/or HBsAg positive, more preferably an expected mother who is HBeAg positive and HBsAg positive.

One embodiment of the present invention relates a PAPD5 inhibitor, in particular a nucleic acid molecule that inhibits the expression and/or activity of PAPD5, for use in the treatment and/or prevention of a HBV infection, in particular a chronic HBV infection. A further embodiment of the present invention relates to a combined preparation comprising an inhibitor of PAPD5 and an inhibitor of PAPD7 for use in the treatment and/or prevention of a HBV infection, in particular a chronic HBV infection. In a preferred embodiment the combined composition for use in treatment and/or prevention of a HBV infection comprises a) a nucleic acid molecule which inhibits expression and/or activity PAPD5; and b) a nucleic acid molecule which inhibits expression and/or activity of PAPD7. Thus, the present invention relates to a combined preparation comprising an inhibitor of PAPD5 and an inhibitor of PAPD7 for simultaneous or sequential use in the treatment and/or prevention of a HBV infection.

The present invention also relates to a combined preparation comprising a) a nucleic acid molecule which inhibits expression and/or activity PAPD5; and b) a nucleic acid molecule which inhibits expression and/or activity of PAPD7. It is envisaged in context of the invention that said combined preparation is used for treating (e.g. ameliorating) a HBV infection. The definitions disclosed herein in connection with the inhibitor of the present invention apply, mutatis mutandis, to the combined preparation of the present invention. The combined preparation may comprise a molecule that is a PAPD5 inhibitor and a separate molecule that is a PAPD7 inhibitor (e.g. two separate RNAi molecules, such as siRNA molecules, shRNA and antisense oligonucleotides, or two separate small molecules). These two separate inhibitors may be formulated within one unit, e.g., within one pill or vial. Alternatively, these two separate inhibitors may be formulated separately, in separate units, e.g. separate pills or vials. The two separate inhibitors may be administered together, (i.e. simultaneously) or separately (i.e. sequentially) provided that the synergistic effect of the two inhibitors is achieved. In one aspect of the invention the combined preparation leads to a reduction of secretion of HBsAg and HBeAg of at least 50% as compared to the no drug control (i.e. compared to cells or subjects to which no drug is administrated).

The present invention also relates to a pharmaceutical composition for use in the treatment and/or prevention of a HBV infection, wherein the pharmaceutical composition comprises (i) the inhibitor of the invention; or the combined preparation of the invention; and (ii) optionally a pharmaceutically acceptable carrier.

Accordingly, the present invention relates to a method of treating and/or preventing a HBV infection, wherein the method comprises administering an effective amount of the inhibitor of the invention, in particular a nucleic acid molecule, a conjugate of the inhibitor, the pharmaceutical composition of the invention, or of the combined preparation of the invention to a subject in need of such a treatment.

The invention also provides for the use of the inhibitor of the invention, in particular a nucleic acid molecule, a conjugate of the inhibitor, the pharmaceutical composition of the invention, or of the combined preparation of the invention for the manufacture of a medicament. In preferred embodiments the medicament is manufactured in a dosage form for subcutaneous administration and for the combined preparation the ratio of the PAPD5 inhibitor and the PAPD7 inhibitor is 1:1 by weight.

The invention also provides for the use of the inhibitor of the invention, in particular a nucleic acid molecule, a conjugate of the inhibitor, the pharmaceutical composition of the invention, or of the combined preparation of the invention as described for the manufacture of a medicament wherein the medicament is in a dosage form for intravenous administration and for the combined preparation the ratio of the PAPD5 inhibitor and the PAPD7 inhibitor is 1:1 by weight.

The inhibitor of the invention, the combined preparation of the invention, or the pharmaceutical composition of the invention may be used in a combination therapy. For example, the inhibitor of the invention, the combined preparation of the invention, or the pharmaceutical composition of the invention may be combined with other anti-HBV agents such as interferon alpha-2b, interferon alpha-2a, and interferon alphacon-1 (pegylated and unpegylated), ribavirin, lamivudine (3TC), entecavir, tenofovir, telbivudine (LdT), adefovir, or other emerging anti-HBV agents such as a HBV RNA replication inhibitor, a HBsAg secretion inhibitor, a HBV capsid inhibitor, an antisense oligomer (e.g. as described in WO2012/145697 and WO 2014/179629), a siRNA (e.g. described in WO 2005/014806, WO 2012/024170, WO 2012/2055362, WO 2013/003520, WO 2013/159109, WO 2017/027350 and WO2017/015175), a HBV therapeutic vaccine, a HBV prophylactic vaccine, a HBV antibody therapy (monoclonal or polyclonal), or TLR 2, 3, 7, 8 or 9 agonists for the treatment and/or prophylaxis of HBV.

The appended examples demonstrate that down regulation of PAPD5 and/or PAPD7 goes along with a reduction in the production of HBsAg and HBeAg as well as of intracellular HBV mRNA in HBV infected cells. These results indicate that the amount and/or activity of PAPD5 and/or PAPD7 can be used for monitoring therapeutic success during the treatment of a HBV infection, e.g. if treatment with an inhibitor of PAPD5 and/or PAPD7 is ongoing or has been performed. Thus, the present invention relates to a method for monitoring the therapeutic success during the treatment of a HBV infection, wherein the method comprises:

(a) analyzing in a sample obtained from a test subject the amount and/or activity of PAPD5 and/or PAPD7;

(b) comparing said amount and/or activity with reference data corresponding to the amount and/or activity of PAPD5 and/or PAPD7 of at least one reference subject; and (c) predicting therapeutic success based on the comparison step (b).

In the monitoring method of the invention the test subject may be a human being who receives medication for a HBV infection or has received medication for a HBV infection. The medication may comprise anti-HBV agents as described above. The medication may also comprise an inhibitor of PAPD5 and/or PAPD7.

In the monitoring method of the invention the reference data may correspond to the amount and/or activity of PAPD5 and/or PAPD7 in a sample of at least one reference subject. Said sample may be blood or a liver biopsy.

One aspect of the invention relates to the monitoring method of the invention, wherein the at least one reference subject has a HBV infection but did not receive medication for a HBV infection; and wherein in step (c) a decreased amount and/or activity of PAPD5 and/or PAPD7 of the test subject as compared to the reference data indicates therapeutic success in the treatment of a HBV infection. For example, said decreased amount and/or activity of PAPD5 and/or PAPD7 may mean that the amount and/or activity of PAPD5 and/or PAPD7 in the sample of the test subject is 0 to 90% of the amount and/or activity of PAPD5 and/or PAPD7 in the sample of the at least one reference subject. For example, said decreased amount and/or activity of PAPD5 and/or PAPD7 may be 0 to 80%, preferably 0 to 70%, more preferably 0 to 60%, even more preferably 0 to 50%, even more preferably 0 to 40%, even more preferably 0 to 30, even more preferably 0 to 20%, and most preferably 0 to 10% of the amount and/or activity of PAPD5 and/or PAPD7 in the sample of the at least one reference subject.

Another aspect of the invention relates to the monitoring method of the invention, wherein the at least one reference subject has a HBV infection and has received medication for a HBV infection; and wherein in step (c) an identical or similar amount and/or activity of PAPD5 and/or PAPD7 of the test subject as compared to the reference data indicates therapeutic success in the treatment of a HBV infection. A further aspect of the invention relates to the monitoring method of the invention, wherein the at least one reference subject does not have a HBV infection; and wherein in step (c) an identical or similar amount and/or activity of PAPD5 and/or PAPD7 of the test subject as compared to the reference data indicates therapeutic success in the treatment of a HBV infection. An identical or similar amount and/or activity of PAPD5 and/or PAPD7 may mean that the amount and/or activity of PAPD5 and/or PAPD7 in the sample of the test subject is 90-110% of the amount and/or activity of PAPD5 and/or PAPD7 in the sample of the at least one reference subject. For example, said identical or similar amount and/or activity of PAPD5 and/or PAPD7 may be 95-105% of the amount and/or activity of PAPD5 and/or PAPD7 in the sample of the at least one reference subject.

Also encompassed by the present invention is a cell or a non-human animal (e.g. a mouse, rat, ferret or rabbit) with increased, reduced or absent PAPD5 and/or PAPD7 expression that can be used for identifying and/or characterizing a compound that prevents and/or treats (e.g. ameliorates) a HBV infection. For example, said cell or non-human animal may comprise an exogenous nucleotide sequence encoding PAPD5 and/or PAPD7, e.g. cloned into an expression vector and operable linked to an exogenous promoter. Said cell or non-human animal may overexpress PAPD5 and/or PAPD7, preferably PAPD5 and PAPD7. Alternatively, said cell or non-human animal may have a knock-down of PAPD5 and/or PAPD7, preferably of PAPD5 and PAPD7.

EMBODIMENTS OF THE INVENTION

Thus, the present invention relates to the following items:

1. A method for identifying a compound that prevents, ameliorates and/or inhibits a hepatitis B virus (HBV) infection, comprising
   a. contacting a test compound with a cell expressing PAPD5 and/or PAPD7
   b. measuring the expression and/or activity of PAPD5 and/or PAPD7 in the presence and absence of said test compound; and
   c. identifying a compound that reduces the expression and/or activity of PAPD5 or PAPD7 as a compound that prevents, ameliorates and/or inhibits a HBV infection.
2. The method of item 1, further comprising the step of testing the ability of combinations of compounds identified in c) to reduce the expression and/or activity of PAPD5 and PAPD7.
3. The method of item 1 or 2, wherein PAPD5 is a PAPD5 target nucleic acid.
4. The method of item 3, wherein the PAPD5 target nucleic acid comprises or consists of
   a. a nucleotide sequence of SEQ ID NO: 4 or 5 or 10, or natural variant thereof;
   b. a nucleotide sequence having at least 80% identity to a nucleotide sequence of a.), wherein the polypeptide expressed from the nucleic acid sequence has poly-A polymerase function;
   c. a nucleotide sequence comprising or consisting of SEQ ID NO: 4, 5 or 10;
   d. a nucleotide sequence encoding the amino acid sequence of SEQ ID NO: 1 or 2;
   e. a nucleotide sequence encoding an amino acid sequence having at least 80% identity to SEQ ID NO: 1 or 2, wherein the polynucleotide encodes a polypeptide that has poly-A polymerase function;
   f. a nucleotide sequence encoding an enzymatically active fragment of SEQ ID NO: 1 or 2, such as SEQ ID NO: 7 or 8; or
   g. a nucleotide sequence encoding an amino acid sequence having at least 80% identity to an amino acid sequence of an enzymatically active fragment of SEQ ID NO: 1 or 2, such as SEQ ID NO: 7 or 8, wherein the polynucleotide encodes a polypeptide that has poly-A polymerase function;
5. The method of item 1 or 2, wherein PAPD7 is a PAPD7 target nucleic acid.
6. The method of item 5, wherein the PAPD7 target nucleic acid comprises or consists of
   a. a nucleotide sequence of SEQ ID NO: 6 or 11, or natural variant thereof;
   b. a nucleotide sequence having at least 80% identity to a nucleotide sequence of (a.), wherein the polypeptide expressed from the nucleic acid sequence has poly-A polymerase function;
   c. a nucleotide sequence comprising or consisting of SEQ ID NO: 6 or 11;
   d. the nucleotide sequence encoding the amino acid sequence of SEQ ID NO: 3;
   e. a nucleotide sequence encoding an amino acid sequence having at least 80% identity to SEQ ID NO: 3, wherein the polynucleotide encodes a polypeptide that has poly-A polymerase function;
   f. the nucleotide sequence encoding an enzymatically active fragment of SEQ ID NO: 3, such as SEQ ID NO: 9; or
   g. a nucleotide sequence encoding an amino acid sequence having at least 80% identity to an amino acid sequence of an enzymatically active fragment of SEQ ID NO: 3, such as SEQ ID NO: 9, wherein the polynucleotide encodes a polypeptide that has poly-A polymerase function.
7. The method of any one of items 1 to 6, wherein said cell is an eukaryotic cell.
8. The method of any one of items 1 to 7, wherein the compound that inhibits propagation of HBV inhibits secretion of HBV surface antigen (HBsAg), inhibits secretion of HBV envelope antigen (HBeAg), and/or inhibits production of intracellular HBV mRNA or HBV DNA.
9. The method of any one of items 1 to 8, wherein the test compound is a screening library of nucleic acid molecules selected from
   a. single stranded antisense oligonucleotides, or
   b. siRNA molecules; and
   c. shRNA molecules.
10. The method of any one of items 1 to 9, wherein the compound identified in step c. of item 1 reduce PAPD5 or PAPD7 mRNA expression by at least 50%.
11. The method of any one of items 1 to 10, wherein the test compound is a combined preparation of a nucleic acid molecule capable of reducing PAPD5 and a nucleic acid molecule capable of reducing PAPD7.
12. The method of item 11, wherein the combined preparation reduce HBV surface antigen (HBsAg), HBV envelope antigen (HBeAg), and/or intracellular HBV mRNA or HBV DNA by at least 70%.
13. The method of any one of items 1 to 12, which additionally comprises the step of comparing the test compound to a control.
14. The method of item 13, wherein said control is an inactive test compound that does not reduce the expression and/or activity of PAPD5 or PAPD7.
15. The method of any one of items 1 to 14, wherein the activity of PAPD5 and PAPD7 is the poly-A polymerase function.
16. An inhibitor of PAPD5 or PAPD7 for use in treating and/or preventing a HBV infection, wherein said inhibitor is
    a. a RNA interference (RNAi) molecule against PAPD5 or PAPD7; or
    b. a genome editing machinery, comprising:
       i. a site-specific DNA nuclease or a polynucleotide encoding a site-specific DNA nuclease; and
       ii. a guide RNA or a polynucleotide encoding a guide RNA.
17. The inhibitor for the use according to item 16, wherein the inhibitor is an RNAi molecule selected from the group consisting of:
    a. a single stranded antisense oligonucleotide;
    b. a siRNA molecule; and
    c. a shRNA molecule.
18. The inhibitor for the use according to item 16 or 17, wherein the inhibitor is a combined preparation comprising
    a. a RNAi molecule which inhibits expression and/or activity of PAPD5; and
    b. a RNAi molecule which inhibits expression and/or activity of PAPD7.
19. The inhibitor for the use according to any one of items 16 to 18, wherein the inhibitor reduces secretion of HBsAg and HBeAg.

20. The inhibitor for the use according to item any one of items 16 to 18, wherein the inhibitor reduces production of intracellular HBV mRNA or HBV DNA.

21. The inhibitor for the use according to any one of items 16 to 20, wherein the inhibitor inhibits development of chronic HBV infection and/or reduces the infectiousness of a HBV infected person.

22. An antisense oligonucleotide or siRNA molecule which comprises or consists of a contiguous nucleotide sequence of 10 to 30 nucleotides in length, wherein the contiguous nucleotide sequence is at least 80% complementarity to PAPD5 target nucleic acid and the antisense oligonucleotide capable of reducing expression of PAPD5.

23. A nucleic acid molecule which comprises or consists of a contiguous nucleotide sequence of 10 to 30 nucleotides in length wherein the contiguous nucleotide sequence is at least 80% complementarity to PAPD7 target nucleic acid and the antisense oligonucleotide capable of reducing expression of PAPD7.

24. The nucleic acid molecule of item 23, wherein the nucleic acid molecule is a single stranded antisense oligonucleotide.

25. The antisense oligonucleotide of item 22, wherein the oligonucleotide is capable of hybridizing to a target nucleic acid of selected from the group consisting of SEQ ID NO: 4, 5 and 10 with a ΔG° below −10 kcal.

26. The antisense oligonucleotide of item 23 or 24, wherein the oligonucleotide is capable of hybridizing to a target nucleic acid of selected from SEQ ID NO: 6 or 11 with a ΔG° below −10 kcal.

27. The antisense oligonucleotide of any one of items 22 to 26, wherein the target nucleic acid is RNA.

28. The antisense oligonucleotide of item 27, wherein the RNA is mRNA.

29. The antisense oligonucleotide of item 28, wherein the mRNA is pre-mRNA or mature mRNA.

30. The antisense oligonucleotide of any one of items 22-29, wherein the contiguous nucleotide sequence comprises or consists of from 12 to 22 nucleotides.

31. The antisense oligonucleotide of item 30, wherein the contiguous nucleotide sequence comprises or consists of from 14-20 nucleotides.

32. The antisense oligonucleotide of any one of items 22-31, wherein the antisense oligonucleotide comprises or consists of 12 to 25 nucleotides in length.

33. The antisense oligonucleotide of any one of items 22-32, wherein the oligonucleotide or contiguous nucleotide sequence is single stranded.

34. The antisense oligonucleotide of any one of items 22-33 wherein the oligonucleotide is neither siRNA nor self-complementary.

35. The antisense oligonucleotide of any one of items 22 or 25, wherein the contiguous nucleotide sequence comprises or consists of a sequence selected from SEQ ID NO: 12-131.

36. The antisense oligonucleotide of item 35, wherein the contiguous nucleotide sequence comprises or consists of a sequence selected from SEQ ID NO: 15, 18, 23, 25, 26, 30, 32, 39, 54, 56, 58, 65, 80, 88, 92, 93, 111, 115, 116 and 118.

37. The nucleic acid molecule or antisense oligonucleotide of any one of item 23, 24 or 26, wherein the contiguous nucleotide sequence comprises or consists of a sequence selected from SEQ ID NO: 132-151.

38. The antisense oligonucleotide of item 37, wherein the contiguous nucleotide sequence comprises or consists of a sequence selected from SEQ ID NO: 153, 155, 168, 171, 172, 174, 183, 184, 188, 190, 191, 194, 195, 197, 221, 224, 229, 232, 239, and 244.

39. The antisense oligonucleotide molecule of any one of items 22-38, wherein the contiguous nucleotide sequence has zero to three mismatches compared to the target nucleic acid it is complementary to.

40. The antisense oligonucleotide of item 39, wherein the contiguous nucleotide sequence has one mismatch compared to the target nucleic acid.

41. The antisense oligonucleotide of item 39, wherein the contiguous nucleotide sequence is fully complementary to the target nucleic acid sequence.

42. The antisense oligonucleotide of any one of items 22-41, comprising one or more modified nucleosides.

43. The antisense oligonucleotide of item 42, wherein the one or more modified nucleoside is a high-affinity modified nucleoside.

44. The antisense oligonucleotide of any one of items 22-43, wherein the antisense oligonucleotide comprises at least one modified internucleoside linkage.

45. The antisense oligonucleotide of item 44, wherein the modified internucleoside linkage is nuclease resistant.

46. The antisense oligonucleotide of item 44 or 45, wherein at least 50% of the internucleoside linkages within the contiguous nucleotide sequence are phosphorothioate internucleoside linkages or boranophosphate internucleoside linkages.

47. The antisense oligonucleotide of item 44 or 45, wherein all the internucleoside linkages within the contiguous nucleotide sequence are phosphorothioate internucleoside linkages.

48. The antisense oligonucleotide of any one of items 22-47, wherein the oligonucleotide is capable of recruiting RNase H.

49. The antisense oligonucleotide of item 48, wherein the oligonucleotide is a gapmer.

50. The antisense oligonucleotide of item 48 or 49, wherein the oligonucleotide is a gapmer of formula 5'-F-G-F'-3', where region F and F' independently comprise or consist of 1-4 modified nucleosides and G is a region between 6 and 17 nucleosides which are capable of recruiting RNaseH.

51. The antisense oligonucleotide of any one of items 42-44 or 50, wherein the modified nucleoside is a 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

52. The antisense oligonucleotide of item 50 or 51, wherein one or more of the modified nucleosides in region F and F' is a LNA nucleoside.

53. The antisense oligonucleotide of item 52, wherein all the modified nucleosides in region F and F' are LNA nucleosides.

54. The antisense oligonucleotide of item 53, wherein region F and F' consist of LNA nucleosides.

55. The antisense oligonucleotide of any one of items 51-54, wherein the LNA nucleoside is selected from beta-D-oxy-LNA, alpha-L-oxy-LNA, beta-D-amino-LNA, alpha-L-amino-LNA, beta-D-thio-LNA, alpha-L-thio-LNA, (S)cET, (R)cET beta-D-ENA and alpha-L-ENA.

56. The oligonucleotide of any one of items 51-54, wherein the LNA nucleoside is oxy-LNA.

57. The antisense oligonucleotide of any one of items 51-56, wherein the LNA nucleoside is beta-D-oxy-LNA.

58. The antisense oligonucleotide of any one of items 51-54, wherein the LNA nucleoside is thio-LNA.

59. The antisense oligonucleotide of any one of items 51-54, wherein the LNA nucleoside is amino-LNA.

60. The antisense oligonucleotide of any one of items 51-54, wherein the LNA nucleoside is cET.

61. The antisense oligonucleotide of any one of items 51-54, wherein the LNA nucleoside is ENA.

62. The antisense oligonucleotide of item 52, wherein at least one of region F or F' further comprises at least one 2' substituted modified nucleoside independently selected from the group consisting of 2'-O-alkyl-RNA, 2'-O-methyl-RNA, 2'-alkoxy-RNA, 2'-O-methoxyethyl-RNA, 2'-amino-DNA and 2'-fluoro-DNA.

63. The antisense oligonucleotide of any one of items 52-62, wherein the RNaseH recruiting nucleosides in region G are independently selected from DNA, alpha-L-LNA, C4' alkylated DNA, ANA and 2' F-ANA and UNA.

64. The antisense oligonucleotide of item 50 or 63, wherein the nucleosides in region G are DNA nucleosides.

65. The antisense oligonucleotide of any one of items 22 or 25, wherein the antisense oligonucleotide is selected from CMP ID NO: 12_1 to 131_1.

66. The antisense oligonucleotide of item 65, wherein the antisense compound are selected from CMP ID NO: 15_1, 18_1, 23_1, 25_1, 26_1, 30_, 32_1, 39_1, 54_1, 56_1, 58_1, 65_1, 80_1, 88_1, 92_1, 93_1, 111_1, 115_1, 116_1 and 118_1.

67. The antisense oligonucleotide of items 24 wherein the antisense oligonucleotide is selected from CMP ID NO: 132 to 151_1.

68. The antisense oligonucleotide of item 67, wherein the antisense compound are selected from CMP ID NO: 153_1, 155_1, 168_1, 171_1, 172_1, 174_1, 183_1, 184_1, 188_1, 190_1, 191_1, 194_1, 195_1, 197_1, 221_1, 224_1, 229_1, 232_1, 239_1, and 244_1.

69. The siRNA molecule of item 22, wherein the siRNA molecule is targeting a PAPD5 target sequence selected from one or more of SEQ ID NO: 252, 253, 254 and 255

70. The nucleic acid molecule of item 23, wherein the nucleic acid molecule is an siRNA molecule targeting a PAPD7 target sequence selected from one or more of SEQ ID NO: 256, 257, 258 and 259.

71. A conjugate comprising the antisense oligonucleotide or siRNA according to any one of claims 22-70, and at least one conjugate moiety covalently attached to said oligonucleotide.

72. The conjugate of item 71, wherein the conjugate moiety is selected from carbohydrates, cell surface receptor ligands, drug substances, hormones, lipophilic substances, polymers, proteins, peptides, toxins, vitamins, viral proteins or combinations thereof.

73. The conjugate of item 71 or 72, wherein the conjugate moiety is capable of binding to the asialoglycoprotein receptor.

74. The conjugate of any one of item 71-73, comprising a linker which is positioned between the antisense oligonucleotide and the conjugate moiety.

75. The conjugate of item 74, wherein the linker is a physiologically labile linker.

76. The conjugate of item 75, wherein the physiologically labile linker is nuclease susceptible linker.

77. The conjugate of item 75 or 76, wherein the oligonucleotide has the formula D'-F-G-F' or F-G-F'-D", wherein F, F' and G are as defined in any one of items 52-65 and D' or D" comprises 1, 2 or 3 DNA nucleosides with phosphorothioate internucleoside linkages.

78. A combined preparation comprising:

a. a RNAi molecule which inhibits expression and/or activity of PAPD5; and
b. a RNAi molecule which inhibits expression and/or activity of PAPD7.

79. The combined preparation of item 78, wherein the RNAi molecules are selected from items 22-70 or a conjugate of any one of items 71-77.

80. The combined preparation of item 78, wherein the RNAi molecule in a) is an antisense compounds of item 36 or 66 and where the RNAi molecule in b) is an antisense compounds of item 38 or 68.

81. A pharmaceutical composition comprising the antisense oligonucleotide or siRNA molecule of any one of items 22-70, or a conjugate of any one of items 71-77, or a combined preparation of item 78-80 and optionally a pharmaceutically acceptable diluent, carrier, salt and/or adjuvant.

82. An in vivo or in vitro method for modulating PAPD5 and/or PAPD7 expression in a target cell which is expressing PAPD5 and/or PAPD7, said method comprising administering an antisense oligonucleotide or siRNA molecule of item 22-70 or a conjugate of item 71-77, or a combined preparation of item 78 or 79, or the pharmaceutical composition of item 81 in an effective amount to said cell.

83. A method for treating or preventing a disease comprising administering a therapeutically or prophylactically effective amount of an antisense oligonucleotide or siRNA molecule of item 22-70 or a conjugate of item 71-77 or a combined preparation of item 78-80, or the pharmaceutical composition of item 81 to a subject suffering from or susceptible to the disease.

84. The antisense oligonucleotide or siRNA molecule of item 22-70 or a conjugate of item 71-77 or a combined preparation of item 78-80, or the pharmaceutical composition of item 81, for use as a medicament for treatment or prevention of a disease in a subject.

85. Use of the oligonucleotide of oligonucleotide or siRNA molecule of item 22-70 or a conjugate of item 71-77 or a combined preparation of item 78-80, for the preparation of a medicament for treatment or prevention of a disease in a subject.

86. The method, the antisense oligonucleotide or the use of any one of items 83-85, wherein the PAPD5 and/or PAPD7 is reduced by at least 30%, or at least or at least 40%, or at least 50%, or at least 60%, or at least 70%, or at least 80%, or at least 90%, or at least 95% compared to the expression without the antisense oligonucleotide or siRNA molecule of item 22-70 or a conjugate of item 71-77, or a combined preparation of item 78-80.

87. The method, the antisense oligonucleotide or the use of items 83-85, wherein the disease is selected from HBV infection, in particular chronic HBV infection.

88. A method for monitoring the therapeutic success during the treatment of a HBV infection, wherein the method comprises:

a. analyzing in a sample obtained from a test subject the amount and/or activity of PAPD5 and/or PAPD7;
b. comparing said amount and/or activity with reference data corresponding to the amount and/or activity of PAPD5 and/or PAPD7 of at least one reference subject; and
c. predicting therapeutic success based on the comparison step (b).

89. The monitoring method of item 88, wherein the test subject is a human being who receives medication for a HBV infection or has received medication for a HBV infection.

90. The monitoring method of item 88 or 89, wherein the reference data corresponds to the amount and/or activity of PAPD5 and/or PAPD7 in a sample of at least one reference subject.

91. The monitoring method of any one of items 88 to 90, wherein the at least one reference subject has a HBV infection but did not receive medication for a HBV infection; and wherein in step (c) a decreased amount and/or activity of PAPD5 and/or PAPD7 of the test subject as compared to the reference data indicates therapeutic success in the treatment of a HBV infection.

92. The monitoring method of item 91, wherein said decreased amount and/or activity of PAPD5 and/or PAPD7 means that the amount and/or activity of PAPD5 and/or PAPD7 in the sample of the test subject is 0 to 90% of the amount and/or activity of PAPD5 and/or PAPD7 in the sample of the at least one reference subject.

93. The monitoring method of any one of items 88 to 90, wherein the at least one reference subject has a HBV infection and has received medication for a HBV infection; and wherein in step (c) an identical or similar amount and/or activity of PAPD5 and/or PAPD7 of the test subject as compared to the reference data indicates therapeutic success in the treatment of a HBV infection.

94. The monitoring method of any one of items 88 to 90, wherein the at least one reference subject does not have a HBV infection; and wherein in step (c) an identical or similar amount and/or activity of PAPD5 and/or PAPD7 of the test subject as compared to the reference data indicates therapeutic success in the treatment of a HBV infection.

95. The monitoring method of item 93 or 94, wherein said identical or similar amount and/or activity of PAPD5 and/or PAPD7 means that the amount and/or activity of PAPD5 and/or PAPD7 in the sample of the test subject is 90-110% of the amount and/or activity of PAPD5 and/or PAPD7 in the sample of the at least one reference subject.

Pharmaceutical Compositions

As described above, the invention relates to a composition comprising an inhibitor of PAPD5 alone or in combination with a PAPD7 inhibitor for use in treating and/or preventing a HBV infection. The inhibitor is preferably a nucleic acid molecule as defined herein. Specifically, a combined preparation comprising an inhibitor of PAPD5 and an inhibitor of PAPD7 for use in the treatment and/or prevention of a HBV infection is contemplated; and a pharmaceutical composition comprising said inhibitor composition or said combined preparation. Said pharmaceutical composition (i.e. medicament) optionally comprises a pharmaceutically acceptable carrier. Said pharmaceutical composition may further comprise a therapeutically acceptable diluent, salt, excipient and/or adjuvant.

A typical pharmaceutical composition is prepared by mixing a PAPD5 inhibitor alone or with a PAPD7 inhibitor and a carrier or excipient. Suitable carriers and excipients are well known to those skilled in the art and are described in detail in, e.g., Ansel, Ansel's Pharmaceutical Dosage Forms and Drug Delivery Systems, Philadelphia: Lippincott, Williams & Wilkins, 2004; Gennaro, Remington: The Science and Practice of Pharmacy, Philadelphia: Lippincott, Williams & Wilkins, 2000; and Rowe, Handbook of Pharmaceutical Excipients, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to improve appearance of the drug or aid in the manufacturing of the pharmaceutical product (i.e., medicament). For example, the pharmaceutical composition of the invention may be formulated by mixing an inhibitor of PAPD5 and/or an inhibitor of PAPD7 at ambient temperature at an appropriate pH, and with the desired degree of purity, with physiologically acceptable carriers, i.e., carriers that are non-toxic to recipients at the dosages and concentrations employed into a suitable administration form. The pharmaceutical composition of the invention may be sterile.

For nucleic acid molecules suitable formulations are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990). WO 2007/031091 provides further suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, Organic Process Research & Development 2000, 4, 427-435 or in Ansel, In: Pharmaceutical Dosage Forms and Drug Delivery Systems, 6th ed. (1995), pp. 196 and 1456-1457. For example, the pharmaceutically acceptable salt of the compounds provided herein may be a sodium salt.

The pharmaceutical composition of the invention is formulated, dosed, and administered in a fashion consistent with good medical practice. Factors for consideration in this context include the particular mammal being treated, the clinical condition of the individual patient, the site of delivery of the agent, the method of administration, the scheduling of administration, the age and sex of the patients and other factors known to medical practitioners. Herein, an "effective amount" (also known as "(therapeutically) effective dose") means the amount of a compound that will elicit the biological or medical response of a subject that is being sought by a medical doctor or other clinician. The "effective amount" of the inhibitor of the invention, the combined preparation of the invention, or the pharmaceutical composition of the invention will be governed by such considerations, and is the minimum amount necessary to inhibit HBsAg and/or HBeAg. For example, such amount may be below the amount that is toxic to the cells of the recipient, or to the mammal as a whole.

For example, if the PAPD5 inhibitor or the PAPD7 inhibitor is/an antisense oligonucleotide, then the pharmaceutically effective amount administered is a dose of 0.1-15 mg/kg, such as from 0.2-10 mg/kg, such as from 0.25-5 mg/kg. The administration can be once a week, every $2^{nd}$ week, every third week or even once a month.

The nucleic acid molecules or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, intramuscular, intracerebral, intracerebroventricular or intrathecal).

In a preferred embodiment the nucleic acid molecule or pharmaceutical compositions of the present invention are administered by a parenteral route including intravenous, intraarterial, subcutaneous, intraperitoneal or intramuscular injection or infusion, intrathecal or intracranial, e.g. intracerebral or intraventricular, intravitreal administration. In one embodiment the active oligonucleotide or oligonucleotide conjugate is administered intravenously. In another embodiment the active nucleic acid molecule or nucleic acid molecule conjugate is administered subcutaneously.

The inhibitor of the invention, the combined preparation of the invention, or the pharmaceutical composition of the invention is useful in the prevention and/or treatment of an HBV invention. They preferably inhibit secretion of HBsAg and/or HBeAg, most preferably of HBsAg and HBeAg.

Definitions

Nucleotide Sequence

The term "nucleotide sequence" or "polynucleotide" is commonly known in the art and comprises molecules comprising or consisting of naturally occurring molecules such as DNA and RNA as well as nucleic acid analogues such as, e.g., oligonucleotides thiophosphates, substituted ribo-oligonucleotides, LNA molecules, PNA molecules, GNA (glycol nucleic acid) molecules, TNA (threose nucleic acid) molecules, morpholino polynucleotides, or nucleic acids with modified backbones such as polysiloxane, and 2'-O-(2-methoxy) ethyl-phosphorothioate, or a nucleic acid with substituents, such as methyl-, thio-, sulphate, benzoyl-, phenyl-, amino-, propyl-, chloro-, and methanocarbanucleosides, or a reporter molecule to facilitate its detection. Furthermore, the term "nucleotide sequence" is to be construed equivalently with the term "nucleic acid molecule" in context of the present invention and may inter alia refer to DNA, RNA, PNA or LNA or hybrids thereof or any modification thereof that is known in the art (see, e.g., U.S. Pat. Nos. 5,525,711, 4,711,955, 5,792,608 or EP 302175 for examples of modifications). Nucleic acid residues comprised by the nucleic acid sequence described and provided herein may be naturally occurring nucleic acid residues or artificially produced nucleic acid residues. Examples for nucleic acid residues are adenine (A), guanine (G), cytosine (C), thymine (T), uracil (U), xanthine (X), and hypoxanthine (HX). As understood by the person of skill in the art, thymine (T) and uracil (U) may be used interchangeably depending on the respective type of polynucleotide. For example, as the skilled person is aware of, a thymine (T) as part of a DNA corresponds to an uracil (U) as part of the corresponding transcribed mRNA. The polynucleotides described and provided herein may be single- or double-stranded, linear or circular, natural or synthetic.

The nucleotide sequences provided herein may be cloned into a vector. The term "vector" as used herein includes plasmids, cosmids, viruses, bacteriophages and other vectors commonly used in genetic engineering. In a preferred embodiment, these vectors are suitable for the transformation of cells, like mammalian cells or yeast cells. Herein, the vector may be an expression vector. Generally, expression vectors have been widely described in the literature. They may comprise a selection marker gene and a replication-origin ensuring replication in the host, a promoter, and a termination signal for transcription. Between the promoter and the termination signal there may be at least one restriction site or a polylinker which enables the insertion of a nucleic acid sequence desired to be expressed. Non-limiting examples for the vector into which a nucleotide sequence provided herein may be cloned are adenoviral, adeno-associated viral (AAV), lentiviral, HIV-based lentiviral, nonviral minicircle-vectors, or other vectors for bacterial and eukaryotic expression systems.

Nucleic Acid Molecule

The term "nucleic acid molecule" or "therapeutic nucleic acid molecule" as used herein is defined as it is generally understood by the skilled person as a molecule comprising two or more covalently linked nucleosides (i.e. a nucleotide sequence). The nucleic acid molecule(s) referred to in the method of the invention are generally therapeutic oligonucleotides below 50 nucleotides in length. The nucleic acid molecules may be or comprise an antisense oligonucleotide, or may be another oligomeric nucleic acid molecule, such as a CRISPR RNA, a siRNA, shRNA, an aptamer, or a ribozyme. Nucleic acid molecules are compositions that are commonly made in the laboratory by solid-phase chemical synthesis followed by purification. When referring to a sequence of the nucleic acid molecule, reference is made to the sequence or order of nucleobase moieties, or modifications thereof, of the covalently linked nucleotides or nucleosides. The nucleic acid molecule of the invention is man-made, and is chemically synthesized, and is typically purified or isolated. The nucleic acid molecule of the invention may comprise one or more modified nucleosides or nucleotides.

In some embodiments, the nucleic acid molecule of the invention comprises or consists of 8 to 40 nucleotides in length, such as from 9 to 35, such as from 10 to 30, such as from 11 to 22, such as from 12 to 20, such as from 13 to 18 or 14 to 16 contiguous nucleotides in length. In some embodiments, the nucleic acid molecule or contiguous nucleotide sequence thereof comprises or consists of 22 or less nucleotides, such as 20 or less nucleotides, such as 18 or less nucleotides, such as 14, 15, 16 or 17 nucleotides. It is to be understood that any range given herein includes the range endpoints. Accordingly, if a nucleic acid molecule is said to include from 10 to 30 nucleotides, both 10 and 30 nucleotides are included.

In some embodiments, the contiguous nucleotide sequence comprises or consists of 8, 9, 10, 11, 12, 13, 14, 15, 16, 17, 18, 19, 20, 21, 22, 23, 24, 25, 26, 27, 28, 29 or 30 contiguous nucleotides in length The nucleic acid molecule(s) are typically for modulating the expression of a target nucleic acids in a mammal. In some embodiments the nucleic acid molecules, such as for siRNAs, shRNAs and antisense oligonucleotides, are typically for inhibiting the expression of a target nucleic acid. The nucleic acid molecules, when combined, may therefore be effective at modulating the expression of one or more target nucleic acids in a mammal.

In one embodiment of the invention the nucleic acid molecule is selected from a RNAi agent, such as a siRNA, shRNA or an antisense oligonucleotide. In preferred embodiments the nucleic acid molecule is a high affinity modified antisense oligonucleotide.

In some embodiments the nucleic acid molecule is a phosphorothioate nucleic acid molecule. In some embodiments the nucleic acid molecule comprises phosphorothioate internucleoside linkages.

In some embodiments the nucleic acid molecule(s) may be conjugated to non-nucleosidic moieties (conjugate moieties).

A library of nucleic acid molecules is to be understood as a collection of variant nucleic acid molecules. The purpose of the library of nucleic acid molecules can vary. In some embodiments, the library of nucleic acid molecules is composed of oligonucleotides with different nucleobase sequences, for example it may be a library of nucleic acid molecules which are designed across a target nucleic acid (e.g. a RNA sequence), for example a library of antisense oligonucleotides or siRNA molecules may be generated by a mRNA gene-walk with the purpose of identifying regions on the target nucleic acid where nucleic acid molecules efficiently modulate the target nucleic acid. In some embodiments, the library of nucleic acid molecules is composed of oligonucleotides with overlapping nucleobase sequence targeting a specific region on the target nucleic acid with the purpose of identifying the most potent sequence within the library of nucleic acid molecules. In some embodiments, the library of nucleic acid molecules is a library of nucleic acid molecule design variants (child nucleic acid molecules) of a parent or ancestral nucleic acid molecule, wherein the nucleic acid molecule design variants retaining the core nucleobase sequence of the parent nucleic acid molecule.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides. An antisense oligonucleotide is a single stranded oligonucleotide with minimal or no internal duplex formation. A siRNA molecule generally consists of 2 complementary oligonucleotide stands (a sense strand and an antisense strand) that forms a double stranded molecule. A shRNA molecule is an oligonucleotide which is generally longer than antisense oligonucleotides and which form an internal duplex (hairpin) structure within the molecule.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded.

RNAi

Herein, the term "RNA interference (RNAi) molecule" refers to any molecule inhibiting RNA expression or translation, including the nucleic acid molecules defined herein. A small interfering RNA (siRNA) is a double-stranded RNA molecule that, by binding complementary mRNA after transcription, leads to their degradation and loss in translation. A small hairpin RNA (shRNA) is an artificial RNA molecule with a hairpin structure which upon expression is able to reduce mRNA via the DICER and RNA reducing silencing complex (RISC). RNAi molecules can be designed on the base of the RNA sequence of the gene of interest. Corresponding RNAi can then be synthesized chemically or by in vitro transcription, or expressed from a vector or PCR product siRNA and shRNA molecules are generally between 20 and 50 nucleotides in length, such as between 25 and 35 nucleotides in length, and interacts with the endonuclease known as Dicer which is believed to processes dsRNA into 19•-23 base pair short interfering RNAs with characteristic two base 3' overhangs which are then incorporated into an RNA-induced silencing complex (RISC). Effective extended forms of Dicer substrates have been described in U.S. Pat. Nos. 8,349,809 and 8,513,207, hereby incorporated by reference. Upon binding to the appropriate target mRNA, one or more endonucleases within the RISC cleave the target to induce silencing. RNAi agents may be chemically modified using modified internucleotide linkages and high affinity nucleosides, such as 2'-4' bicyclic ribose modified nucleosides, including LNA and cET.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence and may optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkage

The term "modified internucleoside linkage" is defined as generally understood by the skilled person as linkages other than phosphodiester (PO) linkages, that covalently couples two nucleosides together. Nucleotides with modified internucleoside linkage are also termed "modified nucleotides". In some embodiments, the modified internucleoside linkage increases the nuclease resistance of the nucleic acid molecules of the invention compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides as well as siRNA's for in vivo use, and may serve to protect against nuclease cleavage at regions of DNA or RNA nucleosides in the oligonucleotide or siRNA of the invention, for example within the gap region of a gapmer oligonucleotide, as well as in regions of modified nucleosides.

In an embodiment, the nucleic acid molecule, e.g. antisense oligonucleotide, shRNA or siRNA, comprises one or more internucleoside linkages modified from the natural phosphodiester to a linkage that is for example more resistant to nuclease attack. Nuclease resistance may be determined by incubating the oligonucleotide in blood serum or by using a nuclease resistance assay (e.g. snake venom phosphodiesterase (SVPD), both are well known in the art. Internucleoside linkages which are capable of enhancing the nuclease resistance of an oligonucleotide are referred to as nuclease resistant internucleoside linkages. In some embodiments at least 50% of the internucleoside linkages in the antisense oligonucleotide, or contiguous nucleotide sequence thereof, are modified, such as at least 60%, such as at least 70%, such as at least 80 or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

Modified internucleoside linkages may be selected from the group comprising phosphorothioate, diphosphorothioate and boranophosphate. In some embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage.

A phosphorothioate internucleoside linkage is particularly useful due to nuclease resistance, beneficial pharmakokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide comprises one or more neutral internucleoside linkage, particularly a internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from $-O-P(O)_2-O-$, $-O-P(O,S)-O-$, $-O-P(S)_2-O-$, $-S-P(O)_2-O-$, $-S-P(O,S)-O-$, $-S-P(S)_2-O-$, $-O-P(O)_2-S-$, $-O-P(O,S)-S-$, $-S-P(O)_2-S-$, $-O-PO(RH)-O-$, $O-PO(OCH_3)-O-$, $-O-PO(NR^H)-O-$, $-O-PO(OCH_2CH_2S-R)-O-$, $-O-PO(BH_3)-O-$, $-O-PO(NHR^H)-O-$, $-O-P(O)_2-NR^H-$, $-NR^H-P(O)_2-O-$, $-NR^H-CO-O-$, $-NR^H-CO-NR^H-$, and/or the internucleoside linker may be selected form the group consisting of: $-O-CO-O-$, $-O-CO-NR^H-$, $-NR^H-CO-CH_2-$, $-O-CH_2-CO-NR^H-$, $-O-CH_2-CH_2-NR^H-$, $CO-NR^H-CH_2-$, $-CH_2-NR^HCO-$, $-O-CH_2-CH_2-S-$, $-S-CH_2-CH_2-O-$, $-S-CH_2-CH_2-S-$, $-CH_2-SO_2-CH_2-$, $-CH_2-CO-NR^H-$, $-O-CH_2-CH_2-NR^H-CO-$, $-CH_2-NCH_3-O-CH_2-$, where RH is selected from hydrogen and C1-4-alkyl.

Nuclease resistant linkages, such as phosphothioate linkages, are particularly useful in antisense oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the antisense oligonucleotide are phosphorothioate and/or boranophosphate linkages. Preferably, all the internucleoside linkages in the oligonucleotide are phosphorothioate linkages.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide or modified nucleic acid molecule describes an oligonucleotide or nucleic acid molecule comprising one or more sugar-modified nucleosides and/or modified internucleoside linkages. The term "chimeric" is a term that has been used in the literature to describe oligonucleotides or nucleic acid molecules with modified nucleosides, in particular gapmer oligonucleotides.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol. 45 page 2055 and Bergstrom (2009) Current Protocols in Nucleic Acid Chemistry Suppl. 37 1.4.1).

The term "% complementary" as used herein, refers to the number of nucleotides in percent of a contiguous nucleotide sequence in a nucleic acid molecule (e.g. oligonucleotide) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences (when aligned with the target sequence 5'-3' and the oligonucleotide sequence from 3'-5'), dividing by the total number of nucleotides in the oligonucleotide and multiplying by 100. In such a comparison a nucleobase/nucleotide which does not align (form a base pair) is termed a mismatch. Preferably, insertions and deletions are not allowed in the calculation of % complementarity of a contiguous nucleotide sequence.

The term "fully complementary", refers to 100% complementarity.

The following is an example of an oligonucleotide (SEQ ID NO: 12) that is fully complementary to a region of a target nucleic acid (SEQ ID NO: 10).

```
1651 cccttagttaaacacatctacccttgacca 1680 (Pos. 1651-1690 of SEQ ID NO: 10)
            ||||||||||||||||||
   1 --3'-TCAATTTGTGTAGATGGGA-5'---    19 (SEQ ID NO: 12)
```

Identity

In context of the present invention, the term "identity" or "percent identity" means that amino acid or nucleotide sequences have identities of at least 80%, preferably at least 90%, more preferably at least 95%, even more preferably at least 98%, and even more preferably at least 99% identity to the sequences shown herein, e.g. those of SEQ ID NO: 1, 2, or 3, wherein the higher identity values are preferred upon the lower ones. In accordance with the present invention, the term "identity/identities" or "percent identity/identities" in the context of two or more nucleic acid or amino acid sequences, refers to two or more sequences that are the same, or that have a specified percentage of amino acid residues or nucleotides that are the same (e.g., at least 80%, at least 90%, at least 95%, at least 98%, or at least 99% identity with the amino acid sequences of, e.g., SEQ ID NO: 1, 2, 3, 7, 8 or 9 or with the nucleotide sequences of, e.g., SEQ ID NO: 4, 5, 6, 10 or 11), when compared and aligned for maximum correspondence over a window of comparison, or over a designated region as measured using a sequence comparison algorithm as known in the art, or by manual alignment and visual inspection.

For amino acid sequences, preferably the described identity exists over a region that is at least about 50 amino acids, preferably at least 100 amino acids, more preferably at least 400 amino acids, more preferably at least 500 amino acids, more preferably at least 600 amino acids and most preferably all amino acids in length.

In case of nucleotide sequences, the described identity most preferably exists over a region that is at least 100 nucleotides, preferably at least 1,000 nucleotides, more preferably at least 2,000 nucleotides and most preferably all nucleotides in length. However, for nucleic acid molecules, which generally are below 50 nucleotides, the identity can be assessed over a significantly shorter region. Generally, the percentage identity of nucleic acid molecules is calculated by counting the number of aligned bases that are identical between the two sequences dividing by the total number of nucleotides in the nucleic acid molecule and multiplying by 100. Percent identity=(Matches×100)/Length of aligned region. Preferably, insertions and deletions are not allowed in the calculation of % identity of a contiguous nucleotide sequence in a nucleic acid molecule.

Those having skills in the art will know how to determine percent identity between/among sequences using, for example, algorithms such as those based on CLUSTALW computer program (Thompson, 1994, Nucl Acids Res, 2: 4673-4680) or FASTDB (Brutlag, 1990, Comp App Biosci, 6: 237-245), as known in the art. Also available to those having skills in this art are the BLAST and BLAST 2.0 algorithms (Altschul, 1997, Nucl Acids Res 25: 3389-3402; Altschul, 1993, J Mol Evol, 36: 290-300; Altschul, 1990, J Mol Biol 215: 403-410). For example, BLAST 2.0, which stands for Basic Local Alignment Search Tool BLAST (Altschul, 1997, loc. cit.; Altschul, 1993, loc. cit.; Altschul, 1990, loc. cit.), can be used to search for local sequence alignments. BLAST, as discussed above, produces alignments of both nucleotide and amino acid sequences to determine sequence similarity. Because of the local nature of the alignments, BLAST is especially useful in determining exact matches or in identifying similar sequences. Analogous computer techniques using BLAST (Altschul, 1997, loc. cit.; Altschul, 1993, loc. cit.; Altschul, 1990, loc. cit.) are used to search for identical or related molecules in nucleotide databases such as GenBank or EMBL.

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy ΔG° is a more accurate representation of binding affinity and is related to the dissociation constant ($K_d$) of the reaction by $\Delta G°=-RT \ln(K_d)$, where R is the gas constant and T is the absolute temperature. Therefore, a very low ΔG° of the reaction between an oligonucleotide and the target nucleic acid reflects a strong hybridization between the oligonucleotide and target nucleic acid. ΔG° is the energy associated with a reaction where aqueous concentrations are 1M, the pH is 7, and the temperature is 37° C. The hybridization of oligonucleotides to a target nucleic acid is a spontaneous reaction and for spontaneous reactions ΔG° is less than zero. ΔG° can be measured experimentally, for example, by use of the isothermal titration calorimetry (ITC) method as described in Hansen et al., 1965, *Chem. Comm.* 36-38 and Holdgate et al., 2005, *Drug Discov Today*. The skilled person will know that commercial equipment is available for ΔG° measurements. ΔG° can also be estimated numerically by using the nearest neighbor model as described by SantaLucia, 1998, *Proc Natl Acad Sci USA.* 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated ΔG° values below −10 kcal for oligonucleotides that are 10-30 nucleotides in length. In some embodiments the degree or strength of hybridization is measured by the standard state Gibbs free energy ΔG°. The oligonucleotides may hybridize to a target nucleic acid with estimated ΔG° values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

Target Nucleic Acid

According to the present invention, the target nucleic acid is a nucleic acid which encodes mammalian PAPD5 or PAPD7 and may for example be a gene, a RNA, a mRNA, and pre-mRNA, a mature mRNA or a cDNA sequence. The target may therefore be referred to as a PAPD5 or PAPD7 target nucleic acid. The oligonucleotide or nucleic acid molecule of the invention may for example target exon regions of a mammalian PAPD5 or PAPD7, or may for example target intron region in the PAPD5 or PAPD7 pre-mRNA. Suitably, the target nucleic acid encodes a PAPD5 or PAPD7 protein, in particular mammalian PAPD5 or PAPD7, such as human PAPD5 or PAPD7 (See for example tables 1A and B and Table 2A and B) which provides the mRNA and pre-mRNA sequences for human, monkey, rat and pig PAPD5 or PAPD7).

In some embodiments, the target nucleic acid is selected from the group consisting of SEQ ID NO: 4, 5 or 10 or naturally occurring variants thereof (e.g. sequences encoding a mammalian PAPD5).

In some embodiments, the target nucleic acid is selected from the group consisting of SEQ ID NO: 6 or 11 or naturally occurring variants thereof (e.g. sequences encoding a mammalian PAPD7).

If employing the oligonucleotide of the invention in research or diagnostics the target nucleic acid may be a cDNA or a synthetic nucleic acid derived from DNA or RNA.

For in vivo or in vitro application, the oligonucleotide of the invention is typically capable of inhibiting the expression of the PAPD5 or PAPD7 target nucleic acid in a cell which is expressing the PAPD5 or PAPD7 target nucleic acid. The contiguous sequence of nucleobases of the oligonucleotide of the invention is typically complementary to the PAPD5 or PAPD7 target nucleic acid, as measured across the length of the oligonucleotide, optionally with the exception of one or two mismatches, and optionally excluding nucleotide based linker regions which may link the oligonucleotide to an optional functional group such as a conjugate, or other non-complementary terminal nucleotides (e.g. region D' or D"). The target nucleic acid may, in some embodiments, be a RNA or DNA, such as a messenger RNA, such as a mature mRNA or a pre-mRNA. In some embodiments the target nucleic acid is a RNA or DNA which encodes mammalian PAPD5 or PAPD7 protein, such as human PAPD5 or PAPD7, e.g. the human PAPD5 mRNA sequence, such as that disclosed as SEQ ID NO 4, 5 or 10 or the human PAPD7 mRNA sequence, such as that disclosed as SEQ ID NO 6 or 11. Further information on exemplary target nucleic acids is provided in tables 1A and B and Table 2A and B.

TABLE 1A

Genome and assembly information for PAPD5 across species.

| Species | Chr. | Band | Strand | Genomic coordinates Start | End | ensembl_gene_id | Assembly |
|---|---|---|---|---|---|---|---|
| Human | 16 | q12.1 | fwd | 50152918 | 50235310 | ENSG00000121274 | GRCh38.p7 |
| mouse | 8 | C3 | fwd | 88199213 | 88259722 | ENSMUSG00000036779 | GRCm38.p5 |
| Rat | 19 | p11 | rev | 19771677 | 19832812 | ENSRNOG00000024212 | Rnor_6.0 |

TABLE 1B

| Genome and assembly information for PAPD7 across species. | | | | | | | |
|---|---|---|---|---|---|---|---|
| | | | | Genomic coordinates | | | |
| Species | Chr | Band | Strand | Start | End | ensembl_gene_id | Assembly |
| Human | 5 | p15.31 | fwd | 6713007 | 6757048 | ENSG00000112941 | GRCh38.p7 |
| mouse | 13 | B3 | rev | 69497959 | 69534617 | ENSMUSG00000034575 | GRCm38.p5 |
| Rat | 1 | p11 | fwd | 36400443 | 36433238 | ENSRNOG00000017613 | Rnor_6.0 |

Fwd = forward strand.
Rev = reverse strand.
The genome coordinates provide the pre-mRNA sequence (genomic sequence).

Target Sequence

The term "target sequence" as used herein refers to a sequence of nucleotides present in the target nucleic acid which comprises the nucleobase sequence which is complementary to the oligonucleotide or nucleic acid molecule of the invention. In some embodiments, the target sequence consists of a region on the target nucleic acid which is complementary to the contiguous nucleotide sequence of the oligonucleotide of the invention (i.e. a sub-sequence).

The oligonucleotide or nucleic acid molecule of the invention comprises a contiguous nucleotide sequence which is complementary to or hybridizes to a region on the target nucleic acid, such as a target sequence described herein.

The target nucleic sequence to which the oligonucleotide is complementary to or hybridizes to generally comprises a stretch of contiguous nucleobases of at least 10 nucleotides. The contiguous nucleotide sequence is between 10 to 50 nucleotides, such as 12-30, such as 13 to 25, such as 14 to 20, such as 15 to 18 contiguous nucleotides.

Naturally Occurring Variant

The term "naturally occurring variant" refers to variants of PAPD5 or PAPD7 gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms, and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian PAPD5 target nucleic acid, such as a target nucleic acid selected form the group consisting of SEQ ID NO: 4, 5 or 10.

In some embodiments, the naturally occurring variants have at least 95% such as at least 98% or at least 99% homology to a mammalian PAPD5 target nucleic acid, such as a target nucleic acid selected form the group consisting of SEQ ID NO: 6 or 11.

Numerous single nucleotide polymorphisms are known in the PAPD5 or PAPD7 gene, for example those disclosed in Table 2A (human premRNA start/reference sequence is SEQ ID NO: 10) and Table 2B human premRNA start/reference sequence is SEQ ID NO: 11).

TABLE 2A

| PAPD5 polymorphisms (naturally occurring variants) | | |
|---|---|---|
| minor allele | Minor allele frequency | Start on SEQ ID NO: 10 |
| G | 0.00399361 | 29 |
| G | 0.000199681 | 34 |
| T | 0.000399361 | 39 |
| A | 0.000599042 | 62 |
| A | 0.000599042 | 97 |
| G | 0.000199681 | 141 |
| A | 0.000199681 | 142 |
| T | 0.000199681 | 158 |
| A | 0.0241613 | 235 |
| A | 0.00239617 | 279 |
| — | 0.214058 | 370 |
| G | 0.000798722 | 450 |
| CAGCA | 0.000798722 | 603 |
| A | 0.0223642 | 1028 |
| C | 0.000199681 | 1044 |
| A | 0.0189696 | 1068 |
| T | 0.000199681 | 1181 |
| T | 0.0249601 | 1199 |
| T | 0.000998403 | 1258 |
| A | 0.000199681 | 1261 |
| T | 0.000599042 | 1441 |
| T | 0.000199681 | 1443 |
| C | 0.000599042 | 1469 |
| A | 0.000399361 | 1535 |

TABLE 2B

| PAPD7 polymorphisms (naturally occurring variants) | | |
|---|---|---|
| minor allele | Minor allele frequency | Start on SEQ ID NO: 11 |
| A | 0.293331 | 21 |
| T | 0.00119808 | 50 |
| T | 0.000199681 | 64 |
| A | 0.00279553 | 127 |
| A | 0.0597045 | 224 |
| G | 0.000199681 | 234 |
| T | 0.000599042 | 270 |
| A | 0.128994 | 284 |
| C | 0.000399361 | 316 |
| T | 0.000199681 | 349 |
| G | 0.00778754 | 362 |
| A | 0.000199681 | 409 |
| G | 0.000199681 | 425 |
| A | 0.000199681 | 448 |
| T | 0.000199681 | 473 |
| C | 0.000199681 | 491 |
| C | 0.327676 | 564 |
| T | 0.0203674 | 606 |
| — | 0.389577 | 837 |
| — | 0.00139776 | 1317 |
| T | 0.000599042 | 1331 |
| T | 0.000199681 | 1475 |
| T | 0.000399361 | 1483 |
| C | 0.01877 | 1673 |

TABLE 2B-continued

| PAPD7 polymorphisms (naturally occurring variants) | | |
|---|---|---|
| minor allele | Minor allele frequency | Start on SEQ ID NO: 11 |
| A | 0.000199681 | 1682 |
| T | 0.00339457 | 1726 |
| GGTCCTGGCCGGCGCCCGC | 0.258586 | 1736 |
| G | 0.000599042 | 1760 |
| C | 0.000199681 | 1777 |
| G | 0.000399361 | 1780 |
| T | 0.000199681 | 1852 |
| T | 0.000199681 | 1861 |
| T | 0.000199681 | 1889 |
| C | 0.000399361 | 1923 |
| G | 0.000399361 | 1962 |
| T | 0.0147764 | 1987 |
| G | 0.000998403 | 1996 |
| T | 0.000399361 | 2036 |

Modulation of Expression

The term "modulation of expression" as used herein is to be understood as an overall term for a nucleic acid molecules ability to alter the amount of PAPD5 or PAPD7 when compared to the amount of PAPD5 or PAPD7 before administration of the nucleic acid molecule. Alternatively modulation of expression may be determined by reference to a control experiment. It is generally understood that the control is an individual or target cell treated with a saline composition or an individual or target cell treated with a non-targeting or nucleic acid molecule (mock). It may however also be an individual treated with the standard of care.

One type of modulation is a nucleic acid molecules ability to inhibit, down-regulate, reduce, suppress, remove, stop, block, prevent, lessen, lower, avoid or terminate expression of PAPD5 or PAPD7, e.g. by degradation of mRNA or blockage of transcription.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T^m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The nucleic acid molecule of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of nucleic acid molecules, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into oligonucleotides, such as enhanced nucleoside resistance and enhanced affinity.

2' Modified Nucleosides.

A 2' sugar modified nucleoside is a nucleoside which has a substituent other than H or —OH at the 2' position (2' substituted nucleoside) or comprises a 2' linked biradicle, and includes 2' substituted nucleosides and LNA (2'-4' biradicle bridged) nucleosides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

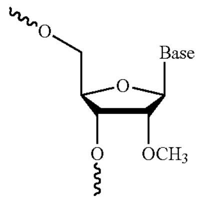

2'-O-Me

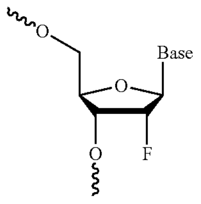

2'-F-RNA

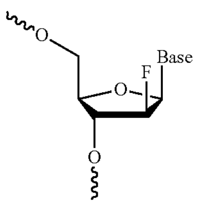

2'-F-ANA

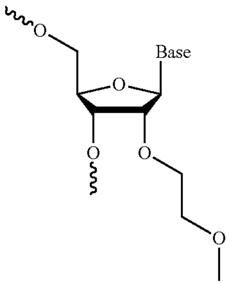

2'-O-MOE

-continued

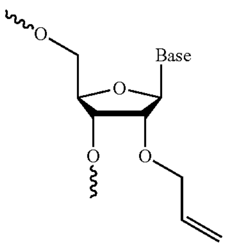

2′-O-Allyl

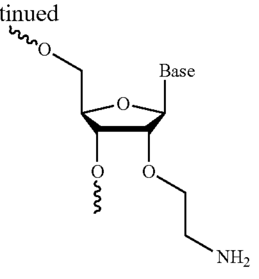

2′-O-Ethylamine

Locked Nucleic Acid Nucleosides (LNA).

LNA nucleosides are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

In some embodiments, the modified nucleoside or the LNA nucleosides of the oligomer of the invention has a general structure of the formula I or II:

Formula I

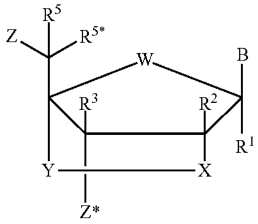

β-D or

Formula II

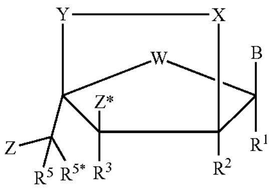

α-L wherein W is selected from —O—, —S—, —N($R^a$)—, —C($R^aR^b$)—, such as, in some embodiments —O—;

B designates a nucleobase or modified nucleobase moiety;

Z designates an internucleoside linkage to an adjacent nucleoside, or a 5'-terminal group;

Z* designates an internucleoside linkage to an adjacent nucleoside, or a 3'-terminal group;

X designates a group selected from the list consisting of —C($R^aR^b$)—, —C($R^a$)═C($R^b$)—, —C($R^a$)═N—, —O—, —Si($R^a$)$_2$—, —S—, —$SO_2$—, —N($R^a$)—, and >C═Z In some embodiments, X is selected from the group consisting of: —O—, —S—, NH—, N$R^aR^b$, —$CH_2$—, C$R^aR^b$, —C(═$CH_2$)—, and —C(═C$R^aR^b$)—

In some embodiments, X is —O—

Y designates a group selected from the group consisting of —C($R^aR^b$)—, —C($R^a$)═C($R^b$)—, —C($R^a$)═N—, —O—, —Si($R^a$)$_2$—, —S—, —$SO_2$—, —N($R^a$)—, and >C═Z In some embodiments, Y is selected from the group consisting of: —$CH_2$—, —C($R^aR^b$)—, —$CH_2CH_2$—, —C($R^aR^b$)—C($R^aR^b$)—, —$CH_2CH_2CH_2$—, —C($R^aR^b$)C($R^aR^b$)C($R^aR^b$)—, —C($R^a$)═C($R^b$)—, and —C($R^a$)═N—

In some embodiments, Y is selected from the group consisting of: —$CH_2$—, —CH$R^a$—, —$CHCH_3$—, C$R^aR^b$— or —X—Y— together designate a bivalent linker group (also referred to as a radicle) together designate a bivalent linker group consisting of 1, 2, 3 or 4 groups/atoms selected from the group consisting of —C($R^aR^b$)—, —C($R^a$)═C($R^b$)—, —C($R^a$)═N—, —O—, —Si($R^a$)$_2$—, —S—, —$SO_2$—, —N($R^a$)—, and >C═Z, In some embodiments, —X—Y— designates a biradicle selected from the groups consisting of: —X—$CH_2$—, —X—C$R^aR^b$—, —X—CH$R^{a-}$, —X—C($HCH_3$)$^-$, —O—Y—, —O—$CH_2$—, —S—$CH_2$—, —NH—$CH_2$—, —O—$CHCH_3$—, —$CH_2$—O—$CH_2$, —O—CH($CH_3CH_3$)—, —O—$CH_2$—$CH_2$—, O$CH_2$—$CH_2$—$CH_2$—, —O—$CH_2OCH_2$—, —O—N$CH_2$—, —C(═$CH_2$)—$CH_2$—, —N$R^a$—$CH_2$—, N—O—$CH_2$, —S—C$R^aR^b$— and —S—CH$R^a$—.

In some embodiments —X—Y— designates —O—$CH_2$— or —O—CH($CH_3$)—.

wherein Z is selected from —O—, —S—, and —N($R^a$)—, and $R^a$ and, when present $R^b$, each is independently selected from hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkytthio, halogen, where aryl and heteroaryl may be optionally substituted and where two geminal substituents $R^a$ and $R^b$ together may designate optionally substituted methylene (═$CH_2$), wherein for all chiral centers, asymmetric groups may be found in either R or S orientation.

wherein $R^1$, $R^2$, $R^3$, $R^5$ and $R^{5*}$ are independently selected from the group consisting of: hydrogen, optionally substituted $C_{1-6}$-alkyl, optionally substituted $C_{2-6}$-alkenyl, optionally substituted $C_{2-6}$-alkynyl, hydroxy, $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkytthio, halogen, where aryl and heteroaryl may be optionally substituted, and where two geminal substituents together may designate oxo, thioxo, imino, or optionally substituted methylene.

In some embodiments $R^1$, $R^2$, $R^3$, $R^5$ and $R^{5*}$ are independently selected from $C_{1-6}$ alkyl, such as methyl, and hydrogen.

In some embodiments $R^1$, $R^2$, $R^3$, $R^5$ and $R^{5*}$ are all hydrogen.

In some embodiments $R^1$, $R^2$, $R^3$, are all hydrogen, and either $R^5$ and $R^{5*}$ is also hydrogen and the other of $R^5$ and $R^{5*}$ is other than hydrogen, such as $C_{1-6}$ alkyl such as methyl.

In some embodiments, $R^a$ is either hydrogen or methyl. In some embodiments, when present, $R^b$ is either hydrogen or methyl.

In some embodiments, one or both of $R^a$ and $R^b$ is hydrogen

In some embodiments, one of $R^a$ and $R^b$ is hydrogen and the other is other than hydrogen In some embodiments, one of $R^a$ and $R^b$ is methyl and the other is hydrogen In some embodiments, both of $R^a$ and $R^b$ are methyl.

In some embodiments, the biradicle —X—Y— is —O—$CH_2$—, W is O, and all of $R^1$, $R^2$, $R^3$, $R^5$ and $R^{5*}$ are all hydrogen. Such LNA nucleosides are disclosed in WO99/014226, WO00/66604, WO98/039352 and WO2004/046160 which are all hereby incorporated by reference, and include what are commonly known as beta-D-oxy LNA and alpha-L-oxy LNA nucleosides.

In some embodiments, the biradicle —X—Y— is —S—$CH_2$—, W is O, and all of $R^1$, $R^2$, $R^3$, $R^5$ and $R^{5*}$ are all hydrogen. Such thio LNA nucleosides are disclosed in WO99/014226 and WO2004/046160 which are hereby incorporated by reference.

In some embodiments, the biradicle —X—Y— is —NH—$CH_2$—, W is O, and all of $R^1$, $R^2$, $R^3$, $R^5$ and $R^{5*}$ are all hydrogen. Such amino LNA nucleosides are disclosed in WO99/014226 and WO2004/046160 which are hereby incorporated by reference.

In some embodiments, the biradicle —X—Y— is —O—$CH_2$—$CH_2$— or —O—$CH_2$—$CH_2$— $CH_2$—, W is O, and all of $R^1$, $R^2$, $R^3$, $R^5$ and $R^{5*}$ are all hydrogen. Such LNA nucleosides are disclosed in WO00/047599 and Morita et al, Bioorganic & Med. Chem. Lett. 12 73-76, which are hereby incorporated by reference, and include what are commonly known as 2'-O-4'C-ethylene bridged nucleic acids (ENA).

In some embodiments, the biradicle —X—Y— is —O—$CH_2$—, W is O, and all of $R^1$, $R^2$, $R^3$, and one of $R^5$ and $R^{5*}$ are hydrogen, and the other of $R^5$ and $R^{5*}$ is other than hydrogen such as $C_{1-6}$ alkyl, such as methyl. Such 5' substituted LNA nucleosides are disclosed in WO2007/134181 which is hereby incorporated by reference.

In some embodiments, the biradicle —X—Y— is —O—$CR^aR^b$—, wherein one or both of $R^a$ and $R^b$ are other than hydrogen, such as methyl, W is O, and all of $R^1$, $R^2$, $R^3$, and one of $R^5$ and $R^{5*}$ are hydrogen, and the other of $R^5$ and $R^{5*}$ is other than hydrogen such as $C_{1-6}$ alkyl, such as methyl. Such bis modified LNA nucleosides are disclosed in WO2010/077578 which is hereby incorporated by reference.

In some embodiments, the biradicle —X—Y— designate the bivalent linker group —O—$CH(CH_2OCH_3)$-(2' O-methoxyethyl bicyclic nucleic acid—Seth at al., 2010, J. Org. Chem. Vol 75(5) pp. 1569-81). In some embodiments, the biradicle —X—Y— designate the bivalent linker group —O—$CH(CH_2CH_3)$-(2'O-ethyl bicyclic nucleic acid—Seth at al., 2010, J. Org. Chem. Vol 75(5) pp. 1569-81). In some embodiments, the biradicle —X—Y— is —O—$CHR^a$—, W is O, and all of $R^1$, $R^2$, $R^3$, $R^5$ and $R^{5*}$ are all hydrogen. Such 6' substituted LNA nucleosides are disclosed in WO10036698 and WO07090071 which are both hereby incorporated by reference.

In some embodiments, the biradicle —X—Y— is —O—$CH(CH_2OCH_3)$—, W is O, and all of $R^1$, $R^2$, $R^3$, $R^5$ and $R^{5*}$ are all hydrogen. Such LNA nucleosides are also known as cyclic MOEs in the art (cMOE) and are disclosed in WO07090071.

In some embodiments, the biradicle —X—Y— designate the bivalent linker group —O—$CH(CH_3)$—. —in either the R- or S-configuration. In some embodiments, the biradicle —X—Y— together designate the bivalent linker group —O—$CH_2$—O—$CH_2$— (Seth at al., 2010, J. Org. Chem). In some embodiments, the biradicle —X—Y— is —O—CH($CH_3$)—, W is O, and all of $R^1$, $R^2$, $R^3$, $R^5$ and $R^{5*}$ are all hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L) which are both hereby incorporated by reference).

In some embodiments, the biradicle —X—Y— is —O—$CR^aR^b$—, wherein in neither $R^a$ or $R^b$ is hydrogen, W is O, and all of $R^1$, $R^2$, $R^3$, $R^5$ and $R^{5*}$ are all hydrogen. In some embodiments, $R^a$ and $R^b$ are both methyl. Such 6' di-substituted LNA nucleosides are disclosed in WO 2009006478 which is hereby incorporated by reference.

In some embodiments, the biradicle —X—Y— is —S—$CHR^a$—, W is O, and all of $R^1$, $R^2$, $R^3$, $R^5$ and $R^{5*}$ are all hydrogen. Such 6' substituted thio LNA nucleosides are disclosed in WO11156202 which is hereby incorporated by reference. In some 6' substituted thio LNA embodiments $R^a$ is methyl.

In some embodiments, the biradicle —X—Y— is —C(=$CH_2$)—C($R^aR^b$)—, such as —C(=$CH_2$)—$CH_2$—, or —C(=$CH_2$)—CH($CH_3$)—W is O, and all of $R^1$, $R^2$, $R^3$, $R^5$ and $R^{5*}$ are all hydrogen. Such vinyl carbo LNA nucleosides are disclosed in WO8154401 and WO09067647 which are both hereby incorporated by reference.

In some embodiments the biradicle —X—Y— is —N(—$OR^a$)—, W is O, and all of $R^1$, $R^2$, $R^3$, $R^5$ and $R^{5*}$ are all hydrogen. In some embodiments $R^a$ is $C_{1-6}$ alkyl such as methyl. Such LNA nucleosides are also known as N substituted LNAs and are disclosed in WO2008/150729 which is hereby incorporated by reference. In some embodiments, the biradicle —X—Y— together designate the bivalent linker group —O—$NR^a$—$CH_3$—(Seth at al., 2010, J. Org. Chem). In some embodiments the biradicle —X—Y— is —N($R^a$)—, W is O, and all of $R^1$, $R^2$, $R^3$, $R^5$ and $R^{5*}$ are all hydrogen. In some embodiments $R^a$ is $C_{1-6}$ alkyl such as methyl.

In some embodiments, one or both of $R^5$ and $R^{5*}$ is hydrogen and, when substituted the other of $R^5$ and $R^{5*}$ is $C_{1-6}$ alkyl such as methyl. In such an embodiment, $R^1$, $R^2$, $R^3$, may all be hydrogen, and the biradicle —X—Y— may be selected from —O—$CH_2$— or —O—C($HCR^a$)—, such as —O—C($HCH_3$)—. In some embodiments, the biradicle is —$CR^aR^b$—O—$CR^aR^b$—, such as $CH_2$—O—$CH_2$—, W is O and all of $R^1$, $R^2$, $R^3$, $R^5$ and $R^{5*}$ are all hydrogen. In some embodiments $R^a$ is C01 alkyl such as methyl. Such LNA nucleosides are also known as conformationally restricted nucleotides (CRNs) and are disclosed in WO2013036868 which is hereby incorporated by reference.

In some embodiments, the biradicle is —O—$CR^aR^b$—O—$CR^aR^b$—, such as O—$CH_2$—O—$CH_2$—, W is O and all of $R^1$, $R^2$, $R^3$, $R^5$ and $R^{5*}$ are all hydrogen. In some embodiments $R^a$ is $C_{1-6}$ alkyl such as methyl. Such LNA nucleosides are also known as COC nucleotides and are disclosed in Mitsuoka et al., Nucleic Acids Research 2009 37(4), 1225-1238, which is hereby incorporated by reference.

It will be recognized than, unless specified, the LNA nucleosides may be in the beta-D or alpha-L stereoisoform.

Certain examples of LNA nucleosides are presented in Scheme 1.

Scheme 1

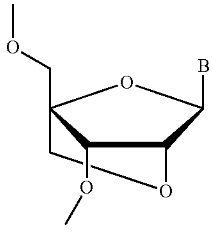

β-D-oxy LNA

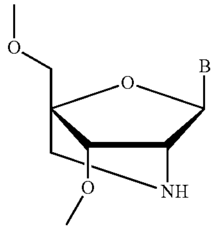

β-D-amino LNA

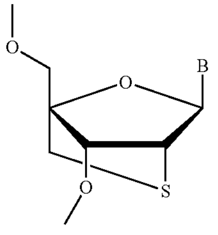

β-D-thio LNA

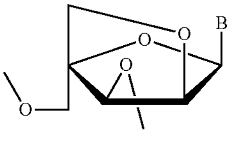

α-L-oxy LNA

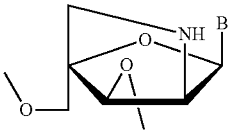

α-L-amino LNA

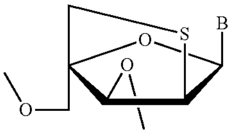

α-L-thio LNA

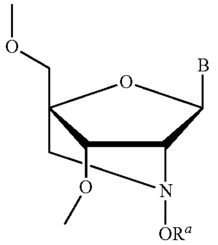

β-D-amino substituted LNA

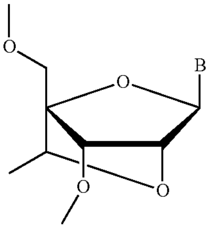

6′methyl β-D-oxy LNA

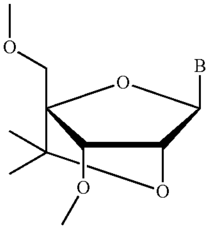

6′dimethyl β-D-oxy LNA

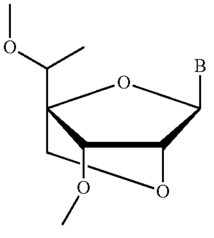

5′ methyl β-D-oxy LNA

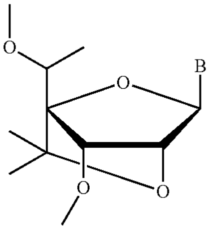

5′methyl, 6′dimethyl β-D-oxy LNA

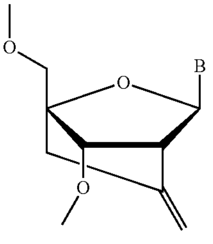

Carbocyclic(vinyl) β-D-LNA

-continued

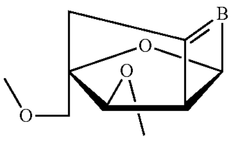

Carbocyclic(vinyl) α-L-LNA

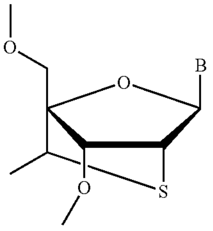

6′ methyl thio β-D LNA

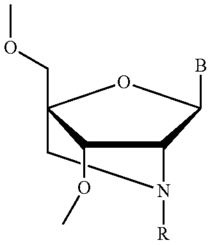

Substituted β-D-amino LNA

As illustrated in the examples, in some embodiments of the invention the LNA nucleosides in the oligonucleotides are beta-D-oxy-LNA nucleosides.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference).

Gapmer

The term gapmer as used herein refers to an antisense oligonucleotide which comprises a region of RNase H recruiting oligonucleotides (gap) which is flanked 5' and 3' by regions which comprise one or more affinity enhancing modified nucleosides (flanks or wings). Various gapmer designs are described herein. Headmers and tailmers are oligonucleotides capable of recruiting RNase H where one of the flanks is missing, i.e. only one of the ends of the oligonucleotide comprises affinity enhancing modified nucleosides. For headmers the 3' flank is missing (i.e. the 5' flank comprises affinity enhancing modified nucleosides) and for tailmers the 5' flank is missing (i.e. the 3' flank comprises affinity enhancing modified nucleosides).

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer or mixed flank gapmer refers to a LNA gapmer wherein at least one of the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA and 2'-F-ANA nucleoside(s). In some embodiments the mixed wing gapmer has one flank which comprises only LNA nucleosides (e.g. 5' or 3') and the other flank (3' or 5' respectfully) comprises 2' substituted modified nucleoside(s) and optionally LNA nucleosides.

Conjugate

The term conjugate as used herein refers to an oligonucleotide which is covalently linked to a non-nucleotide moiety (conjugate moiety or region C or third region).

Conjugation of the oligonucleotide of the invention to one or more non-nucleotide moieties may improve the pharmacology of the oligonucleotide, e.g. by affecting the activity, cellular distribution, cellular uptake or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue or cell type and thereby enhance the effectiveness of the oligonucleotide in that organ, tissue or cell type. A the same time the conjugate may serve to reduce activity of the oligonucleotide in non-target cell types, tissues or organs, e.g. off target activity or activity in non-target cell types, tissues or organs. WO 93/07883 and WO2013/033230 provides suitable conjugate moieties, which are hereby incorporated by reference. Further suitable conjugate moieties are those capable of binding to the asialoglycoprotein receptor (ASGPr). In particular tri-valent N-acetylgalactosamine conjugate moieties are suitable for binding to the ASGPr, see for example WO 2014/076196, WO 2014/207232 and WO 2014/179620 (hereby incorporated by reference).

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103, each of which is incorporated herein by reference in its entirety.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof.

Conjugate Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety to an oligonucleotide (e.g. the termini of region A or C).

In some embodiments of the invention the conjugate or oligonucleotide conjugate of the invention may optionally, comprise a linker region which is positioned between the oligonucleotide and the conjugate moiety. In some embodiments, the linker between the conjugate and oligonucleotide is biocleavable.

Biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA. Phosphodiester containing biocleavable linkers are described in more detail in WO 2014/076195 (hereby incorporated by reference).

Conjugates may also be linked to the oligonucleotide via non biocleavable linkers, or in some embodiments the conjugate may comprise a non-cleavable linker which is covalently attached to the biocleavable linker. Linkers that are not necessarily biocleavable but primarily serve to covalently connect a conjugate moiety to an oligonucleotide or biocleavable linker. Such linkers may comprise a chain structure or an oligomer of repeating units such as ethylene glycol, amino acid units or amino alkyl groups. In some embodiments the linker (region Y) is an amino alkyl, such as a $C_2$-$C_{36}$ amino alkyl group, including, for example $C_6$ to $C_{12}$ amino alkyl groups. In some embodiments the linker (region Y) is a $C_6$ amino alkyl group. Conjugate linker groups may be routinely attached to an oligonucleotide via use of an amino modified oligonucleotide, and an activated ester group on the conjugate group.

Treatment

The terms “treatment”, “treating”, “treats” or the like are used herein to generally mean obtaining a desired pharmacological and/or physiological effect. This effect is therapeutic in terms of partially or completely curing a disease and/or adverse effect attributed to the disease. The term “treatment” as used herein covers any treatment of a disease in a subject and includes: (a) inhibiting the disease, i.e. arresting its development like the inhibition of increase of HBsAg and/or HBeAg; or (b) ameliorating (i.e. relieving) the disease, i.e. causing regression of the disease, like the repression of HBsAg and/or HBeAg production. Thus, a compound that ameliorates and/or inhibits a HBV infection is a compound that treats a HBV invention. Preferably, the term “treatment” as used herein relates to medical intervention of an already manifested disorder, like the treatment of an already defined and manifested HBV infection.

Prevention

Herein the term "preventing", "prevention" or "prevents" relates to a prophylactic treatment, i.e. to a measure or procedure the purpose of which is to prevent, rather than to cure a disease. Prevention means that a desired pharmacological and/or physiological effect is obtained that is prophylactic in terms of completely or partially preventing a disease or symptom thereof. Accordingly, herein "preventing a HBV infection" includes preventing a HBV infection from occurring in a subject, and preventing the occurrence of symptoms of a HBV infection. In the present invention in particular the prevention of HBV infection in children from HBV infected mothers are contemplated.

Patient

For the purposes of the present invention the "subject" (or "patient") may be a vertebrate. In context of the present invention, the term "subject" includes both humans and other animals, particularly mammals, and other organisms. Thus, the herein provided means and methods are applicable to both human therapy and veterinary applications. Accordingly, herein the subject may be an animal such as a mouse, rat, hamster, rabbit, guinea pig, ferret, cat, dog, chicken, sheep, bovine species, horse, camel, or primate. Preferably, the subject is a mammal. More preferably the subject is human.

HBV Infection

The term "hepatitis B virus infection" or "HBV infection" is commonly known in the art and refers to an infectious disease that is caused by the hepatitis B virus (HBV) and affects the liver. A HBV infection can be an acute or a chronic infection. Some infected persons have no symptoms during the initial infection and some develop a rapid onset of sickness with vomiting, yellowish skin, tiredness, dark urine and abdominal pain ("Hepatitis B Fact sheet No 204". who.int. July 2014. Retrieved 4 Nov. 2014). Often these symptoms last a few weeks and can result in death. It may take 30 to 180 days for symptoms to begin. In those who get infected around the time of birth 90% develop a chronic hepatitis B infection while less than 10% of those infected after the age of five do ("Hepatitis B FAQs for the Public—Transmission", U.S. Centers for Disease Control and Prevention (CDC), retrieved 2011-11-29). Most of those with chronic disease have no symptoms; however, cirrhosis and liver cancer may eventually develop (Chang, 2007, Semin Fetal Neonatal Med, 12: 160-167). These complications result in the death of 15 to 25% of those with chronic disease ("Hepatitis B Fact sheet No 204". who.int. July 2014, retrieved 4 Nov. 2014). Herein, the term "HBV infection" includes the acute and chronic hepatitis B infection. The term "HBV infection" also includes the asymptotic stage of the initial infection, the symptomatic stages, as well as the asymptotic chronic stage of the HBV infection.

Enzymatically Active Fragments

Herein, an enzymatically active fragment of SEQ ID NO: 1 or 2 (i.e. of PAPD5) relates to those polypeptides that comprise a stretch of contiguous amino acid residues of SEQ ID NO: 1 or 2 (i.e. of PAPD5) and that retain a biological activity (i.e. functionality) of PAPD5, particularly the poly-A polymerase function. In line with this, herein, an enzymatically active fragment of SEQ ID NO: 3 (i.e. of PAPD7) relates to those polypeptides that comprise a stretch of contiguous amino acid residues of SEQ ID NO: 3 (i.e. of PAPD7) and that retain a biological activity (i.e. functionality) of PAPD7, particularly the poly-A polymerase function. Examples for enzymatically active fragments of PAPD5 and PAPD7 are the nucleotidyltransferase domain and the Cid1 poly A polymerase.

Polypeptide

Herein, term "polypeptide" includes all molecules that comprise or consist of amino acid monomers linked by peptide (amide) bonds. Thus, the term "polypeptide" comprises all amino acid sequences, such as peptides, oliogopeptides, polypeptides and proteins. The "polypeptide" described herein may be a naturally occurring polypeptide or a non-naturally occurring polypeptide. The non-naturally occurring polypeptide may comprise at least one mutation (e.g. amino acid substitution, amino acid deletion or amino acid addition) as compared to the naturally occurring counterpart. The non-naturally occurring polypeptide may also be cloned in a vector and/or be operable linked to a promoter that is not the natural promoter of said polypeptide. Said promoter may be a constitutively active promoter. The term "amino acid" or "residue" as used herein includes both L- and D-isomers of the naturally occurring amino acids as well as of other amino acids (e.g., non-naturally-occurring amino acids, amino acids which are not encoded by nucleic acid sequences, synthetic amino acids etc.). Examples of naturally-occurring amino acids are alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophane (Trp; W), tyrosine (Tyr; Y), valine (Val; V). Post-translationally modified naturally-occurring amino acids are dehydrobutyrine (Dhb) and labionin (Lab). Examples for non-naturally occurring amino acids are described above. The non-naturally occurring polypeptide may comprise one or more non-amino acid substituents, or heterologous amino acid substituents, compared to the amino acid sequence of a naturally occurring form of the polypeptide, for example a reporter molecule or another ligand, covalently or non-covalently bound to the amino acid sequence.

Compound

Herein, the term "compound" means any nucleic acid molecule, such as RNAi molecules according to the invention or any conjugate comprising such a nucleic acid molecule. For example, herein the compound may be an RNAi molecule against PAPD5 or PAPD7, in particular an antisense oligonucleotide, a siRNA or a shRNA.

Composition

The term "composition" may also be used to describe a nucleic acid molecule compound. A nucleic acid molecule composition has less than 20% impurities, preferably less than 15% or 10% impurities, more preferably less than 9, 8, 7 or 6% impurities, most preferably less than 5% impurities. The impurities are typically nucleic acid molecules which are one or two nucleotides shorter (n−1 or n−2) than the primary nucleic acid molecule component.

Inhibitor

The term "inhibitor" is known in the art and relates to a compound/substance or composition capable of fully or partially preventing or reducing the physiologic function (i.e. the activity) of (a) specific protein(s) (e.g. of PAPD5 and/or PAPD7). In the context of the present invention, an "inhibitor" of PAPD5 or PAPD7 is capable of preventing or reducing the activity/function of PAPD5 or PAPD7, respectively, by preventing or reducing the expression of the PAPD5 or PAPD7 gene products. Thus, an inhibitor of PAPD5 or PAPD7 may lead to a decreased expression level of PAPD5 or PAPD7 (e.g. decreased level of PAPD5 or PAPD7 mRNA, or of PAPD5 or PAPD7 protein) which is reflected in a decreased functionality (i.e. activity) of PAPD5 or PAPD7, wherein said function comprises the poly-A polymerase function. An inhibitor of PAPD5 or PAPD7, in the context of the present invention, accordingly, may also encompass transcriptional repressors of PAPD5 or PAPD7 expression that are capable of reducing the level of PAPD5 or PAPD7. Preferred inhibitors are nucleic acid molecules of the invention.

Measuring

Herein, the term "measuring" also means "analyzing" or "determining" (i.e. detecting and/or quantifying). For example, the term "measuring the expression and/or activity of PAPD5 and/or PAPD7" means determining the amount of PAPD5 and/or PAPD7 expression and/or activity, for example, determining the amount of the PAPD5 and/or PAPD7 polypeptide (i.e. protein). Methods for measuring (i.e. determining) the amount and/or activity of PAPD5 and/or PAPD7 protein are known in the art and described herein above. In line with this, the term "measuring whether a test compound inhibits propagation of HBV" means analyzing or determining (i.e. detecting and/or quantifying) whether a test compound or composition inhibits propagation of HBV.

The present invention is further described by reference to the non-limiting figures and examples.

EXAMPLES

The Examples illustrate the invention.

Material and Methods

Oligonucleotide Motif Sequences and Oligonucleotide Compounds

TABLE 3 list of oligonucleotide motif sequences (indicated by SEQ ID NO) targeting the human PAPD5 transcript (SEQ ID NO: 10), designs of these, as well as specific antisense oligonucleotide compounds (indicated by CMP ID NO) designed based on the motif sequence.

| SEQ ID NO | Motif Sequence | Design | Oligonucleotide Compound | CMP ID NO | Start ID NO: 10 | dG |
|---|---|---|---|---|---|---|
| 12 | agggtagatgtgtttaact | 2-14-3 | AGggtagatgtgtttaACT | 12_1 | 1656 | -22 |
| 13 | cagcctaaacttagtgg | 3-12-2 | CAGcctaaacttagtGG | 13_1 | 2000 | -21 |
| 14 | aagccctcaatgtaaaacac | 2-14-4 | AAgccctcaatgtaaaACAC | 14_1 | 2446 | -22 |
| 15 | aatagcaagtagaggagag | 3-13-3 | AATagcaagtagaggaGAG | 15_1 | 3059 | -21 |
| 16 | aaataaggatactggcga | 2-12-4 | AAataaggatactgGCGA | 16_1 | 4036 | -21 |
| 17 | gagggaacacataataaaag | 4-14-2 | GAGGgaacacataataaaAG | 17_1 | 4484 | -20 |
| 18 | gtaatacctctcacattc | 2-12-4 | GTaatacctctcacATTC | 18_1 | 5928 | -21 |
| 19 | agtaacaccaatctcattg | 2-13-4 | AGtaacaccaatctcATTG | 19_1 | 6652 | -21 |
| 20 | gtgacagtattcaatgatc | 2-13-4 | GTgacagtattcaatGATC | 20_1 | 7330 | -22 |
| 21 | cagttccgtatcaccaac | 2-13-3 | CAgttccgtatcaccAAC | 21_1 | 7702 | -22 |
| 22 | aagtctaactcaaagccatc | 2-15-3 | AAgtctaactcaaagccATC | 22_1 | 8292 | -21 |
| 23 | aggcttccattttattgaa | 2-14-3 | AGgcttccattttattGAA | 23_1 | 8625 | -22 |
| 24 | ttttagaaaacgaggcta | 2-12-4 | TTttagaaaacgagGCTA | 24_1 | 9866 | -20 |
| 25 | gtattcttattcttgct | 3-12-2 | GTAttcttattcttgCT | 25_1 | 10254 | -20 |
| 26 | attattcccacagtaaga | 4-12-2 | ATTAttcccacagtaaGA | 26_1 | 10881 | -22 |
| 27 | aacaacaaacaggatgggc | 3-14-2 | AACaacaaacaggatggGC | 27_1 | 11370 | -21 |
| 28 | atatccacaatattctgat | 4-13-2 | ATATccacaatattctgAT | 28_1 | 11790 | -20 |
| 29 | aaagaaataatgtcgtctgg | 2-14-4 | AAagaaataatgtcgtCTGG | 29_1 | 12413 | -20 |
| 30 | ccagagtaaacaaatcc | 3-11-3 | CCAgagtaaacaaaTCC | 30_1 | 12718 | -21 |
| 31 | attcaacatttttagtcacc | 2-15-3 | ATtcaacatttttagtcACC | 31_1 | 13555 | -21 |
| 32 | tttggtaattcttttttttag | 3-14-3 | TTTggtaattctttttttTAG | 32_1 | 14297 | -20 |
| 33 | caatgaggaaacaagagtca | 2-14-4 | CAatgaggaaacaagaGTCA | 33_1 | 15137 | -22 |
| 34 | ttcaaaataatgtgggaggt | 3-14-3 | TTCaaaataatgtgggaGGT | 34_1 | 15695 | -22 |
| 35 | ggatatttgatacggcaaat | 2-15-3 | GGatatttgatacggcaAAT | 35_1 | 16145 | -20 |
| 36 | ctataagaagcaaaccc | 3-11-3 | CTAtaagaagcaaaCCC | 36_1 | 16714 | -21 |

TABLE 3 -continued list of oligonucleotide motif sequences (indicated by SEQ ID NO) targeting the human PAPD5 transcript (SEQ ID NO: 10), designs of these, as well as specific antisense oligonucleotide compounds (indicated by CMP ID NO) designed based on the motif sequence.

| SEQ ID NO | Motif Sequence | Design | Oligonucleotide Compound | CMP ID NO | Start ID NO: 10 | dG |
|---|---|---|---|---|---|---|
| 37 | atataattcacgtttcactt | 3-14-3 | ATAtaattcacgtttcaCTT | 37_1 | 17097 | -21 |
| 38 | aatgattcacatgaaggtta | 3-14-3 | AATgattcacatgaaggTTA | 38_1 | 17420 | -20 |
| 39 | gttaggattttgctatg | 2-11-4 | GTtaggattttgcTATG | 39_1 | 18299 | -20 |
| 40 | gtacaaatatcaaccgtat | 3-13-3 | GTAcaaatatcaaccgTAT | 40_1 | 18669 | -21 |
| 41 | cacactatttcaagatgcta | 3-15-2 | CACactatttcaagatgcTA | 41_1 | 19681 | -22 |
| 42 | cacctatacaatggagtatt | 3-14-3 | CACctatacaatggagtATT | 42_1 | 20352 | -22 |
| 43 | atcatacgtcattagagaac | 2-14-4 | ATcatacgtcattagaGAAC | 43_1 | 20721 | -21 |
| 44 | cagaacagatactttgcca | 2-15-2 | CAgaacagatactttgcCA | 44_1 | 21111 | -22 |
| 45 | aagaatggttggttaaggg | 2-14-3 | AAgaatggttggttaaGGG | 45_1 | 21782 | -21 |
| 46 | agaattggtaaactggactg | 4-14-2 | AGAAttggtaaactggacTG | 46_1 | 22378 | -22 |
| 47 | agaattatattggctgg | 3-11-3 | AGAattatattggcTGG | 47_1 | 23160 | -20 |
| 48 | cctaaaccagacagaaaaga | 2-15-3 | CCtaaaccagacagaaaAGA | 48_1 | 23993 | -22 |
| 49 | accaattagagcagaaatc | 4-13-2 | ACCAattagagcagaaaTC | 49_1 | 24813 | -21 |
| 50 | ttctaaataacagatgggtc | 3-14-3 | TTCtaaataacagatggGTC | 50_1 | 25047 | -21 |
| 51 | tttataatttttttccatct | 3-14-3 | TTTataatttttttccaTCT | 51_1 | 26080 | -20 |
| 52 | gcaaatatcagattaacctc | 4-14-2 | GCAAatatcagattaaccTC | 52_1 | 26625 | -22 |
| 53 | aacggtatggcagaagacaa | 3-14-3 | AACggtatggcagaagaCAA | 53_1 | 26973 | -22 |
| 54 | ttcaacctttactgcat | 4-11-2 | TTCAacctttactgcAT | 54_1 | 27813 | -20 |
| 55 | actgataaagggcatttcaa | 2-14-4 | ACtgataaagggcattTCAA | 55_1 | 28357 | -22 |
| 56 | cagtaggaatgtggctt | 2-12-3 | CAgtaggaatgtggCTT | 56_1 | 28718 | -21 |
| 57 | ttttatggcagggtttcac | 3-14-2 | TTTtatggcagggtttcAC | 57_1 | 29327 | -21 |
| 58 | tcactgttaaacctcac | 2-11-4 | TCactgttaaaccTCAC | 58_1 | 29902 | -20 |
| 59 | caattttctaattcaatggt | 4-14-2 | CAATtttctaattcaatgGT | 59_1 | 30704 | -20 |
| 60 | aagatataattcacccact | 4-13-2 | AAGAtataattcacccaCT | 60_1 | 31008 | -22 |
| 61 | gccacataaaggataaagt | 2-13-4 | GCcacataaaggataAAGT | 61_1 | 31348 | -22 |
| 62 | cccattagaagtaaggtga | 2-15-2 | CCcattagaagtaaggtGA | 62_1 | 32367 | -22 |
| 63 | atgtaaattaaaacttccc | 2-13-4 | ATgtaaattaaaactTCCC | 63_1 | 32632 | -21 |
| 64 | tgagagcataaaagtacgga | 3-15-2 | TGAgagcataaaagtacgGA | 64_1 | 32945 | -22 |
| 65 | ttcacaacaggtaaaggg | 4-12-2 | TTCAcaacaggtaaagGG | 65_1 | 33593 | -21 |
| 66 | tgcattcctaagtaacataa | 2-14-4 | TGcattcctaagtaacATAA | 66_1 | 34801 | -21 |
| 67 | agagaaaagtgatgagggaa | 3-14-3 | AGAgaaaagtgatgaggGAA | 67_1 | 35368 | -22 |
| 68 | atacggatcaccagctaaa | 3-14-2 | ATAcggatcaccagctaAA | 68_1 | 36131 | -21 |
| 69 | catgttatgcacagaagat | 2-13-4 | CAtgttatgcacagaAGAT | 69_1 | 36712 | -22 |
| 70 | cgctgaagaactaagtatta | 2-14-4 | CGctgaagaactaagtATTA | 70_1 | 37282 | -20 |
| 71 | caaacagatggtggtgata | 3-14-2 | CAAacagatggtggtgaTA | 71_1 | 37870 | -20 |
| 72 | agtagccattaggatg | 3-11-2 | AGTagccattaggaTG | 72_1 | 38478 | -20 |

TABLE 3 -continued list of oligonucleotide motif sequences (indicated by SEQ ID NO) targeting the human PAPD5 transcript (SEQ ID NO: 10), designs of these, as well as specific antisense oligonucleotide compounds (indicated by CMP ID NO) designed based on the motif sequence.

| SEQ ID NO | Motif Sequence | Design | Oligonucleotide Compound | CMP ID NO | Start ID NO: 10 | dG |
|---|---|---|---|---|---|---|
| 73 | atacacaggctccataata | 2-14-3 | ATacacaggctccataATA | 73_1 | 39639 | -22 |
| 74 | gattttgtatagtccacaa | 3-15-2 | GATUttgtatagtccacAA | 74_1 | 40178 | -21 |
| 75 | gcatctataaaaaagggaca | 2-14-4 | GCatctataaaaaaggGACA | 75_1 | 41042 | -22 |
| 76 | agtgcaagtatcgct | 2-10-3 | AGtgcaagtatcGCT | 76_1 | 41734 | -20 |
| 77 | ccaaaagaatcaagttcgta | 3-15-2 | CCAaaagaatcaagttcgTA | 77_1 | 42442 | -21 |
| 78 | cctcagaccaaatttattt | 2-13-4 | CCtcagaccaaatttATTT | 78_1 | 43203 | -22 |
| 79 | ttcaacaagcatctattgta | 3-14-3 | TTCaacaagcatctattGTA | 79_1 | 43663 | -22 |
| 80 | caaaggttgttgtactct | 3-12-3 | CAAaggttgttgtacTCT | 80_1 | 44220 | -21 |
| 81 | tcataaatctttttccacg | 3-14-2 | TCAtaaatctttttccaCG | 81_1 | 44756 | -20 |
| 82 | cttgttacggatttaatgtg | 2-15-3 | CTtgttacggatttaatGTG | 82_1 | 45042 | -21 |
| 83 | gctataaaaatagaagcc | 3-12-3 | GCTataaaaatagaaGCC | 83_1 | 46202 | -22 |
| 84 | tccttagcaaactaaacat | 3-13-3 | TCCttagcaaactaaaCAT | 84_1 | 47142 | -22 |
| 85 | agcaaaaggcaggtattcaa | 3-15-2 | AGCaaaaggcaggtattcAA | 85_1 | 47843 | -22 |
| 86 | gaatccatttacatattcac | 3-14-3 | GAAtccatttacatattCAC | 86_1 | 48267 | -21 |
| 87 | tccagtatccaaaacatac | 2-13-4 | TCcagtatccaaaacATAC | 87_1 | 49256 | -21 |
| 88 | agcttaaagaagaacggtt | 4-13-2 | AGCTtaaagaagaacggTT | 88_1 | 49688 | -22 |
| 89 | cacaacgtgcctacctt | 2-13-2 | CAcaacgtgcctaccTT | 89_1 | 50508 | -22 |
| 90 | ccagaatccaagaaaatgg | 3-14-2 | CCAgaatccaagaaaatGG | 90_1 | 50764 | -21 |
| 91 | tcacctcgaactaaacaagt | 2-16-2 | TCacctcgaactaaacaaGT | 91_1 | 51561 | -21 |
| 92 | gtatctttctgtactatt | 2-12-4 | GTatctttctgtacTATT | 92_1 | 52461 | -21 |
| 93 | gtcattctactaacaaacg | 4-13-2 | GTCAttctactaacaaaCG | 93_1 | 53305 | -21 |
| 94 | tggaaaaggaagaaccatt | 2-13-4 | TGgaaaaggaagaacCATT | 94_1 | 53865 | -20 |
| 95 | aatacaactcttccgtgat | 2-13-4 | AAtacaactcttccgTGAT | 95_1 | 54638 | -22 |
| 96 | aataccctgacgagctg | 2-12-3 | AAtaccctgacgagCTG | 96_1 | 54942 | -22 |
| 97 | tcataaaacatgatccttgc | 3-15-2 | TCAtaaaacatgatccttGC | 97_1 | 55741 | -22 |
| 98 | ctaaagcagatccatagaa | 3-13-3 | CTAaagcagatccataGAA | 98_1 | 56277 | -21 |
| 99 | agactataacttttgctaca | 3-15-2 | AGActataacttttgctaCA | 99_1 | 56942 | -22 |
| 100 | agcaatgacttgaacatagt | 2-16-2 | AGcaatgacttgaacataGT | 100_1 | 57369 | -20 |
| 101 | ataaaacaagcatacgggc | 3-14-2 | ATAaaacaagcatacggGC | 101_1 | 58146 | -21 |
| 102 | atgagataccagcagatag | 2-15-2 | ATgagataccagcagatAG | 102_1 | 58588 | -20 |
| 103 | agaagaaatcctgagtaatc | 4-14-2 | AGAAgaaatcctgagtaaTC | 103_1 | 59089 | -21 |
| 104 | ccctaaaaagtgacgta | 3-12-2 | CCCtaaaaagtgacgTA | 104_1 | 59461 | -21 |
| 105 | ttaagttagatcacggc | 4-11-2 | TTAAgttagatcacgGC | 105_1 | 59970 | -20 |
| 106 | gtggatacagaaagcca | 2-12-3 | GTggatacagaaagCCA | 106_1 | 60738 | -22 |
| 107 | gtatcggcaggagatt | 3-10-3 | GTAtcggcaggagATT | 107_1 | 61038 | -21 |

TABLE 3 -continued list of oligonucleotide motif sequences (indicated by SEQ ID NO) targeting the human PAPD5 transcript (SEQ ID NO: 10), designs of these, as well as specific antisense oligonucleotide compounds (indicated by CMP ID NO) designed based on the motif sequence.

| SEQ ID NO | Motif Sequence | Design | Oligonucleotide Compound | CMP ID NO | Start ID NO: 10 | dG |
|---|---|---|---|---|---|---|
| 108 | taactaattgattccattgc | 4-14-2 | TAACtaattgattccattGC | 108_1 | 61868 | -22 |
| 109 | agaagaacggaaattgcc | 3-13-2 | AGAagaacggaaattgCC | 109_1 | 62418 | -21 |
| 110 | ataatgattttcctatcc | 4-12-2 | ATAAtgattttcctatCC | 110_1 | 62822 | -20 |
| 111 | atggttttgtggagaagg | 2-13-3 | ATggttttgtggagaAGG | 111_1 | 63000 | -22 |
| 112 | tgctgctgtgaaaagaaatg | 2-14-4 | TGctgctgtgaaaagaAATG | 112_1 | 63697 | -21 |
| 113 | gtgtccaatttttttattat | 2-14-3 | GTgtccaatttttttatTAT | 113_1 | 64377 | -20 |
| 114 | gatggaatcaactgtgtagt | 2-16-2 | GAtggaatcaactgtgtaGT | 114_1 | 65307 | -21 |
| 115 | gatggtgacaaattattct | 4-13-2 | GATGgtgacaaattattCT | 115_1 | 65894 | -22 |
| 116 | tgcttttgggaatcttt | 2-11-4 | TGcttttgggaatCTTT | 116_1 | 66650 | -21 |
| 117 | gatgtcctacaatgaacacg | 2-15-3 | GAtgtcctacaatgaacACG | 117_1 | 68024 | -22 |
| 118 | gtacaaggacaaagtaacc | 3-13-3 | GTAcaaggacaaagtaACC | 118_1 | 68732 | -22 |
| 119 | tgaaacgcctatctcta | 4-11-2 | TGAAacgcctatctcTA | 119_1 | 69029 | -21 |
| 120 | atactatttatgcttatgga | 3-15-2 | ATActatttatgcttatgGA | 120_1 | 69796 | -21 |
| 121 | ttgtaatcaaggcaataagg | 3-14-3 | TTGtaatcaaggcaataAGG | 121_1 | 70770 | -21 |
| 122 | gaagtccaataacgcaga | 4-12-2 | GAAGtccaataacgcaGA | 122_1 | 71091 | -22 |
| 123 | atatccaatctctatatgtg | 3-15-2 | ATAtccaatctctatatgTG | 123_1 | 72013 | -21 |
| 124 | gccttacacaagactatatt | 2-15-3 | GCcttacacaagactatATT | 124_1 | 73444 | -22 |
| 125 | tgctgaattttatgttaac | 4-13-2 | TGCTgaattttatgttaAC | 125_1 | 73823 | -21 |
| 126 | cacaagatgatgggtttaag | 2-14-4 | CAcaagatgatgggttTAAG | 126_1 | 74559 | -22 |
| 127 | ttagtggtttgggtgc | 2-12-2 | TTagtggtttgggtGC | 127_1 | 75043 | -20 |
| 128 | agattgttaccttactgat | 2-14-3 | AG attgttaccttactGAT | 128_1 | 76110 | -21 |
| 129 | tattacaaatatcaatctcc | 3-14-3 | TATtacaaatatcaatcTCC | 129_1 | 76931 | -21 |
| 130 | taccaaaagcatagagtgg | 3-14-2 | TACcaaaagcatagagtGG | 130_1 | 77605 | -21 |
| 131 | aattatcttcccgctac | 2-11-4 | AAttatcttcccgCTAC | 131_1 | 78652 | -22 |

Motif sequences represent the contiguous sequence of nucleobases present in the oligonucleotide.

Designs refer to the gapmer design, F-G-F', where each number represents the number of consecutive modified nucleosides, e.g. 2' modified nucleosides (first number-5' flank), followed by the number of DNA nucleosides (second number-gap region), followed by the number of modified nucleosides, e.g 2' modified nucleosides (third number-3' flank), optionally preceded by or followed by further repeated regions of DNA and LNA, which are not necessarily part of the contiguous sequence that is complementary to the target nucleic acid.

TABLE 4 list of oligonucleotide motif sequences (indicated by SEQ ID NO) targeting the human PAPD7 transcript (SEQ ID NO: 11), designs of these, as well as specific antisense oligonucleotide compounds (indicated by CMP ID NO) designed based on the motif sequence.

| SEQ ID NO | motif sequence | Design | Oligonucleotide Compound | CMP ID NO | Start ID NO: 11 | dG |
|---|---|---|---|---|---|---|
| 132 | gttgggtggaataggca | 2-13-2 | GTtgggtggaataggCA | 132_1 | 132 | -22 |
| 133 | tcgatttcccgttccaa | 2-13-2 | TCgatttcccgttccAA | 133_1 | 1962 | -21 |
| 134 | acaacctacacataaattgc | 3-15-2 | ACAacctacacataaattGC | 134_1 | 2510 | -21 |
| 135 | actataagaactcccaaca | 2-13-4 | ACtataagaactcccAACA | 135_1 | 2668 | -21 |
| 136 | gagaaaaagagttacaagc | 4-13-2 | GAGAaaaagagttacaaGC | 136_1 | 2695 | -20 |
| 137 | aactggagggagagaagag | 4-13-2 | AACTggagggagagaagAG | 137_1 | 2883 | -22 |
| 138 | tttctaagagcagaggtaca | 2-15-3 | TTtctaagagcagaggtACA | 138_1 | 3090 | -22 |
| 139 | agaagtaacaagagcct | 4-11-2 | AGAAgtaacaagagcCT | 139_1 | 3463 | -20 |
| 140 | agtatcaaaccagacctc | 2-13-3 | AGtatcaaaccagacCTC | 140_1 | 3795 | -22 |
| 141 | ccacaaccgaaagactt | 4-11-2 | CCACaaccgaaagacTT | 141_1 | 4205 | -22 |
| 142 | aatacacactgcattttca | 2-13-4 | AAtacacactgcattTTCA | 142_1 | 4336 | -20 |
| 143 | ccaggtagatagcacag | 2-13-2 | CCaggtagatagcacAG | 143_1 | 4686 | -21 |
| 144 | ccatgacaaagtaacaacag | 2-14-4 | CCatgacaaagtaacaACAG | 144_1 | 4821 | -22 |
| 145 | cagaatttcctttgagtta | 2-14-3 | CAg aatttcctttg agTTA | 145_1 | 5134 | -21 |
| 146 | ccttcgcaagaaagaattga | 2-16-2 | CCttcgcaagaaagaattGA | 146_1 | 5263 | -21 |
| 147 | tcatacatacacgcttct | 2-14-2 | TCatacatacacgcttCT | 147_1 | 5577 | -20 |
| 148 | tgcgaaaagattggagg | 2-11-4 | TGcgaaaagattgGAGG | 148_1 | 5945 | -21 |
| 149 | cacaggacgcttacatgaat | 2-16-2 | CAcaggacgcttacatgaAT | 149_1 | 6235 | -22 |
| 150 | gctgtttttttttcttaac | 3-14-2 | GCTgtttttttttcttaAC | 150_1 | 6352 | -21 |
| 151 | accataagtgagtgttctt | 2-14-3 | ACcataagtgagtgttCTT | 151_1 | 6834 | -22 |
| 152 | acacaagcccatagaaacag | 2-16-2 | ACacaagcccatagaaacAG | 152_1 | 7158 | -21 |
| 153 | cagtagtaaccaccaag | 2-11-4 | CAgtagtaaccacCAAG | 153_1 | 7447 | -22 |
| 154 | cctgcaaacttttatttat | 2-14-3 | CCtgcaaacttttattTAT | 154_1 | 7708 | -21 |
| 155 | acttagtaatagcagca | 2-12-3 | ACttagtaatagcaGCA | 155_1 | 8074 | -20 |
| 156 | atgaatactccgaagactt | 2-13-4 | ATgaatactccgaagACTT | 156_1 | 8249 | -21 |
| 157 | aaagaaaaggatcacaagcc | 3-14-3 | AAAgaaaaggatcacaaGCC | 157_1 | 8784 | -22 |
| 158 | agacagaaatcacctaaca | 3-14-2 | AGAcagaaatcacctaaCA | 158_1 | 8887 | -20 |
| 159 | tagaacagacattattcatc | 3-14-3 | TAGaacagacattattcATC | 159_1 | 9506 | -20 |
| 160 | agttacacggagcagcac | 2-14-2 | AGttacacggagcagcAC | 160_1 | 9664 | -22 |
| 161 | cactatacacagaacactat | 3-14-3 | CACtatacacagaacacTAT | 161_1 | 9770 | -22 |
| 162 | agctgtctaaatacatgg | 2-12-4 | AG ctgtctaaatacATGG | 162_1 | 10000 | -21 |
| 163 | atgaacctattttatgcttc | 3-14-3 | ATGaacctattttatgcTTC | 163_1 | 10206 | -22 |
| 164 | accatcattaacctgcgt | 2-14-2 | ACcatcattaacctgcGT | 164_1 | 10318 | -22 |
| 165 | agtaaagtgcccagatgt | 2-14-2 | AGtaaagtgcccagatGT | 165_1 | 10568 | -22 |
| 166 | ttccctatgaaatcctcaa | 3-14-2 | TTCcctatgaaatcctcAA | 166_1 | 10781 | -21 |
| 167 | cactcttcatagaatgcaac | 2-14-4 | CActcttcatagaatgCAAC | 167_1 | 10917 | -22 |

TABLE 4 -continued list of oligonucleotide motif sequences (indicated by SEQ ID NO) targeting the human PAPD7 transcript (SEQ ID NO: 11), designs of these, as well as specific antisense oligonucleotide compounds (indicated by CMP ID NO) designed based on the motif sequence.

| SEQ ID NO | motif sequence | Design | Oligonucleotide Compound | CMP ID NO | Start ID NO: 11 | dG |
|---|---|---|---|---|---|---|
| 168 | aatgcttaatttttctctct | 2-14-4 | AAtgcttaatttttctCTCT | 168_1 | 11084 | -22 |
| 169 | ttagagacgatgcctataac | 3-14-3 | TTAgagacgatgcctatAAC | 169_1 | 11308 | -22 |
| 170 | tgaatagttcccatagatt | 4-13-2 | TGAAtagttcccatagaTT | 170_1 | 11585 | -21 |
| 171 | cagcataattgttttcttt | 3-13-3 | CAGcataattgttttcTTT | 171_1 | 12330 | -21 |
| 172 | atgtcattatgttttagtt | 4-13-2 | ATGTcattatgttttagTT | 172_1 | 12634 | -21 |
| 173 | cagcagtatctcttagaa | 2-13-3 | CAgcagtatctcttaGAA | 173_1 | 12902 | -21 |
| 174 | cggtaagggttcggtg | 2-12-2 | CGgtaagggttcggTG | 174_1 | 13126 | -21 |
| 175 | catgaaccacattaggaac | 4-13-2 | CATGaaccacattaggaAC | 175_1 | 13383 | -21 |
| 176 | cattcaacacacacgacaa | 2-13-4 | CAttcaacacacacgACAA | 176_1 | 13578 | -21 |
| 177 | aagtatccaagactcaaga | 2-13-4 | AAgtatccaagactcAAGA | 177_1 | 13889 | -20 |
| 178 | ccacagaaacaccgag | 4-10-2 | CCACagaaacaccgAG | 178_1 | 14100 | -22 |
| 179 | tggaaaagggaagggaaga | 3-14-2 | TGGaaaagggaagggaaGA | 179_1 | 14179 | -21 |
| 180 | agagagtccgaagcctg | 2-13-2 | AGagagtccgaagccTG | 180_1 | 14432 | -22 |
| 181 | atgggaaaggtaacgagc | 3-13-2 | ATGggaaaggtaacgaGC | 181_1 | 14616 | -22 |
| 182 | ctatcctacaagtccgaa | 3-13-2 | CTAtcctacaagtccgAA | 182_1 | 15471 | -22 |
| 183 | cattgcttttataatccta | 4-13-2 | CATTgcttttataatccTA | 183_1 | 15816 | -22 |
| 184 | ctttttaaggacaggagg | 4-12-2 | CTTTttaaggacaggaGG | 184_1 | 15988 | -21 |
| 185 | gatgaaagataagtgagcat | 2-14-4 | GAtgaaagataagtgaGCAT | 185_1 | 16395 | -22 |
| 186 | gaagcctgtaataattaagc | 2-14-4 | GAagcctgtaataattAAGC | 186_1 | 17007 | -22 |
| 187 | caccctagtaaagcaaac | 4-12-2 | CACCctagtaaagcaaAC | 187_1 | 17151 | -22 |
| 188 | gcaaatgtaagccttttt | 3-13-2 | GCAaatgtaagcctttTT | 188_1 | 17303 | -21 |
| 189 | acctgacagctaccgac | 2-13-2 | ACctgacagctaccgAC | 189_1 | 17498 | -22 |
| 190 | aagagtgggttgtaagc | 2-12-3 | AAgagtgggttgtaAGC | 190_1 | 17963 | -20 |
| 191 | tagtgaaaatatttggagtt | 2-14-4 | TAgtgaaaatatttggAGTT | 191_1 | 18101 | -20 |
| 192 | tttcagcaccttaaaccc | 2-14-2 | TTtcagcaccttaaacCC | 192_1 | 18518 | -22 |
| 193 | ttaagggaaaggaaacgtca | 4-14-2 | TTAAgggaaaggaaacgtCA | 193_1 | 18747 | -21 |
| 194 | gtaggtaaagggcaaaggaa | 3-15-2 | GTAggtaaagggcaaaggAA | 194_1 | 19007 | -22 |
| 195 | gtgaattaaagccaaagc | 2-12-4 | GTgaattaaagccaAAGC | 195_1 | 19252 | -21 |
| 196 | tgtttttgtattttagtat | 3-13-3 | TGTUttgtattttagTAT | 196_1 | 19476 | -20 |
| 197 | gaggtttttttagtgaatt | 2-14-4 | GAggttttttttagtgAATT | 197_1 | 19722 | -21 |
| 198 | gaggagctaaacggaca | 3-12-2 | GAGgagctaaacggaCA | 198_1 | 20062 | -22 |
| 199 | gtttagtcttatgttctcac | 2-16-2 | GTttagtcttatgttctcAC | 199_1 | 20623 | -21 |
| 200 | caaatactgaatatgcccg | 2-14-3 | CAaatactgaatatgcCCG | 200_1 | 20726 | -22 |
| 201 | accatttaaatcgccaac | 3-12-3 | ACCatttaaatcgccAAC | 201_1 | 20926 | -21 |
| 202 | cagtaagagtagcccaacaa | 2-16-2 | CAgtaagagtagcccaacAA | 202_1 | 21234 | -22 |

TABLE 4 -continued list of oligonucleotide motif sequences (indicated by SEQ ID NO) targeting the human PAPD7 transcript (SEQ ID NO: 11), designs of these, as well as specific antisense oligonucleotide compounds (indicated by CMP ID NO) designed based on the motif sequence.

| SEQ ID NO | motif sequence | Design | Oligonucleotide Compound | CMP ID NO | Start ID NO: 11 | dG |
|---|---|---|---|---|---|---|
| 203 | taacggcaacatcaaatagc | 4-14-2 | TAACggcaacatcaaataGC | 203_1 | 22017 | -22 |
| 204 | actgagcaccaactacac | 2-13-3 | ACtgagcaccaactaCAC | 204_1 | 22592 | -22 |
| 205 | cctaattttatgtatcacat | 2-14-4 | CCtaattttatgtatcACAT | 205_1 | 23074 | -22 |
| 206 | ctaggaattataacaaatca | 4-14-2 | CTAGgaattataacaaatCA | 206_1 | 23462, 23509 | -20 |
| 207 | actccaaagaacatactcac | 2-14-4 | ACtccaaagaacatacTCAC | 207_1 | 24628 | -22 |
| 208 | taagagaaacaatcacacca | 3-14-3 | TAAgagaaacaatcacaCCA | 208_1 | 24935 | -22 |
| 209 | tgtcctaaaatatcagcag | 2-14-3 | TGtcctaaaatatcagCAG | 209_1 | 26022 | -21 |
| 210 | cttttaatgagacagtgca | 2-15-2 | CTtttaatgagacagtgCA | 210 1 | 26212 | -20 |
| 211 | ttgtagcataagatggaaag | 4-14-2 | TTGTagcataagatggaaAG | 211 1 | 26500 | -21 |
| 212 | aaactgtagccaataactgt | 3-14-3 | AAActgtagccaataacTGT | 212 1 | 26945 | -21 |
| 213 | attcatcctaacacaagtag | 2-15-3 | ATtcatcctaacacaagTAG | 213 1 | 27117 | -22 |
| 214 | cacgaaaggaacagctaag | 4-13-2 | CACGaaaggaacagctaAG | 214 1 | 27264 | -21 |
| 215 | acaacaggcaagtacc | 4-10-2 | ACAAcaggcaagtaCC | 215 1 | 27411 | -20 |
| 216 | gctaaacactataaggat | 3-12-3 | GCTaaacactataagGAT | 216 1 | 27505 | -21 |
| 217 | cccgtaagcatttgagaa | 2-14-2 | CCcgtaagcatttgagAA | 217 1 | 27831 | -21 |
| 218 | agccaatatgcgacagtaac | 2-16-2 | AGccaatatgcgacagtaAC | 218 1 | 28146 | -22 |
| 219 | taaccaaaacaatcagtgtc | 3-14-3 | TAAccaaaacaatcagtGTC | 219 1 | 28777 | -20 |
| 220 | aacagggaacaggagtta | 3-12-3 | AACagggaacaggagTTA | 220_1 | 29195 | -20 |
| 221 | atttatcaacttccacc | 2-11-4 | ATttatcaacttcCACC | 221_1 | 29906 | -22 |
| 222 | cgtttaagaccaggcac | 4-11-2 | CGTTtaagaccaggcAC | 222_1 | 30020 | -22 |
| 223 | acaaaggaactcaggaagag | 3-15-2 | ACAaaggaactcaggaagAG | 223_1 | 30424 | -20 |
| 224 | tcacagacaagcaccaa | 4-11-2 | TCACagacaagcaccAA | 224_1 | 31150 | -20 |
| 225 | tacttttaaaacacgtagg | 4-14-2 | TACTttttaaaacacgtaGG | 225_1 | 31329 | -21 |
| 226 | gcacaatcacaaagaccaa | 4-13-2 | GCACaatcacaaagaccAA | 226_1 | 31531 | -22 |
| 227 | tcagtaaagaacagaggc | 2-13-3 | TCagtaaagaacagaGGC | 227_1 | 31820 | -20 |
| 228 | catatttccaccacacaag | 2-15-2 | CAtatttccaccacacaAG | 228_1 | 32222 | -21 |
| 229 | agtaaaccactgtcca | 2-11-3 | AGtaaaccactgtCCA | 229_1 | 32601 | -21 |
| 230 | tcctctttggcgatata | 2-12-3 | TCctctttggcgatATA | 230_1 | 33337 | -21 |
| 231 | cataaatacccctgaatac | 2-14-3 | CAtaaatacccctgaaTAC | 231_1 | 33986 | -20 |
| 232 | cgattttatcaccaaca | 4-11-2 | CGATtttatcaccaaCA | 232_1 | 34175 | -20 |
| 233 | acaatcaggttaagtgtgga | 2-16-2 | ACaatcaggttaagtgtgGA | 233_1 | 34771 | -21 |
| 234 | gaagccaaagactacca | 3-12-2 | GAAgccaaagactacCA | 234_1 | 35096 | -20 |
| 235 | tggtagggactgaattttaa | 2-15-3 | TGgtagggactgaattttTAA | 235_1 | 35850 | -21 |
| 236 | cggtagtcaatcacc | 2-10-3 | CGgtagtcaatcACC | 236_1 | 36584 | -20 |
| 237 | ctatcaaaattatttcacct | 2-14-4 | CTatcaaaattatttcACCT | 237_1 | 36886 | -22 |

TABLE 4 -continued list of oligonucleotide motif sequences (indicated by SEQ ID NO) targeting the human PAPD7 transcript (SEQ ID NO: 11), designs of these, as well as specific antisense oligonucleotide compounds (indicated by CMP ID NO) designed based on the motif sequence.

| SEQ ID NO | motif sequence | Design | Oligonucleotide Compound | CMP ID NO | Start ID NO: 11 | dG |
|---|---|---|---|---|---|---|
| 238 | acgaaaatttagcatcctaa | 3-14-3 | ACG aaaatttagcatccTAA | 238_1 | 37041 | -20 |
| 239 | tggtaaacactgggc | 2-11-2 | TGgtaaacactggGC | 239_1 | 38059 | -19 |
| 240 | gattgttggttgtcatg | 3-11-3 | GATtgttggttgtcATG | 240_1 | 38173 | -21 |
| 241 | aattataccccacatttca | 3-14-2 | AATtataccccacatttCA | 241_1 | 38806 | -22 |
| 242 | tgcaattagacacgttacg | 2-13-4 | TGcaattagacacgtTACG | 242_1 | 39004 | -22 |
| 243 | ggcaaccaattaaacta | 4-11-2 | GGCAaccaattaaacTA | 243_1 | 40226 | -21 |
| 244 | cagttttatgctaatca | 4-11-2 | CAGTtttatgctaatCA | 244_1 | 40272 | -20 |
| 245 | gcaaaggaggagcggaataa | 2-16-2 | GCaaaggaggagcggaatAA | 245_1 | 40707 | -21 |
| 246 | aaacagaagtaagaaggtcc | 2-14-4 | AAacagaagtaagaagGTCC | 246_1 | 41156 | -22 |
| 247 | tccacttatccatagaaa | 2-12-4 | TCcacttatccataGAAA | 247_1 | 41477 | -20 |
| 248 | gctttgacgaacaggaaat | 2-14-3 | GCtttgacgaacaggaAAT | 248_1 | 42282 | -21 |
| 249 | ttccgaccaaaagaaaagac | 4-14-2 | TTCCgaccaaaagaaaagAC | 249_1 | 42632 | -21 |
| 250 | gcgacacgatccgttaaa | 3-13-2 | GCGacacgatccgttaAA | 250_1 | 43104 | -22 |
| 251 | ccccgttttaaaaac | 4-9-2 | CCCCgttttaaaaAC | 251_1 | 43334 | -20 |

Motif sequences represent the contiguous sequence of nucleobases present in the oligonucleotide.

Designs refer to the gapmer design, F-G-F', where each number represents the number of consecutive modified nucleosides, e.g. 2' modified nucleosides (first number-5' flank), followed by the number of DNA nucleosides (second number-gap region), followed by the number of modified nucleosides, e.g 2' modified nucleosides (third number-3' flank), optionally preceded by or followed by further repeated regions of DNA and LNA, which are not necessarily part of the contiguous sequence that is complementary to the target nucleic acid.

Compound Chemistry

Each one compound from the two chemical series DHQ and THP were synthesized to be suitable for the Y3H screening performed by HYBRIGENICS SERVICES SAS. Both compounds included PEG5 linker and were tagged with a Trimethoprim (TMP) anchor ligand (Table 5).

TABLE 5

TMP-tagged small molecule compound IDs

| | Hybrigenics ID | Structure |
|---|---|---|
| DHQ compound-TMP | HBX129653 | 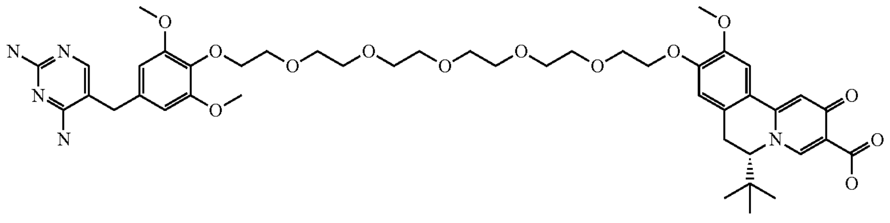 [SMILES: COc1cc2c(cc1OCCOCCOCCOCCOCCOCCOc1c(OC)cc(Cc3cnc(N)nc3N)cc1OC)C[C@@H](C(C)(C)C)n1cc(C(=O)O)c(=O)cc1-2] |

TABLE 5-continued

| TMP-tagged small molecule compound IDs | | |
|---|---|---|
| | Hybrigenics ID | Structure |
| THP compound-TMP | HBX129654 | 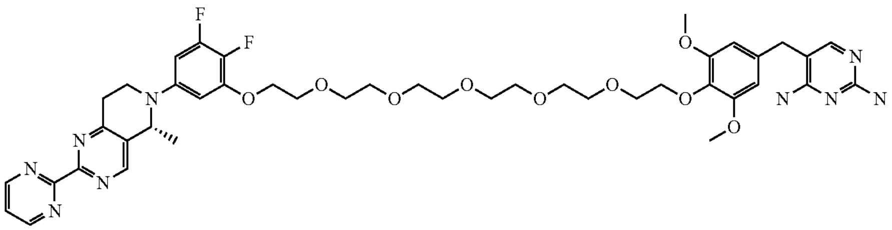 [SMILES: COc1cc(Cc2cnc(N)nc2N)cc(OC)c1OCCOCCOCCOCCOCCOCCOc1cc(N2CCc3nc(-c4ncccn4)ncc3[C@H]2C)cc(F)c1F] |

Y3H ULTImate YChemH™ Screen

The two compounds were provided by Roche to HYBRIGENICS SERVICES SAS and tested for permeability and toxicity. Compounds were then screened against HYBRIGENICS's cDNA Human placenta library (PLA). The screens were carried out according to the optimized cell-to-cell mating protocol developed for Hybrigenics ULTImate Y2H™ using at different compound concentration (Table 6).

TABLE 6

| YChemH screens IDs | | | | |
|---|---|---|---|---|
| | Hybrigenics ID | YChemH Project | YChemH screen Project ID | Probe concentration |
| DHQ compound | HBX129653 | hgx4240 | PLA_RP6_hgx4240v1_pB409_A | 5 μM |
| THP compound | HBX129654 | hgx4241 | PLA_RP6_hgx4241v1_pB409_A | 10 μM |

Y3H ULTImate YChemH™ Dependency Assay

Clones obtained from the screen were picked in 96-well format and clones positive for growth under selective conditions (HIS+) were evaluated in a dependency assay using spot assays. Only clones that were able to grow on selective medium in the presence of the tagged compound were being picked up, processed (cell lysis, PCR, gene sequencing) and mapped for protein alignment using Blast analysis.

Y3H ULTImate YChemH™ 1-by-1 Validation Experiment—Prey Fragments

In this validation step each one identified fragment prey and one chemical probe (HBX129653, HBX129654) is tested in a 1-by-1 experiment. The plasmids from 3 selected preys from the screening library were extracted from the yeast cells, amplified in *E. coli* and re-transformed into YHGX13 yeast cells. For each interaction, DO1, 1/10, 1/100 and 1/1000 of the diploid yeast culture expressing both hook and prey constructs were spotted on a selective medium without tryptophan, leucine and histidine and supplemented with the chemical probe and FK506. Interactions were tested in duplicate. One plate was used per chemical compound and concentration (DMSO, 5, 10 and 20 μM of HBX129653, 5, 10 and 20 μM of HBX129654, 5 μM of HBX24786 Trimethoprim (TMP) and 5 μM of HBX129634 (TMP-PEG5-OH)). Plates were incubated at 30° C. for 3 days.

Y3H ULTImate YChemH™ 1-by-1 Validation Experiment—Full Length Proteins

The coding sequence of full-length PAPD5var1 (NM_001040284.2) and PAPD7varX1 (XM_005248234.2) were reconstituted from an N-terminal codon-optimized gene fragment (to remove high GC content) and commercially available clones of the C-terminal regions of the proteins and cloned in frame with the Gal4 Activation Domain (AD) into plasmid pP7 (AD-Prey), derived from the original pGADGH (Bartel et al., 1993 in Cellular interactions in development: A practical approach. ed. Hartley, D. A., Oxford University Press, Oxford, pp. 153-179). The constructs were checked by sequencing the entire inserts.

For each prey, a mini-mating was carried out between YHGX13 (Y187 ade2-101::loxP-kanMX-loxP, mata) transformed with the prey plasmids and YPT6AT yeast cells (mata) transformed with the DHFR hook (Dihydrofolate reductase) to produce a diploid yeast culture. For each interaction, DO1, 1/10, 1/100 and 1/1000 of the diploid yeast culture expressing both hook and prey constructs were spotted on a selective medium without tryptophan, leucine and histidine and supplemented with the chemical probe and FK506. Interactions were tested in duplicate. One plate was used per chemical compound and concentration (DMSO, 5, 10 and 20 μM of HBX129653, 5, 10 and 20 μM of HBX129654, 5 μM of HBX24786 Trimethoprim (TMP) and 5 μM of HBX129634 (TMP-PEG5-OH)). Plates were incubated at 30° C. for 3 days.

Y3H ULTImate YChemH™—Competition with Free Compound

The competition assay is based on the previously described 1-by-1 validation with a constant concentration for the chemical probe (HBX129653, HBX 129654) and increasing concentrations of the parent compound of the chemical probe (MOL653, MOL654) or its inactive enantiomer (INACT653, INACT654) (Table 7). The competition assays were performed on selective medium at 8 concentrations of the free compound (0, 0.25, 0.5, 1, 2, 5, 10 and 20 μM) and a consistent concentration for the tagged Y3H-compound (1 μM).

TABLE 7

| YChemH competition IDs | | |
|---|---|---|
| | Hybrigenics ID | Structure |
| DHQ compound-active | MOL653 | 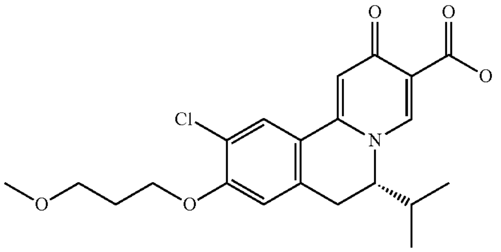 Formula (III) |
| DHQ compound-inactive | INACT653 | 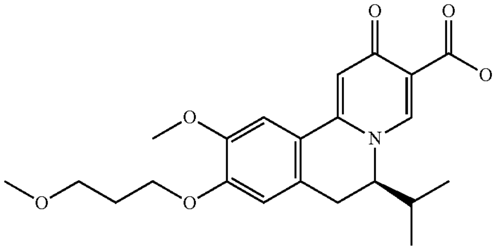 [SMILES: COCCCOc1cc2c(cc1OC)-c1cc(=O)c(C(=O)O)cn1[C@@H](C(C)C)C2] |
| THP compound-active | MOL654 | 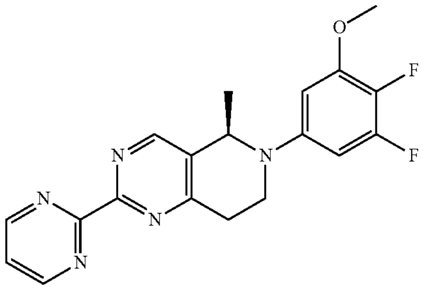 Formula (IV) |
| THP compound-inactive | INACT654 | 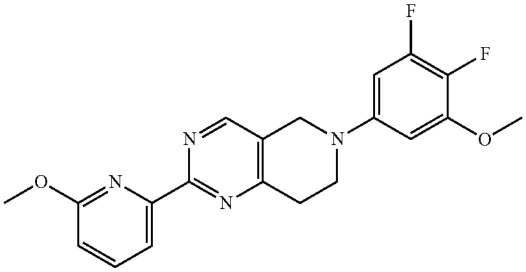 |

HepaRG Cell Culture

HepaRG cells (Biopredics International, Rennes, France, Cat #HPR101) were cultured at 37° C. in a humidified atmosphere with 5% CO2 in complete HepaRG growth medium consisting of William's E Medium (GIBCO), Growth Medium Supplement (Biopredics, Cat #ADD710) and 1% (v/v) GlutaMAX-I (Gibco #32551) and 1× Pen/Strep (Gibco, #15140) for 2 weeks. To initiate differentiation, 0.9% (v/v) DMSO (Sigma-Aldrich, D2650) was added to the growth medium on confluent cells. After one week, medium was replaced by complete differentiation medium (HepaRG growth medium supplemented with 1.8% (v/v) DMSO) in which cells were maintained for approximately 4 weeks with differentiation medium renewal every 7 days. Differentiated HepaRG cells (dHepaRG), displayed hepatocyte-like cell islands surrounded by monolayer of biliary-like cells. Prior to HBV infection and compound treatment, dHepaRG cells were seeded into collagen I coated 96-well plates (Gibco, Cat #A11428-03) at 60,000 cells per well in 100 μL of complete differentiation medium. Cells were allowed to recover their differentiated phenotype in 96-well plates for approximately 1 week after plating prior to HBV infection.

HBV Infection of dHepaRG Cells dHepaRG cells were infected with HBV particles at an MOI of 30. The HBV particles were produced from HBV-producing HepG2.2.15 cells (Sells et al 1987 Proc Natl Acad Sci USA 84, 1005-1009). dHepaRG culture conditions, differentiation and HBV infection have been described previously (Hantz, 2009, J. Gen. Virol., 2009, 90: 127-135). In brief complete differentiation medium (HepaRG growth medium consisting of William's E Medium (GIBCO), Growth Medium Supplement (Biopredics, Cat #ADD710) and 1% (v/v) GlutaMAX-I (Gibco #32551) and 1× Pen/Strep (Gibco, #15140), supplemented with 1.8% (v/v) DMSO), containing 4% PEG-8000 and virus stock (20 to 30 GE/cell) was added (120 μL/well). One day post-infection, the cells were washed three times with phosphate-buffered saline and medium (complete differentiation medium) was replaced every two days during the experiment.

siRNA Treatment of HBV-Infected HepaRG

A pool of four different siRNAs was acquired from GE Dharmacon (ON TARGETplus) (Table 8).

TABLE 8

Overview siRNAs

| ON TARGETplus | siRNA (Cat.No.) | Target Sequence | SEQ ID NO |
|---|---|---|---|
| siPAPD5 | J-010011-05 | CAUCAAUGCUUUAUAUCGA | 252 |
| (Cat. No. # | J-010011-06 | GGACGACACUUCAAUUAUU | 253 |
| L-010011-00- | J-010011-07 | GAUAAAGGAUGGUGGUUCA | 254 |
| 0010) | J-010011-08 | GAAUAGACCUGAGCCUUCA | 255 |
| siPAPD7 | J-009807-05 | GGAGUGACGUUGAUUCAGA | 256 |
| (Cat. No. # | J-009807-06 | CGGAGUUCAUCAAGAAUUA | 257 |
| L-009807-00- | J-009807-07 | CGGAGUUCAUCAAGAAUUA | 258 |
| 0005) | J-009807-08 | GCGAAUAGCCACAUGCAAU | 259 |

One day before infection with HBV cells and 4 days after infection cells were treated with the siRNA pool either against PAPD5, PAPD7, both or the non-targeting siRNA as control. The siRNAs (25 nM each) were transfected using DharmaFect 4 (GE Dharmacon; Cat. No. T-2004-01) and OPTI-MEM (Thermo Scientific; Cat. No. 51985034) according to manufacturer's protocol. The experiment was run for 11 days.

HBV Antigen Measurements

To evaluate the impact on HBV antigen expression and secretion, supernatants were collected on Day 11. HBV HBsAg and HBeAg levels were measured using CLIA ELISA Kits (Autobio Diagnostic #CL0310-2, #CL0312-2), according to the manufacturer's protocol. Briefly, 25 μL of supernatant per well were transferred to the respective antibody coated microtiter plate and 25 μL of enzyme conjugate reagent were added. The plate was incubated for 60 min on a shaker at room temperature before the wells were washed five times with washing buffer using an automatic washer. 25 μL of substrate A and B were added to each well. The plates were incubated on a shaker for 10 min at room temperature before luminescence was measured using an Envision luminescence reader (Perkin Elmer).

Cell Viability

After the removal of supernatant media from the HBV infected dHepaRG cells, cells were incubated with CellTiterGlo One Solution (Promega) to measure cell viability.

After LNA oligonucleotide treatments of HBV infected dHepaRG cells, cell viability was measured using the Cell Counting kit-8 (Sigma-Aldrich, #96992) according to the manufacturer's protocol. Briefly, Medium was removed from the cells and replaced by 110 μL of medium containing 9% Cell Counting kit-8. Cells were incubated for 1 h at 37° C. The supernatant was transferred into a new 96 wells plate and the absorbance at 450 nm was measured using an Envision luminescence reader (Perkin Elmer).

Real-Time PCR for Intracellular mRNA

For intracellular mRNA isolation, dHepaRG were washed once with PBS (Gibco) and lysed using the MagNA Pure "96 Cellular RNA Large Volume Kit" (Roche #05467535001). The lystates may be stored at −80° C. For the real-time qPCR reaction an AB7900 HT sequence detection system (Applied Biosystems), the TaqMan® Gene Expression Master Mix (ThermoFisher Scientific) were used. For detection of HBV mRNA HBV core-specific primer (Integrated DNA Technologies) (Table 9) and to measure reduction of PAPD5 and PAPD7, in the presence of siRNA, gene-specific TaqMan® Expression Assay probes (ThermoFisher Scientific; PAPD5 Cat. No. 4331182; PAPD7 Cat. No. 4331182) were used. Samples were normalized using TaqMan® Expression Assay probe against b-Actin (ThermoFisher Scientific; PAPD5 Cat. No. 4331182).

TABLE 9

HBV core specific TaqMan probes

| | Name | Dye | Sequence | SEQ ID NO |
|---|---|---|---|---|
| HBV core Primer | Forward (F3_HBVcore) | | CTG TGC CTT GGG TGG CTT T | 265 |
| | Reverse (R3_HBVcore) | | AAG GAA AGA AGT CAG AAG GCAAAA | 266 |
| | Probe (P3_HBVcore) | FAM-MGB | AGC TCC AAA/ZEN/ TTC TTT ATA AGG GTC GAT GTC CAT G | 267 |

HBV DNA Extraction and Quantification from Virus Preparation

HBV DNA extraction is performed using the QIAamp UltraSens Virus kit (Qiagen, #53704) according to the manufacturer's protocol with the following optimizations. 30 μL and 3 μL of the virus sample are diluted into 1 mL of PBS before adding buffer AC. The first centrifugation step is done for 45 min at full speed and 4° C. HBV DNA is quantified in duplicate by qPCR using a QuantStudio 12K Flex (Applied Biosystems), the TaqMan Gene Expression Master Mix (Applied Biosystems, #4369016) and a premix 1:1:0.5 of the primers indicated in Table 9 above and probe reconstituted at 100 μM. The qPCR is performed using the following settings: UDG incubation (2 min, 50° C.), enzyme activation (10 min, 95° C.) and qPCR (40 cycles with 15 sec, 95° C. for denaturation and 1 min, 60° C. for annealing and extension). Genomes equivalent calculation is based on a standard curve generated from HBV genotype D plasmid dilutions with known concentrations.

Oligonucleotide Synthesis

Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on an Oligomaker 48 at 1 μmol scale. At the end of the synthesis, the oligonucleotides are cleaved from the solid support using aqueous ammonia for 5-16 hours at 60'C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl- C(Bz), LNA-A(Bz), LNA-G(dmf), or LNA-T) is performed by using a solution of 0.1 M of the 5'-O-DMT-protected amidite in acetonitrile and DCI (4,5-dicyanoimidazole) in acetonitrile (0.25 M) as activator. For the final cycle, a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphordiester linkages can be introduced using 0.02 M iodine in THF/Pyridine/water 7:2:1. The rest of the reagents are the ones typically used for oligonucleotide synthesis.

For post solid phase synthesis conjugation a commercially available C6 aminolinker phorphoramidite can be used in the last cycle of the solid phase synthesis and after deprotection and cleavage from the solid support the aminolinked deprotected oligonucleotide is isolated. The conjugates are introduced via activation of the functional group using standard synthesis methods.

Purification by RP-HPLC:

The crude compounds are purified by preparative RP-HPLC on a Phenomenex Jupiter C18 10μ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations

DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography $T_m$ Assay:

Oligonucleotide and RNA target (phosphate linked, PO) duplexes are diluted to 3 mM in 500 ml RNase-free water and mixed with 500 ml 2× $T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Example 1: DHQ and THP Binds to PAPD5 and PAPD7

PAPD5/7 were Identified in Y3H Ultimate YChemH Screen as Common Interaction Partner of DHQ and THP Both proteins PAPD5 (variant 1: NP_001035374; variant 2: NP_001035375) and PAPD7 (XP_005248291) were identified by a numerous number of fragments in the Y3H screen for both compounds (DHQ and THP) as described in the Materials and Method section. The identified proteins were ranked with a confidence score of A (scale A-D) by HYBRIGENICS (Table 10).

TABLE 10

YChemH screen results for PAPD5/7

| | Hybrigenics ID | Protein prey identified | # of fragments | Confidence score |
|---|---|---|---|---|
| DHQ compound | HBX129653 | PAPD5 variant 1 | 28 | A |
| | | PAPD5 variant 2 | 1 | N/A |
| | | PAPD7 | 12 | A |
| THP compound | HBX129654 | PAPD5 variant 1 | 5 | N/A |
| | | PAPD5 variant 2 | 49 | A |
| | | PAPD7 | 24 | A |

PAPD5/7 Interaction with DHQ and THP could be Confirmed Using Y3H ULTImate YChemH 1-by-1 Validation of Identified Prey Fragments and Further with Full Length Proteins In a first validation step three fragments identified in the first screen were selected for the 1-by-1 validation assay (as described in the Materials and Method section) and tested at three different concentrations (5, 10 and 201M) (Table 11).

TABLE 11 interacting fragment selected for validation assay

| Interaction # | Prey fragment ID | Protein Prey |
|---|---|---|
| A | PLA_RP6_hgx4240v1_pB409_A-15 | PAPD7 |
| B | PLA_RP6_hgx4241v1_pB409_A-112 | PAPD5 variant 1 |
| C | PLA_RP6_hgx4240v1_pB409_A-24 | PAPD5 variant 2 |

All three fragments could be validated as specific binders for DHQ and THP already at the lowest tested concentration (FIG. 1).

In a second validation step, full length proteins for PAPD5 and PAPD7 were synthesized and used for 1-by-1 validation (as described in the Materials and Method section) with DHQ and THP (Table 12).

TABLE 12

Reference ID for full length protein prey used in 1-by-1 validation assay

| Interaction # | HYBRIGENICS Reference | Protein Prey |
|---|---|---|
| A | hgx4386v1_pP7 | PAPD5 var1 full length |
| B | hgx4388v2_pP7 | PAPD7 var1 full length |

Figure 2:
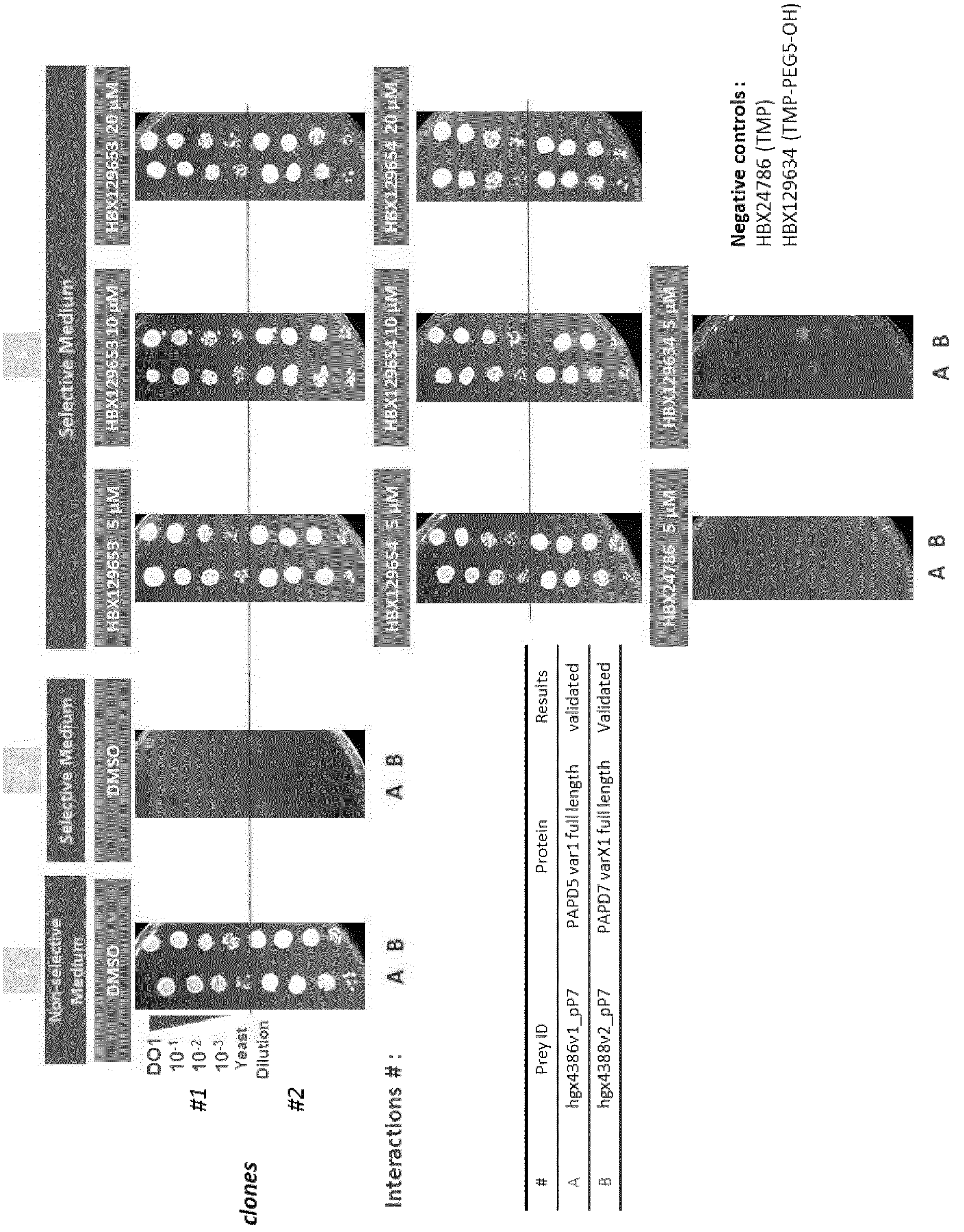
FIG. 2: Pictures from 1-by-1 experiment with HBX129653/HBX129654 chemical probes and PAPD5/7 full length proteins.

The interaction between these full length proteins and the DHQ and THP compounds were confirmed at the lowest tested concentration and shown to be specific for the chemical probes (FIG. 2).

PAPD5/7 Interaction with DHQ and THP in Y3H can be Competed by Both Free Active Compound, but not the Inactive Enantiomer After validation of binding of DHQ and THP to protein fragments and full length PAPD5 and PAPD7 the binding was confirmed in a Y3H ULTImate YChenH competition experiment (as described in the Materials and Method section) using either inactive or active free compound (Table 13). A decrease of loss of yeast growth in the presence of the parent active compound, but not in the presence of the inactive enantiomer, means that the parent compound competes with the chemical probe and interacts with the protein target.

Figure 3:
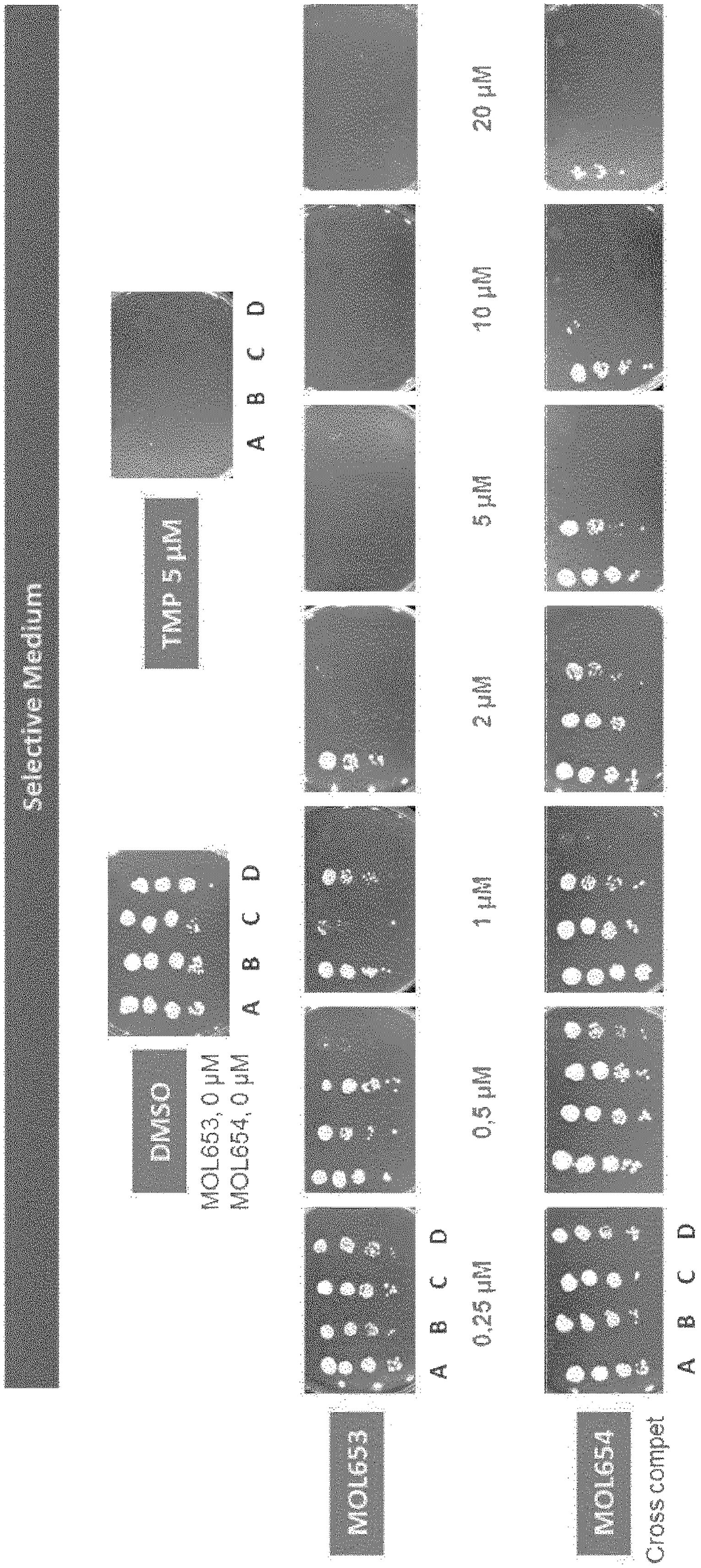
FIG. 3: Pictures from competition assay using HBX129653 (DHQ) and MOL653/654 for competition
Figure 4:
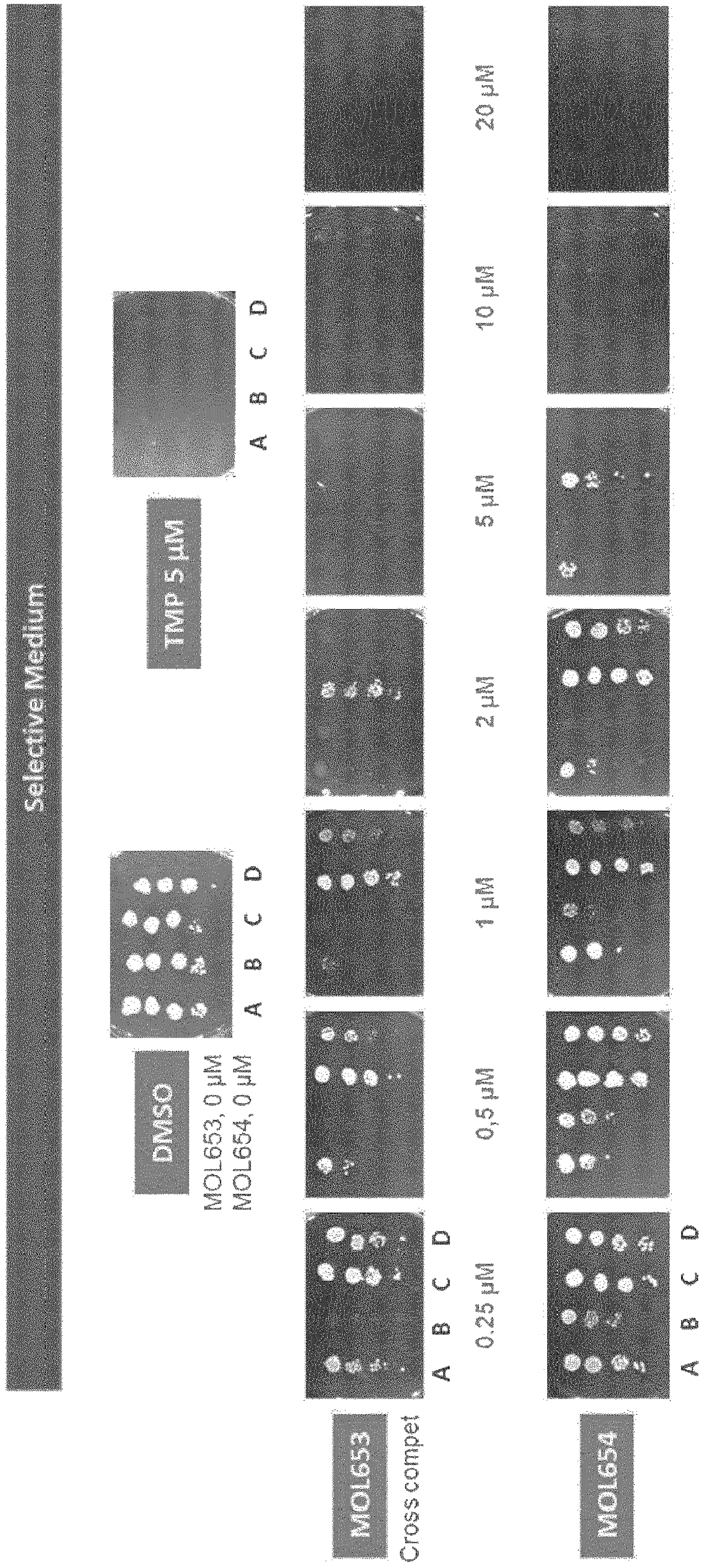
FIG. 4: Pictures from competition assay using HBX129654 (THP) and MOL653/654 for competition
Figure 5:
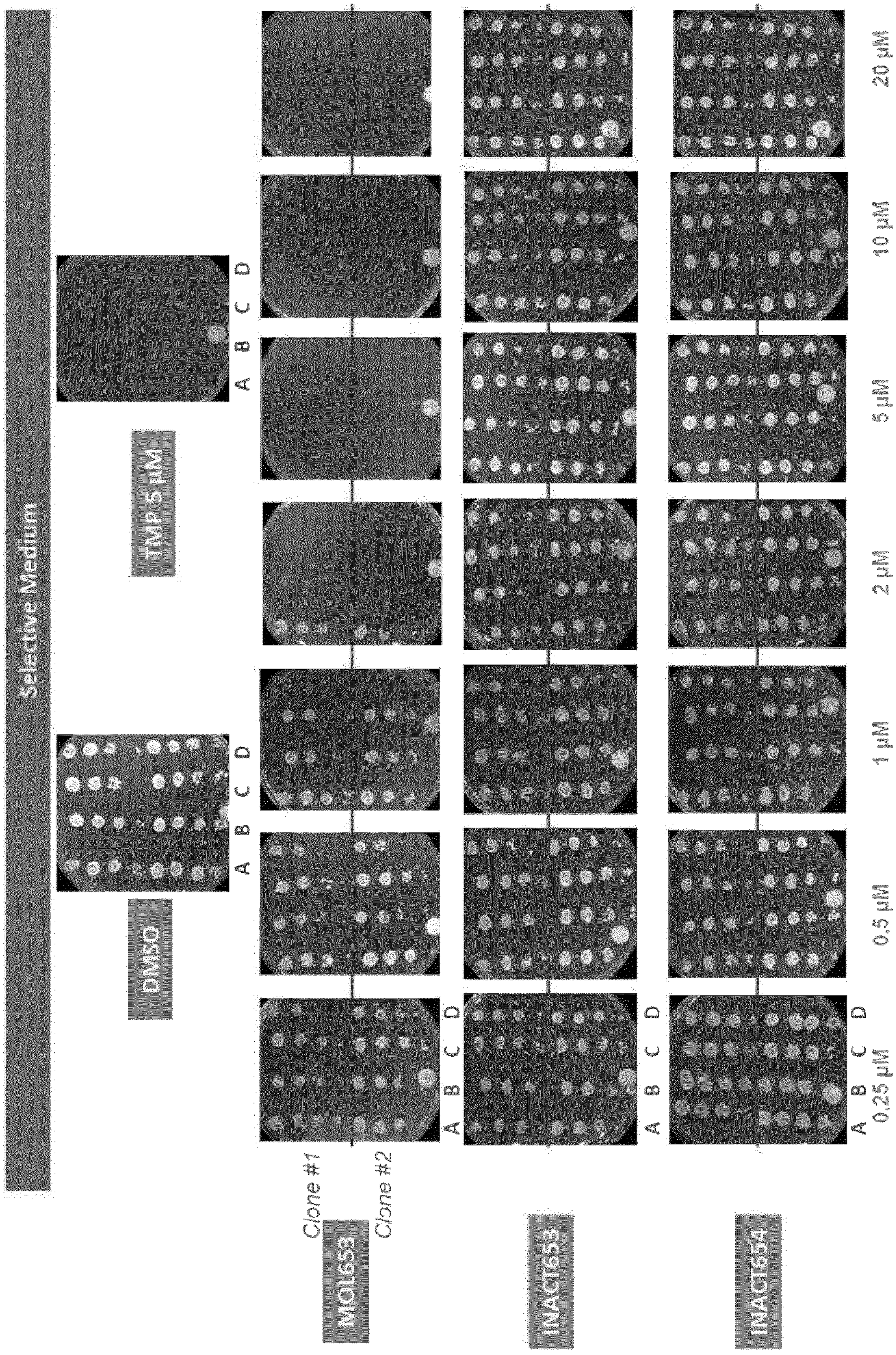
FIG. 5: Pictures from competition assay using HBX129653 (DHQ) and INACT653/INACT654 for competition. MOL653 was included as positive control.
Figure 6:
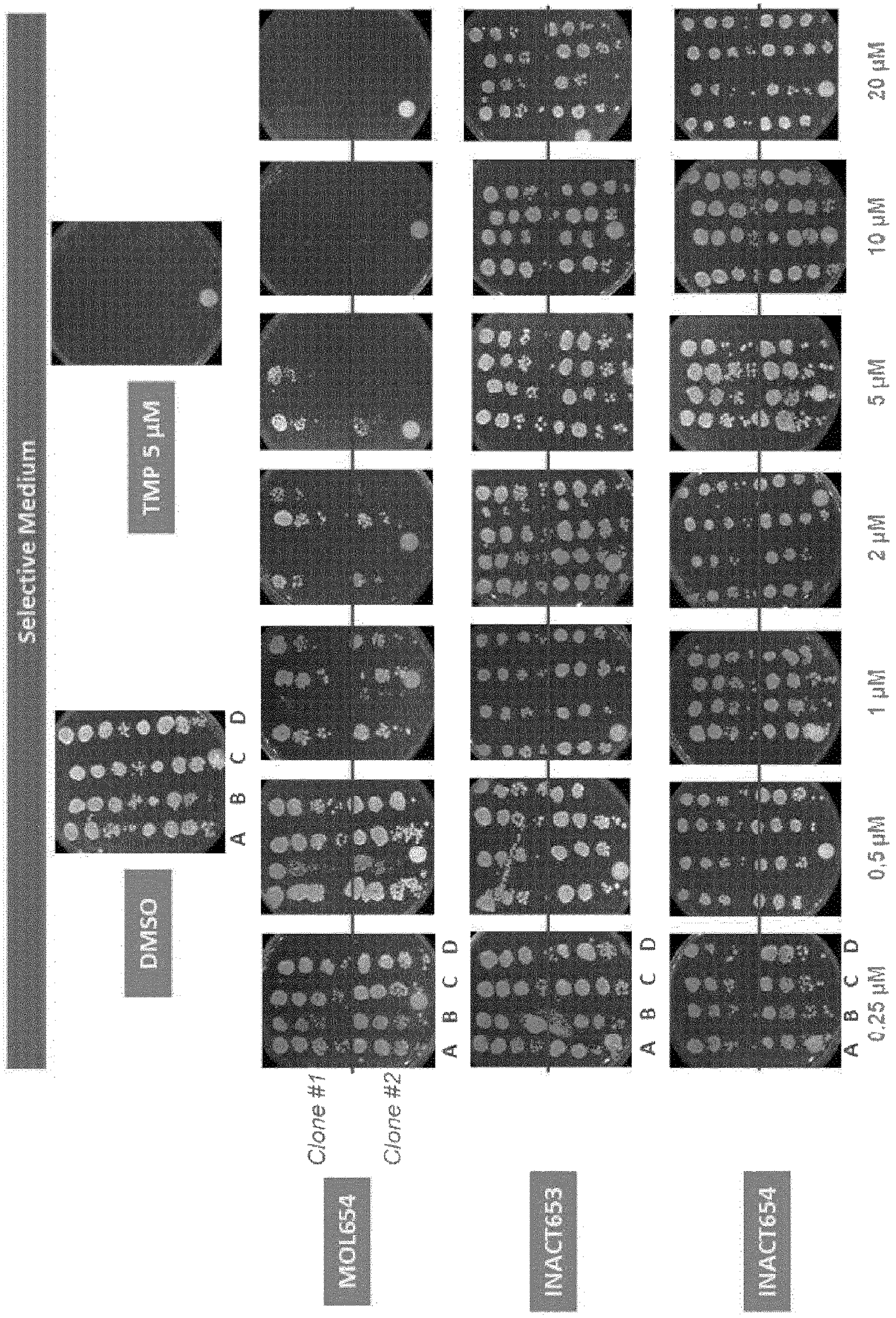
FIG. 6: Pictures from competition assay using HBX129654 (THP) and INACT653/INACT654 for competition. MOL653 was included as positive control.

For all tested compounds toxicity on non-selective medium at the highest concentration (20M) was tested using CellTiter-Glo Luminescent Cell Viability Assay (Promega) according to the manufacturer's protocol. No toxicity was observed at this concentration for any compound as yeast growth was not affected (data not shown). For both active free parent compounds (DHQ and THP, MOL653 and MOL654, respectively) competition could be observed, with lower concentration needed for competing the binding to the full length protein than for the fragment interactions (FIG. 3+4). Successful cross competition suggests a shared binding side for DHQ and THP to PAPD5/7 or at least binding in close proximity to each other.

TABLE 13

Reference ID for protein prey used in competition assay

| Interaction # | Prey fragment ID | Protein Prey |
|---|---|---|
| A | PLA_RP6_hgx4241v1_pB409_A-112 | PAPD5 var1 experimental fragment |
| B | hgx4386v1_pP7 | PAPD5 var1 full length |
| C | PLA_RP6_hgx4240v1_pB409_A-15 | PAPD7 varX1 experimental fragment |
| D | hgx4388v2_pP7 | PAPD7 varX1 full length |

Example 2: Inhibition of PAPD5 and/or PAPD7 with siRNA Results in Effective Treatment of HBV Infection To correlate the binding of DHQ and THP to PAPD5/7 and the impact of these two proteins on HBV gene expression, we used RNAi technology to reduce these proteins in naturally HBV infected dHepaRG and to monitor the impact of this reduction on viral parameters. For that we used siRNA pools against PAPD5 and PAPD7 (see table 8) in HBV infected dHepaRG cells as described in the Materials and methods section.

Figure 7:
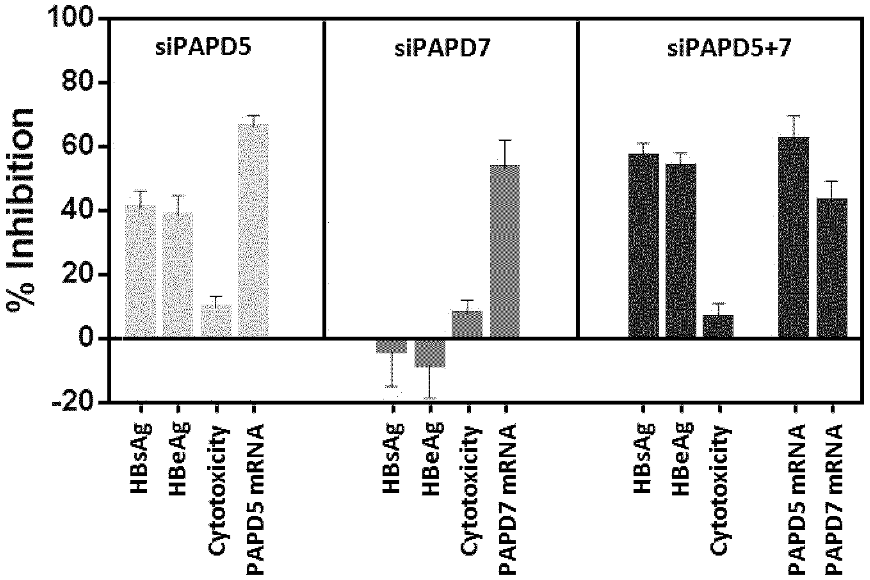
FIG. 7: (A) SiRNA knock-down (KD) of PAPD5 and PAPD7 in HBV-infected dHepaRG leads to reduction in HBV expression. Differentiated HepaRG cells were infected with HBV and treated with siRNA against either PAPD5, PAPD7 or both (25 nM each) one day prior to HBV infection and on day 4 post infection. Supernatant were harvested on day 11, levels of HBsAg and HBeAg secreted in the supernatant were measured by ELISA and normalized to non-treated control. Cell toxicity and inhibition of gene expression was measured subsequently and also normalized to the non-treated control. (B) The same experiment as described in (A) was performed, with the exception that only the level of HBsAg secreted in the supernatant was measured.
Figure 7:
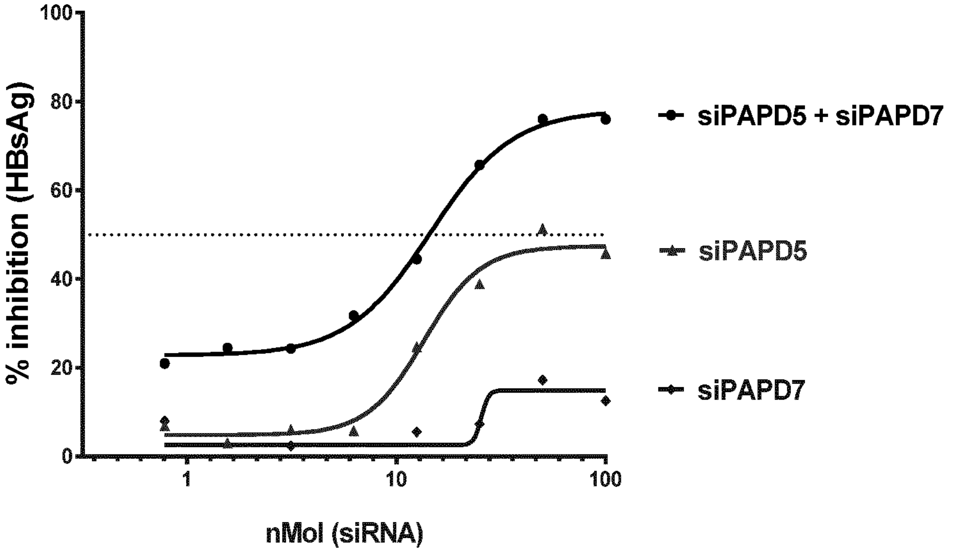

Reduction of PAPD5 led to inhibition of viral expression measured by secreted HBsAg and HBeAg as well as intracellular HBV mRNA (measured using CLIA ELISA and real-time PCR as described in the Materials and Methods section). While the reduction of PAPD5 mRNA dramatically reduced HBV gene expression, inhibition of PAPD7 had a modest effect on HBV expression (FIG. 7). However, an enhanced synergistic anti-HBV activity was observed when siRNA against PAPD7 and PAPD5 were combined (FIG. 7), suggesting a compensative role for PAPD7 in the absence of PAPD5.

Example 3: DHQ and THP Effectively Reduces HBsAg and HBeAg

The potency of DHQ and THP and their variants against HBV infection were measured in HepG2.2.15 cells using HBsAg and HBeAg as read out.

HepG2.2.15 cells (Sells et al 1987 Proc Natl Acad Sci USA 84, 1005-1009) were cultured in 96 well plates (15.000 cells/well in 100 uL) in DMEM+GluTaMax-1 (GiBCO Cat. NO. 10569), 1% Pen Strep (Gibco Cat. No. 15140), 10% FBS (Clontech Cat. No. 631106), Geneticin 0.25 ug/ml (Invitrogen 10131035). The compounds were tested using three-fold serial dilutions in DMSO with a top concentration of 100 μM and 9 serial dilutions. Each compound was tested in quadricate. The cells were incubated for 3 days, supernatants were collected and HBsAg and HBeAg were measured as described in the Materials and Methods section.

The $IC_{50}$ values of the tested compounds in the reduction of secretion of HBsAg and HBeAg are shown in the following:

HBX129653 (DHQ-TMP): $IC_{50}$ HBsAg 1.181 uM

HBX129654 (THP-TMP): $IC_{50}$ HBsAg 0.299 uM

MOL653 (DHQ-free-active): $IC_{50}$ HBsAg 0.003 uM; $IC_{50}$ HBeAg 0.007 uM

MOL654 (THP-free-active): $IC_{50}$ HBsAg 0.003 uM

INACT653 (DHQ-free-inactive): $IC_{50}$ HBsAg 3.15 uM

INACT654 (THP-free-inactive): $IC_{50}$ HBsAg>25 uM

Example 4: Screening for In Vitro Efficacy of Antisense Oligonucleotides Targeting PAPD5

An oligonucleotide screen was done across the PAPD5 mRNA using 16 to 20mer gapmers. Efficacy testing was performed in an in vitro experiment in HeLa cells.

Cell Lines

HeLa cell line was purchased from European Collection of Authenticated Cell Cultures (ECACC, #93021013) and maintained as recommended by the supplier in a humidified incubator at 37° C. with 5% CO2. For assays, 2,500 cells/well were seeded in a 96 multi well plate in Eagle's Minimum Essential Medium (Sigma, M2279) with 10% fetal bovine serum (FBS), 2 mM Glutamin AQ, 1% NEAA, 25 μg/ml Gentamicin.

Oligonucleotide Efficacy

Figure 8:
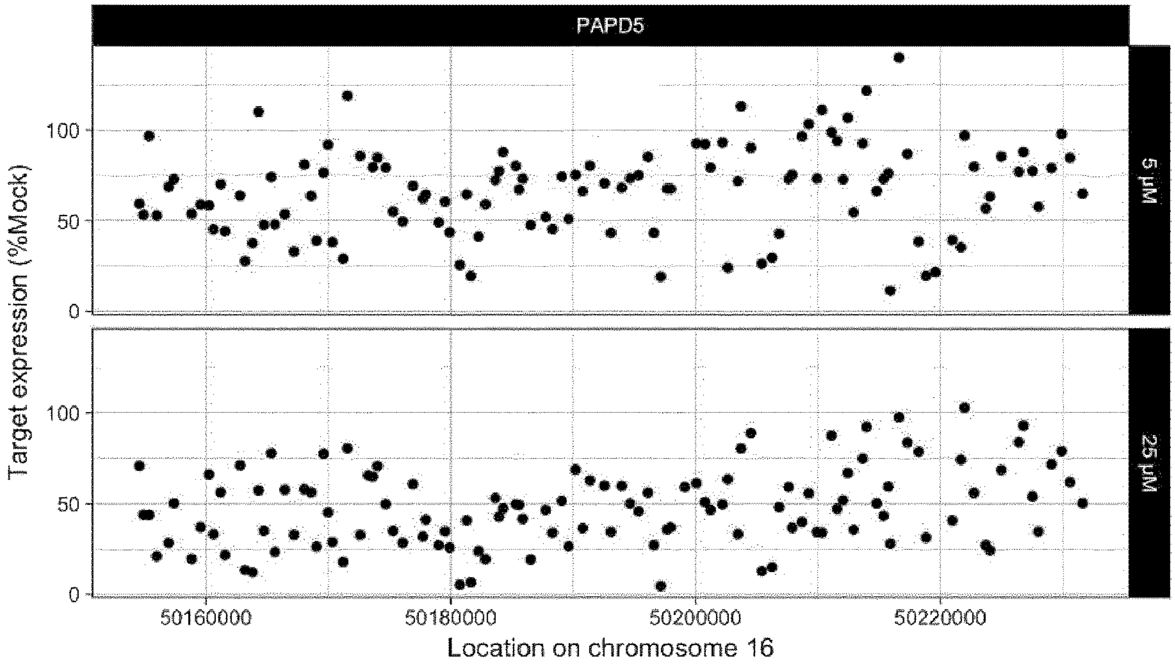
FIG. 8: Representation of the ability of the oligonucleotides, tested in example 4, to reduce the expression of PAPD5 in HeLa cell cultures. Each oligonucleotide is represented by a dot indicating its location on the PAPD5 mRNA by chromosomal position. The oligonucleotide concentrations were 5 and 25 microM as indicated in the right hand side each plot.

Cells were incubated for 24 hours before addition of oligonucleotides dissolved in PBS. Final concentration of oligonucleotides was 5 and 25 μM, the final culture volume was 100 μl/well. The cells were harvested 3 days after addition of oligonucleotide compounds and RNA was extracted using the PureLink Pro 96 RNA Purification kit (Ambion), according to the manufacturer's instructions. After RNA/LNA duplex denaturation (90° C., 40 sec) QPCR was done with a one-step protocol (qScript™ XLT One-Step RT-qPCR ToughMix®, Low ROX™ from Quanta Bioscience, #95134-500) in a duplex set up with TaqMan primer assays for the gene of interest PAPD5 (Hs00223727_m1, FAM-MGB, Life Technologies) and a house keeping gene GUSB (Hu_4326320E, VIC-MGB, Life Technologies) following the recommendations of the provider. The relative PAPD5 mRNA expression level is shown in table 14 as % of average control samples (PBS-treated cells). FIG. 8 presents the target knockdown achieved with the individual oligonucleotide compounds across the PAPAD5 encoding sequence.

TABLE 14 in vitro efficacy of anti-PAPD5 compounds (single experiment withduplex QPCR). PAPD5 mRNA levels are normalized to GUSB in HeLac ells and shown as % of control (PBS treated cells).

| CMP ID NO | Concentration µM | % mRNA of control Avg | sd | Compound (CMP) | Start on SEQ ID NO 10 |
|---|---|---|---|---|---|
| 12_1 | 25 | 70.8 | 9.3 | AGggtagatgtgtttaACT | 1656 |
| 12_1 | 5 | 59.3 | 11.7 | AGggtagatgtgtttaACT | 1656 |
| 13_1 | 25 | 43.9 | 0.2 | CAGcctaaacttagtGG | 2000 |
| 13_1 | 5 | 53.2 | 18.1 | CAGcctaaacttagtGG | 2000 |
| 14_1 | 25 | 43.9 | 8.8 | AAgccctcaatgtaaaACAC | 2446 |
| 14_1 | 5 | 96.6 | 8.1 | AAgccctcaatgtaaaACAC | 2446 |
| 15_1 | 25 | 21.1 | 3.2 | AATagcaagtagaggaGAG | 3059 |
| 15_1 | 5 | 52.9 | 17.1 | AATagcaagtagaggaGAG | 3059 |
| 16_1 | 25 | 28.5 | 7.3 | AAataaggatactgGCGA | 4036 |
| 16_1 | 5 | 68.6 | 16.4 | AAataaggatactgGCGA | 4036 |
| 17_1 | 25 | 50.2 | 20.4 | GAGGgaacacataataaaAG | 4484 |
| 17_1 | 5 | 72.9 | 29.0 | GAGGgaacacataataaaAG | 4484 |
| 18_1 | 25 | 19.7 | 4.0 | GTaatacctctcacATTC | 5928 |
| 18_1 | 5 | 53.8 | 14.0 | GTaatacctctcacATTC | 5928 |
| 19_1 | 25 | 37.0 | 8.4 | AGtaacaccaatctcATTG | 6652 |
| 19_1 | 5 | 58.8 | 10.7 | AGtaacaccaatctcATTG | 6652 |
| 20_1 | 25 | 66.1 | 5.3 | GTgacagtattcaatGATC | 7330 |
| 20_1 | 5 | 58.4 | 12.5 | GTgacagtattcaatGATC | 7330 |
| 21_1 | 25 | 33.2 | 3.1 | CAgttccgtatcaccAAC | 7702 |
| 21_1 | 5 | 45.3 | 11.6 | CAgttccgtatcaccAAC | 7702 |
| 22_1 | 25 | 56.3 | 6.7 | AAgtctaactcaaagccATC | 8292 |
| 22_1 | 5 | 70.1 | 16.8 | AAgtctaactcaaagccATC | 8292 |
| 23_1 | 25 | 21.7 | nd | AGgcttccattttattGAA | 8625 |
| 23_1 | 5 | 44.3 | 0.5 | AGgcttccattttattGAA | 8625 |
| 24_1 | 25 | 71.2 | 10.2 | TTttagaaaacgagGCTA | 9866 |
| 24_1 | 5 | 63.8 | 10.6 | TTttagaaaacgagGCTA | 9866 |
| 25_1 | 25 | 13.4 | 0.1 | GTAttcttattcttgCT | 10254 |
| 25_1 | 5 | 27.9 | 10.6 | GTAttcttattcttgCT | 10254 |
| 26_1 | 25 | 12.0 | 0.9 | ATTAttcccacagtaaGA | 10881 |
| 26_1 | 5 | 37.7 | 1.1 | ATTAttcccacagtaaGA | 10881 |
| 27_1 | 25 | 57.5 | 4.4 | AACaacaaacaggatggGC | 11370 |
| 27_1 | 5 | 110.0 | 2.2 | AACaacaaacaggatggGC | 11370 |
| 28_1 | 25 | 35.2 | 0.8 | ATATccacaatattctgAT | 11790 |
| 28_1 | 5 | 47.7 | 1.2 | ATATccacaatattctgAT | 11790 |
| 29_1 | 25 | 77.8 | 32.7 | AAagaaataatgtcgtCTGG | 12413 |

TABLE 14 -continued in vitro efficacy of anti-PAPD5 compounds (single experiment withduplex QPCR). PAPD5 mRNA levels are normalized to GUSB in HeLac ells and shown as % of control (PBS treated cells).

| CMP ID NO | Concentration µM | % mRNA of control Avg | sd | Compound (CMP) | Start on SEQ ID NO 10 |
|---|---|---|---|---|---|
| 29_1 | 5 | 73.9 | 2.5 | AAagaaataatgtcgtCTGG | 12413 |
| 30_1 | 25 | 23.4 | 4.0 | CCAgagtaaacaaaTCC | 12718 |
| 30_1 | 5 | 48.0 | 2.0 | CCAgagtaaacaaaTCC | 12718 |
| 31_1 | 25 | 57.7 | 10.6 | ATtcaacatttttagtcACC | 13555 |
| 31_1 | 5 | 53.6 | 4.8 | ATtcaacatttttagtcACC | 13555 |
| 32_1 | 25 | 32.8 | 5.7 | TTTggtaattcttt1ltTAG | 14297 |
| 32_1 | 5 | 33.1 | 5.4 | TTTggtaattcttt1ltTAG | 14297 |
| 33_1 | 25 | 58.0 | nd | CAatgaggaaacaagaGTCA | 15137 |
| 33_1 | 5 | 80.9 | 17.9 | CAatgaggaaacaagaGTCA | 15137 |
| 34_1 | 25 | 56.3 | 9.0 | TTCaaaataatgtgggaGGT | 15695 |
| 34_1 | 5 | 63.6 | 2.7 | TTCaaaataatgtgggaGGT | 15695 |
| 35_1 | 25 | 26.4 | 1.9 | GGatatttgatacggcaAAT | 16145 |
| 35_1 | 5 | 39.1 | 10.1 | GGatatttgatacggcaAAT | 16145 |
| 36_1 | 25 | 77.5 | 12.6 | CTAtaagaagcaaaCCC | 16714 |
| 36_1 | 5 | 76.6 | 2.7 | CTAtaagaagcaaaCCC | 16714 |
| 37_1 | 25 | 45.3 | 4.5 | ATAtaattcacgtttcaCTT | 17097 |
| 37_1 | 5 | 91.9 | nd | ATAtaattcacgtttcaCTT | 17097 |
| 38_1 | 25 | 28.9 | 2.7 | AATgattcacatgaaggTTA | 17420 |
| 38_1 | 5 | 38.2 | 2.2 | AATgattcacatgaaggTTA | 17420 |
| 39_1 | 25 | 18.0 | 4.7 | GTtaggattttgcTATG | 18299 |
| 39_1 | 5 | 29.2 | 4.1 | GTtaggattttgcTATG | 18299 |
| 40_1 | 25 | 80.4 | 2.0 | GTAcaaatatcaaccgTAT | 18669 |
| 40_1 | 5 | 118.8 | 10.4 | GTAcaaatatcaaccgTAT | 18669 |
| 41_1 | 25 | 32.8 | 7.7 | CACactatttcaagatgcTA | 19681 |
| 41_1 | 5 | 85.6 | 4.8 | CACactatttcaagatgcTA | 19681 |
| 42_1 | 25 | 65.6 | 20.2 | CACctatacaatggagtATT | 20352 |
| 43_1 | 25 | 64.9 | 12.3 | ATcatacgtcattagaGAAC | 20721 |
| 43_1 | 5 | 79.4 | 25.2 | ATcatacgtcattagaGAAC | 20721 |
| 44_1 | 25 | 70.7 | 2.6 | CAgaacagatactttgcCA | 21111 |
| 44_1 | 5 | 84.7 | 5.5 | CAgaacagatactttgcCA | 21111 |
| 45_1 | 25 | 49.8 | 11.9 | AAgaatggttggttaaGGG | 21782 |
| 45_1 | 5 | 79.2 | 4.3 | AAgaatggttggttaaGGG | 21782 |
| 46_1 | 25 | 35.1 | 0.0 | AGAAttggtaaactggacTG | 22378 |
| 46_1 | 5 | 55.1 | 7.7 | AGAAttggtaaactggacTG | 22378 |
| 47_1 | 25 | 28.4 | 3.9 | AGAattatattggcTGG | 23160 |

TABLE 14 -continued in vitro efficacy of anti-PAPD5 compounds
(single experiment withduplex QPCR).
PAPD5 mRNA levels are normalized to GUSB in HeLac ells
and shown as % of control (PBS treated cells).

| CMP ID NO | Concentration µM | % mRNA of control Avg | sd | Compound (CMP) | Start on SEQ ID NO 10 |
|---|---|---|---|---|---|
| 47_1 | 5 | 49.6 | 2.2 | AGAattatattggcTGG | 23160 |
| 48_1 | 25 | 60.8 | 13.7 | CCtaaaccagacagaaaAGA | 23993 |
| 48_1 | 5 | 69.1 | 5.0 | CCtaaaccagacagaaaAGA | 23993 |
| 49_1 | 25 | 31.9 | 4.7 | ACCAattagagcagaaaTC | 24813 |
| 49_1 | 5 | 62.2 | 1.0 | ACCAattagagcagaaaTC | 24813 |
| 50_1 | 25 | 41.3 | 6.5 | TTCtaaataacagatggGTC | 25047 |
| 50_1 | 5 | 64.4 | 21.7 | TTCtaaataacagatggGTC | 25047 |
| 51_1 | 25 | 27.1 | 5.9 | TTTataattttttccaTCT | 26080 |
| 51 1 | 5 | 49.1 | 7.7 | TTTataattttttccaTCT | 26080 |
| 52_1 | 25 | 34.9 | 6.8 | GCAAatatcagattaaccTC | 26625 |
| 52_1 | 5 | 60.5 | 3.1 | GCAAatatcagattaaccTC | 26625 |
| 53_1 | 25 | 25.9 | 0.8 | AACggtatggcagaagaCAA | 26973 |
| 53_1 | 5 | 43.6 | 2.2 | AACggtatggcagaagaCAA | 26973 |
| 54_1 | 25 | 5.1 | 0.1 | TTCAacctttactgcAT | 27813 |
| 54_1 | 5 | 25.7 | 3.1 | TTCAacctttactgcAT | 27813 |
| 55_1 | 25 | 40.8 | 0.9 | ACtgataaagggcattTCAA | 28357 |
| 55_1 | 5 | 64.5 | 1.6 | ACtgataaagggcattTCAA | 28357 |
| 56_1 | 25 | 6.4 | 2.3 | CAgtaggaatgtggCTT | 28718 |
| 56_1 | 5 | 19.6 | 0.7 | CAgtaggaatgtggCTT | 28718 |
| 57_1 | 25 | 23.9 | 0.4 | TTTtatggcagggtttcAC | 29327 |
| 57_1 | 5 | 41.2 | 7.9 | TTTtatggcagggtttcAC | 29327 |
| 58_1 | 25 | 19.6 | 0.7 | TCactgttaaaccTCAC | 29902 |
| 58_1 | 5 | 59.0 | 12.9 | TCactgttaaaccTCAC | 29902 |
| 59_1 | 25 | 53.1 | 4.8 | CAATtttctaattcaatgGT | 30704 |
| 59_1 | 5 | 72.4 | 29.8 | CAATtttctaattcaatgGT | 30704 |
| 60_1 | 25 | 42.8 | 2.0 | AAGAtataattcacccaCT | 31008 |
| 60_1 | 5 | 77.3 | 13.7 | AAGAtataattcacccaCT | 31008 |
| 61_1 | 25 | 47.4 | 2.7 | GCcacataaaggataAAGT | 31348 |
| 61_1 | 5 | 87.8 | 12.8 | GCcacataaaggataAAGT | 31348 |
| 62_1 | 25 | 49.8 | 2.7 | CCcattagaagtaaggtGA | 32367 |
| 62_1 | 5 | 80.1 | 11.1 | CCcattagaagtaaggtGA | 32367 |
| 63_1 | 25 | 49.4 | 1.1 | ATgtaaattaaaactTCCC | 32632 |
| 63_1 | 5 | 67.2 | 1.7 | ATgtaaattaaaactTCCC | 32632 |
| 64_1 | 25 | 41.7 | 1.7 | TGAgagcataaaagtacgGA | 32945 |
| 64_1 | 5 | 73.1 | 6.3 | TGAgagcataaaagtacgGA | 32945 |

TABLE 14 -continued in vitro efficacy of anti-PAPD5 compounds (single experiment withduplex QPCR). PAPD5 mRNA levels are normalized to GUSB in HeLac ells and shown as % of control (PBS treated cells).

| CMP ID NO | Concentration µM | % mRNA of control Avg | sd | Compound (CMP) | Start on SEQ ID NO 10 |
|---|---|---|---|---|---|
| 65_1 | 25 | 19.4 | 0.2 | TTCAcaacaggtaaagGG | 33593 |
| 65_1 | 5 | 47.7 | 3.3 | TTCAcaacaggtaaagGG | 33593 |
| 66_1 | 25 | 46.6 | 0.2 | TGcattcctaagtaacATAA | 34801 |
| 66_1 | 5 | 52.0 | 5.3 | TGcattcctaagtaacATAA | 34801 |
| 67_1 | 25 | 34.1 | 10.4 | AGAgaaaagtgatgaggGAA | 35368 |
| 67_1 | 5 | 45.5 | 2.0 | AGAgaaaagtgatgaggGAA | 35368 |
| 68_1 | 25 | 51.7 | 3.6 | ATAcggatcaccagctaAA | 36131 |
| 68_1 | 5 | 74.2 | 18.8 | ATAcggatcaccagctaAA | 36131 |
| 69_1 | 25 | 26.5 | 3.5 | CAtgttatgcacagaAGAT | 36712 |
| 69_1 | 5 | 51.0 | 1.4 | CAtgttatgcacagaAGAT | 36712 |
| 70_1 | 25 | 68.8 | 11.0 | CGctgaagaactaagtATTA | 37282 |
| 70_1 | 5 | 75.2 | 6.7 | CGctgaagaactaagtATTA | 37282 |
| 71_1 | 25 | 36.5 | 5.1 | CAAacagatggtggtgaTA | 37870 |
| 71_1 | 5 | 66.3 | 6.4 | CAAacagatggtggtgaTA | 37870 |
| 72_1 | 25 | 62.8 | 9.4 | AGTagccattaggaTG | 38478 |
| 72_1 | 5 | 80.2 | 3.1 | AGTagccattaggaTG | 38478 |
| 73_1 | 25 | 59.9 | 11.1 | ATacacaggctccataATA | 39639 |
| 73_1 | 5 | 70.6 | 9.5 | ATacacaggctccataATA | 39639 |
| 74_1 | 25 | 34.5 | 9.7 | GATUttgtatagtccacAA | 40178 |
| 74_1 | 5 | 43.3 | 6.9 | GATUttgtatagtccacAA | 40178 |
| 75_1 | 25 | 59.8 | 0.2 | GCatctataaaaaaggGACA | 41042 |
| 75_1 | 5 | 68.1 | 2.9 | GCatctataaaaaaggGACA | 41042 |
| 76_1 | 25 | 50.0 | 1.8 | AGtgcaagtatcGCT | 41734 |
| 76_1 | 5 | 73.2 | 0.1 | AGtgcaagtatcGCT | 41734 |
| 77_1 | 25 | 45.8 | 3.2 | CCAaaagaatcaagttcgTA | 42442 |
| 77_1 | 5 | 75.0 | 14.2 | CCAaaagaatcaagttcgTA | 42442 |
| 78_1 | 25 | 56.1 | 4.5 | CCtcagaccaaatttATTT | 43203 |
| 78_1 | 5 | 85.1 | 1.8 | CCtcagaccaaatttATTT | 43203 |
| 79_1 | 25 | 27.1 | 3.4 | TTCaacaagcatctattGTA | 43663 |
| 79_1 | 5 | 43.3 | 1.1 | TTCaacaagcatctattGTA | 43663 |
| 80_1 | 25 | 4.4 | 1.8 | CAAaggttgttgtacTCT | 44220 |
| 80_1 | 5 | 19.2 | 3.4 | CAAaggttgttgtacTCT | 44220 |
| 81_1 | 25 | 35.9 | 11.3 | TCAtaaatctttttccaCG | 44756 |
| 81_1 | 5 | 67.6 | 0.7 | TCAtaaatctttttccaCG | 44756 |
| 82_1 | 25 | 36.9 | 2.1 | CTtgttacggatttaatGTG | 45042 |

TABLE 14 -continued in vitro efficacy of anti-PAPD5 compounds (single experiment withduplex QPCR). PAPD5 mRNA levels are normalized to GUSB in HeLac ells and shown as % of control (PBS treated cells).

| CMP ID NO | Concentration µM | % mRNA of control Avg | sd | Compound (CMP) | Start on SEQ ID NO 10 |
|---|---|---|---|---|---|
| 82_1 | 5 | 67.5 | 10.5 | CTtgttacggatttaatGTG | 45042 |
| 83_1 | 25 | 59.1 | 8.2 | GCTataaaaatagaaGCC | 46202 |
| 84_1 | 25 | 61.3 | 3.4 | TCCttagcaaactaaaCAT | 47142 |
| 84_1 | 5 | 92.6 | 0.3 | TCCttagcaaactaaaCAT | 47142 |
| 85_1 | 25 | 51.0 | 1.9 | AGCaaaaggcaggtattcAA | 47843 |
| 85_1 | 5 | 92.2 | 5.5 | AGCaaaaggcaggtattcAA | 47843 |
| 86_1 | 25 | 46.6 | 2.8 | GAAtccatttacatattCAC | 48267 |
| 86_1 | 5 | 79.2 | 0.9 | GAAtccatttacatattCAC | 48267 |
| 87_1 | 25 | 49.7 | 0.0 | TCcagtatccaaaacATAC | 49256 |
| 87_1 | 5 | 93.1 | 2.8 | TCcagtatccaaaacATAC | 49256 |
| 88_1 | 25 | 63.4 | 7.0 | AGCTtaaagaagaacggTT | 49688 |
| 88_1 | 5 | 24.2 | 15.8 | AGCTtaaagaagaacggTT | 49688 |
| 89_1 | 25 | 33.3 | 12.3 | CAcaacgtgcctaccTT | 50508 |
| 89_1 | 5 | 71.9 | 32.7 | CAcaacgtgcctaccTT | 50508 |
| 90_1 | 25 | 80.3 | 18.2 | CCAgaatccaagaaaatGG | 50764 |
| 90_1 | 5 | 112.9 | 36.7 | CCAgaatccaagaaaatGG | 50764 |
| 91_1 | 25 | 88.9 | 10.3 | TCacctcgaactaaacaaGT | 51561 |
| 91_1 | 5 | 90.1 | 5.9 | TCacctcgaactaaacaaGT | 51561 |
| 92_1 | 5 | 26.4 | 7.9 | GTatctttctgtacTATT | 52461 |
| 93_1 | 25 | 15.1 | 7.2 | GTCAttctactaacaaaCG | 53305 |
| 93_1 | 5 | 29.7 | 15.4 | GTCAttctactaacaaaCG | 53305 |
| 94_1 | 25 | 48.1 | 20.2 | TGgaaaaggaagaacCATT | 53865 |
| 94_1 | 5 | 42.8 | 34.7 | TGgaaaaggaagaacCATT | 53865 |
| 95_1 | 25 | 59.2 | 3.6 | AAtacaactcttccgTGAT | 54638 |
| 95_1 | 5 | 73.0 | 9.2 | AAtacaactcttccgTGAT | 54638 |
| 96_1 | 25 | 36.8 | nd | AAtaccctgacgagCTG | 54942 |
| 96_1 | 5 | 75.2 | 4.1 | AAtaccctgacgagCTG | 54942 |
| 97_1 | 25 | 40.0 | 20.5 | TCAtaaaacatgatccttGC | 55741 |
| 97_1 | 5 | 96.4 | 3.0 | TCAtaaaacatgatccttGC | 55741 |
| 98_1 | 25 | 55.7 | 1.0 | CTAaagcagatccataGAA | 56277 |
| 98_1 | 5 | 103.3 | 24.2 | CTAaagcagatccataGAA | 56277 |
| 99_1 | 25 | 34.5 | 16.3 | AGActataacttttgctaCA | 56942 |
| 99_1 | 5 | 73.1 | 6.0 | AGActataacttttgctaCA | 56942 |
| 100_1 | 25 | 34.1 | nd | AGcaatgacttgaacataGT | 57369 |
| 100_1 | 5 | 110.9 | 22.8 | AGcaatgacttgaacataGT | 57369 |

TABLE 14 -continued in vitro efficacy of anti-PAPD5 compounds (single experiment withduplex QPCR). PAPD5 mRNA levels are normalized to GUSB in HeLac ells and shown as % of control (PBS treated cells).

| CMP ID NO | Concentration µM | % mRNA of control Avg | sd | Compound (CMP) | Start on SEQ ID NO 10 |
|---|---|---|---|---|---|
| 101_1 | 25 | 87.5 | 16.7 | ATAaaacaagcatacggGC | 58146 |
| 101_1 | 5 | 98.8 | 15.0 | ATAaaacaagcatacggGC | 58146 |
| 102_1 | 25 | 47.2 | 11.2 | ATgagataccagcagatAG | 58588 |
| 102_1 | 5 | 94.0 | 8.9 | ATgagataccagcagatAG | 58588 |
| 103_1 | 25 | 52.0 | 4.5 | AGAAgaaatcctgagtaaTC | 59089 |
| 103_1 | 5 | 72.7 | 0.6 | AGAAgaaatcctgagtaaTC | 59089 |
| 104_1 | 25 | 67.0 | 9.6 | CCCtaaaaagtgacgTA | 59461 |
| 104_1 | 5 | 106.7 | 9.6 | CCCtaaaaagtgacgTA | 59461 |
| 105_1 | 25 | 35.8 | 4.4 | TTAAgttagatcacgGC | 59970 |
| 105_1 | 5 | 54.6 | 9.3 | TTAAgttagatcacgGC | 59970 |
| 106_1 | 25 | 74.8 | 3.5 | GTggatacagaaagCCA | 60738 |
| 106_1 | 5 | 92.6 | 3.2 | GTggatacagaaagCCA | 60738 |
| 107_1 | 25 | 92.2 | 6.9 | GTAtcggcaggagATT | 61038 |
| 107_1 | 5 | 121.5 | 31.7 | GTAtcggcaggagATT | 61038 |
| 108_1 | 25 | 50.2 | 10.6 | TAACtaattgattccattGC | 61868 |
| 108_1 | 5 | 66.4 | 4.6 | TAACtaattgattccattGC | 61868 |
| 109_1 | 25 | 43.3 | 8.4 | AGAagaacggaaattgCC | 62418 |
| 109_1 | 5 | 72.9 | 4.1 | AGAagaacggaaattgCC | 62418 |
| 110_1 | 25 | 59.3 | 0.2 | ATAAtgattttcctatCC | 62822 |
| 110_1 | 5 | 76.0 | 3.6 | ATAAtgattttcctatCC | 62822 |
| 111_1 | 25 | 28.0 | 0.4 | ATggttttgtggagaAGG | 63000 |
| 111_1 | 5 | 11.3 | 10.2 | ATggttttgtggagaAGG | 63000 |
| 112_1 | 25 | 97.4 | 4.2 | TGctgctgtgaaaagaAATG | 63697 |
| 112_1 | 5 | 139.8 | 0.6 | TGctgctgtgaaaagaAATG | 63697 |
| 113_1 | 25 | 83.7 | 7.7 | GTgtccaattttttatTAT | 64377 |
| 113_1 | 5 | 86.7 | 0.4 | GTgtccaattttttatTAT | 64377 |
| 114_1 | 25 | 78.7 | 8.5 | GAtggaatcaactgtgtaGT | 65307 |
| 114_1 | 5 | 38.6 | 17.3 | GAtggaatcaactgtgtaGT | 65307 |
| 115_1 | 25 | 31.4 | 3.6 | GATGgtgacaaattattCT | 65894 |
| 115_1 | 5 | 19.6 | 4.4 | GATGgtgacaaattattCT | 65894 |
| 116_1 | 5 | 21.7 | nd | TGcttttgggaatCTTT | 66650 |
| 117_1 | 25 | 40.8 | 18.6 | GAtgtcctacaatgaacACG | 68024 |
| 117_1 | 5 | 39.4 | 10.3 | GAtgtcctacaatgaacACG | 68024 |
| 118_1 | 25 | 74.2 | 11.3 | GTAcaaggacaaagtaACC | 68732 |
| 118_1 | 5 | 35.4 | 7.7 | GTAcaaggacaaagtaACC | 68732 |

TABLE 14 -continued in vitro efficacy of anti-PAPD5 compounds (single experiment withduplex QPCR). PAPD5 mRNA levels are normalized to GUSB in HeLac ells and shown as % of control (PBS treated cells).

| CMP ID NO | Concentration µM | % mRNA of control Avg | sd | Compound (CMP) | Start on SEQ ID NO 10 |
|---|---|---|---|---|---|
| 119_1 | 25 | 102.8 | 9.8 | TGAAacgcctatctcTA | 69029 |
| 119_1 | 5 | 96.9 | 2.6 | TGAAacgcctatctcTA | 69029 |
| 120_1 | 25 | 56.0 | 2.4 | ATActatttatgcttatgGA | 69796 |
| 120_1 | 5 | 79.7 | 2.5 | ATActatttatgcttatgGA | 69796 |
| 121_1 | 25 | 27.1 | 0.9 | TTGtaatcaaggcaataAGG | 70770 |
| 121_1 | 5 | 56.8 | 3.8 | TTGtaatcaaggcaataAGG | 70770 |
| 122_1 | 25 | 24.4 | 1.4 | GAAGtccaataacgcaGA | 71091 |
| 122_1 | 5 | 63.3 | 14.8 | GAAGtccaataacgcaGA | 71091 |
| 123_1 | 25 | 68.6 | 11.3 | ATAtccaatctctatatgTG | 72013 |
| 123_1 | 5 | 85.3 | 6.3 | ATAtccaatctctatatgTG | 72013 |
| 124_1 | 25 | 83.9 | 0.8 | GCcttacacaagactatATT | 73444 |
| 124_1 | 5 | 77.0 | 43.8 | GCcttacacaagactatATT | 73444 |
| 125_1 | 25 | 93.0 | 7.4 | TGCTgaattttatgttaAC | 73823 |
| 125_1 | 5 | 87.9 | 4.7 | TGCTgaattttatgttaAC | 73823 |
| 126_1 | 25 | 53.9 | 8.5 | CAcaagatgatgggttTAAG | 74559 |
| 126_1 | 5 | 77.5 | 2.5 | CAcaagatgatgggttTAAG | 74559 |
| 127_1 | 25 | 34.7 | 10.4 | TTagtggtttgggtGC | 75043 |
| 127_1 | 5 | 57.6 | 9.4 | TTagtggtttgggtGC | 75043 |
| 128_1 | 25 | 71.7 | nd | AGattgttaccttactGAT | 76110 |
| 128_1 | 5 | 78.9 | 0.6 | AGattgttaccttactGAT | 76110 |
| 129_1 | 25 | 79.0 | 8.9 | TATtacaaatatcaatcTCC | 76931 |
| 129_1 | 5 | 97.7 | nd | TATtacaaatatcaatcTCC | 76931 |
| 130_1 | 25 | 61.9 | 1.5 | TACcaaaagcatagagtGG | 77605 |
| 130_1 | 5 | 84.6 | 1.9 | TACcaaaagcatagagtGG | 77605 |
| 131_1 | 25 | 50.3 | 1.8 | AAttatcttcccgCTAC | 78652 |
| 131_1 | 5 | 64.9 | 13.4 | AAttatcttcccgCTAC | 78652 |

Example 5: Screening for In Vitro Efficacy of Antisense Oligonucleotides Targeting PAPD7

The oligonucleotide screen across the PAPD7 mRNA was conducted essentially as described in Example 4, with the substitution of the TaqMan primer assays for the gene of interest PAPD7 (Hs00173159_m1, FAM-MGB, Life Technologies).

Figure 9:
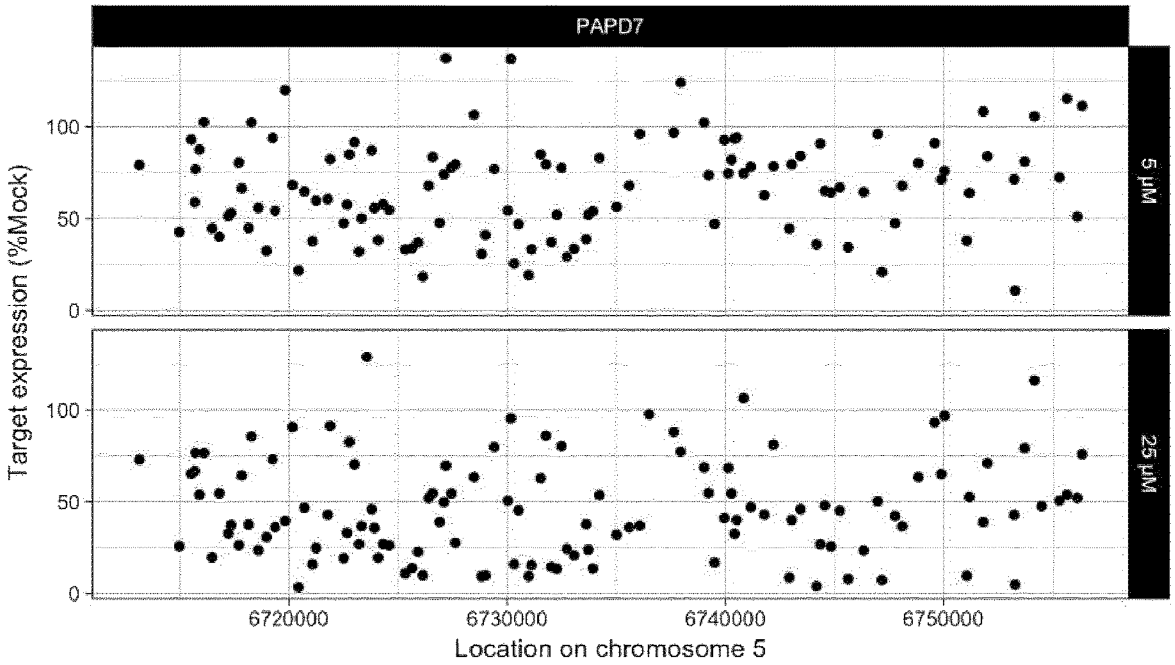
FIG. 9: Representation of the ability of the oligonucleotides, tested in example 5, to reduce the expression of PAPD7 in HeLa cell cultures. Each oligonucleotide is represented by a dot indicating its location on the PAPD7 mRNA by chromosomal position. The oligonucleotide concentrations were 5 and 25 microM as indicated in the right hand side each plot.

The relative PAPD7 mRNA expression level is shown in table 15 as % of average control samples (PBS-treated cells). FIG. 9 presents the target knockdown achieved with the individual oligonucleotide compounds across the PAPAD5 encoding sequence.

TABLE 15 in vitro efficacy of anti-PAPD7 compounds (single experiment with duplex QPCR). PAPD5 mRNA levels are normalized to GUSB in HeLa cells and shown as % of control (PBS treated cells).

| CMP ID NO | Concentration uM | % mRNA of control Avg | sd | Compound (CMP) | Start on SEQ ID NO 10 |
|---|---|---|---|---|---|
| 132_1 | 25 | 72.8 | 4.0 | GTtgggtggaataggCA | 132 |
| 132_1 | 5 | 79.1 | 0.3 | GTtgggtggaataggCA | 132 |
| 133_1 | 25 | 25.6 | 1.4 | TCgatttcccgttccAA | 1962 |
| 133_1 | 5 | 42.7 | 0.7 | TCgatttcccgttccAA | 1962 |
| 134_1 | 25 | 65.2 | 2.3 | ACAacctacacataaattGC | 2510 |
| 134_1 | 5 | 93.0 | 1.1 | ACAacctacacataaattGC | 2510 |
| 135_1 | 25 | 66.7 | 0.6 | ACtataagaactcccAACA | 2668 |
| 135_1 | 5 | 58.9 | 13.0 | ACtataagaactcccAACA | 2668 |
| 136_1 | 25 | 76.6 | 5.0 | GAGAaaaagagttacaaGC | 2695 |
| 136_1 | 5 | 76.8 | 16.6 | GAGAaaaagagttacaaGC | 2695 |
| 137_1 | 25 | 53.7 | 12.7 | AACTggagggagagaagAG | 2883 |
| 137_1 | 5 | 87.5 | 20.1 | AACTggagggagagaagAG | 2883 |
| 138_1 | 25 | 76.5 | 2.2 | TTtctaagagcagaggtACA | 3090 |
| 138_1 | 5 | 102.6 | 44.0 | TTtctaagagcagaggtACA | 3090 |
| 139_1 | 25 | 19.6 | 0.2 | AGAAgtaacaagagcCT | 3463 |
| 139_1 | 5 | 44.6 | 20.4 | AGAAgtaacaagagcCT | 3463 |
| 140_1 | 25 | 54.6 | 3.0 | AGtatcaaaccagacCTC | 3795 |
| 140_1 | 5 | 39.9 | 9.9 | AGtatcaaaccagacCTC | 3795 |
| 141_1 | 25 | 32.6 | 5.1 | CCACaaccgaaagacTT | 4205 |
| 141_1 | 5 | 51.2 | 1.9 | CCACaaccgaaagacTT | 4205 |
| 142_1 | 25 | 37.2 | 3.1 | AAtacacactgcattTTCA | 4336 |
| 142_1 | 5 | 53.1 | 1.7 | AAtacacactgcattTTCA | 4336 |
| 143_1 | 25 | 26.2 | 6.0 | CCaggtagatagcacAG | 4686 |
| 143_1 | 5 | 80.5 | 4.2 | CCaggtagatagcacAG | 4686 |
| 144_1 | 25 | 64.2 | 4.8 | CCatgacaaagtaacaACAG | 4821 |
| 144_1 | 5 | 66.4 | 0.7 | CCatgacaaagtaacaACAG | 4821 |
| 145_1 | 25 | 37.4 | 3.1 | CAgaatttcctttgagTTA | 5134 |
| 145_1 | 5 | 44.8 | 4.7 | CAgaatttcctttgagTTA | 5134 |
| 146_1 | 25 | 85.5 | 4.1 | CCttcgcaagaaagaattGA | 5263 |
| 146_1 | 5 | 102.4 | 4.7 | CCttcgcaagaaagaattGA | 5263 |

TABLE 15 -continued in vitro efficacy of anti-PAPD7 compounds (single experiment with duplex QPCR). PAPD5 mRNA levels are normalized to GUSB in HeLa cells and shown as % of control (PBS treated cells).

| CMP ID NO | Concentration uM | % mRNA of control Avg | sd | Compound (CMP) | Start on SEQ ID NO 10 |
|---|---|---|---|---|---|
| 147_1 | 25 | 23.5 | 2.3 | TCatacatacacgcttCT | 5577 |
| 147_1 | 5 | 55.8 | 6.5 | TCatacatacacgcttCT | 5577 |
| 148_1 | 25 | 30.6 | 5.8 | TGcgaaaagattgGAGG | 5945 |
| 148_1 | 5 | 32.4 | 5.1 | TGcgaaaagattgGAGG | 5945 |
| 149_1 | 25 | 72.9 | 11.4 | CAcaggacgcttacatgaAT | 6235 |
| 149_1 | 5 | 93.9 | 15.5 | CAcaggacgcttacatgaAT | 6235 |
| 150_1 | 25 | 36.1 | 2.0 | GCTgttttttttcttaAC | 6352 |
| 150_1 | 5 | 54.3 | 10.9 | GCTgttttttttcttaAC | 6352 |
| 151_1 | 25 | 39.5 | 2.5 | ACcataagtgagtgttCTT | 6834 |
| 151_1 | 5 | 120.0 | 8.9 | ACcataagtgagtgttCTT | 6834 |
| 152_1 | 25 | 90.6 | 9.7 | ACacaagcccatagaaacAG | 7158 |
| 152_1 | 5 | 68.2 | 7.9 | ACacaagcccatagaaacAG | 7158 |
| 153_1 | 25 | 3.4 | 0.2 | CAgtagtaaccacCAAG | 7447 |
| 153_1 | 5 | 21.6 | 4.8 | CAgtagtaaccacCAAG | 7447 |
| 154_1 | 25 | 46.6 | 0.7 | CCtgcaaacttttattTAT | 7708 |
| 154_1 | 5 | 64.7 | 3.1 | CCtgcaaacttttattTAT | 7708 |
| 155_1 | 25 | 15.7 | 1.3 | ACttagtaatagcaGCA | 8074 |
| 155_1 | 5 | 37.6 | 2.1 | ACttagtaatagcaGCA | 8074 |
| 156_1 | 25 | 24.7 | 0.3 | ATgaatactccgaagACTT | 8249 |
| 156_1 | 5 | 59.8 | 3.1 | ATgaatactccgaagACTT | 8249 |
| 157_1 | 25 | 42.7 | 5.2 | AAAgaaaaggatcacaaGCC | 8784 |
| 157_1 | 5 | 60.5 | 3.2 | AAAgaaaaggatcacaaGCC | 8784 |
| 158_1 | 25 | 91.4 | 19.9 | AGAcagaaatcacctaaCA | 8887 |
| 158_1 | 5 | 82.3 | 4.9 | AGAcagaaatcacctaaCA | 8887 |
| 159_1 | 25 | 19.2 | 2.4 | TAGaacagacattattcATC | 9506 |
| 159_1 | 5 | 47.4 | 10.0 | TAGaacagacattattcATC | 9506 |
| 160_1 | 25 | 33.0 | 5.2 | AGttacacggagcagcAC | 9664 |
| 160_1 | 5 | 57.4 | 3.6 | AGttacacggagcagcAC | 9664 |
| 161_1 | 25 | 82.6 | 22.1 | CACtatacacagaacacTAT | 9770 |
| 161_1 | 5 | 85.0 | 7.0 | CACtatacacagaacacTAT | 9770 |
| 162_1 | 25 | 70.4 | 2.3 | AGctgtctaaatacATGG | 10000 |
| 162_1 | 5 | 91.7 | 16.8 | AG ctgtctaaatacATGG | 10000 |
| 163_1 | 25 | 26.7 | 0.6 | ATGaacctattttatgcTTC | 10206 |
| 163_1 | 5 | 31.9 | 1.8 | ATGaacctattttatgcTTC | 10206 |
| 164_1 | 25 | 36.5 | 5.5 | ACcatcattaacctgcGT | 10318 |

TABLE 15 -continued in vitro efficacy of anti-PAPD7 compounds (single experiment with duplex QPCR). PAPD5 mRNA levels are normalized to GUSB in HeLa cells and shown as % of control (PBS treated cells).

| CMP ID NO | Concentration uM | % mRNA of control Avg | sd | Compound (CMP) | Start on SEQ ID NO 10 |
|---|---|---|---|---|---|
| 164_1 | 5 | 50.0 | 0.5 | ACcatcattaacctgcGT | 10318 |
| 165_1 | 25 | 129.2 | 5.9 | AGtaaagtgcccagatGT | 10568 |
| 166_1 | 25 | 45.8 | 3.3 | TTCcctatgaaatcctcAA | 10781 |
| 166_1 | 5 | 87.1 | 14.5 | TTCcctatgaaatcctcAA | 10781 |
| 167_1 | 25 | 35.6 | 2.8 | CActcttcatagaatgCAAC | 10917 |
| 167_1 | 5 | 55.6 | 9.1 | CActcttcatagaatgCAAC | 10917 |
| 168_1 | 25 | 19.4 | 4.9 | AAtgcttaatttttctCTCT | 11084 |
| 168_1 | 5 | 38.2 | 1.9 | AAtgcttaatttttctCTCT | 11084 |
| 169_1 | 25 | 26.8 | 4.1 | TTAgagacgatgcctatAAC | 11308 |
| 169_1 | 5 | 57.6 | 2.5 | TTAgagacgatgcctatAAC | 11308 |
| 170_1 | 25 | 26.1 | 2.2 | TGAAtagttcccatagaTT | 11585 |
| 170_1 | 5 | 54.7 | 1.8 | TGAAtagttcccatagaTT | 11585 |
| 171_1 | 25 | 10.8 | 0.6 | CAGcataattgttttcTTT | 12330 |
| 171_1 | 5 | 33.1 | 1.3 | CAGcataattgttttcTTT | 12330 |
| 172_1 | 25 | 13.8 | 2.2 | ATGTcattatgllttagTT | 12634 |
| 172_1 | 5 | 33.8 | 3.1 | ATGTcattatgllttagTT | 12634 |
| 173_1 | 25 | 22.6 | 2.5 | CAgcagtatctcttaGAA | 12902 |
| 173_1 | 5 | 36.8 | 1.8 | CAgcagtatctcttaGAA | 12902 |
| 174_1 | 25 | 9.7 | 0.4 | CGgtaagggttcggTG | 13126 |
| 174_1 | 5 | 18.2 | 0.0 | CGgtaagggttcggTG | 13126 |
| 175_1 | 25 | 51.9 | 3.5 | CATGaaccacattaggaAC | 13383 |
| 175_1 | 5 | 67.8 | 15.0 | CATGaaccacattaggaAC | 13383 |
| 176_1 | 25 | 54.6 | 0.0 | CAttcaacacacacgACAA | 13578 |
| 176_1 | 5 | 83.5 | 0.3 | CAttcaacacacacgACAA | 13578 |
| 177_1 | 25 | 38.9 | 1.1 | AAgtatccaagactcAAGA | 13889 |
| 177_1 | 5 | 47.6 | 3.4 | AAgtatccaagactcAAGA | 13889 |
| 178_1 | 25 | 49.8 | 9.4 | CCACagaaacaccgAG | 14100 |
| 178_1 | 5 | 74.0 | 21.3 | CCACagaaacaccgAG | 14100 |
| 179_1 | 25 | 69.6 | 0.2 | TGGaaaagggaagggaaGA | 14179 |
| 179_1 | 5 | 137.8 | 15.7 | TGGaaaagggaagggaaGA | 14179 |
| 180_1 | 25 | 54.5 | 0.1 | AGagagtccgaagccTG | 14432 |
| 180_1 | 5 | 77.7 | 18.8 | AGagagtccgaagccTG | 14432 |
| 181_1 | 25 | 27.6 | 5.5 | ATGggaaaggtaacgaGC | 14616 |
| 181_1 | 5 | 79.5 | nd | ATGggaaaggtaacgaGC | 14616 |
| 182_1 | 25 | 63.3 | 1.9 | CTAtcctacaagtccgAA | 15471 |

TABLE 15 -continued in vitro efficacy of anti-PAPD7 compounds (single experiment with duplex QPCR). PAPD5 mRNA levels are normalized to GUSB in HeLa cells and shown as % of control (PBS treated cells).

| CMP | Concentration | % mRNA of control | | | Start on |
|---|---|---|---|---|---|
| ID NO | uM | Avg | sd | Compound (CMP) | SEQ ID NO 10 |
| 182_1 | 5 | 106.6 | 12.5 | CTAtcctacaagtccgAA | 15471 |
| 183_1 | 25 | 9.2 | 0.6 | CATTgcttttataatccTA | 15816 |
| 183_1 | 5 | 30.6 | 3.1 | CATTgcttttataatccTA | 15816 |
| 184_1 | 25 | 9.7 | 1.0 | CTTTttaaggacaggaGG | 15988 |
| 184_1 | 5 | 40.9 | 0.7 | CTTTttaaggacaggaGG | 15988 |
| 185_1 | 25 | 79.7 | 0.2 | GAtgaaagataagtgaGCAT | 16395 |
| 185_1 | 5 | 76.9 | 2.5 | GAtgaaagataagtgaGCAT | 16395 |
| 186_1 | 25 | 50.5 | 17.3 | GAagcctgtaataattAAGC | 17007 |
| 186_1 | 5 | 54.4 | 10.9 | GAagcctgtaataattAAGC | 17007 |
| 187_1 | 25 | 95.4 | 6.2 | CACCctagtaaagcaaAC | 17151 |
| 187_1 | 5 | 137.3 | 37.9 | CACCctagtaaagcaaAC | 17151 |
| 188_1 | 25 | 15.8 | 2.5 | GCAaatgtaagcctttTT | 17303 |
| 188_1 | 5 | 25.3 | 0.4 | GCAaatgtaagcctttTT | 17303 |
| 189_1 | 25 | 45.4 | 2.3 | ACctgacagctaccgAC | 17498 |
| 189_1 | 5 | 46.8 | 12.3 | ACctgacagctaccgAC | 17498 |
| 190_1 | 25 | 9.3 | 1.5 | AAgagtgggttgtaAGC | 17963 |
| 190_1 | 5 | 19.1 | 2.0 | AAgagtgggttgtaAGC | 17963 |
| 191_1 | 25 | 15.3 | 2.6 | TAgtgaaaatatttggAGTT | 18101 |
| 191_1 | 5 | 33.2 | 4.5 | TAgtgaaaatatttggAGTT | 18101 |
| 192_1 | 25 | 62.7 | 7.6 | TTtcagcaccttaaacCC | 18518 |
| 192_1 | 5 | 84.9 | 12.6 | TTtcagcaccttaaacCC | 18518 |
| 193_1 | 25 | 86.0 | 24.0 | TTAAgggaaaggaaacgtCA | 18747 |
| 193_1 | 5 | 79.5 | 6.2 | TTAAgggaaaggaaacgtCA | 18747 |
| 194_1 | 25 | 14.4 | 1.0 | GTAggtaaagggcaaaggAA | 19007 |
| 194_1 | 5 | 37.1 | 4.6 | GTAggtaaagggcaaaggAA | 19007 |
| 195_1 | 25 | 13.4 | 0.5 | GTgaattaaagccaAAGC | 19252 |
| 195_1 | 5 | 51.9 | 9.1 | GTgaattaaagccaAAGC | 19252 |
| 196_1 | 25 | 80.3 | 21.3 | TGTUttgtattttagTAT | 19476 |
| 196_1 | 5 | 77.5 | 23.0 | TGTUttgtattttagTAT | 19476 |
| 197_1 | 25 | 24.2 | 1.1 | GAggtttlltttagtgAATT | 19722 |
| 197_1 | 5 | 29.0 | 2.4 | GAggtttlltttagtgAATT | 19722 |
| 198_1 | 25 | 20.6 | 1.7 | GAGgagctaaacggaCA | 20062 |
| 198_1 | 5 | 33.4 | 6.4 | GAGgagctaaacggaCA | 20062 |
| 199_1 | 25 | 37.7 | 4.0 | GTttagtcttatgttctcAC | 20623 |
| 199_1 | 5 | 38.8 | 5.6 | GTttagtcttatgttctcAC | 20623 |

TABLE 15 -continued in vitro efficacy of anti-PAPD7 compounds (single experiment with duplex QPCR). PAPD5 mRNA levels are normalized to GUSB in HeLa cells and shown as % of control (PBS treated cells).

| CMP ID NO | Concentration uM | % mRNA of control Avg | sd | Compound (CMP) | Start on SEQ ID NO 10 |
|---|---|---|---|---|---|
| 200_1 | 25 | 23.8 | 2.1 | CAaatactgaatatgcCCG | 20726 |
| 200_1 | 5 | 52.0 | 10.0 | CAaatactgaatatgcCCG | 20726 |
| 201_1 | 25 | 13.6 | 0.4 | ACCatttaaatcgccAAC | 20926 |
| 201_1 | 5 | 54.0 | 8.8 | ACCatttaaatcgccAAC | 20926 |
| 202_1 | 25 | 53.5 | 2.6 | CAgtaagagtagcccaacAA | 21234 |
| 202_1 | 5 | 82.9 | 0.9 | CAgtaagagtagcccaacAA | 21234 |
| 203_1 | 25 | 31.9 | 8.8 | TAACggcaacatcaaataGC | 22017 |
| 203_1 | 5 | 56.3 | 4.2 | TAACggcaacatcaaataGC | 22017 |
| 204_1 | 25 | 35.9 | 5.8 | ACtgagcaccaactaCAC | 22592 |
| 204_1 | 5 | 67.9 | 10.4 | ACtgagcaccaactaCAC | 22592 |
| 205_1 | 25 | 36.8 | 1.7 | CCtaattttatgtatcACAT | 23074 |
| 205_1 | 5 | 96.2 | 8.4 | CCtaattttatgtatcACAT | 23074 |
| 206_1 | 25 | 97.7 | 1.3 | CTAGgaattataacaaatCA | 23462 |
| | | | | | 23509 |
| 207_1 | 25 | 88.0 | 17.6 | ACtccaaagaacatacTCAC | 24628 |
| 207_1 | 5 | 97.0 | 4.8 | ACtccaaagaacatacTCAC | 24628 |
| 208_1 | 25 | 77.3 | 18.8 | TAAgagaaacaatcacaCCA | 24935 |
| 208_1 | 5 | 124.2 | 2.5 | TAAgagaaacaatcacaCCA | 24935 |
| 209_1 | 25 | 68.6 | 6.7 | TGtcctaaaatatcagCAG | 26022 |
| 209_1 | 5 | 102.4 | 4.6 | TGtcctaaaatatcagCAG | 26022 |
| 210_1 | 25 | 54.8 | 0.4 | CTtttaatgagacagtgCA | 26212 |
| 210_1 | 5 | 73.6 | 1.8 | CTtttaatgagacagtgCA | 26212 |
| 211_1 | 25 | 16.7 | 1.1 | TTGTagcataagatggaaAG | 26500 |
| 211_1 | 5 | 47.0 | 1.3 | TTGTagcataagatggaaAG | 26500 |
| 212_1 | 25 | 41.0 | 0.2 | AAActgtagccaataacTGT | 26945 |
| 212_1 | 5 | 92.7 | 9.4 | AAActgtagccaataacTGT | 26945 |
| 213_1 | 25 | 68.3 | 1.6 | ATtcatcctaacacaagTAG | 27117 |
| 213_1 | 5 | 74.6 | 6.7 | ATtcatcctaacacaagTAG | 27117 |
| 214_1 | 25 | 54.5 | 0.3 | CACGaaaggaacagctaAG | 27264 |
| 214_1 | 5 | 82.0 | 13.5 | CACGaaaggaacagctaAG | 27264 |
| 215_1 | 25 | 32.4 | 1.7 | ACAAcaggcaagtaCC | 27411 |
| 215_1 | 5 | 93.5 | 2.7 | ACAAcaggcaagtaCC | 27411 |
| 216_1 | 25 | 40.0 | 2.5 | GCTaaacactataagGAT | 27505 |
| 216_1 | 5 | 94.1 | 0.1 | GCTaaacactataagGAT | 27505 |
| 217_1 | 25 | 106.4 | 4.9 | CCcgtaagcatttgagAA | 27831 |

TABLE 15 -continued in vitro efficacy of anti-PAPD7 compounds (single experiment with duplex QPCR). PAPD5 mRNA levels are normalized to GUSB in HeLa cells and shown as % of control (PBS treated cells).

| CMP ID NO | Concentration uM | % mRNA of control Avg | sd | Compound (CMP) | Start on SEQ ID NO 10 |
|---|---|---|---|---|---|
| 217_1 | 5 | 74.6 | 2.5 | CCcgtaagcatttgagAA | 27831 |
| 218_1 | 25 | 47.0 | 1.4 | AGccaatatgcgacagtaAC | 28146 |
| 218_1 | 5 | 78.1 | 2.2 | AGccaatatgcgacagtaAC | 28146 |
| 219_1 | 25 | 42.8 | 0.3 | TAAccaaaacaatcagtGTC | 28777 |
| 219_1 | 5 | 62.6 | 1.1 | TAAccaaaacaatcagtGTC | 28777 |
| 220_1 | 25 | 81.1 | 20.6 | AACagggaacaggagTTA | 29195 |
| 220_1 | 5 | 78.4 | 3.3 | AACagggaacaggagTTA | 29195 |
| 221_1 | 25 | 8.6 | 1.3 | ATttatcaacttcCACC | 29906 |
| 221_1 | 5 | 44.4 | 7.4 | ATttatcaacttcCACC | 29906 |
| 222_1 | 25 | 40.0 | 1.7 | CGTTtaagaccaggcAC | 30020 |
| 222_1 | 5 | 79.5 | 8.0 | CGTTtaagaccaggcAC | 30020 |
| 223_1 | 25 | 45.9 | 6.2 | ACAaaggaactcaggaagAG | 30424 |
| 223_1 | 5 | 84.1 | 9.3 | ACAaaggaactcaggaagAG | 30424 |
| 224_1 | 25 | 3.8 | 0.0 | TCACagacaagcaccAA | 31150 |
| 224_1 | 5 | 35.8 | 0.3 | TCACagacaagcaccAA | 31150 |
| 225_1 | 25 | 26.7 | 1.0 | TACTttttaaaacacgtaGG | 31329 |
| 225_1 | 5 | 90.9 | 3.5 | TACTttttaaaacacgtaGG | 31329 |
| 226_1 | 25 | 47.9 | 0.4 | GCACaatcacaaagaccAA | 31531 |
| 226_1 | 5 | 65.0 | 9.4 | GCACaatcacaaagaccAA | 31531 |
| 227_1 | 25 | 25.4 | 0.6 | TCagtaaagaacagaGGC | 31820 |
| 227_1 | 5 | 64.2 | 1.5 | TCagtaaagaacagaGGC | 31820 |
| 228_1 | 25 | 45.1 | 2.0 | CAtatttccaccacacaAG | 32222 |
| 228_1 | 5 | 66.9 | 5.1 | CAtatttccaccacacaAG | 32222 |
| 229_1 | 25 | 7.8 | 0.9 | AGtaaaccactgtCCA | 32601 |
| 229_1 | 5 | 34.2 | 2.7 | AGtaaaccactgtCCA | 32601 |
| 230_1 | 25 | 23.4 | 1.2 | TCctctttggcgatATA | 33337 |
| 230_1 | 5 | 64.4 | 3.6 | TCctctttggcgatATA | 33337 |
| 231_1 | 25 | 50.2 | 4.4 | CAtaaatacccctgaaTAC | 33986 |
| 231_1 | 5 | 96.2 | 6.9 | CAtaaatacccctgaaTAC | 33986 |
| 232_1 | 25 | 7.2 | 0.8 | CGATtttatcaccaaCA | 34175 |
| 232_1 | 5 | 20.8 | 2.3 | CGATtttatcaccaaCA | 34175 |
| 233_1 | 25 | 42.1 | 1.5 | ACaatcaggttaagtgtgGA | 34771 |
| 233_1 | 5 | 47.4 | 7.5 | ACaatcaggttaagtgtgGA | 34771 |
| 234_1 | 25 | 36.5 | 14.4 | GAAgccaaagactacCA | 35096 |
| 234_1 | 5 | 67.8 | 4.2 | GAAgccaaagactacCA | 35096 |

TABLE 15 -continued in vitro efficacy of anti-PAPD7 compounds (single experiment with duplex QPCR). PAPD5 mRNA levels are normalized to GUSB in HeLa cells and shown as % of control (PBS treated cells).

| CMP ID NO | Concentration uM | % mRNA of control Avg | sd | Compound (CMP) | Start on SEQ ID NO 10 |
|---|---|---|---|---|---|
| 235_1 | 25 | 63.4 | 6.2 | TGgtagggactgaatttTAA | 35850 |
| 235_1 | 5 | 80.3 | 0.4 | TGgtagggactgaatttTAA | 35850 |
| 236_1 | 25 | 93.2 | 3.6 | CGgtagtcaatcACC | 36584 |
| 236_1 | 5 | 91.2 | 12.4 | CGgtagtcaatcACC | 36584 |
| 237_1 | 25 | 65.0 | 13.9 | CTatcaaaattatttcACCT | 36886 |
| 237_1 | 5 | 71.2 | 6.8 | CTatcaaaattatttcACCT | 36886 |
| 238_1 | 25 | 96.9 | 0.6 | ACGaaaatttagcatccTAA | 37041 |
| 238_1 | 5 | 75.9 | 13.5 | ACGaaaatttagcatccTAA | 37041 |
| 239_1 | 25 | 9.5 | 1.7 | TGgtaaacactggGC | 38059 |
| 239_1 | 5 | 37.9 | 1.5 | TGgtaaacactggGC | 38059 |
| 240_1 | 25 | 52.4 | 0.7 | GATtgttggttgtcATG | 38173 |
| 240_1 | 5 | 63.9 | 3.4 | GATtgttggttgtcATG | 38173 |
| 241_1 | 25 | 38.8 | 0.7 | AATtataccccacatttCA | 38806 |
| 241_1 | 5 | 108.3 | 7.0 | AATtataccccacatttCA | 38806 |
| 242_1 | 25 | 71.1 | 1.1 | TGcaattagacacgtTACG | 39004 |
| 242_1 | 5 | 83.9 | 3.6 | TGcaattagacacgtTACG | 39004 |
| 243_1 | 25 | 42.7 | 2.6 | GGCAaccaattaaacTA | 40226 |
| 243_1 | 5 | 71.3 | 1.9 | GGCAaccaattaaacTA | 40226 |
| 244_1 | 25 | 4.6 | 0.9 | CAGTtttatgctaatCA | 40272 |
| 244_1 | 5 | 10.6 | 1.7 | CAGTtttatgctaatCA | 40272 |
| 245_1 | 25 | 79.2 | 7.3 | GCaaaggaggagcggaatAA | 40707 |
| 245_1 | 5 | 81.1 | 7.2 | GCaaaggaggagcggaatAA | 40707 |
| 246_1 | 25 | 116.1 | 0.8 | AAacagaagtaagaagGTCC | 41156 |
| 246_1 | 5 | 105.7 | 10.4 | AAacagaagtaagaagGTCC | 41156 |
| 247_1 | 25 | 47.5 | 5.3 | TCcacttatccataGAAA | 41477 |
| 248_1 | 25 | 50.6 | 3.5 | GCtttgacgaacaggaAAT | 42282 |
| 248_1 | 5 | 72.3 | 0.8 | GCtttgacgaacaggaAAT | 42282 |
| 249_1 | 25 | 53.7 | 2.7 | TTCCgaccaaaagaaaagAC | 42632 |
| 249_1 | 5 | 115.4 | 21.3 | TTCCgaccaaaagaaaagAC | 42632 |
| 250_1 | 25 | 51.9 | 0.3 | GCGacacgatccgttaAA | 43104 |
| 250_1 | 5 | 50.9 | 3.1 | GCGacacgatccgttaAA | 43104 |
| 251_1 | 25 | 75.9 | 2.7 | CCCCgttttaaaaAC | 43334 |
| 251_1 | 5 | 111.5 | 3.0 | CCCCgttttaaaaAC | 43334 |

Example 6: Effect on HBV Infected dHepaRG Cells Using Selected Antisense Oligonucleotides Targeting PAPD5 or PAPD7 Delivered to the Cells by Gymnosis A selection of the most efficacious oligonucleotides from Example 4 and 5 were selected to test their effect on HBV propagation parameters in HBV infected dHepaRG cells.

HBV infected dHepaRG cells (described in the Materials and Methods section, HBV infection of dHepaRG cells) were cultured in 96-well plates. One day post HBV infection 20 μM of oligonucleotide was delivered to the cells using unassisted uptake (gymnosis). A total of 40 oligonucleotides were tested, 20 targeting PAPD5 and 20 targeting PAPD7. The experiments were conducted in triplicate, with PBS controls. The oligonucleotide treatment was repeated at day 4 and 7 including medium replacement (this differs from the every 2 day replacement described in the Materials and Method section).

At day 11 post-infection, supernatants were harvested and HBsAg and HBeAg levels were assessed using the CLIA ELISA assay (see Materials and Methods, HBV antigen measurements). Cell viability was measured as described in the Materials and Method section, Cell viability. mRNA was extracted from the cells using a MagNA Pure robot and the MagNA Pure 96 Cellular RNA Large Volume Kit (Roche, #05467535001) according to the manufacturer's protocol. HBV mRNA and PAPD5 or PAPD7 mRNA was quantified in technical duplicate by qPCR using a QuantStudio 12K Flex (Applied Biosystems), the TaqMan RNA-to-CT 1-Step Kit (Applied Biosystems, #4392938), Human ACTB endogenous control (Applied Biosystems, #4310881E). Taqman reagents were used together with the following commercial ThermoFisher Scientific primers (HBV Pa03453406_s1; PAPD5 Hs00900790_m1; and PAPD7 Hs00173159_m1). The mRNA expression was analyzed using the comparative cycle threshold 2-ΔΔCt method normalized to the reference gene ACTB (ThermoFisher Scientific 4310881 E) and to PBS treated cells.

The effects of the oligonucleotide treatment on the PAPD5 or PAPD7 mRNA as well as the effect on the HBV propagation parameter HBsAg are shown in Table 16 and Table 17.

TABLE 16 in vitro effect of PAPD5 targeting compounds on target mRNA and HBsAg (average of 3)

| CMP ID NO | % mRNA inhibition Avg | sd | % HBsAg Inhibition Avg | sd | Compound (CMP) | Start on SEQ ID NO 10 |
|---|---|---|---|---|---|---|
| 15_1 | 79.1 | 8.5 | -9.7 | 5.7 | AATagcaagtagaggaGAG | 3059 |
| 18_1 | 94.0 | 1.6 | -5.3 | 6.0 | GTaatacctctcacATTC | 5928 |
| 23_1 | 95.9 | 0.8 | 45.8 | 3.9 | AGgcttccattttattGAA | 8625 |
| 25_1 | 98.5 | 0.3 | 4.4 | 7.1 | GTAttcttattcttgCT | 10254 |
| 26_1 | 97.5 | 0.4 | 20.9 | 7.0 | ATTAttcccacagtaaGA | 10881 |
| 30_1 | 89.2 | 3.5 | -13.2 | 1.9 | CCAgagtaaacaaaTCC | 12718 |
| 32_1 | 93.6 | 1.1 | 0.8 | 12.0 | TTTggtaattctttttTAG | 14297 |
| 39_1 | 72.1 | 5.6 | -19.4 | 9.9 | GTtaggattttgcTATG | 18299 |

TABLE 16 -continued in vitro effect of PAPD5 targeting compounds on target mRNA and HBsAg (average of 3)

| CMP ID NO | % mRNA inhibition Avg | sd | % HBsAg Inhibition Avg | sd | Compound (CMP) | Start on SEQ ID NO 10 |
|---|---|---|---|---|---|---|
| 54_1 | 91.0 | 1.6 | 5.2 | 4.9 | TTCAacctttactgcAT | 27813 |
| 56_1 | 95.6 | 1.0 | 5.5 | 6.6 | CAgtaggaatgtggCTT | 28718 |
| 58_1 | 82.2 | 2.6 | -18.6 | 17.5 | TCactgttaaaccTCAC | 29902 |
| 65_1 | 51.1 | 6.0 | -36.8 | 15.4 | TTCAcaacaggtaaagGG | 33593 |
| 80_1 | 89.4 | 1.6 | 9.4 | 9.9 | CAAaggttgttgtacTCT | 44220 |
| 88_1 | 22.6 | 10.7 | -20.1 | 13.8 | AGCTtaaagaagaacggTT | 49688 |
| 92_1 | 93.1 | 1.7 | -8.1 | 6.5 | GTatctttctgtacTATT | 52461 |
| 93_1 | 67.3 | 5.5 | -14.8 | 2.5 | GTCAttctactaacaaaCG | 53305 |
| 111_1 | 72.0 | 4.6 | -27.6 | 8.7 | ATggttttgtggagaAGG | 63000 |
| 115_1 | 61.7 | 6.9 | 25.8 | 9.4 | GATGgtgacaaattattCT | 65894 |
| 116_1 | 97.2 | 0.7 | 11.2 | 9.5 | TGcttttgggaatCTTT | 66650 |
| 118_1 | 44.4 | 15.0 | -24.2 | 24.1 | GTAcaaggacaaagtaACC | 68732 |

TABLE 17 in vitro effect of PAPD7 targeting compounds on target mRNA and HBsAg Average of 3).

| CMP ID NO | % mRNA inhibition Avg | sd | % HBsAg Inhibition Avg | sd | Compound (CMP) | Start on SEQ ID NO 11 |
|---|---|---|---|---|---|---|
| 153_1 | 87.5 | 2.1 | -32.3 | 9.5 | CAgtagtaaccacCAAG | 7447 |
| 155_1 | 83.6 | 3.0 | -35.8 | 13.5 | ACttagtaatagcaGCA | 8074 |
| 168_1 | 96.0 | 1.0 | -45.2 | 9.5 | AAtgcttaatttttctCTCT | 11084 |
| 171_1 | 96.3 | 0.8 | -34.4 | 15.3 | CAGcataattgttttcTTT | 12330 |
| 172_1 | 96.0 | 0.8 | -45.0 | 12.5 | ATGTcattatgttttagTT | 12634 |
| 174_1 | 87.0 | 1.5 | -28.8 | 4.8 | CGgtaagggttcggTG | 13126 |
| 183_1 | 96.3 | 0.7 | -31.7 | 11.6 | CATTgcttttataatccTA | 15816 |
| 184_1 | 85.3 | 1.9 | -46.6 | 11.2 | CTTTttaaggacaggaGG | 15988 |
| 188_1 | 89.2 | 0.8 | -34.8 | 20.7 | GCAaatgtaagcctttTT | 17303 |
| 190_1 | 92.0 | 0.9 | -31.5 | 15.7 | AAgagtgggttgtaAGC | 17963 |
| 191_1 | 93.4 | 0.4 | -36.2 | 21.8 | TAgtgaaaatatttggAGTT | 18101 |
| 194_1 | 65.4 | 4.0 | -37.3 | 17.4 | GTAggtaaagggcaaaggAA | 19007 |
| 195_1 | 85.9 | 3.8 | -39.2 | 14.6 | GTgaattaaagccaAAGC | 19252 |
| 197_1 | 94.0 | 1.3 | -24.9 | 15.5 | GAggtttttttagtgAATT | 19722 |
| 221_1 | 99.1 | 0.3 | -36.4 | 4.7 | ATttatcaacttcCACC | 29906 |
| 224_1 | 97.7 | 0.6 | -22.1 | 16.0 | TCACagacaagcaccAA | 31150 |

TABLE 17 -continued in vitro effect of PAPD7 targeting compounds on target mRNA and HBsAg Average of 3).

| CMP | % mRNA inhibition | | % HBsAg Inhibition | | | Start on SEQ ID |
|---|---|---|---|---|---|---|
| ID NO | Avg | sd | Avg | sd | Compound (CMP) | NO 11 |
| 229_1 | 96.6 | 0.7 | 60.5 | 4.6 | AGtaaaccactgtCCA | 32601 |
| 232_1 | 95.5 | 1.5 | -48.3 | 31.0 | CGATtttatcaccaaCA | 34175 |
| 239_1 | 93.1 | 1.3 | -31.6 | 3.7 | TGgtaaacactggGC | 38059 |
| 244_1 | 98.7 | 0.3 | -26.9 | 8.5 | CAGTtttatgctaatCA | 40272 |

From these data it can be seen that the inhibition of the PAPD5 mRNA (table 16) and PAPD7 mRNA (table 17) was very efficient for most of the oligonucleotide compounds.

The observed effect of PAPD5 and PAPD7 mRNA reduction on HBsAg levels is however less pronounced even in cells treated for 11 days after un-assisted delivery of oligonucleotide. Here only PAPD5 targeting CMP ID NO: 23_1, 26_1 and 115_1 showed clear HBsAg inhibition and of the PAPD7 targeting compounds only CPM ID NO: 229_1 showed clear HBsAg inhibition. Without being bound by theory this could be due to a slow onset of the effect caused by the target knock down on the HBsAg inhibition in the present assay and thus, for some compounds, HBsAg inhibition would not be seen unless assayed at a later time point.

Example 7: Effect on HBV Infected dHepaRG Cells Using a Combined Preparation of a PAPD5 and a PAPD7 Targeting Antisense Oligonucleotide Delivered to the Cells by Gymnosis In Example 2 it was observed that mixing a pool of PAPD7 targeting siRNA's with a pool of PAPD5 targeting siRNA's resulted in a synergistic anti-HBV activity. The present example sets out to investigate whether a similar synergy can be observed when combining two individual single stranded antisense oligonucleotides, where one targets PAPD5 and one targets PAPD7.

The experiment was conducted as described in Example 6 with the change that instead of adding individual oligonucleotides, a combination of two oligonucleotides were added to the cells, such that 20 μM of one oligonucleotide targeting PAPD5 was added together with 20 μM of a second oligonucleotide targeting PAPD7. Only HBsAg was measured for the combinations.

The combination of oligonucleotides can be seen in table 18, including the results on the HBV propagation parameters, HBsAg inhibition.

TABLE 18 in vitro effect combinations of PAPD5 and PAPD7 targeting compounds on HBsAg (average of 3). The HBsAg inhibition results from table 16 and 17 on the individual compounds are also included in this table for ease of comparing the individual treatment with the combination treatment.

| CMP ID NO | % HBsAg inhibition combination | | % HBsAg inhibition PAPD5 | | % HBsAg inhibition PAPD7 | |
|---|---|---|---|---|---|---|
| combination | Avg | sd | Avg | sd | Avg | sd |
| 15_1 + 184_1 | −14.9 | 13.0 | −9.7 | 5.7 | −46.6 | 11.2 |
| 15_1 + 221_1 | −8.1 | 2.9 | −9.7 | 5.7 | −36.4 | 4.7 |
| 18_1 + 184_1 | −8.0 | 1.8 | −5.3 | 6.0 | −46.6 | 11.2 |
| 18_1 + 221_1 | 22.0 | 10.8 | −5.3 | 6.0 | −36.4 | 4.7 |
| 23_1 + 172_1 | 48.4 | 6.3 | 45.8 | 3.9 | −45.0 | 12.5 |
| 23_1 + 188_1 | 47.2 | 14.3 | 45.8 | 3.9 | −34.8 | 20.7 |
| 25_1 + 174_1 | 31.3 | 7.8 | 4.4 | 7.1 | −28.8 | 4.8 |
| 25_1 + 183_1 | 58.5 | 9.9 | 4.4 | 7.1 | −31.7 | 11.6 |
| 26_1 + 174_1 | 8.4 | 2.6 | 20.9 | 7.0 | −28.8 | 4.8 |
| 26_1 + 183_1 | 38.5 | 11.2 | 20.9 | 7.0 | −31.7 | 11.6 |
| 30_1 + 172_1 | −19.1 | 11.2 | −13.2 | 1.9 | −45.0 | 12.5 |
| 30_1 + 188_1 | −8.6 | 5.0 | −13.2 | 1.9 | −34.8 | 20.7 |
| 32_1 + 155_1 | 21.0 | 1.2 | 0.8 | 12.0 | −35.8 | 13.5 |
| 32_1 + 195_1 | 8.3 | 4.7 | 0.8 | 12.0 | −39.2 | 14.6 |
| 39_1 + 224_1 | −10.7 | 10.0 | −19.4 | 9.9 | −22.1 | 16.0 |
| 39_1 + 229_1 | 48.3 | 4.8 | −19.4 | 9.9 | 60.5 | 4.6 |
| 54_1 + 190_1 | 8.3 | 9.1 | 5.2 | 4.9 | −31.5 | 15.7 |
| 54_1 + 232_1 | 29.4 | 2.4 | 5.2 | 4.9 | −48.3 | 31.0 |
| 56_1 + 153_1 | 45.0 | 9.5 | 5.5 | 6.6 | −32.3 | 9.5 |
| 56_1 + 244_1 | 60.5 | 5.9 | 5.5 | 6.6 | −26.9 | 8.5 |
| 58_1 + 171_1 | −8.0 | 17.8 | −18.6 | 17.5 | −34.4 | 15.3 |
| 58_1 + 239_1 | −14.2 | 13.0 | −18.6 | 17.5 | −31.6 | 3.7 |
| 65_1 + 171_1 | −21.2 | 4.5 | −36.8 | 15.4 | −34.4 | 15.3 |
| 65_1 + 239_1 | −26.4 | 2.3 | −36.8 | 15.4 | −31.6 | 3.7 |
| 80_1 + 153_1 | 53.6 | 5.1 | 9.4 | 9.9 | −32.3 | 9.5 |
| 80_1 + 244_1 | 65.4 | 7.3 | 9.4 | 9.9 | −26.9 | 8.5 |
| 88_1 + 168_1 | −16.4 | 7.9 | −20.1 | 13.8 | −45.2 | 9.5 |
| 88_1 + 197_1 | −9.7 | 9.0 | −20.1 | 13.8 | −24.9 | 15.5 |
| 92_1 + 190_1 | 34.6 | 7.2 | −8.1 | 6.5 | −31.5 | 15.7 |
| 92_1 + 232_1 | 23.4 | 11.6 | −8.1 | 6.5 | −48.3 | 31.0 |
| 93_1 + 224_1 | 12.8 | 5.6 | −14.8 | 2.5 | −22.1 | 16.0 |
| 93_1 + 229_1 | 27.7 | 10.3 | −14.8 | 2.5 | 60.5 | 4.6 |
| 111_1 + 191_1 | −20.0 | 7.0 | −27.6 | 8.7 | −36.2 | 21.8 |
| 111_1 + 194_1 | −22.2 | 5.6 | −27.6 | 8.7 | −37.3 | 17.4 |
| 115_1 + 191_1 | 4.8 | 5.4 | 25.8 | 9.4 | −36.2 | 21.8 |
| 115_1 + 194_1 | −6.7 | 13.3 | 25.8 | 9.4 | −37.3 | 17.4 |
| 116_1 + 155_1 | 39.2 | 2.2 | 11.2 | 9.5 | −35.8 | 13.5 |
| 116_1 + 195_1 | 22.9 | 9.5 | 11.2 | 9.5 | −39.2 | 14.6 |
| 118_1 + 168_1 | −9.8 | 11.5 | −24.2 | 24.1 | −45.2 | 9.5 |
| 118_1 + 197_1 | 4.6 | 10.5 | −24.2 | 24.1 | −24.9 | 15.5 |

Figure 10:
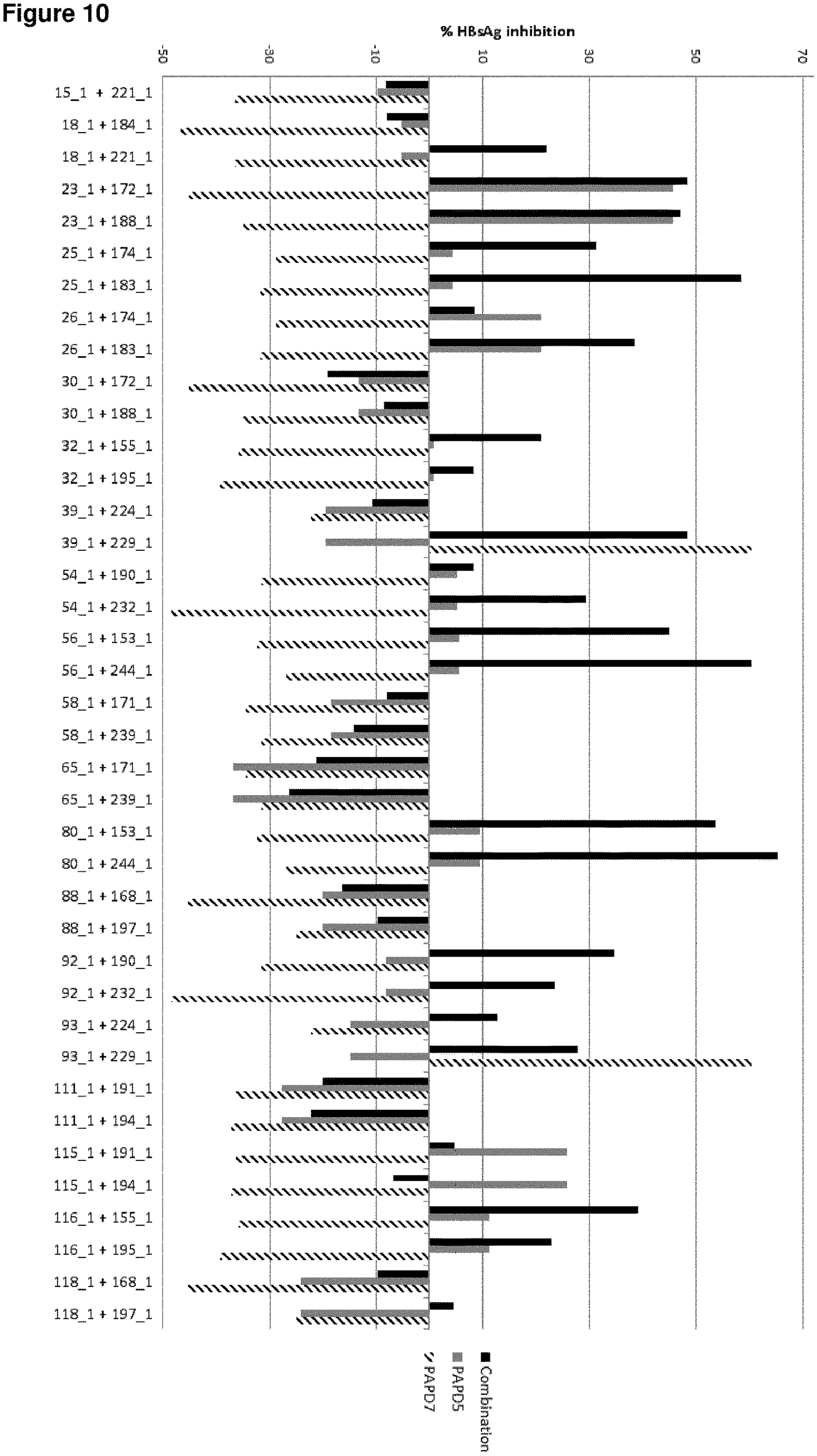
FIG. 10: Representation of the inhibition of HBsAg in HBV infected HepaRG cells with combinations oligonucleotides targeting PAPD5 and PAPD7 (20 μM each) compared to the inhibition obtained using a single oligonucleotide (20 μM) present in the combination. The assay was conducted with gymnosis.

The results are also summarized in FIG. 10. Of the 40 combinations tested above 18 resulted in an apparent synergistic effect on the HBsAg inhibition. 7 of these synergistic combinations are with oligonucleotides that individually did not produce any effect on HBsAg inhibition in the current assay. From this experiment it can be concluded that the combination of PAPD5 and a PAPD7 targeting oligonucleotides have a high likelihood of producing a synergistic effect on HBsAg inhibition.

Example 8: Repeat of Selected Combinations from Example 7

The experiment in example 7 was repeated with the oligonucleotide combinations indicated in table 19.

TABLE 19 in vitro effect combinations of PAPD5 and PAPD7 targeting compounds on HBsAg (average of 3). The HBsAg inhibition results from table 16 and 17 on the individual compounds are also included in this table for ease of comparing the individual treatment with the combination treatment.

| CMP ID NO | % HBsAg inhibition combination | | % HBsAg inhibition PAPD5 | | % HBsAg inhibition PAPD7 | |
|---|---|---|---|---|---|---|
| combination | Avg | sd | Avg | sd | Avg | sd |
| 23_1 + 172_1 | 57.4 | 13.2 | 45.8 | 3.9 | −45.0 | 12.5 |
| 23_1 + 188_1 | 63.6 | 8.0 | 45.8 | 3.9 | −34.8 | 20.7 |
| 25_1 + 174_1 | 36.2 | 14.5 | 4.4 | 7.1 | −28.8 | 4.8 |
| 25_1 + 183_1 | 80.3 | 1.3 | 4.4 | 7.1 | −31.7 | 11.6 |
| 39_1 + 229_1 | 33.9 | 18.5 | −19.4 | 9.9 | 60.5 | 4.6 |
| 54_1 + 232_1 | 56.0 | 8.5 | 5.2 | 4.9 | −48.3 | 31.0 |
| 56_1 + 153_1 | 55.4 | 6.5 | 5.5 | 6.6 | −32.3 | 9.5 |
| 80_1 + 153_1 | 53.2 | 9.3 | 9.4 | 9.9 | −32.3 | 9.5 |
| 80_1 + 244_1 | 74.3 | 5.1 | 9.4 | 9.9 | −26.9 | 8.5 |
| 92_1 + 190_1 | 27.8 | 9.9 | −8.1 | 6.5 | −31.5 | 15.7 |
| 116_1 + 155_1 | 31.6 | 1.1 | 11.2 | 9.5 | −35.8 | 13.5 |

From these data it can be seen that the synergistic effect observed in example 7 is repeatable.

Example 9: Effect on HBV Infected dHepaRG Cells Using Selected Antisense Oligonucleotides Targeting PAPD5 or PAPD7 Delivered to the Cells by Transfection In the following experiment it was investigated whether similar synergistic results could be achieved using transfection of the oligonucleotides into HBV infected dHepaRG cells instead of unassisted delivery.

Twelve PAPD5 targeting oligonucleotides (table 20) and thirteen PAPD7 targeting oligonucleotides (table 21) were tested individually using the transfection assay described here. Oligonucleotides were transfected in a 96-well plate format at a final concentration of 500 nM per well in differentiated HepaRG cells one day post-infection with HBV (described in the Materials and Methods section, HBV infection of dHepaRG cells). Prior to transfection, medium was replaced with 100 uL penicillin/streptomycin free complete differentiation medium. For single oligonucleotide treatment, oligonucleotide was diluted in Opti-MEM+Glutamax-I reduced serum medium (Gibco, #51985) and incubated at a ratio 1:1 with Lipofectamine RNAiMax (Invitrogen, #56532) for 5 minutes at room temperature according to the manufacturer's instructions. From this LNA-transfection reagent mixture, 20 μl was then added on top of the cells. After 3 days, medium was replaced with a complete differentiation medium. At day 5 post-transfection, HBsAg was measured as described in the materials and method section, PAPD5 and PAPD7 mRNA was measured as described in Example 6.

In addition some of the PAPD5 and PAPD7 oligonucleotides were tested in combination (table 22). The oligonucleotides were co-transfected into the HBV infected HepaRG cells using the same protocol as single treatment with 500 nM of each oligonucleotide in the final concentration.

TABLE 20 in vitro effect of PAPD5 targeting compounds on target mRNA and HBsAg

| CMP ID NO | % mRNA inhibition Avg | sd | % HBsAg Inhibition Avg | sd | Compound (CMP) | Start on SEQ ID NO 10 |
|---|---|---|---|---|---|---|
| 23_1 | 70.3 | 4.0 | 89.2 | 8.7 | AGgcttccattttattGAA | 8625 |
| 25_1 | 81.0 | 2.9 | 3.9 | 12.6 | GTAttcttattcttgCT | 10254 |
| 26_1 | 85.6 | 1.8 | 52.7 | 14.0 | ATTAttcccacagtaaGA | 10881 |
| 39_1 | 69.3 | 5.8 | 14.3 | 10.0 | GTtaggattttgcTATG | 18299 |
| 54_1 | 75.6 | 3.6 | 31.6 | 16.5 | TTCAacctttactgcAT | 27813 |
| 56_1 | 90.7 | 1.4 | 67.4 | 5.3 | CAgtaggaatgtggCTT | 28718 |
| 58_1 | 39.3 | 11.1 | -4.1 | 14.6 | TCactgttaaaccTCAC | 29902 |
| 65_1 | 81.1 | 4.8 | 32.3 | 34.5 | TTCAcaacaggtaaagGG | 33593 |
| 80_1 | 90.9 | 1.7 | 33.2 | 8.7 | CAAaggttgttgtacTCT | 44220 |
| 92_1 | 80.5 | 1.9 | 15.3 | 19.1 | GTatctttctgtacTATT | 52461 |
| 93_1 | 72.2 | 4.3 | 37.3 | 12.5 | GTCAttctactaacaaaCG | 53305 |
| 116_1 | 81.6 | 4.8 | 10.8 | 10.3 | TGcttttgggaatCTTT | 66650 |

TABLE 21 in vitro effect of PAPD7 targeting compounds on target mRNA and HBsAg

| CMP ID NO | % mRNA inhibition Avg | sd | % HBsAg Inhibition Avg | sd | Compound (CMP) | Start on SEQ ID NO 11 |
|---|---|---|---|---|---|---|
| 153_1 | 67.0 | 8.3 | -17.8 | 9.4 | CAgtagtaaccacCAAG | 7447 |
| 155_1 | 86.3 | 4.2 | 0.1 | 31.9 | ACttagtaatagcaGCA | 8074 |
| 171_1 | 66.8 | 13.2 | -5.8 | 6.6 | CAGcataattgttttcTTT | 12330 |
| 172_1 | 94.5 | 1.2 | 12.1 | 6.8 | ATGTcattatgttttagTT | 12634 |
| 174_1 | 58.6 | 7.3 | -6.8 | 21.9 | CGgtaagggttcggTG | 13126 |
| 183_1 | 74.1 | 5.0 | 6.7 | 23.6 | CATTgcttttataatccTA | 15816 |
| 188_1 | 72.8 | 4.7 | 26.9 | 4.6 | GCAaatgtaagcctttTT | 17303 |
| 190_1 | 75.2 | 4.9 | 87.7 | 1.0 | AAgagtgggttgtaAGC | 17963 |
| 224_1 | 72.6 | 4.4 | 4.3 | 24.1 | TCACagacaagcaccAA | 31150 |
| 229_1 | 48.0 | 6.4 | 27.8 | 24.9 | AGtaaaccactgtCCA | 32601 |
| 232_1 | 64.0 | 4.0 | -15.1 | 38.3 | CGATtttatcaccaaCA | 34175 |
| 239_1 | 91.9 | 3.7 | 88.0 | 7.0 | TGgtaaacactggGC | 38059 |
| 244_1 | 70.0 | 3.6 | -12.9 | 11.3 | CAGTtttatgctaatCA | 40272 |

TABLE 22 in vitro effect of combinations of PAPD5 and PAPD7 targeting compounds. The HBsAg inhibition results from table 20 and 21 on the individual compounds are also included in this table for ease of comparing the individual treatment with the combination treatment

| CMP ID NO | % HBsAg inhibition combination | | CMP ID NO | % HBsAg inhibition | | CMP ID NO | % HBsAg inhibition | |
|---|---|---|---|---|---|---|---|---|
| combination | Avg | sd | PAPD5 | Avg | sd | PAPD7 | Avg | sd |
| 23_1 + 172_1 | 44.1 | 6.9 | 23_1 | 89.2 | 8.7 | 172_1 | 12.1 | 6.8 |
| 23_1 + 188_1 | 76.6 | 12.0 | 23_1 | 89.2 | 8.7 | 188_1 | 26.9 | 4.6 |
| 25_1 + 174_1 | 33.0 | 22.1 | 25_1 | 3.9 | 12.6 | 174_1 | −6.8 | 21.9 |
| 25_1 + 183_1 | 75.3 | 7.8 | 25_1 | 3.9 | 12.6 | 183_1 | 6.7 | 23.6 |
| 39_1 + 229_1 | 77.4 | 13.3 | 39_1 | 14.3 | 10.0 | 229_1 | 27.8 | 24.9 |
| 54_1 + 232_1 | 79.9 | 6.5 | 54_1 | 31.6 | 16.5 | 232_1 | −15.1 | 38.3 |
| 56_1 + 153_1 | 95.6 | 1.2 | 56_1 | 67.4 | 5.3 | 153_1 | −17.8 | 9.4 |
| 56_1 + 244_1 | 89.2 | 4.8 | 56_1 | 67.4 | 5.3 | 244_1 | −12.9 | 11.3 |
| 80_1 + 153_1 | 85.5 | 2.3 | 80_1 | 33.2 | 8.7 | 153_1 | −17.8 | 9.4 |
| 80_1 + 244_1 | 82.8 | 6.7 | 80_1 | 33.2 | 8.7 | 244_1 | −12.9 | 11.3 |
| 92_1 + 190_1 | 90.5 | 1.9 | 92_1 | 15.3 | 19.1 | 190_1 | 87.7 | 1.0 |
| 116_1 + 155_1 | 87.5 | 2.5 | 116_1 | 10.8 | 10.3 | 155_1 | 0.1 | 31.9 |

Figure 11:
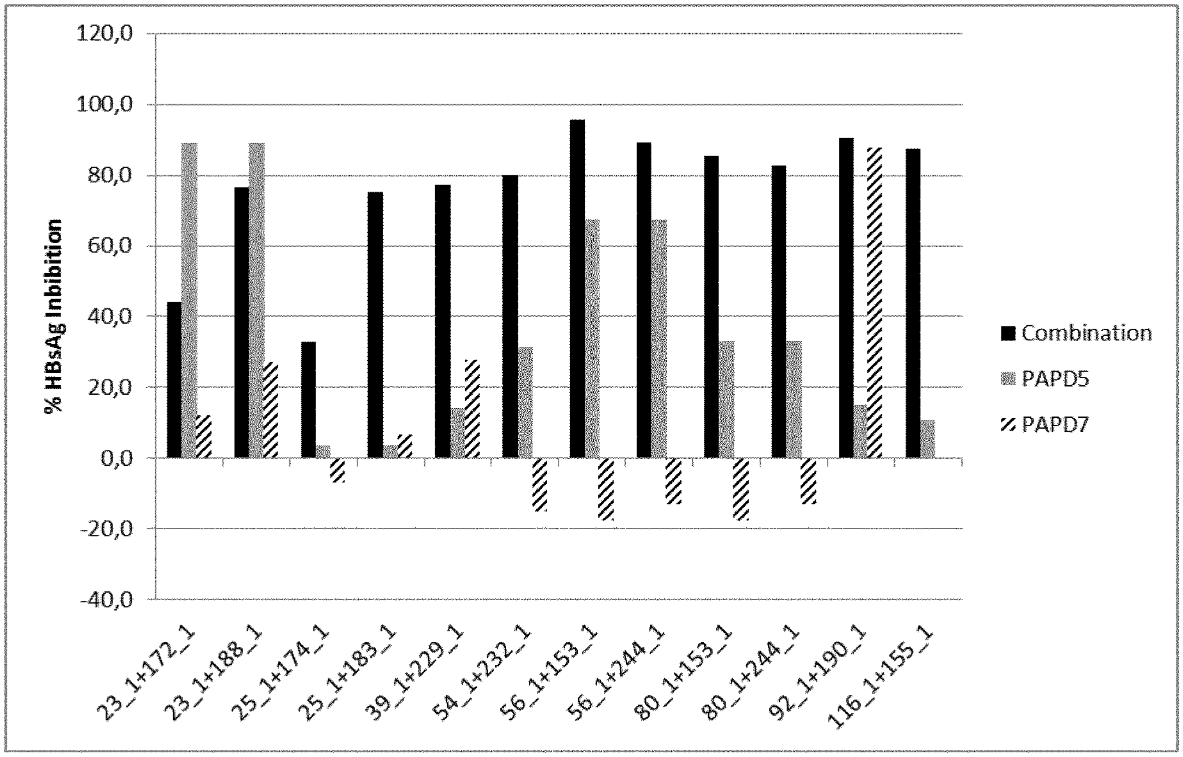
FIG. 11: Representation of the inhibition of HBsAg in HBV infected HepaRG cells with combinations oligonucleotides targeting PAPD5 and PAPD7 (500 nM each) compared to the inhibition obtained using a single oligonucleotide (500 nM) from the combination. The assay was conducted with transfection.

From these data it can be seen that when using a transfection assay 6 out of the 12 oligonucleotides targeting PAPD5 have a clear effect on HBsAg inhibition, which is considerably more than observed with the gymnotic assay in example 6. Also the number of PAPD7 targeting compounds that have an effect on the HBsAg inhibition has been increased using the transfection assay such that 4 out of 12 compounds have a clear effect on HBsAg inhibition. The data from the combinations are summarized in table 22 and FIG. 11. From these data it can be seen that 9 of the 12 tested combinations produce an apparent synergistic effect on the HBsAg inhibition.

The invention claimed is:

1. A method for the treatment of Hepatitis B virus infection in a subject, said method comprising administering an effective amount of a composition comprising a nucleic acid molecule which directly inhibits expression and/or activity of PAP associated domain containing 5 (PAPD5) to the subject; wherein the nucleic acid molecule is independently selected from the group consisting of:

a. single stranded antisense oligonucleotide;

b. siRNA molecule; and c. shRNA molecule.

2. The method of claim 1, wherein said composition is a combined preparation further comprising:

a. nucleic acid molecule which directly inhibits expression and/or activity of PAP associated domain containing 7 (PAPD7).

3. The method of claim 2, wherein the nucleic acid molecule is selected from:

a. single stranded antisense oligonucleotide comprising a contiguous nucleotide sequence of 10 to 30 nucleotides in length with at least 80% complementarity to a PAPD5 target nucleic acid and which is capable of reducing expression of PAPD5; and b. single stranded antisense oligonucleotide comprising a contiguous nucleotide sequence of 10 to 30 nucleotides in length with at least 80% complementarity to a PAPD7 target nucleic acid and which is capable of reducing expression of PAPD7.

4. The method of claim 2 wherein the nucleic acid molecule comprises a contiguous nucleotide sequence of 10 to 30 nucleotides in length wherein the contiguous nucleotide sequence is 100% complementary to a PAPD7 target nucleic acid and the nucleic acid molecule is capable of reducing expression of PAPD7.

5. The nucleic method of claim 4, wherein the nucleic acid molecule is a single stranded antisense oligonucleotide.

6. The method of claim 5, wherein the oligonucleotide is a gapmer of formula 5'-F-G-F'-3', where region F and F' independently comprise 1-7 2' sugar modified nucleosides and G is a region between 6 and 16 nucleosides which are capable of recruiting RNaseH.

7. The method according to claim 5 wherein the antisense oligonucleotide is a conjugate comprising at least one conjugate moiety covalently attached to said oligonucleotide.

8. The method of claim 4, wherein the contiguous nucleotide sequence comprises phosphorothioate internucleoside linkages.

9. The method of claim 1, wherein the composition reduces secretion of HBsAg, HBeAg and/or inhibits production of intracellular HBV mRNA or HBV DNA.

10. The method of claim 1, wherein the composition inhibits development of chronic HBV infection and/or reduces the infectiousness of a HBV infected person.

11. The method of claim 10, wherein the composition that inhibits propagation of HBV inhibits secretion of HBV surface antigen (HBsAg), and/or inhibits secretion of HBV envelope antigen (HBeAg), and/or inhibits production of intracellular HBV mRNA.

12. The method of claim 1 wherein the nucleic acid molecule is a single stranded antisense oligonucleotide which comprises a contiguous nucleotide sequence of 10 to 30 nucleotides in length wherein the contiguous nucleotide sequence is 100% complementary to a PAPD5 target nucleic acid and the antisense oligonucleotide is capable of reducing expression of PAPD5.

13. The method of claim 12, wherein the antisense oligonucleotide comprises one or more 2' sugar modified nucleoside(s).

14. The method of claim 13, wherein the one or more 2' sugar modified nucleoside(s) is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

15. The method of claim 13, wherein the one or more 2' sugar modified nucleoside(s) is a LNA nucleoside.

16. The method of claim 12, wherein the contiguous nucleotide sequence comprises phosphorothioate internucleoside linkages.

17. The method of claim 12, wherein the oligonucleotide is a gapmer of formula 5'-F-G-F'-3', where region F and F' independently comprise 1-7 2' sugar modified nucleosides and G is a region between 6 and 16 nucleosides which are capable of recruiting RNaseH.

18. The method according to claim 12 wherein the antisense oligonucleotide is a conjugate comprising at least one conjugate moiety covalently attached to said oligonucleotide.

* * * * *

SEQUENCE LISTING

```
<160> NUMBER OF SEQ ID NOS: 267

<210> SEQ ID NO 1
<211> LENGTH: 698
<212> TYPE: PRT
<213> ORGANISM: Homo sapiens

<400> SEQUENCE: 1

Met Arg Pro Arg Pro Arg Ser Ala Pro Gly Lys Pro Arg Arg Arg Ser
1               5                   10                  15

Arg Ala Arg Leu Arg Ser Ser Arg Thr Pro Ser Gly Gly Ala Ser Gly
            20                  25                  30

Gly Gly Gly Ser Ser Ser Ser Ser Ser Thr Ala Thr Gly Gly Ser Gly
        35                  40                  45

Ser Ser Thr Gly Ser Pro Gly Gly Ala Ala Ser Ala Pro Ala Pro Ala
    50                  55                  60

Pro Ala Gly Met Tyr Arg Ser Gly Glu Arg Leu Leu Gly Ser His Ala
65                  70                  75                  80

Leu Pro Ala Glu Gln Arg Asp Phe Leu Pro Leu Glu Thr Thr Asn Asn
                85                  90                  95

Asn Asn Asn His His Gln Pro Gly Ala Trp Ala Arg Arg Ala Gly Ser
            100                 105                 110

Ser Ala Ser Ser Pro Pro Ser Ala Ser Ser Ser Pro His Pro Ser Ala
        115                 120                 125

Ala Val Pro Ala Ala Asp Pro Ala Asp Ser Ala Ser Gly Ser Ser Asn
    130                 135                 140

Lys Arg Lys Arg Asp Asn Lys Ala Ser Thr Tyr Gly Leu Asn Tyr Ser
145                 150                 155                 160

Leu Leu Gln Pro Ser Gly Gly Arg Ala Ala Gly Gly Gly Arg Ala Asp
                165                 170                 175
```

-continued

```
Gly Gly Gly Val Val Tyr Ser Gly Thr Pro Trp Lys Arg Arg Asn Tyr
            180                 185                 190

Asn Gln Gly Val Val Gly Leu His Glu Glu Ile Ser Asp Phe Tyr Glu
        195                 200                 205

Tyr Met Ser Pro Arg Pro Glu Glu Glu Lys Met Arg Met Glu Val Val
    210                 215                 220

Asn Arg Ile Glu Ser Val Ile Lys Glu Leu Trp Pro Ser Ala Asp Val
225                 230                 235                 240

Gln Ile Phe Gly Ser Phe Lys Thr Gly Leu Tyr Leu Pro Thr Ser Asp
                245                 250                 255

Ile Asp Leu Val Val Phe Gly Lys Trp Glu Asn Leu Pro Leu Trp Thr
            260                 265                 270

Leu Glu Glu Ala Leu Arg Lys His Lys Val Ala Asp Glu Asp Ser Val
        275                 280                 285

Lys Val Leu Asp Lys Ala Thr Val Pro Ile Ile Lys Leu Thr Asp Ser
    290                 295                 300

Phe Thr Glu Val Lys Val Asp Ile Ser Phe Asn Val Gln Asn Gly Val
305                 310                 315                 320

Arg Ala Ala Asp Leu Ile Lys Asp Phe Thr Lys Lys Tyr Pro Val Leu
                325                 330                 335

Pro Tyr Leu Val Leu Val Leu Lys Gln Phe Leu Leu Gln Arg Asp Leu
            340                 345                 350

Asn Glu Val Phe Thr Gly Gly Ile Gly Ser Tyr Ser Leu Phe Leu Met
        355                 360                 365

Ala Val Ser Phe Leu Gln Leu His Pro Arg Glu Asp Ala Cys Ile Pro
    370                 375                 380

Asn Thr Asn Tyr Gly Val Leu Leu Ile Glu Phe Phe Glu Leu Tyr Gly
385                 390                 395                 400

Arg His Phe Asn Tyr Leu Lys Thr Gly Ile Arg Ile Lys Asp Gly Gly
                405                 410                 415

Ser Tyr Val Ala Lys Asp Glu Val Gln Lys Asn Met Leu Asp Gly Tyr
            420                 425                 430

Arg Pro Ser Met Leu Tyr Ile Glu Asp Pro Leu Gln Pro Gly Asn Asp
        435                 440                 445

Val Gly Arg Ser Ser Tyr Gly Ala Met Gln Val Lys Gln Ala Phe Asp
    450                 455                 460

Tyr Ala Tyr Val Val Leu Ser His Ala Val Ser Pro Ile Ala Lys Tyr
465                 470                 475                 480

Tyr Pro Asn Asn Glu Thr Glu Ser Ile Leu Gly Arg Ile Ile Arg Val
                485                 490                 495

Thr Asp Glu Val Ala Thr Tyr Arg Asp Trp Ile Ser Lys Gln Trp Gly
            500                 505                 510

Leu Lys Asn Arg Pro Glu Pro Ser Cys Asn Gly Asn Gly Val Thr Leu
        515                 520                 525

Ile Val Asp Thr Gln Gln Leu Asp Lys Cys Asn Asn Asn Leu Ser Glu
    530                 535                 540

Glu Asn Glu Ala Leu Gly Lys Cys Arg Ser Lys Thr Ser Glu Ser Leu
545                 550                 555                 560

Ser Lys His Ser Ser Asn Ser Ser Ser Gly Pro Val Ser Ser Ser Ser
                565                 570                 575

Ala Thr Gln Ser Ser Ser Ser Asp Val Asp Ser Asp Ala Thr Pro Cys
            580                 585                 590
```

```
Lys Thr Pro Lys Gln Leu Leu Cys Arg Pro Ser Thr Gly Asn Arg Val
        595                 600                 605

Gly Ser Gln Asp Val Ser Leu Glu Ser Ser Gln Ala Val Gly Lys Met
    610                 615                 620

Gln Ser Thr Gln Thr Thr Asn Thr Ser Asn Ser Thr Asn Lys Ser Gln
625                 630                 635                 640

His Gly Ser Ala Arg Leu Phe Arg Ser Ser Ser Lys Gly Phe Gln Gly
                645                 650                 655

Thr Thr Gln Thr Ser His Gly Ser Leu Met Thr Asn Lys Gln His Gln
            660                 665                 670

Gly Lys Ser Asn Asn Gln Tyr Tyr His Gly Lys Lys Arg Lys His Lys
        675                 680                 685

Arg Asp Ala Pro Leu Ser Asp Leu Cys Arg
    690                 695


<210> SEQ ID NO 2
<211> LENGTH: 698
<212> TYPE: PRT
<213> ORGANISM: Homo sapiens

<400> SEQUENCE: 2

Met Arg Pro Arg Pro Arg Ser Ala Pro Gly Lys Pro Arg Arg Arg Ser
1               5                   10                  15

Arg Ala Arg Leu Arg Ser Ser Arg Thr Pro Ser Gly Gly Ala Ser Gly
            20                  25                  30

Gly Gly Gly Ser Ser Ser Ser Ser Ser Thr Ala Thr Gly Gly Ser Gly
        35                  40                  45

Ser Ser Thr Gly Ser Pro Gly Gly Ala Ala Ser Ala Pro Ala Pro Ala
    50                  55                  60

Pro Ala Gly Met Tyr Arg Ser Gly Glu Arg Leu Leu Gly Ser His Ala
65                  70                  75                  80

Leu Pro Ala Glu Gln Arg Asp Phe Leu Pro Leu Glu Thr Thr Asn Asn
                85                  90                  95

Asn Asn Asn His His Gln Pro Gly Ala Trp Ala Arg Arg Ala Gly Ser
            100                 105                 110

Ser Ala Ser Ser Pro Pro Ser Ala Ser Ser Ser Pro His Pro Ser Ala
        115                 120                 125

Ala Val Pro Ala Ala Asp Pro Ala Asp Ser Ala Ser Gly Ser Ser Asn
    130                 135                 140

Lys Arg Lys Arg Asp Asn Lys Ala Ser Thr Tyr Gly Leu Asn Tyr Ser
145                 150                 155                 160

Leu Leu Gln Pro Ser Gly Gly Arg Ala Ala Gly Gly Gly Arg Ala Asp
                165                 170                 175

Gly Gly Gly Val Val Tyr Ser Gly Thr Pro Trp Lys Arg Arg Asn Tyr
            180                 185                 190

Asn Gln Gly Val Val Gly Leu His Glu Glu Ile Ser Asp Phe Tyr Glu
        195                 200                 205

Tyr Met Ser Pro Arg Pro Glu Glu Glu Lys Met Arg Met Glu Val Val
    210                 215                 220

Asn Arg Ile Glu Ser Val Ile Lys Glu Leu Trp Pro Ser Ala Asp Val
225                 230                 235                 240

Gln Ile Phe Gly Ser Phe Lys Thr Gly Leu Tyr Leu Pro Thr Ser Asp
                245                 250                 255

Ile Asp Leu Val Val Phe Gly Lys Trp Glu Asn Leu Pro Leu Trp Thr
            260                 265                 270
```

-continued

```
Leu Glu Glu Ala Leu Arg Lys His Lys Val Ala Asp Glu Asp Ser Val
        275                 280                 285

Lys Val Leu Asp Lys Ala Thr Val Pro Ile Ile Lys Leu Thr Asp Ser
    290                 295                 300

Phe Thr Glu Val Lys Val Asp Ile Ser Phe Asn Val Gln Asn Gly Val
305                 310                 315                 320

Arg Ala Ala Asp Leu Ile Lys Asp Phe Thr Lys Lys Tyr Pro Val Leu
                325                 330                 335

Pro Tyr Leu Val Leu Val Leu Lys Gln Phe Leu Leu Gln Arg Asp Leu
            340                 345                 350

Asn Glu Val Phe Thr Gly Gly Ile Gly Ser Tyr Ser Leu Phe Leu Met
        355                 360                 365

Ala Val Ser Phe Leu Gln Leu His Pro Arg Glu Asp Ala Cys Ile Pro
    370                 375                 380

Asn Thr Asn Tyr Gly Val Leu Leu Ile Glu Phe Phe Glu Leu Tyr Gly
385                 390                 395                 400

Arg His Phe Asn Tyr Leu Lys Thr Gly Ile Arg Ile Lys Asp Gly Gly
                405                 410                 415

Ser Tyr Val Ala Lys Asp Glu Val Gln Lys Asn Met Leu Asp Gly Tyr
            420                 425                 430

Arg Pro Ser Met Leu Tyr Ile Glu Asp Pro Leu Gln Pro Gly Asn Asp
        435                 440                 445

Val Gly Arg Ser Ser Tyr Gly Ala Met Gln Val Lys Gln Ala Phe Asp
    450                 455                 460

Tyr Ala Tyr Val Val Leu Ser His Ala Val Ser Pro Ile Ala Lys Tyr
465                 470                 475                 480

Tyr Pro Asn Asn Glu Thr Glu Ser Ile Leu Gly Arg Ile Ile Arg Val
                485                 490                 495

Thr Asp Glu Val Ala Thr Tyr Arg Asp Trp Ile Ser Lys Gln Trp Gly
            500                 505                 510

Leu Lys Asn Arg Pro Glu Pro Ser Cys Asn Gly Asn Gly Val Thr Leu
        515                 520                 525

Ile Val Asp Thr Gln Gln Leu Asp Lys Cys Asn Asn Asn Leu Ser Glu
    530                 535                 540

Glu Asn Glu Ala Leu Gly Lys Cys Arg Ser Lys Thr Ser Glu Ser Leu
545                 550                 555                 560

Ser Lys His Ser Ser Asn Ser Ser Ser Gly Pro Val Ser Ser Ser Ser
                565                 570                 575

Ala Thr Gln Ser Ser Ser Ser Asp Val Asp Ser Asp Ala Thr Pro Cys
            580                 585                 590

Lys Thr Pro Lys Gln Leu Leu Cys Arg Pro Ser Thr Gly Asn Arg Val
        595                 600                 605

Gly Ser Gln Asp Val Ser Leu Glu Ser Ser Gln Ala Val Gly Lys Met
    610                 615                 620

Gln Ser Thr Gln Thr Thr Asn Thr Ser Asn Ser Thr Asn Lys Ser Gln
625                 630                 635                 640

His Gly Ser Ala Arg Leu Phe Arg Ser Ser Ser Lys Gly Phe Gln Gly
                645                 650                 655

Thr Thr Gln Thr Ser His Gly Ser Leu Met Thr Asn Lys Gln His Gln
            660                 665                 670

Gly Lys Ser Asn Asn Gln Tyr Tyr His Gly Lys Lys Arg Lys His Lys
        675                 680                 685
```

Arg Asp Ala Pro Leu Ser Asp Leu Cys Arg
690 695

<210> SEQ ID NO 3
<211> LENGTH: 792
<212> TYPE: PRT
<213> ORGANISM: Homo sapiens

<400> SEQUENCE: 3

Met Asp Pro Arg Val Ala Trp Ile Gln Pro Glu Gln Lys Gly Pro Ala
1 5 10 15

Asn Ala Leu Trp Met Gln Ile Trp Glu Thr Ser Gln Gly Val Gly Arg
20 25 30

Gly Gly Ser Gly Phe Ala Ser Tyr Phe Cys Leu Asn Ser Pro Ala Leu
35 40 45

Asp Thr Ala Ala Ala Ala Gly Ala Ala Gly Arg Gly Ser Gly Gly Leu
50 55 60

Gly Pro Ala Leu Pro Ala Ala Ser Pro Pro Pro Pro Gly Pro Thr Ala
65 70 75 80

Pro Ala Ala Leu Pro Pro Ala Leu Leu Thr Ala Leu Gly Pro Ala Ala
85 90 95

Glu Gly Ala Arg Arg Leu His Lys Ser Pro Ser Leu Ser Ser Ser Ser
100 105 110

Ser Ser Ser Ser Ser Asn Ala Glu Ser Gly Thr Glu Ser Pro Gly Cys
115 120 125

Ser Ser Ser Ser Ser Ser Ser Ala Ser Leu Gly Arg Pro Gly Gly Gly
130 135 140

Arg Gly Gly Ala Phe Phe Asn Phe Ala Asp Gly Ala Pro Ser Ala Pro
145 150 155 160

Gly Thr Ala Asn Gly His Pro Gly Pro Arg Gly Pro Ala Pro Ala Gly
165 170 175

Ser Pro Ser Gln His Gln Phe His Pro Gly Arg Arg Lys Arg Glu Asn
180 185 190

Lys Ala Ser Thr Tyr Gly Leu Asn Tyr Leu Leu Ser Gly Ser Arg Ala
195 200 205

Ala Ala Leu Ser Gly Gly Gly Gly Pro Gly Ala Gln Ala Pro Arg Pro
210 215 220

Gly Thr Pro Trp Lys Ser Arg Ala Tyr Ser Pro Gly Ile Gln Gly Leu
225 230 235 240

His Glu Glu Ile Ile Asp Phe Tyr Asn Phe Met Ser Pro Cys Pro Glu
245 250 255

Glu Ala Ala Met Arg Arg Glu Val Val Lys Arg Ile Glu Thr Val Val
260 265 270

Lys Asp Leu Trp Pro Thr Ala Asp Val Gln Ile Phe Gly Ser Phe Ser
275 280 285

Thr Gly Leu Tyr Leu Pro Thr Ser Asp Ile Asp Leu Val Val Phe Gly
290 295 300

Lys Trp Glu Arg Pro Pro Leu Gln Leu Leu Glu Gln Ala Leu Arg Lys
305 310 315 320

His Asn Val Ala Glu Pro Cys Ser Ile Lys Val Leu Asp Lys Ala Thr
325 330 335

Val Pro Ile Ile Lys Leu Thr Asp Gln Glu Thr Glu Val Lys Val Asp
340 345 350

Ile Ser Phe Asn Met Glu Thr Gly Val Arg Ala Ala Glu Phe Ile Lys
355 360 365

-continued

```
Asn Tyr Met Lys Lys Tyr Ser Leu Leu Pro Tyr Leu Ile Leu Val Leu
    370                 375                 380

Lys Gln Phe Leu Leu Gln Arg Asp Leu Asn Glu Val Phe Thr Gly Gly
385                 390                 395                 400

Ile Ser Ser Tyr Ser Leu Ile Leu Met Ala Ile Ser Phe Leu Gln Leu
                405                 410                 415

His Pro Arg Ile Asp Ala Arg Arg Ala Asp Glu Asn Leu Gly Met Leu
            420                 425                 430

Leu Val Glu Phe Phe Glu Leu Tyr Gly Arg Asn Phe Asn Tyr Leu Lys
        435                 440                 445

Thr Gly Ile Arg Ile Lys Glu Gly Gly Ala Tyr Ile Ala Lys Glu Glu
    450                 455                 460

Ile Met Lys Ala Met Thr Ser Gly Tyr Arg Pro Ser Met Leu Cys Ile
465                 470                 475                 480

Glu Asp Pro Leu Leu Pro Gly Asn Asp Val Gly Arg Ser Ser Tyr Gly
                485                 490                 495

Ala Met Gln Val Lys Gln Val Phe Asp Tyr Ala Tyr Ile Val Leu Ser
            500                 505                 510

His Ala Val Ser Pro Leu Ala Arg Ser Tyr Pro Asn Arg Asp Ala Glu
        515                 520                 525

Ser Thr Leu Gly Arg Ile Ile Lys Val Thr Gln Glu Val Ile Asp Tyr
    530                 535                 540

Arg Arg Trp Ile Lys Glu Lys Trp Gly Ser Lys Ala His Pro Ser Pro
545                 550                 555                 560

Gly Met Asp Ser Arg Ile Lys Ile Lys Glu Arg Ile Ala Thr Cys Asn
                565                 570                 575

Gly Glu Gln Thr Gln Asn Arg Glu Pro Glu Ser Pro Tyr Gly Gln Arg
            580                 585                 590

Leu Thr Leu Ser Leu Ser Ser Pro Gln Leu Leu Ser Ser Gly Ser Ser
        595                 600                 605

Ala Ser Ser Val Ser Ser Leu Ser Gly Ser Asp Val Asp Ser Asp Thr
    610                 615                 620

Pro Pro Cys Thr Thr Pro Ser Val Tyr Gln Phe Ser Leu Gln Ala Pro
625                 630                 635                 640

Ala Pro Leu Met Ala Gly Leu Pro Thr Ala Leu Pro Met Pro Ser Gly
                645                 650                 655

Lys Pro Gln Pro Thr Thr Ser Arg Thr Leu Ile Met Thr Thr Asn Asn
            660                 665                 670

Gln Thr Arg Phe Thr Ile Pro Pro Pro Thr Leu Gly Val Ala Pro Val
        675                 680                 685

Pro Cys Arg Gln Ala Gly Val Glu Gly Thr Ala Ser Leu Lys Ala Val
    690                 695                 700

His His Met Ser Ser Pro Ala Ile Pro Ser Ala Ser Pro Asn Pro Leu
705                 710                 715                 720

Ser Ser Pro His Leu Tyr His Lys Gln His Asn Gly Met Lys Leu Ser
                725                 730                 735

Met Lys Gly Ser His Gly His Thr Gln Gly Gly Gly Tyr Ser Ser Val
            740                 745                 750

Gly Ser Gly Gly Val Arg Pro Pro Val Gly Asn Arg Gly His His Gln
        755                 760                 765

Tyr Asn Arg Thr Gly Trp Arg Arg Lys Lys His Thr His Thr Arg Asp
    770                 775                 780
```

```
Ser Leu Pro Val Ser Leu Ser Arg
785                 790


<210> SEQ ID NO 4
<211> LENGTH: 8114
<212> TYPE: DNA
<213> ORGANISM: Homo sapiens

<400> SEQUENCE: 4

acaacgcgct ccctgcgggg cgggcggcaa cctccatgcg gcctcgtcca cgctcagcac     60

cggggaagcc gaggcggaga agccgcgcgc gcctcagaag ctcccggacg cccagcggcg    120

gcgcgagcgg cggcggcggc agcagcagca gcagcagcac ggccaccggc gggagcggca    180

gcagcaccgg cagccccggc ggcgcggcct cggccccggc cccggccccg gccggcatgt    240

atcgctccgg ggagcgcctg ctgggcagcc acgcgctgcc cgcggagcag cgggacttcc    300

tgcccctaga gacgaccaac aacaacaaca accaccacca gcccggggcc tgggcccgcc    360

gggcgggctc ctcggcgtcc tcgcctccct cggcgtcctc gtccccgcac ccttcggccg    420

ccgtccccgc cgccgatcca gccgattcgg cctcgggcag cagcaacaag aggaagcgcg    480

acaacaaggc cagcacgtat ggactcaact acagcctgct gcagcccagc ggagggcggg    540

ccgcgggggg cggccgagca gacggcggcg gggtcgtgta cagcgggacc ccgtggaaac    600

ggaggaacta caaccaggga gtcgtgggtc tgcatgaaga aatcagtgat ttttatgaat    660

acatgtctcc aagacctgag gaggagaaga tgcggatgga ggtggtgaac aggatcgaga    720

gtgtaattaa ggagctctgg cccagcgctg acgtccagat atttggaagt tttaaaactg    780

gactttattt acctactagt gacatcgacc tagtggtgtt tgggaagtgg gagaacctac    840

ccctctggac tctggaagaa gctcttcgga aacacaaagt cgcagatgag gattcggtga    900

aagttttaga caaagcaact gtacctatta ttaaattaac agattctttt actgaagtga    960

aagttgatat cagctttaat gtacagaatg gcgtgagagc agctgacctc atcaaagatt   1020

ttaccaagaa atatcctgta ttgccatact tggttttagt attgaaacaa ttcctattgc   1080

agagggacct taatgaagta tttacaggtg gaattggttc ttatagtctc tttttaatgg   1140

cagtcagttt ccttcagtta catcccaggg aagatgcttg catccccaat acaaactatg   1200

gtgttctctt aatagaattt tttgaattat atggacgaca cttcaattat ttaaagactg   1260

gcatccggat aaaggatggt ggttcatatg tggccaaaga tgaagtacag aaaaatatgc   1320

tagatggcta caggccatca atgctttata tcgaagatcc tttacaacca ggtaacgatg   1380

ttggaaggag ttcatatggg gccatgcaag tgaagcaggc ctttgattat gcctacgttg   1440

ttttgagtca tgctgtatca ccaatagcaa agtactatcc caacaatgaa acagaaagca   1500

tactaggtag aataattaga gtaacagatg aagttgccac atatagagat tggatatcaa   1560

agcagtgggg cttgaagaat agacctgagc cttcatgcaa tggaaatggt gttaccttga   1620

tagtagatac tcagcagtta gataaatgta ataataatct atctgaagaa aatgaagccc   1680

ttggaaaatg tagaagtaaa acctcggaat ctcttagtaa acactcttca aactcttcat   1740

caggtccagt gtcgtcctct tctgccacac agtccagctc tagtgatgta gattccgatg   1800

caacaccatg caaaaccccg aaacagctgc tttgccgtcc gtccactggg aaccgagtag   1860

ggtcgcaaga tgtatccttg gagtcctctc aggcagttgg gaaaatgcaa agcacccaaa   1920

ccactaacac atccaacagc accaacaaat ctcagcatgg atcagcaagg ctctttcgtt   1980

cttccagcaa aggcttccaa ggtacaactc aaacaagcca tggttccttg atgacaaaca   2040
```

-continued aacaacatca aggcaaatcc aataatcagt attaccatgg caaaaagagg aaacacaaga 2100
gggacgcgcc cctctcagac ctctgtagat agtcagcgct gcgcggtgga ctgtcttctc 2160
tgtgcaatga tctcatgctc aggacagttg cgcagggact cctgggagat attcaggagc 2220
ctcacactgt tcagacgttg acttagcaac tgcgtttttt cccagctcgc cacagaatgg 2280
atcatgaaga ctgacaactg caaaaaaaac aaaacaaaac aaaaaaaaaa gcaagcaaaa 2340
aagagggaaa aaaaaggctg cttatttgat aagtcatatg ctacaacagg gtcattttaa 2400
gatttaaagc ttgaatgtaa aataaatata tttctcattg gctttatgca gagttatagg 2460
gaatagtatt cagtgttggt agggtgatag aaacaaaaaa cagtatcaga ggatgaggtg 2520
gggaaggaaa acaaaggtat ctgataggaa gtccagattc caaaggggaa agtgatctgt 2580
gcatgttttt tttttaaata tttttgcata tatttaccat tttattgtgt gtatatatag 2640
aagaccatat aggagattga tatttgtaat agtggatttg ttaataatac tttttacata 2700
acattactgt ttaaattgta aacagatttt ttctcaggat tagtttgaaa aataatctaa 2760
attgtcatct taacatccat atatagggaa gtgattagtt ctattactca atttgttttt 2820
ctcagcattg aaatgactta atagaaccct tgtgtcctgc tgcaaaaatt tttcctctct 2880
aaagaaaagg tttatggtgg caaatgatgt ttattttatt ttgtaaaaaa aaaaaaaatgt 2940
actatgtact tttgtgtaaa cactgaaaaa tctctggtca tctccgagaa ttaacttgca 3000
actgttttct atagtgctgt cgtcttgggc aatgggcaat tacatgactt tgtgtttgct 3060
tcctttgcag tctttttttt ttccccccat ttcttcctaa taggaaaaaa aaaaaaaaaa 3120
aggtcaccca tgtctggtct cattcctgtt gcagtgaaac ttcgagttcc acagactttg 3180
catgctggct tctctaaccc tgtgtgctgc gtgtgcctgt ttctcatctc ttattctttt 3240
taaaattcat gcttaactac tgtgggagaa taactgtaaa cagctttaat taaatcatac 3300
ttataaaaaa ctattttctt atattccact ctatgctttt ggtattgttg atctttacaa 3360
attaaatggt ctttgataat ggatctattt tgtattgcct tattaagacc aaatacttct 3420
tgtcatccca ttctttatcc tcttctttca tggaattgtt atcgttaatt aaaacttttt 3480
taaacattgg cttgtttcaa tcatactgta aattttggtt gtagtcagct ttgagtgcaa 3540
tgagatgtat aattctgtta tcattacctg ttgagtttga aactcagttg ggaatattta 3600
atataataga atgtaagtga catttctgaa aatgcttttct ttcagggtga aagctcttat 3660
gtttagcatc aatgtgtatg gctctgttaa atgcagccat ttctgagacg agattctttt 3720
atatatatat acatataaag tactattggc ttttaggagt ttcttttata tacatttatg 3780
aaatactgaa gaccaatcag accattaatg gacacttagt gtaacttttt ataaagaaaa 3840
taatgctaaa gtaagaccaa aactgatgtc atcactgaaa ttaacaattt tcaatatgtt 3900
catattttaa ttcacaatgg aaaaatgtgt tccaaaactg gaaactcata gtactcgtgt 3960
aaactgtgga agatttcaaa tgtgatgtta ttttgacaat gttttaaatt ttagagtcac 4020
attttattct gatcagaatt tttattgaga tgttgagctt ttgtttttga aactagtttg 4080
tcataacatt gtgcataatc acagtattta ttttctagga caattgtgaa tgtgtagact 4140
tatgtttact gctaagggaa caattattta taaaataata ttaaatccag tattagctgc 4200
ctatttcaga cacttaatac ttgcagagat ctatgttaca tttaccacac tgaagttttt 4260
tttgttgttt tttgtttgtt tttaaagaat caccctcatt gttgaaagta aatgtactct 4320
tagggtgcga atattagtgt tccaataagc atgtgattat attaaggtgg tggtagcggg 4380
aagataattc tgattccatt gggaatctta ggttttcgta aatttattgg gaaaatagtt 4440

-continued

```
tttcctgtac tgctgaagtt tctttttggt aaacagtatc tttctaaaag aaaaaagcat   4500
gaaggagaaa ttgaggtgtg tatacatttc ctcaaatgac cagcattgta ttcgtgaata   4560
ctgtgtatct tgcagtgaac agtgtggaag ctgttcattt ttcaatctga agtaaaatac   4620
tttcaagaac ttttagtttg cctgctcatt tgttttatac atttcatcta tttgactcct   4680
atcttatttc ttttttgagt tttaatactt cctatatttt gtgaatatat cagaaatgtg   4740
tcatttatat attagagtcc attcatatcc atgaatcata accttccttt gctaatactt   4800
gttgaatggg attttacaaa ttctccctca ctctggtgac atttctcagg cagtcatgta   4860
tgtgtacctg gccattagaa atattaatat ttaaagactg ttttttagag gagctgatgg   4920
gttggtgagg tgtcagcaca aaatcttact ggttatgttt tgatgataaa agtatatcca   4980
ttttttccct ccagctttaa ggtgactgtg aaggtgcctg gttttgaatg tctttgtttg   5040
gtttggagat gtcgcactca gttttcaaat ctagcttgga tctgtaggac ctatgttttt   5100
tacaagtaat tgccctccag tcttcaacag ttgattctgt tttattttta tcctgttttg   5160
agtgtacttt acctttactt gcattttgag cctcattaat atttaggtta tttgatttgg   5220
ctccagatat tcctagatct gcacagggca aaacatgggc tatagggtga gcatttttaa   5280
ttgtcttttt ctgctggaac cttatatctc tccatgtgtt ttctgctcct tccctccccc   5340
atgaaatggt aagtgtgact tgtgtttgcc tgaacctgtg gactagtgtt tggggtttct   5400
ggaaacacta gagggtcaga aaagagtaat gaccaccgtg acgtgcagga ttctcttgct   5460
gtgacatgtt cattgcaaag ccctctccag tgactaggag gtgtagttat taaggttgat   5520
ctgttagaaa tcaccattat taggtattag tggtagatgt tgctgatact tttattggtc   5580
atgactacat ctcagtttta ctttaatatt gatctatagt ttgatcagtt ccttgaattc   5640
taatatgttg atttctcagt gtttctgtca ctaaccaaga atgtttctag gcagttggtt   5700
gcttcacagt caaaactaaa tggtaaacta tcaaaaatac attcccaatt ttgctgtgat   5760
aaatattgaa atgttaaaat taatgaacag aagaatttat tcttacccat ctattcttgt   5820
tctcctagtt cattaaactt tcagttattg gaaaggcaca ttctcaaagt attttatgag   5880
caaaatattc tataaatgcg tctaacaaac ctaattgaat ataaaagtta tatttagtag   5940
ttactgttga tagtaatttt catcagggtc atagttcatc tagtaaaata tttagagaat   6000
gatgttaaca ttccagcatt aaagtgggaa caaagattta tatatgaaat tccttaaaag   6060
agttcatctt gccttggttt ctgaccctca agactctagc tacctgccat cttgtcaaaa   6120
catttgtggg tagaataagt gttaaagatc aaattttaat atgcttctcg atatttaaca   6180
tagctaagaa gccagatttt actgtagaag ttatttacat gatttgaaaa cttgacctaa   6240
ctggaagcct ttttctcagt catcttgttc taagccatct tgacttcaca cccttagcga   6300
cttttctttt ttttttggtc aaagataatg agctaaatat atatagacgt tgaatgttga   6360
caaaattatt aaccagaaaa attgcttata aaggctgctg atctatttga tacctagaat   6420
taaatatttg aggacagttt ttagttaata aactgctaat gtttatttta ctgtctctca   6480
ggtttttggt tttttaaaa aaaatgtgtt tggcctttac attttctact taagtgtgta   6540
ctttattgag tttaaccttg tctgtagcct agtagcctga aagaaaagga gacagaacca   6600
gagagatgga tgtagtgcat tccctttggt tattacacat ttgtggtagc tcctggattt   6660
actgagagat attttagcta tgtcaataag aacagctaat gatgtggaaa tcaggtgttc   6720
tcttgtgtat ttcagtgaac atttttatta gtagttgcat atcatctcta gttccacatt   6780
```

-continued

```
ttaacttaac gtctttgtgg cttcaccact gagctacctt tcactacacc agcttctgtg   6840
tggcctggta acatggaagg tctctcctaa ggacagtctg gacgtatttt gggggaatgt   6900
tatttatctt aaagatgcct agaaacaaaa cgcatatagt accagtgaga aactatgaag   6960
taaacaagtt gctcaggccg ggcatggtgg ctcacgcctg taatcccagc actttgggag   7020
gccgaagcgg gaggatggct tgaggctggg agtttgagac cttcatctct taaaaaaaca   7080
aacaaaaacc tgaatggtga ggtgtggtgg aattgggtag gggagggaaa ggaggacttg   7140
gaaaagcatt ctccaaagcc agcaacttgg tgaagttcag tacttgcctc ttagaggtta   7200
ggccatgcct ttcaaagaga gtgaaatgat gggttatcag ccacattctt ggagttaata   7260
tttttcttca tctttcagtt tgggttctgt gctattcata gttcttccct aagaccattt   7320
cattattacc ttttatattt agttgcaatt tattataata tgttgttttg tccctgaact   7380
taatctccta attttaagat cctctctgat ttttgcatat tgaaacttac agaagtcact   7440
ttaaaaaagt cttttgaaag tcctacaatc ctaaaataaa tcacaagctt gtttgttaga   7500
cgtgtcaaga gtctccagtc tttactacta aaaagcagca ctgccttaac acacattgtt   7560
atgggtgaaa agtgagggac gaccagtgta gtttctggat ataaagtgtg aaggactgtt   7620
gagttaaaca tttttagtgg aatatacata gataacgtgt atttagaaac tttggtgaag   7680
ccagtatttg tttttagtaa ccttttttatg tatttccttc tttgattagc attgtcttca   7740
gtgttaagaa atgtggactc ctgtgaggtg ctggaggttt gaatcatctt gaaaactttc   7800
caatcttgtc tagttaccac tgcagagaca ctaaggaatt taccagaaaa agatatttga   7860
tacaagtgat ttaagaaatc tcaacatttc ctgaggccgt atcactgggc aaccagtgat   7920
gaaaactatg aatgaattgc acacctggaa gattttttaa gctaatgaca gtttcttcaa   7980
agatgtcaat tatttgcctt ggaaatttta taaattgcat ttctatgcac atcggcctct   8040
agtgcttacc actcggttta ttattcataa tctgcaattc aataaaggct ttgtgttttc   8100
atttatcttc aaaa                                                     8114
```

<210> SEQ ID NO 5
<211> LENGTH: 7973
<212> TYPE: DNA
<213> ORGANISM: Homo sapiens

<400> SEQUENCE: 5

```
acaacgcgct ccctgcgggg cgggcggcaa cctccatgcg gcctcgtcca cgctcagcac     60
cggggaagcc gaggcggaga agccgcgcgc gcctcagaag ctcccggacg cccagcggcg    120
gcgcgagcgg cggcggcggc agcagcagca gcagcagcac ggccaccggc gggagcggca    180
gcagcaccgg cagccccggc ggcgcggcct cggccccggc cccggccccg gccggcatgt    240
atcgctccgg ggagcgcctg ctgggcagcc acgcgctgcc cgcggagcag cgggacttcc    300
tgcccctaga gacgaccaac aacaacaaca accaccacca gcccggggcc tgggcccgcc    360
gggcgggctc ctcggcgtcc tcgcctccct cggcgtcctc gtccccgcac ccttcggccg    420
ccgtccccgc cgccgatcca gccgattcgg cctcgggcag cagcaacaag aggaagcgcg    480
acaacaaggc cagcacgtat ggactcaact acagcctgct gcagcccagc ggagggcggg    540
ccgcgggggg cggccgagca gacggcggcg gggtcgtgta cagcgggacc ccgtggaaac    600
ggaggaacta caaccaggga gtcgtgggtc tgcatgaaga aatcagtgat ttttatgaat    660
acatgtctcc aagacctgag gaggagaaga tgcggatgga ggtggtgaac aggatcgaga    720
gtgtaattaa ggagctctgg cccagcgctg acgtccagat atttggaagt tttaaaactg    780
```

```
gactttattt acctactagt gacatcgacc tagtggtgtt tgggaagtgg gagaacctac    840
ccctctggac tctggaagaa gctcttcgga aacacaaagt cgcagatgag gattcggtga    900
aagttttaga caaagcaact gtacctatta ttaaattaac agattctttt actgaagtga    960
aagttgatat cagctttaat gtacagaatg gcgtgagagc agctgacctc atcaaagatt   1020
ttaccaagaa atatcctgta ttgccatact tggttttagt attgaaacaa ttcctattgc   1080
agagggacct taatgaagta tttacaggtg gaattggttc ttatagtctc tttttaatgg   1140
cagtcagttt ccttcagtta catcccaggg aagatgcttg catccccaat acaaactatg   1200
gtgttctctt aatagaattt tttgaattat atggacgaca cttcaattat ttaaagactg   1260
gcatccggat aaaggatggt ggttcatatg tggccaaaga tgaagtacag aaaaatatgc   1320
tagatggcta caggccatca atgctttata tcgaagatcc tttacaacca ggtaacgatg   1380
ttggaaggag ttcatatggg gccatgcaag tgaagcaggc ctttgattat gcctacgttg   1440
ttttgagtca tgctgtatca ccaatagcaa agtactatcc caacaatgaa acagaaagca   1500
tactaggtag aataattaga gtaacagatg aagttgccac atatagagat tggatatcaa   1560
agcagtgggg cttgaagaat agacctgagc cttcatgcaa tggtccagtg tcgtcctctt   1620
ctgccacaca gtccagctct agtgatgtag attccgatgc aacaccatgc aaaaccccga   1680
aacagctgct ttgccgtccg tccactggga accgagtagg gtcgcaagat gtatccttgg   1740
agtcctctca ggcagttggg aaaatgcaaa gcacccaaac cactaacaca tccaacagca   1800
ccaacaaatc tcagcatgga tcagcaaggc tctttcgttc ttccagcaaa ggcttccaag   1860
gtacaactca aacaagccat ggttccttga tgacaaacaa acaacatcaa ggcaaatcca   1920
ataatcagta ttaccatggc aaaaagagga aacacaagag ggacgcgccc ctctcagacc   1980
tctgtagata gtcagcgctg cgcggtggac tgtcttctct gtgcaatgat ctcatgctca   2040
ggacagttgc gcagggactc ctgggagata ttcaggagcc tcacactgtt cagacgttga   2100
cttagcaact gcgtttttc ccagctcgcc acagaatgga tcatgaagac tgacaactgc    2160
aaaaaaaaca aaacaaaaca aaaaaaaaag caagcaaaaa agagggaaaa aaaaggctgc   2220
ttatttgata agtcatatgc tacaacaggg tcattttaag atttaaagct tgaatgtaaa   2280
ataaatatat ttctcattgg ctttatgcag agttataggg aatagtattc agtgttggta   2340
gggtgataga aacaaaaaac agtatcagag gatgaggtgg ggaaggaaaa caaaggtatc   2400
tgataggaag tccagattcc aaaggggaaa gtgatctgtg catgtttttt ttttaaatat   2460
ttttgcatat atttaccatt ttattgtgtg tatatataga agaccatata ggagattgat   2520
atttgtaata gtggatttgt taataatact ttttacataa cattactgtt taaattgtaa   2580
acagattttt tctcaggatt agtttgaaaa ataatctaaa ttgtcatctt aacatccata   2640
tatagggaag tgattagttc tattactcaa tttgttttc tcagcattga aatgacttaa    2700
tagaaccctt gtgtcctgct gcaaaaattt ttcctctcta aagaaaaggt ttatggtggc   2760
aaatgatgtt tattttattt tgtaaaaaaa aaaaaatgta ctatgtactt ttgtgtaaac   2820
actgaaaaat ctctggtcat ctccgagaat taacttgcaa ctgttttcta tagtgctgtc   2880
gtcttgggca atgggcaatt acatgacttt gtgtttgctt cctttgcagt cttttttttt   2940
tccccccatt tcttcctaat aggaaaaaaa aaaaaaaaaa ggtcacccat gtctggtctc   3000
attcctgttg cagtgaaact tcgagttcca cagactttgc atgctggctt ctctaaccct   3060
gtgtgctgcg tgtgcctgtt tctcatctct tattcttttt aaaattcatg cttaactact   3120
```

-continued

```
gtgggagaat aactgtaaac agctttaatt aaatcatact tataaaaaac tattttctta   3180
tattccactc tatgcttttg gtattgttga tctttacaaa ttaaatggtc tttgataatg   3240
gatctatttt gtattgcctt attaagacca aatacttctt gtcatcccat tctttatcct   3300
cttctttcat ggaattgtta tcgttaatta aaactttttt aaacattggc ttgtttcaat   3360
catactgtaa attttggttg tagtcagctt tgagtgcaat gagatgtata attctgttat   3420
cattacctgt tgagtttgaa actcagttgg gaatatttaa tataatagaa tgtaagtgac   3480
atttctgaaa atgctttctt tcagggtgaa agctcttatg tttagcatca atgtgtatgg   3540
ctctgttaaa tgcagccatt tctgagacga gattctttta tatatatata catataaagt   3600
actattggct tttaggagtt tcttttatat acatttatga aatactgaag accaatcaga   3660
ccattaatgg acacttagtg taacttttta taaagaaaat aatgctaaag taagaccaaa   3720
actgatgtca tcactgaaat taacaatttt caatatgttc atattttaat tcacaatgga   3780
aaaatgtgtt ccaaaactgg aaactcatag tactcgtgta aactgtggaa gatttcaaat   3840
gtgatgttat tttgacaatg ttttaaattt tagagtcaca ttttattctg atcagaattt   3900
ttattgagat gttgagcttt tgtttttgaa actagtttgt cataacattg tgcataatca   3960
cagtatttat tttctaggac aattgtgaat gtgtagactt atgtttactg ctaagggaac   4020
aattatttat aaaataatat taaatccagt attagctgcc tatttcagac acttaatact   4080
tgcagagatc tatgttacat ttaccacact gaagtttttt ttgttgtttt ttgtttgttt   4140
ttaaagaatc accctcattg ttgaaagtaa atgtactctt agggtgcgaa tattagtgtt   4200
ccaataagca tgtgattata ttaaggtggt ggtagcggga agataattct gattccattg   4260
ggaatcttag gttttcgtaa atttattggg aaaatagttt ttcctgtact gctgaagttt   4320
ctttttggta aacagtatct ttctaaaaga aaaaagcatg aaggagaaat tgaggtgtgt   4380
atacatttcc tcaaatgacc agcattgtat tcgtgaatac tgtgtatctt gcagtgaaca   4440
gtgtggaagc tgttcatttt tcaatctgaa gtaaaatact ttcaagaact tttagtttgc   4500
ctgctcattt gttttataca tttcatctat ttgactccta tcttatttct tttttgagtt   4560
ttaatacttc ctatattttg tgaatatatc agaaatgtgt catttatata ttagagtcca   4620
ttcatatcca tgaatcataa ccttcctttg ctaatacttg ttgaatggga ttttacaaat   4680
tctccctcac tctggtgaca tttctcaggc agtcatgtat gtgtacctgg ccattagaaa   4740
tattaatatt taaagactgt tttttagagg agctgatggg ttggtgaggt gtcagcacaa   4800
aatcttactg gttatgtttt gatgataaaa gtatatccat tttttccctc cagctttaag   4860
gtgactgtga aggtgcctgg ttttgaatgt ctttgtttgg tttggagatg tcgcactcag   4920
ttttcaaatc tagcttggat ctgtaggacc tatgtttttt acaagtaatt gccctccagt   4980
cttcaacagt tgattctgtt ttattttttat cctgttttga gtgtacttta cctttacttg   5040
cattttgagc ctcattaata tttaggttat ttgatttggc tccagatatt cctagatctg   5100
cacagggcaa aacatgggct atagggtgag catttttaat tgtctttttc tgctggaacc   5160
ttatatctct ccatgtgttt tctgctcctt ccctccccca tgaaatggta agtgtgactt   5220
gtgtttgcct gaacctgtgg actagtgttt ggggtttctg gaaacactag agggtcagaa   5280
aagagtaatg accaccgtga cgtgcaggat tctcttgctg tgacatgttc attgcaaagc   5340
cctctccagt gactaggagg tgtagttatt aaggttgatc tgttagaaat caccattatt   5400
aggtattagt ggtagatgtt gctgatactt ttattggtca tgactacatc tcagttttac   5460
tttaatattg atctatagtt tgatcagttc cttgaattct aatatgttga tttctcagtg   5520
```

tttctgtcac taaccaagaa tgtttctagg cagttggttg cttcacagtc aaaactaaat 5580
ggtaaactat caaaaataca ttcccaattt tgctgtgata aatattgaaa tgttaaaatt 5640
aatgaacaga agaatttatt cttacccatc tattcttgtt ctcctagttc attaaacttt 5700
cagttattgg aaaggcacat tctcaaagta ttttatgagc aaaatattct ataaatgcgt 5760
ctaacaaacc taattgaata taaaagttat atttagtagt tactgttgat agtaattttc 5820
atcagggtca tagttcatct agtaaaatat ttagagaatg atgttaacat tccagcatta 5880
aagtgggaac aaagatttat atatgaaatt ccttaaaaga gttcatcttg ccttggtttc 5940
tgaccctcaa gactctagct acctgccatc ttgtcaaaac atttgtgggt agaataagtg 6000
ttaaagatca aattttaata tgcttctcga tatttaacat agctaagaag ccagatttta 6060
ctgtagaagt tatttacatg atttgaaaac ttgacctaac tggaagcctt tttctcagtc 6120
atcttgttct aagccatctt gacttcacac ccttagcgac ttttcttttt tttttggtca 6180
aagataatga gctaaatata tatagacgtt gaatgttgac aaaattatta accagaaaaa 6240
ttgcttataa aggctgctga tctatttgat acctagaatt aaatatttga ggacagtttt 6300
tagttaataa actgctaatg tttattttac tgtctctcag gtttttggtt tttttaaaaa 6360
aaatgtgttt ggcctttaca ttttctactt aagtgtgtac tttattgagt ttaaccttgt 6420
ctgtagccta gtagcctgaa agaaaaggag acagaaccag agagatggat gtagtgcatt 6480
ccctttggtt attacacatt tgtggtagct cctggattta ctgagagata ttttagctat 6540
gtcaataaga acagctaatg atgtggaaat caggtgttct cttgtgtatt tcagtgaaca 6600
tttttattag tagttgcata tcatctctag ttccacattt taacttaacg tctttgtggc 6660
ttcaccactg agctaccttt cactacacca gcttctgtgt ggcctggtaa catggaaggt 6720
ctctcctaag gacagtctgg acgtattttg ggggaatgtt atttatctta aagatgccta 6780
gaaacaaaac gcatatagta ccagtgagaa actatgaagt aaacaagttg ctcaggccgg 6840
gcatggtggc tcacgcctgt aatcccagca ctttgggagg ccgaagcggg aggatggctt 6900
gaggctggga gtttgagacc ttcatctctt aaaaaaacaa acaaaaacct gaatggtgag 6960
gtgtggtgga attgggtagg ggagggaaag gaggacttgg aaaagcattc tccaaagcca 7020
gcaacttggt gaagttcagt acttgcctct tagaggttag gccatgcctt tcaaagagag 7080
tgaaatgatg ggttatcagc cacattcttg gagttaatat ttttcttcat ctttcagttt 7140
gggttctgtg ctattcatag ttcttcccta agaccatttc attattacct tttatattta 7200
gttgcaattt attataatat gttgttttgt ccctgaactt aatctcctaa ttttaagatc 7260
ctctctgatt tttgcatatt gaaacttaca gaagtcactt taaaaaagtc ttttgaaagt 7320
cctacaatcc taaaataaat cacaagcttg tttgttagac gtgtcaagag tctccagtct 7380
ttactactaa aaagcagcac tgccttaaca cacattgtta tgggtgaaaa gtgagggacg 7440
accagtgtag tttctggata taaagtgtga aggactgttg agttaaacat ttttagtgga 7500
atatacatag ataacgtgta tttagaaact ttggtgaagc cagtatttgt ttttagtaac 7560
ctttttatgt atttccttct ttgattagca ttgtcttcag tgttaagaaa tgtggactcc 7620
tgtgaggtgc tggaggtttg aatcatcttg aaaactttcc aatcttgtct agttaccact 7680
gcagagacac taaggaattt accagaaaaa gatatttgat acaagtgatt taagaaatct 7740
caacatttcc tgaggccgta tcactgggca accagtgatg aaaactatga atgaattgca 7800
cacctggaag attttttaag ctaatgacag tttcttcaaa gatgtcaatt atttgccttg 7860

-continued

```
gaaattttat aaattgcatt tctatgcaca tcggcctcta gtgcttacca ctcggtttat   7920

tattcataat ctgcaattca ataaaggctt tgtgttttca tttatcttca aaa          7973
```

<210> SEQ ID NO 6
<211> LENGTH: 4511
<212> TYPE: DNA
<213> ORGANISM: Homo sapiens

<400> SEQUENCE: 6

```
gggcgcgcgg gccccgcggg ggcggcgcgt ggatggatcc gcgcgtggcc tggatccagc     60

ccgagcagaa ggggccggcc aatgccctgt ggatgcagat ctgggagacc tcgcagggcg    120

tgggccgcgg cggctcgggc ttcgcgtcct atttctgcct caactcgccg gcgctggaca    180

cggcggccgc ggcgggggcg gccgggcggg gcagtggcgg cctgggcccc gcgctgcccg    240

ccgcgtcgcc cccgccgccc ggccccaccg cgcccgccgc gctgccccccc gcgctgctga    300

cggcgctggg gcccgcggcc gagggcgcgc ggcgcttgca caagtcgccg tcgctgtcgt    360

cctcgtcgtc gtcctcctcg tccaacgcgg agtcgggcac cgagagcccc ggctgctcgt    420

cgtcgtcctc cagcagcgcc tcgctgggcc ggccgggcgg cggccgcggc ggcgccttct    480

tcaacttcgc cgacggcgcg cccagcgccc ctggcacagc caacgggcac cccgggccgc    540

gcggccccgc gcccgccggc tccccgtcgc agcaccagtt ccacccgggt cgccggaaac    600

gcgagaacaa ggccagcacc tacggcctca actacctgct gtccggcagc cgcgcggccg    660

ctctcagcgg agggggcggc cccggggccc aggcgccgcg gcccggcacc ccgtggaaga    720

gccgcgcgta cagcccgggc atccagggac tacatgagga aataattgac ttttataact    780

tcatgtcccc ttgtcctgaa gaagcagcta tgagaagaga ggtggtgaaa cggatcgaaa    840

ctgtggtgaa agacctttgg ccgacggctg atgtacagat atttggcagc tttagtacag    900

gtctttatct tccaactagc gacatagacc tggtggtctt cgggaaatgg gagcgtcctc    960

ctttacagct gctggagcaa gccctgcgga agcacaacgt ggctgagccg tgttccatca   1020

aagtccttga caaggctacg gtaccaataa taaagctcac agatcaggag actgaagtga   1080

aagttgacat cagctttaac atggagacgg gcgtccgggc agcggagttc atcaagaatt   1140

acatgaagaa atattcattg ctgccttact tgattttagt attgaaacag ttccttctgc   1200

agagggacct gaatgaagtt tttacaggtg gaattagctc atacagccta attttaatgg   1260

ccattagctt tctacagttg catccaagaa ttgatgcccg gagagctgat gaaaaccttg   1320

gaatgcttct tgtagaattt tttgaactct atgggagaaa ttttaattac ttgaaaaccg   1380

gtattagaat caaagaagga ggtgcctata tcgccaaaga ggagatcatg aaagccatga   1440

ccagcgggta cagaccgtcg atgctgtgca ttgaggaccc cctgctgcca gggaatgacg   1500

ttggccggag ctcctatggc gccatgcagg tgaagcaggt cttcgattat gcctacatag   1560

tgctcagcca tgctgtgtca ccgctggcca ggtcctatcc aaacagagac gccgaaagta   1620

ctttaggaag aatcatcaaa gtaactcagg aggtgattga ctaccggagg tggatcaaag   1680

agaagtgggg cagcaaagcc cacccgtcgc caggcatgga cagcaggatc aagatcaaag   1740

agcgaatagc cacatgcaat ggggagcaga cgcagaaccg agagcccgag tctccctatg   1800

gccagcgctt gactttgtcg ctgtccagcc cccagctcct gtcttcaggc tcctcggcct   1860

cttctgtgtc ttcactttct gggagtgacg ttgattcaga cacaccgccc tgcacaacgc   1920

ccagtgttta ccagttcagt ctgcaagcgc cagctcctct catggccggc ttacccaccg   1980

ccttgccaat gcccagtggc aaacctcagc ccaccacttc cagaacactg atcatgacaa   2040
```

-continued

```
ccaacaatca gaccaggttt actatacctc caccgaccct aggggttgct cctgttcctt   2100
gcagacaagc tggtgtagaa ggaactgcgt ctttgaaagc cgtccaccac atgtcttccc   2160
cggccattcc ctcagcgtcc cccaacccgc tctcgagccc tcatctgtat cataagcagc   2220
acaacggcat gaaactgtcc atgaagggct ctcacggcca cacccaaggc ggcggctaca   2280
gctctgtggg tagcggaggt gtgcggcccc ctgtgggcaa caggggacac caccagtata   2340
accgcaccgg ctggaggagg aaaaaacaca cacacacacg ggacagtctg cccgtgagcc   2400
tcagcagata atggctcctg gctgcgtcag cctcccccac ccctctgcag actgccccgc   2460
ggcctcggcc accggcaggg gaaccgagac cagcaccccg cacgtcagcc gggctcgcgg   2520
cacgcccgcc gctgatcact ctgcatgttt cttcgtgtgg tggtcgcgtc catcttcaag   2580
aacagctcgt tgtgctcatc tgtgaagcct tattaaacgt ggacgttgtt ttctgccttc   2640
ccaggattct tccttcagtg ctgaggcagg tcgggctcag gaactgcagg gacgtgaaca   2700
tgcgcttgcg gtttgaggta gccgtgtctg ttccttcgcg gtttgctatt ttcatttcct   2760
gttcgtcaaa gcagcagagg agatcaaacc ccgttcgtgt gtctttcctc cacggataag   2820
cttgggaggt cattgtttta ctgccctcac attttgtttg aaatttcaga actgtttttc   2880
tatgtaaata ttgaaaactt atgatttgtg caataactca gatatttttt atttaatttc   2940
ctattttcac ataagttata tttaagggag gagggaattt tttttaaaca agcttaggtc   3000
ctttcccgag ctgcattttc taagttgggt catcgtgtcg gctggttgtc tgacgagcat   3060
cgttacaaac accatgatga ggggtttggg gttttatttt gatgtctttt cttttggtcg   3120
gaagtgagtg aaggagccag gtcgccctga aggttttcca aagggcttgg ctccagagcc   3180
acctggcaga ctgcccgtgg ccctgctgtc gggccccagg ccgttgtcct gctctgacca   3240
cagagtttta atgttttggt tttcacttct tttaaactgg acaacaaatc cagcatttca   3300
agtgccagaa gtataacttt ctaaggagag aagggttgtc acattataaa atctttagga   3360
aaatgtgaac tggaaaacgc ttcggtcagt tttagtgaca tagcctgtga tgatgggtct   3420
ggtgactatt attgcggacc gtggtaccca gttttaggaa tgtggagaaa ggaattctgt   3480
tgattccgtt gaggaatctg tagcgtatgc attcgttctg ttaagagcaa atctaggaga   3540
agtgcttcag ctgcccagtg cgccgtgggg agtgttttaa cggatcgtgt cgcaggagag   3600
cacagcccag cgttggggcc gggaccgctg gcgcccgacg tcggaagcat acaggtatac   3660
tatgcaagtg tattctgcca caacaaccac tgtctttgtt accttttttt gaacaagaat   3720
atatccatcc tgcctaaccc tgagtttttg gagcaccaca gttgtcctgg gagttggttg   3780
catcttgtag gccatctgac ttcctgtttt taaaacgggg gtctggtctt gctaaacact   3840
acaggtaggt tggtctttga agtccactag tggagaatgt caagacaaga tacttattac   3900
catgacatct gatgcatgtg cagcagtggg gagttctaga ttgatctctg aatgtgatcg   3960
acgcccagca aggacaagct ttaaaatgtc tgcggtctgc ccttttgaag caggactggc   4020
tcactctgtc attgggagct gtcagctgcg actgcaggtt ctctaggagg cattccagaa   4080
tagagtagca cactgtgtct gcagttctcg atgaccgaaa gttatcaaaa atatttaaaa   4140
tatttaaatt gtgaacctat tgataaagaa tatttataaa aactgatctg taggcctgta   4200
ctaatctcta cgcattagca atattgactg taaacccaca ttaaggaaac cactacgggt   4260
ctggcagtgc gtgtcccgtg gggtgtgcat tttaaaactc gattcataga cacaggtacc   4320
atgttccatt tccgtcatgg tgaagcaaat gaattggcct ggctaccact gtggtcgcgt   4380
```

-continued

```
gctacaggtt tgacaaaaag atatcatgtt tcgatttttt tgtgtgtgga caacaatatg   4440

gaagctaaaa ttgacatatt tttatgtaaa gtttttctat tctttgattt ttaataaact   4500

ttggaaacca g                                                        4511


<210> SEQ ID NO 7
<211> LENGTH: 474
<212> TYPE: PRT
<213> ORGANISM: Homo sapiens

<400> SEQUENCE: 7

Thr Tyr Gly Leu Asn Tyr Ser Leu Leu Gln Pro Ser Gly Gly Arg Ala
1               5                   10                  15

Ala Gly Gly Gly Arg Ala Asp Gly Gly Gly Val Val Tyr Ser Gly Thr
            20                  25                  30

Pro Trp Lys Arg Arg Asn Tyr Asn Gln Gly Val Val Gly Leu His Glu
        35                  40                  45

Glu Ile Ser Asp Phe Tyr Glu Tyr Met Ser Pro Arg Pro Glu Glu Glu
    50                  55                  60

Lys Met Arg Met Glu Val Val Asn Arg Ile Glu Ser Val Ile Lys Glu
65                  70                  75                  80

Leu Trp Pro Ser Ala Asp Val Gln Ile Phe Gly Ser Phe Lys Thr Gly
                85                  90                  95

Leu Tyr Leu Pro Thr Ser Asp Ile Asp Leu Val Val Phe Gly Lys Trp
            100                 105                 110

Glu Asn Leu Pro Leu Trp Thr Leu Glu Glu Ala Leu Arg Lys His Lys
        115                 120                 125

Val Ala Asp Glu Asp Ser Val Lys Val Leu Asp Lys Ala Thr Val Pro
    130                 135                 140

Ile Ile Lys Leu Thr Asp Ser Phe Thr Glu Val Lys Val Asp Ile Ser
145                 150                 155                 160

Phe Asn Val Gln Asn Gly Val Arg Ala Ala Asp Leu Ile Lys Asp Phe
                165                 170                 175

Thr Lys Lys Tyr Pro Val Leu Pro Tyr Leu Val Leu Val Leu Lys Gln
            180                 185                 190

Phe Leu Leu Gln Arg Asp Leu Asn Glu Val Phe Thr Gly Gly Ile Gly
        195                 200                 205

Ser Tyr Ser Leu Phe Leu Met Ala Val Ser Phe Leu Gln Leu His Pro
    210                 215                 220

Arg Glu Asp Ala Cys Ile Pro Asn Thr Asn Tyr Gly Val Leu Leu Ile
225                 230                 235                 240

Glu Phe Phe Glu Leu Tyr Gly Arg His Phe Asn Tyr Leu Lys Thr Gly
                245                 250                 255

Ile Arg Ile Lys Asp Gly Gly Ser Tyr Val Ala Lys Asp Glu Val Gln
            260                 265                 270

Lys Asn Met Leu Asp Gly Tyr Arg Pro Ser Met Leu Tyr Ile Glu Asp
        275                 280                 285

Pro Leu Gln Pro Gly Asn Asp Val Gly Arg Ser Ser Tyr Gly Ala Met
    290                 295                 300

Gln Val Lys Gln Ala Phe Asp Tyr Ala Tyr Val Val Leu Ser His Ala
305                 310                 315                 320

Val Ser Pro Ile Ala Lys Tyr Tyr Pro Asn Asn Glu Thr Glu Ser Ile
                325                 330                 335

Leu Gly Arg Ile Ile Arg Val Thr Asp Glu Val Ala Thr Tyr Arg Asp
            340                 345                 350
```

```
Trp Ile Ser Lys Gln Trp Gly Leu Lys Asn Arg Pro Glu Pro Ser Cys
        355                 360                 365

Asn Gly Asn Gly Val Thr Leu Ile Val Asp Thr Gln Gln Leu Asp Lys
    370                 375                 380

Cys Asn Asn Asn Leu Ser Glu Glu Asn Glu Ala Leu Gly Lys Cys Arg
385                 390                 395                 400

Ser Lys Thr Ser Glu Ser Leu Ser Lys His Ser Ser Asn Ser Ser Ser
                405                 410                 415

Gly Pro Val Ser Ser Ser Ser Ala Thr Gln Ser Ser Ser Ser Asp Val
            420                 425                 430

Asp Ser Asp Ala Thr Pro Cys Lys Thr Pro Lys Gln Leu Leu Cys Arg
        435                 440                 445

Pro Ser Thr Gly Asn Arg Val Gly Ser Gln Asp Val Ser Leu Glu Ser
    450                 455                 460

Ser Gln Ala Val Gly Lys Met Gln Ser Thr
465                 470


<210> SEQ ID NO 8
<211> LENGTH: 419
<212> TYPE: PRT
<213> ORGANISM: Homo sapiens

<400> SEQUENCE: 8

Leu Leu Gln Pro Ser Gly Gly Arg Ala Ala Gly Gly Gly Arg Ala Asp
1               5                   10                  15

Gly Gly Gly Val Val Tyr Ser Gly Thr Pro Trp Lys Arg Arg Asn Tyr
            20                  25                  30

Asn Gln Gly Val Val Gly Leu His Glu Glu Ile Ser Asp Phe Tyr Glu
        35                  40                  45

Tyr Met Ser Pro Arg Pro Glu Glu Glu Lys Met Arg Met Glu Val Val
    50                  55                  60

Asn Arg Ile Glu Ser Val Ile Lys Glu Leu Trp Pro Ser Ala Asp Val
65                  70                  75                  80

Gln Ile Phe Gly Ser Phe Lys Thr Gly Leu Tyr Leu Pro Thr Ser Asp
                85                  90                  95

Ile Asp Leu Val Val Phe Gly Lys Trp Glu Asn Leu Pro Leu Trp Thr
            100                 105                 110

Leu Glu Glu Ala Leu Arg Lys His Lys Val Ala Asp Glu Asp Ser Val
        115                 120                 125

Lys Val Leu Asp Lys Ala Thr Val Pro Ile Ile Lys Leu Thr Asp Ser
    130                 135                 140

Phe Thr Glu Val Lys Val Asp Ile Ser Phe Asn Val Gln Asn Gly Val
145                 150                 155                 160

Arg Ala Ala Asp Leu Ile Lys Asp Phe Thr Lys Lys Tyr Pro Val Leu
                165                 170                 175

Pro Tyr Leu Val Leu Val Leu Lys Gln Phe Leu Leu Gln Arg Asp Leu
            180                 185                 190

Asn Glu Val Phe Thr Gly Gly Ile Gly Ser Tyr Ser Leu Phe Leu Met
        195                 200                 205

Ala Val Ser Phe Leu Gln Leu His Pro Arg Glu Asp Ala Cys Ile Pro
    210                 215                 220

Asn Thr Asn Tyr Gly Val Leu Leu Ile Glu Phe Phe Glu Leu Tyr Gly
225                 230                 235                 240

Arg His Phe Asn Tyr Leu Lys Thr Gly Ile Arg Ile Lys Asp Gly Gly
```

```
                245                 250                 255

Ser Tyr Val Ala Lys Asp Glu Val Gln Lys Asn Met Leu Asp Gly Tyr
            260                 265                 270

Arg Pro Ser Met Leu Tyr Ile Glu Asp Pro Leu Gln Pro Gly Asn Asp
        275                 280                 285

Val Gly Arg Ser Ser Tyr Gly Ala Met Gln Val Lys Gln Ala Phe Asp
    290                 295                 300

Tyr Ala Tyr Val Val Leu Ser His Ala Val Ser Pro Ile Ala Lys Tyr
305                 310                 315                 320

Tyr Pro Asn Asn Glu Thr Glu Ser Ile Leu Gly Arg Ile Ile Arg Val
                325                 330                 335

Thr Asp Glu Val Ala Thr Tyr Arg Asp Trp Ile Ser Lys Gln Trp Gly
            340                 345                 350

Leu Lys Asn Arg Pro Glu Pro Ser Cys Asn Gly Pro Val Ser Ser Ser
        355                 360                 365

Ser Ala Thr Gln Ser Ser Ser Ser Asp Val Asp Ser Asp Ala Thr Pro
    370                 375                 380

Cys Lys Thr Pro Lys Gln Leu Leu Cys Arg Pro Ser Thr Gly Asn Arg
385                 390                 395                 400

Val Gly Ser Gln Asp Val Ser Leu Glu Ser Ser Gln Ala Val Gly Lys
                405                 410                 415

Met Gln Ser


<210> SEQ ID NO 9
<211> LENGTH: 320
<212> TYPE: PRT
<213> ORGANISM: Homo sapiens

<400> SEQUENCE: 9

Tyr Ser Pro Gly Ile Gln Gly Leu His Glu Glu Ile Ile Asp Phe Tyr
1               5                   10                  15

Asn Phe Met Ser Pro Cys Pro Glu Glu Ala Ala Met Arg Arg Glu Val
            20                  25                  30

Val Lys Arg Ile Glu Thr Val Val Lys Asp Leu Trp Pro Thr Ala Asp
        35                  40                  45

Val Gln Ile Phe Gly Ser Phe Ser Thr Gly Leu Tyr Leu Pro Thr Ser
    50                  55                  60

Asp Ile Asp Leu Val Val Phe Gly Lys Trp Glu Arg Pro Pro Leu Gln
65                  70                  75                  80

Leu Leu Glu Gln Ala Leu Arg Lys His Asn Val Ala Glu Pro Cys Ser
                85                  90                  95

Ile Lys Val Leu Asp Lys Ala Thr Val Pro Ile Ile Lys Leu Thr Asp
            100                 105                 110

Gln Glu Thr Glu Val Lys Val Asp Ile Ser Phe Asn Met Glu Thr Gly
        115                 120                 125

Val Arg Ala Ala Glu Phe Ile Lys Asn Tyr Met Lys Lys Tyr Ser Leu
    130                 135                 140

Leu Pro Tyr Leu Ile Leu Val Leu Lys Gln Phe Leu Leu Gln Arg Asp
145                 150                 155                 160

Leu Asn Glu Val Phe Thr Gly Gly Ile Ser Ser Tyr Ser Leu Ile Leu
                165                 170                 175

Met Ala Ile Ser Phe Leu Gln Leu His Pro Arg Ile Asp Ala Arg Arg
            180                 185                 190

Ala Asp Glu Asn Leu Gly Met Leu Leu Val Glu Phe Phe Glu Leu Tyr
```

```
        195                 200                 205

Gly Arg Asn Phe Asn Tyr Leu Lys Thr Gly Ile Arg Ile Lys Glu Gly
    210                 215                 220

Gly Ala Tyr Ile Ala Lys Glu Glu Ile Met Lys Ala Met Thr Ser Gly
225                 230                 235                 240

Tyr Arg Pro Ser Met Leu Cys Ile Glu Asp Pro Leu Leu Pro Gly Asn
                245                 250                 255

Asp Val Gly Arg Ser Ser Tyr Gly Ala Met Gln Val Lys Gln Val Phe
            260                 265                 270

Asp Tyr Ala Tyr Ile Val Leu Ser His Ala Val Ser Pro Leu Ala Arg
        275                 280                 285

Ser Tyr Pro Asn Arg Asp Ala Glu Ser Thr Leu Gly Arg Ile Ile Lys
    290                 295                 300

Val Thr Gln Glu Val Ile Asp Tyr Arg Arg Trp Ile Lys Glu Lys Trp
305                 310                 315                 320


<210> SEQ ID NO 10
<211> LENGTH: 82393
<212> TYPE: DNA
<213> ORGANISM: homo sapiens

<400> SEQUENCE: 10

acaacgcgct ccctgcgggg cgggcggcaa cctccatgcg gcctcgtcca cgctcagcac     60

cggggaagcc gaggcggaga agccgcgcgc gcctcagaag ctcccggacg cccaggtacg    120

tgggagcact ccacagatgg cgcaagtacg gttgggccag gcggttgcgg ccccgtcgcg    180

ccgcggcctc tgtgacgcac ggcgaggcct cccgggctgc tgcgcggcgc agcgggggcg    240

gggcgagcgc gtgagggcgg ggcggtgggg gggggggcg gagcgagagg ggcggagccg    300

gcagaggccc cgccccgggg ccggaggagc gaggacgcta cggagcaggc gcgtctcgct    360

gccgccgctg ccgccgccgc cgctcgctct tctgtggagc cgccgccgcc gccgccgcca    420

tttgcacggg gaccccagtg acaggggctc ggcggagggg cggaggggcg gagggagggg    480

gggagggccc gcggagcccc cgagggcggg agcgacgccg ccggcgccgg ccgggctccc    540

tgcgcgaccg cgccgcccgc ggcgggcccc gagcagcagc agcagcagca gcggcagcag    600

cggcagcagc agcagcagcc gaggccgggc gtgcgcctga ggcggcggcg gcggcggccc    660

tgcgggcggc cgggaggggc gggggcagcg gccgccgccg tttgatggat ccgaggatcg    720

cctggtttca gccagagcag ctcggaccgt ccaacagtct gtggatgcag atctgggaga    780

cgacccaggg gctgaggaac ctctacttca accaccactg tcacagcagc ggcggcgcga    840

gcggcggcgg cggcagcagc agcagcagca gcacggccac cggcgggagc ggcagcagca    900

ccggcagccc cggcggcgcg gcctcggccc cggccccggc cccggccggc atgtatcgct    960

ccggggagcg cctgctgggc agccacgcgc tgcccgcgga gcagcgggac ttcctgcccc   1020

tagagacgac caacaacaac aacaaccacc accagcccgg ggcctgggcc cgccgggcgg   1080

gctcctcggc gtcctcgcct ccctcggcgt cctcgtcccc gcacccttcg gccgccgtcc   1140

ccgccgccga tccagccgat tcggcctcgg gcagcagcaa caagaggaag cgcgacaaca   1200

aggccagcac gtatggactc aactacagcc tgctgcagcc cagcggaggg cgggccgcgg   1260

ggggcggccg agcagacggc ggcggggtcg tgtacagcgg gaccccgtgg aaacggagga   1320

actacaacca gggagtcgtg gggtgagtgc tggctctgcg gcccgatggc ctggccggtg   1380

cgaatgcgca gccgggcaca cgcccacaga gggggggttgt gagggtctag gagcggccac   1440
```

-continued

```
ccccacggcc tgccttcgct gctgttgcac gggggtgctg ctggccatcc ccaacccccc   1500
agtcgttcac acctttcccc aagcctcctt agccgtccac accctccgtc tcctgtcctc   1560
ccttagtcgt ccacaccttc ctcccctccc tcttaaccgt ccacaccttc cccaggcccc   1620
cccctttatc cattcactct cctcccatcc cccttagtta aacacatcta cccttgacca   1680
ccaccccgcc tccagccctc cacacctttt tccccatcat cacaactcaa gatgagaccg   1740
cttagcacgg gcctatcatt cattccctga gaacattggt gtgtgagtgt tttttgatgg   1800
tgcaggaccc ggaggtgctt tccttgccaa gaatagaaac atccagaatg ctcctcccca   1860
tcccccaatc ccagacagca attatgtcag ccctgtaagg cattgcctgc tcttgaccct   1920
ttggcccatc tttttatttt taaaaaattc ccatgtcaca gatgccctgt ctatgcagag   1980
ggtggcgtgg gatgggtgac cactaagttt aggctggtga aggtggtgag cccttctgag   2040
gccctgatag aactttccag gagttcatgg tccgcggctc cagcttctca ctgtaaagtt   2100
gtcatcctgg cagaggcagc caatgctttt cattctaggg ggtagagatt tatgctaatg   2160
agtgaatatt gcaccactag tgactttctg tttaaagttc agctcttaga aaatggaatc   2220
ttacctgacc cctagtgaat tatgtacata agcagggaat gtttccaact agatctccct   2280
tcagaagagt ccctgtgctg gaataggtca ctgaatctta tttgttttgt aaaacaaagc   2340
ttttgggtct cgtgggtgtg tgtgtgtgtg tgtgtgtgtg tgtgtgtgtg tgtgtagctt   2400
gagtatggag aaccggcttt caaattgctt ttcatttttc aggttgtgtt ttacattgag   2460
ggctttagca tgcaaatgaa attaccaatt agtaatccca tgtgaacctt ttcctggatt   2520
tattcattca gatctgccct gctttggctg agagagagag ttctgtgtac ctttttgaag   2580
gtctggataa aatgagttgg tgggttccat ctgcttccag tgggctggtg tctgctctat   2640
gctactatta caactcctac cttttgtgga aaatgcagtc aagcgttcta ggactggtgc   2700
tgtggtacat gtcaaacctg ccctcacatt ccagaaaggg aaccctttta gggttgagtc   2760
ctctgttgct aagcttcaag ggtgctctcc atggtcatca cgttttatta aaggcttgtg   2820
gttccatcct gttagcattt ccaagtctac gcgtaaacct gtggtttagt gacaagcaaa   2880
ttgatgttga gggtttctgg tagtttcatt tcacaggagt aagctccagt taggtaatca   2940
ctgtcaacga aaaccttgaa gttccttaat tgcattttac tgaagcctct ttgcatgtgt   3000
ctagcaaaag atataagtcc aagatgctta tttttttttt gataaattag aaattgtcct   3060
ctcctctact tgctatttaa tgcagaagat actctaaaag gttcatattt atacttagaa   3120
gcaagatgtt cttgttcctg attcaaatat attgccctca aagggattag gagaggaatt   3180
ttcatttccc ggagggatta ctgtttaaaa actggttgta aacctcttta aaaactgctt   3240
atcacttcac cagattttcc attcttttgc ctcctccctt agaggatgtc agcagttaat   3300
ttttttttta aattaaaaaa agttcaattc tgagacctcc tagtttcaaa aaatacatta   3360
aacaattccc aagagtgtta agagtgtctg ggtgcttaga aattcttgct ttgattcatg   3420
tattctgatt tttttttttt ttttgagacg gagtttcgct cttgttgccc aggctggagt   3480
gcagtggctc gatctcagct caccgcaacc tctgcctccc aggttcaagc gattctgctg   3540
cctcagcctc ccgagtagct gggattacag gcgcttgcca ccacgcctgg ctaatttttt   3600
atttttagta gagacggggt ttcttcatgt tggtcaggct ggtctcgaac tcctgacctc   3660
aggtgatctg cccgtcttgg cctcccaaag gactgggatt acaggcatga gccaccgtgc   3720
ccggcctcat tatcctgatt tctttttttt cttttgagac tgggtctcac tctgctgcct   3780
aggctggagt ggagtgacgt gatcatagct cactgtatcc tctaactctt gggctcaagt   3840
```

-continued

```
gatcctcctg ccttagcttc ctggagtagc tgggactaca ggcacatgtc accacacctg   3900
cctaattttt ttatttttac tttttgtaga gatggggcct ccatttgttg cctaggctgg   3960
tcttcaaccg gcctcaagca gtcctcccac cttggcctca cagagtgctg ggattatagg   4020
catgagccac cattctcgcc agtatcctta tttcttaact ttagaaagtt tttctatttt   4080
taatataggt atttaaaaaa atctgaattc agagtgcacc tcgatgttat gctgttctga   4140
gattaaatat actaaaactg ttaccattgt tttctgaatt cttaagatgt gactgatagt   4200
tagctaatag gttaacacat tgtggtggtt cttggcctct gaactgatag tccagatggg   4260
gagaggagac cagaaagcat gtgaaaatgg actagaacca tgggacagct atatagtctc   4320
tcgcagctgt cttttgtgtt ctctgcttcc accaaattgg ttgatttatt tagaatgctg   4380
acctcttgca ttgcctaagt ccttgatgtt tttggtttct cctctgaact ctcaaaggta   4440
ctcacttcat gctcttggta tagcccactt atgtttaact ttccttttat tatgtgttcc   4500
ctcttacaca tgacatggac atttctttaa tatgtagagt aagatattgg atttcatcct   4560
aaagtcttca aaataaaact cttgagctca tcatctcaga cttcttcatg tacccacaga   4620
ccagggattt tgtttgcttt ttaaaacatt tttttatttt gtgttttatt atttttaaat   4680
tttaatttaa ttttatggag acagggtctc gctctgttgc ccaggctgga gtgcagtggt   4740
gtgatctcgg ctcactgcag cctttgcctg ggctcaagcc atccacatgc cttggcctcc   4800
cagtgtgctg ggattacagg tgtgagccac tgtgcctggc ctaaatttat ttttttaatt   4860
ttttttgaga cagggtcttg ctctgtcgct caggctggag tgcagtgtca taatcatggg   4920
tcacagcagc cttggcctcc caggctgaag tgaacttccc acctcagcct cctgagtagt   4980
tgggactaca ggcgagtgcc accatgcctg gctcattttg gttttttttg taaagatggg   5040
gtcttgtcat gttgcccatg aaggtctcca actcctggtc caagtgatcc tcccgcctcc   5100
gcctagcaaa atgttgggat tacaggtgtg agccaccatg cctggcctta tttatttatt   5160
taattatgaa tgaatgaatg aattaatgag agggagtctt gctctcttgc ccaggctgga   5220
gtgtggtggc acaatcttgg cccactgcaa cctccgtctc ccaggttcga gcaattctcc   5280
tgcctcagcc tcccgagtaa ctgggattac aggcgcccgc caccatgccc aggtaatttt   5340
tgtattttta gtagagatgg ggtctcacca tgttggccag actggtttcg aacttctgac   5400
ctcaagtgat ctgcccacct tggcttccca aagtgtcagg attacaggca tgagccacca   5460
tgcctggcct ggccttttat gttttaagtt gcttccactg attctcttgg gctttgctcc   5520
cctccagaac tggccatggt ttaggatgct gtccacctgc tgctgcttgt ccatgaaaac   5580
gagccataaa cccttttctt ttgaaagact taattgttta tcactatgga gaaagagggg   5640
atggcaagaa gtagcaaata cagggaattt gcagaacttg gtcttgagcc ctgggtccag   5700
aaacttcttc tggaaggtgc ttggtgtttg tccaagctca tgataggttt ctgttggctg   5760
tactgccaga tctgtagatg cttttttaag gcttggatga cttgttcaaa acaatgtttt   5820
ggagtacaaa tttggctgtg gggacatcaa gaccttgttg ggaaacttgg gtttaaggta   5880
caatttctta aactaggatg gtgggaatgg ggatgtgaag ggagaatgaa tgtgagaggt   5940
attacagggt aaggatggag atgattcaga ttccttaagt ggatttaata atcacactgt   6000
agctttgaac ttgagtgact ggggaaatat ttgtggtgtt tttggaaata agggccagaa   6060
ggactattgg tttgggtaag aagatagtag ggggatgtat aggtggacct gctagtgggg   6120
agctgagatt tggagggctg agatgtagtg ctcttcactg ccgtagggca gtatcctctt   6180
```

gtatgtgcca tcctctagtg cccattgttc atcatgtcat agtaagccca agatgttcat 6240
gcctttttc agcactgcat tagggcttat atctgcttct ctttctctct ctctctcgct 6300
ctcgctccct ccctctctct ctctttctgt ttttttttt tttttagacg gagtttcact 6360
tgtgttgccc aggttggagt gcagtggcgc gatcttggct cattgcaacc tctgactccc 6420
gggttcaagc aattctcctg cctcagcctc ccaagtagct gggattacag gcatgtgcca 6480
ccatgcctaa ttttgtatct ttagtagaga tggggtttct ccatgttggt caggctggtg 6540
tcaaactccc aacatcaggt gatctacctg cctcggccgc ccaaagtgct gggattacag 6600
gcatgagcca ccgcgcccgg cctctctctg cttatttcta cacagtgtta ccaatgagat 6660
tggtgttact gctgggctcc aaagcaatca gacagattaa agtagattga atatgaaaga 6720
atttagaggc ctttttccaa gtgatttgtg ctctatttaa tttctgtgca tttgcagata 6780
tagcccacag taattcttag tgaactagaa ccttcaggtt attgaatttt actgatttgg 6840
gtactgacat gcgcttttaa gaagacatta ggttttctat agtgtagatt gtacactaac 6900
aatataattc atatttaaga atgtctcaaa atttagtata ctgtgttcaa ctaacttaac 6960
tttctttgtt tttttgttt tgttttgttt ttgtttttg agacggagtc ttgctatgcc 7020
acccaggctg gagtgcagtg gcgtgatctt ggcttactgc aacttcaaca ctcctgggtt 7080
caagtgattt tcctgcctca gcctcctgag tagctgggat tacaggcacc cgccaccaca 7140
ccggctaatt tttgtatttt tagtagagac ggggtttcgc cgtgttggcc aggctggtct 7200
tggactcctg actcaaatga tctgcctgcc ttggcctccc acagtgctag gattacagac 7260
atgagccact gcgcccggcc gctaacttaa ctttcattcc acaacttcca tcttttatcc 7320
aaaatctgtg atcattgaat actgtcacca ttaatcattg gcatttcagt gtttggactt 7380
tttttttccc ccttcgtctt tgtggactct tttttaacac tcataaagtt ttaactattg 7440
aaaagcaaag gaaacggtga gtgacttttt ggagtctgtc tacccagtgg tcacacaaaa 7500
ggcttactac attacaggaa agataggatg ggaaagggat actagaaaat tctaagtcag 7560
gaacgggggt gtgtattaga aaaattctga tcctggcatg ccagatggcc ttacatctca 7620
atttcttccg tgaaattcct gccaacaaat catagtgtta gaagtacaga agggtccatg 7680
ggaacagaat ttaagggctc cgttggtgat acggaactga tcagatggtt ctcacttgtt 7740
ctcagataac ctgtatactg aatatcacag gaagggtata gacgtcatgg cagtggttag 7800
atattcttgc acctgctgaa gctgagaaaa ttaaagtaat ttttttccct gtggaaagta 7860
gaaaatcaag cttttgtatg atttcacaca gctttctatt ctctcttttg ttgactctgt 7920
taagagtaac atttagtggt ggaaactatt tcaggatcac acccacaaca ctagagactg 7980
tattaatcac ttacacacac ataggtatag agtaatcttg aaggggctgt aggccaaaga 8040
taatgctttt ttgaagaatt agagactagt taccagcacc tggtatttgc tgtttcctac 8100
agagctgact ggacagccta gagtctgctg aggaattcag aggatggcca gtagaatgtt 8160
ctttccaccc cagaatattt ggtagggact cagctgctgt ggaatgccaa aaaggctttg 8220
agtttgtttc actattctta agattacacg taattgtttt tttgtaagag attatatata 8280
ttcaagttga ggatggcttt gagttagact ttccttaatt tggaatcaca cagcagatga 8340
tacatttatt tccatctgat aagttacttg atgatgtaaa aagacatttg agttaaagat 8400
ttttgggaaa aaagctgaat gttgagccat ttatgttgtg tactggttcc ctattcactt 8460
ggacaatttt aagtcttaaa acaatcttaa ccatgtgcac aagagatttc acatagtatt 8520
tggtaattaa attaaggaat tctagctcaa gtcatgcttt ttgctgaaat agttgtatat 8580

```
atttagtgcg gaaacctgtg ttttcaaatt aatgtaataa aagtttcaat aaaatggaag   8640
cctttattac cgtgtttcaa atgctatgct aaaccttttc catttgttat tatattaacc   8700
tcctcataca tagccctact aattttttta ctttctattt tgaaataatt acagatttat   8760
aggaagttgt gaaaaatagt acagagccca tgttcccttc accaagtttc acctaatggt   8820
agtagctcac ataacgataa tttaatgtca agaaccagga aattgtcatc gttgcaatcc   8880
ataagccttt tttagatttc accagtttca catgtatttg tgtgtgtgtg tatatatata   8940
attgtatgca attttatcat gtgtagatct ggatagccac tgtaacagtc tatagttcta   9000
tatacagagc tactccatca cctcagggct ccctatgcta ccactttata gccgcacgca   9060
cccttccagc aaccactaat ctgtttgcat ctctgtaatt ttgccatttt gagaatgtta   9120
tataaatgga atcatacaga atgtaacttt ggcttttttt cttttaccat acttcctttg   9180
agagccatcc aaattgctgc atgtatcagt agttcatttc tttttactat tgagtagtag   9240
tccatagtat ggctgaacca cacaatttgt ttaaccattt acttattgaa ggacatacca   9300
gaagggtggt ttccagtttt ttggctattg caaataaagc tgctataaac attcatgtat   9360
ataaatattt ttatgtgaat ataaagtttt cattttgggg gaataaatgc ccaaatgttt   9420
ggattgtatg gtaagtgcat gtttggtttt tagagaaact gctgaactat ttattttcta   9480
gaatgactat atcctcttat attcctatca acaatatatg agatatccag tttctctgca   9540
tccttgctag catttagtgt taccactttt ttatttgagc ggttctaata tgtgtagtga   9600
tagcctgttt tgccttatat taatcaataa aaatagcctc atctaatctt aacttttttt   9660
attttaaaac atcttggcag tattgaactt tctcaatgaa aaatctctaa aattgtgact   9720
tgaaaggctt taattttcca gtttttcttt ggttttactc ttagcagtaa cattttaact   9780
tttttttgtc tttgaagtaa ttttcagtgt ttcctttaca tgttgctttt tcttagaaac   9840
tagttactag catgaagtag atctttagcc tcgttttcta aaaacataaa aaagtaaaac   9900
tgtggggttt atttcaaaat tgagagtcct gtcttttcat atgaggatat tttatagtct   9960
gttggcttgg ctatatttta gggagtaaac ctgtggttag tggtttgttg ttggtggtgg  10020
taaagttttc ttacagtatt tttatacctg aataatacct ttagactcta tagaatagat  10080
acttgatctt caaatctatc ctagaataaa ttgttttatc taaacagctt tgtgacctga  10140
gaattgggac ttagtccctt agttttccct tactggccct ttgtagtcac tgttttgatt  10200
ttgtgaaagt aacttaactc ttagcactgt caggtattgt acattcctgc caaagcaaga  10260
ataagaatac ataggattgt gttttaattc tataattagg tgacttttgg ctaatttcca  10320
ggaacttgga cttaataaag tactagtgat aagtttggaa attttagtgt ccttgttctt  10380
tgaagttatt caccctttac tttcttgttt gtttggggtg tttatactac tgtccctaaa  10440
tatagctgaa ataaaggaag aaaaataacc cctgtaatat cactaccagg atataatttc  10500
tttttttttt tttttttga gatggagtct cgctctgtcg cccaccatct cggctcactg  10560
caagctctgc ctcctgggtt cacgccattc tcctgcctca tcctcccgag tagctgggac  10620
tacaggcgcc cgccaccaca cccggcttat tttttgtatt tttagtagag acggggtttc  10680
actgtgttag ccaggatggt cttgatctcc tgatcttgtg atccacctgc ctcggcctcc  10740
caaagtactg ggattacagg catgagccac cgcgcccggc ctgatataat ttctgttaac  10800
agtttgatgt aaatattttt tgacttttta gtgtttttat atatatatat attttatgtt  10860
tttcttttat caatacgcac tcttactgtg ggaataattt taatgttttt aaagagttgg  10920
```

-continued gttttatttg tttattttat tttatagaaa tggggtctcg ccgggtgcga tggctcacgc 10980
ctgtaatccc agtactttgg gaggccaagg caggagcatc acctgaggtc gggagttcga 11040
gaccagcctg accaacatgg ataaaccgcc tctctactaa aaatacaaaa ttagccgggc 11100
gtggtggcac gtgcctgtaa ttccagctac ttgggaggct gaggcaggag aatcacttga 11160
acccggccgg tggaggttgc agtgagcaaa gattgtgcca ttgcactcca tcctgggcag 11220
caagagtgaa acttcatctc aaaaaaaata aaaaataaaa aagaaagaaa gaaagaaatg 11280
ggatctcacc attttggctg gttttgaact tgtggtctca agcagtcttc ctacctcagc 11340
atcccaaagt attgggatta caggtgtgag cccatcctgt ttgttgttgt tcttttgttg 11400
ttgttgtttt tagatgaagt ctccctctgt cacccaggct ggagtgcagt ggcgctatct 11460
tggctcactg caagccccgc cacccaagtt caagcaattt tctgcctcag cctcccgagt 11520
agctgggatt acaggcgccc accaccatac ctggctaatt tttgtatttt tagtggagac 11580
gaggtttcac catattggcc aggctagtct tgagctcctg acctcgtgat ccacctgcct 11640
cggcctccca aagtgctggg attacaggtg tgagccactg cgcctggcct gttgttgttt 11700
aaataaaaga aatttattct cttacagtcg aggccagaac ttagaactgg ttttcaatct 11760
aaattttttt tcttctttgg gagaagggca tcagaatatt gtggatatac tttttgact 11820
taaaaaaaaa ggttttactg ggctgggcat ggtggctcac ctgggattaa ctgcctgtaa 11880
ccttggcact ttgggaggct gaggcaggtg gatcgcttga gtccaggagt tcaagagcag 11940
cttgggtgac atggtgaaac tccgtctcta ccaaaaaaaa aaaattagcc aggcatggtg 12000
atggcgtgcc cttgaagtcc cagctacttg ggaggcttag ctgggaggat cgcttgagac 12060
caagaggcag aggttgcagt gagctaagtt catgccactg cactccagcc tgggtgacag 12120
agcgagacct cgtctgaaaa attttttttt tttttacta atatgacaaa catcttttca 12180
tttcaaatat atttctatac catttttaat atctcattgc ctttagaatg accttgtatt 12240
catagtacat atgtatgtga tattccattt atttattttt tttcttttgt ctttttttgg 12300
ttatattcca ttgatttaat gtaccttaat ttatcttacc aatttcttgt tgaccatttt 12360
gtttccagtc ttttgttttt ttaccagaca tggattaagc tgagcctttg ccccagacga 12420
cattatttct tttttatcag caaaatatgc gtgtaatgaa attagaatta aaaggcaaaa 12480
aaggttatcc tttattttc tacttatttt tattgagata gtaattcaca taccataaat 12540
ttaacccttt taaagtgtac agttcagtgg ttttcatata ttagaaggtt gtacaaccat 12600
cgcaactaat tccagaacat tttcatcacc ccagaaagaa actctgaacc cattatcact 12660
ccccactccc tcacacaccc taaccctggc agtcacatat agactctctg tctctgtgga 12720
tttgtttact ctggaccttt catataagtg gaatcataac agtttgtggc cttttgtgct 12780
tggcttctca aacttatctg tttccaaagg ttatctgtgt cgtagcatgt gtcagtactt 12840
cattcctttt tatggctgaa tattttattg catgtatatg ccacattttg tttatccatt 12900
cacctgtaga aggacattta ggttgtttcc atttttggc tgttatgaat attactgctg 12960
tagacgttca tgtacaagtt tttatgtgaa cgtgttttca tttttcttgg gtatatactt 13020
aagtgaggaa ttcctgggtc ttaagttaac tctctgttta acattttgag gaactgccaa 13080
attatttttt aaagtggctg tgacatttta tattctacca gcagtgaatg aaatttccaa 13140
tttctccaca tacttgacag cacttttttt tttttttttt tttgaggtga agtcttgctt 13200
tattgcccag gctggagtgc agtagcatga tcttggctca ctgcaacctc cacctcccag 13260
gttcaagcaa ttcttgtatc tctcagcctc ccgagtagct gggattacag gcgcatgtca 13320

-continued

```
ccatgcctgg ctaatttttg tattttttat agagacaggg ttttgccatg ttggtcaggc 13380
tggtcttgaa ctcctgattt caagtgatcc acctgcctta gcctcccaga gttctgggat 13440
tacaggcgtg agccactgca cccagtctgc actttcttta ttatctgtct tctttattat 13500
agccaatcta gtgggtatga agtaagtgtg tcatttgtga ttttgattgt tagtggtgac 13560
taaaaatgtt gaatatcttt acatgagctt gttggccatg tgcacatctt tgttggagaa 13620
atatctattc aaatcttttg actattttaa aattgggtta tttatctttt tattgttgag 13680
ctataggagt tctttatttt attttactga gacagggtct tgctctgtca cctaggctgg 13740
agtgtagtga tgccatcttg actcactgca acctctgccc ccaccccagg ctcaagtgat 13800
cctcccacct cagtcagcat cccacagctg ggaccacagg cgcatgccac catgcctggc 13860
taattttttt tttttttttt tttttgtatt ttagtataga cagagtctca ccttattgcc 13920
caggctggtc tcaaactcct gagctgaagc aatccgccca tctcagcttc ccaaagtgct 13980
ggaattagag gcatgagcca ctgtgcctgg cctattttat tttaaagatg aggcctcact 14040
ttgtcaccca ggttggagtg cagtggcgtg atcatagttc actgccattt tgccctcctg 14100
ggctcaaaca gtactcacga ctcatcttcc tgagtagcta ggactgcagg catgtcgcta 14160
gcatgcccag ctaaaacagt tctttatatt ctagatcggg gtgtccaatc ttttgacttc 14220
cctgggccac attagaagaa gaagaattgt cttgggccac acataaaata cactaacagt 14280
aatgacagct gatgagctaa aaaaagaatt accaaaacat ctcataatgt tttaagaaag 14340
tttacaagtt tatgttgggc cacattcaaa gccatcgtgg gcctctggcc gtgggttgga 14400
tgagcttgtt ctaaatgcta gacccttatc agatggatgg tttgtagata tttatcgcat 14460
gctgtgggtt tttttttttt actttctttt aggttttttt ttttcttaaa taattaaact 14520
gattaaaagc tttaatcttt tcattttctt gataatgtct tttaaagcac aaagttttgt 14580
ttcaatgatg tctaatttgt ctattttttt ttctttggtt gcttgtcata cgtaagaaac 14640
tgttgctaaa tccagaatgc tgaagattta cttgtgaact ttgtttcctt ctatgagttt 14700
tatagtttta gctcttgtat ttaggtcttt gatacatttt gaggtttttt tgttgttgtt 14760
gagacagtct tgctctgtcg cccaggctgg agtgcagtgg tgtgatcttg gcttactgca 14820
ccctctgcct cctcggttca agcaattctc atgcttcagc acccgagtag ctcggattac 14880
aggcgtgcac caccaagcct ggctaatttt tgtattttta gtaaagaggg ggcttcacca 14940
tgtttgtcag gttggtcttg aactcctggg ctcaagcaat cctctcatct cggcctcccc 15000
aagtgctggg attacaggca tgagccacca cgcccagcct gttttgagtt catttttaaa 15060
atatggtgtg aggtagaggt cccatttcat tcctttgcct gtgggtatcc agttgtccca 15120
gaaccatttg ttgaaatgac tcttgtttcc tcattgagca atgtcgtgag accctatctc 15180
cataaaaaat aattaaaaaa aaaaaagaat gcagaaggaa acagttttgc caattttgta 15240
gtatttactg acaatttgca tatgtcttta cattctttag ctatttattt ttcttttgaa 15300
ttactgcctt tgttcatttt tcttttggag ttgtttgtct ttttcttatt aatttgtaag 15360
agattttgca aatatataca atttcttttc tctttttttt gagatggagt tttgctcttc 15420
ttgcccaggc tggagtgcag tggcatgatc ttggcttact gcagcctctg cctcctggtt 15480
tcaagagatt cttctgcctc agcttcctga gtagctggga ttacaggtgc ccaccaccac 15540
acccagctaa tttttttttt tttttttgt atttttagta gagactcggt ttcatcatgt 15600
tggccagact ggtctcaaac tcctcacctc agttgatcca cccaccttgg cctcccaaag 15660
```

-continued tgctgggatt acagttgtga gccaccgtgc ctggacctcc cacattattt tgaaacaaat 15720
tccatatcac ataatttctt ttttttgaga cagagtctcg ctctgtcacc caggctggaa 15780
tgctgtggcg tgacctgtgc ttactgtacc ttctgcctcc taggttcaag cgattctcct 15840
gcctcagtct cctgagtagc tgggattaca ggcacgcacc accacacctg gctagttttt 15900
gtatttttag tagagatggg gtttcaacat gttggccagg ctggtcttga actcctggcc 15960
tcaggtggtc cgtccacttc ggcctcccaa agtgctggga ttacaggctt gagccactgc 16020
acccagccaa tatcatataa tttcatataa atagttcttt gtgtatcttt agataaggac 16080
ttaaaagaag gcataatcgt aacaccatta ttaataccta aaagaagtga gcaataaata 16140
attcatttgc cgtatcaaat atccaatgtt catatttcct ccattgtccc ataataattt 16200
ttaaaagttt gctcaaatca aaatccaaac aagattattt caaagcattg tttgaggtac 16260
attttaaatc ttaatttata gatttctctg ctgtctcttt tcccccatat ttatttgttg 16320
aagaaaccaa gcgttgtttc ctgtggactt tcctactctc tggattttgc tggttatatt 16380
cctctggtat cagtttacta tgatcccttt ttcccctgta ttttctgtaa atttgtaact 16440
agatctagag atttgtttag attttgtggg tttttttttt tttttttttt ttttttgcaa 16500
aaatgcatca taaatggtgg tgtgtacatc tctcagaaga cacatatctt aatgtctttt 16560
tgtggtatta gttattaatg attactgcct atatttatta attcattatt tggattgtaa 16620
gtttatgata gtctcttgat gctttttctg ttgttagctg gaatgcttct aaaaggagaa 16680
ggctttcctc ttcaagctac ttggttgtct tgagggtttg cttcttatag ggaaagcagg 16740
ctaagggtga aaaaggaaat agtttctaac tgggtctgtt aatgagctgt caccccaggc 16800
aaagagaagc aaggcaggtc acaggaaagt gaagtgggct tgggatgatt ggtgccccat 16860
gcgtgcatgc atgaagggaa gttaatcctc cctgtagtga actctactgg gcttttggtc 16920
agtagccaag actgtcaagg aagacctttg tcagaagcca tacctggcct ttgcttttag 16980
ctgttggtag ctgaaggaaa ccagaacaga cctatgacct gtgaacttct gctcagtaga 17040
caaagttctc tcagcctaaa ttcagtaagc aggagtaaga tgcttgcttt cccttgaagt 17100
gaaacgtgaa ttatatgttt cttcaacttg tgctaatatt cttttttttt ttgagatgga 17160
gtctcacact gtctcccagg ctggagtgca gtggtgcaat ctccgctcac tgcaacctca 17220
gcctcccgag tagctgggat tacaggcgcc tgccaccacg cctggctaat tttttgtatt 17280
tttagcagag atggggtttc actatgttgg ccaggctgga cttgaactcc tgacctcacg 17340
atctgcctgc ctcggtctcc caaagtgctg ggattacagg cgtgagccac cacacctggg 17400
caacttgtgc taatattctt aaccttcatg tgaatcattc ctgccctcag gctagcataa 17460
cccatacagc cttccttata ggaagatttc ctactgggag tgaatttgtc cagtgattcc 17520
cccaagatat cccccaatca aatattttaa aagtcatcat ttacatgtaa aaactatgta 17580
acaagcatgg tagcagcagc gttaaagaaa tggcagtatg gcccctgtaa gggaaggctc 17640
cagaagatga gccgcactca gcctctaggt cacagctacc ttaggagttt gcagttgttc 17700
ctggggaagt cagtagacaa agctatctct caggcctggg caagataggg attttttttt 17760
tttctttgag atggagtctc accctgtcat ccaggctgga gtgcagcagc atgatctcgg 17820
ttcaccacaa cctccacctc ctgggttcaa gtgattttac tgcctcagcc tcctgagtag 17880
ctgggactac aggtgcgggc catcatgcct ggctcatttt tgtattttta gtagagatgg 17940
ggtttcacca tgttggctag gctagtctca aactcctgac ctcaggtgat ccacctgcct 18000
cccagagtgc tgggattata ggcatgagcc actgtgccca gtgttttttt ttttttaatt 18060
gtagtgacag gatctcactt tgtttcctgg gctattccca aactccaggc ctcaagccgt 18120
cctcctacct tagcctccca gagtgctggg gttacaggtt tgacccactg tgcctagtct 18180
cagaattcat gtttttaaaa gtcactctgt gccaggctca tgcctgtaat cctaatactt 18240
tgggaggctg aggcaggagg gttgcttgag cccaggagtt tgagaccagc ctggaaacca 18300
tagcaaaatc ctaactctac aaaaaataca aaaaatagcc aggtgtggtg gcatgcacct 18360
gtagtcccgg ttacttggga ggctgaagtg caaggatcgc ttgagcctag gaagttgagg 18420
ctgcagtgag ctgtgatcat gccactgcac aacagcctgg gcaacagagt gagaagtaac 18480
tctggctgtg gtggggaaag tggattagtg gagaatggaa gctgggaaac atggtggttc 18540
ttgctaagtc agtatcaagg gatcacagat gagggggcta tttcgtccta ataagggcct 18600
tggtctccca gatagtcatg gatttttcta tttagaagct ccttctcagt ttttcttgcc 18660
caaggcatat acggttgata tttgtacaac acaggctgga tctgtatggg tccacttata 18720
tgtggatttt ttttcaacca aacttggatt aaaaatatag ttgtaggcca ggcacagtga 18780
cttatgcctg taagcctagc actttgggag cccaaggcag gcggatcagc tgaggtcagg 18840
agtttgagac cagcctggcc aatgtggtga aaccatgtgc ctactaaaaa tacaaaaaat 18900
agctgggtgt ggtggtgtgc acttgtaatc ccagctactc aggaggctga agccagagaa 18960
ttgcttgaac ccgggaggtg gaggttgcag tgagctaacg cagcagaggt tgcagtgagc 19020
taacgcagca gaggttgcag tgagccaacg gggtggaggt tgcagtgagc caagattgca 19080
ccaccacact ctagcctgtg tgacagagca agactctgtc tcaaaaataa ataaataaaa 19140
atacagtgta ggccaggtat agtggctcat gcctataatc ccagaacttt gagaggccaa 19200
ggcaggcaga tcagttgaag ccaggagttt gagaccaacc tggctaacat ggtagaaccc 19260
cacctctact aaacagaagt acagaaatta accaggcata ggtggtgcat gcctgtaatc 19320
ccagctgctt gctaaactga ggcaggagaa ttgggaggca gaggttgcag tgagctacga 19380
ttgtgccact ggactccaga ctgggtgaca gagcgagact ctgtctccaa gagaaaaaaa 19440
aaaattgtac ttacaggaca tgaaacccac ctgtacggtg tgctgactgg gagactggag 19500
tatgcatagt tcttggtaaa caaggggatt cctgaaacca atcccctgag tatatggagg 19560
gttgactata tattttaata gaatttatta cttttttttt ttttttagc agttttaggt 19620
ttatggaaaa attgagcagg agtacatagt ttctctatct ccctcacatt tccccattac 19680
tagcatcttg aaatagtgtg gtacatttgt tacaactgaa gagccaaata ttgatacatt 19740
actgttaact aaggtccgta atttacttta gagttcactc ttggtgttgc agtttctatg 19800
agtgttggca aatatatcat gacatgtatc tagcattata gtatcatatt gagtagtttc 19860
actgccctaa aaatcccctt tgttccacct tttcatccct ccatctacct gaacccctga 19920
taaccactga tccttttaca gtctctatag ttttaccttt tacagaatgt catatagttg 19980
gaatcataca gattggcttc tttccatgtt ccttcctggc ttgatagctc ttttcttttt 20040
tttgagatgg agtctcgctc tcgcccaggc tggagtgcag tggcgcaatc ttggctcact 20100
gcaaactctc cgcctcctgg gttcaagcaa ttctcctgtc tcagcctccc aagtagcttg 20160
gactacaggc gcatacctcc cctgcctggc taatgtttgt atttttggta aaggtggggt 20220
tttaccatat tggtcaggct ggtctcaaac acctgtcctc aggtgatcca cccacctcgg 20280
cctcccaaag tgctgggatt acaggcgtga gccaccctgc cctgccagct cttttttttg 20340
tactgctgaa taatactcca ttgtataggt gtatgagttt atctattcac cttctgaagg 20400

-continued

```
acattttggt tgctcctaag ttttggcaat tatgcatgaa gttactataa acatctgtgt  20460
gtaggttttt gtgtggtcat gtttttagct catttggata aataccaagg agcacgattg  20520
ttggatcgta tggtaagagt atgtttagtt ttgtaagaaa ctgccaaact gtctttcagg  20580
gtgactgtac cattttgcat tcccaccagc aatgaatcaa gttcctgtcg ctccacatcc  20640
tcgttagcat ttggtgttgt cagtgttttg gcttttcacc attctaatag atatgtagtg  20700
atatcttgtc ttactttgca gttctctaat gacgtatgat gttgagcatc ttttcatctg  20760
cttatttgtt gttgttgttg ttgtgttgtt cattgaaatg gaatctcgct ctattgccca  20820
ggctggagtg caatggtaca atcttggctc actgcaacct ctgcctcctg ggttcaagtg  20880
attctcctgc ctcagctccc caggtagctg ggattacagg cgcccgccac catgcccggc  20940
tagtttttgt atttttagta gagacaggat ttcaccatgt tggccaggct ggtcttgaac  21000
tcctgacctt aggtgatctg cccgcctcgg cctcccaaag tgctgggatt acaggcgtga  21060
gccactgcgc ctggctttca tctgcttatt tgatatgtgt atatgttatt tggcaaagta  21120
tctgttctga tcttttgccc attttttaat cagattgttc ttttattgct tctggggttc  21180
tttttgtttg cttttttga gacagagtct tgctctgtcg cccagtctgg aatgcagtgg  21240
catgatctca gctcactgcg acctctgctt cctgggttca agtgattctt gtgccttagc  21300
ctcccaaata gctgggatta caagcatgtg ccactgcacc tggctaattt ttgtatttat  21360
agtagggaca gggttttgcc atgttggcca ggctggtctt ggactcctgg tcttcagtga  21420
tccacccacc tttgcctccc aaagtaatga gattacaggc gtgagccacc atgcccggct  21480
tattgttaag ttttaagagt tctttgtata tgtgtatttt ttgattcttt taaaattaat  21540
acttaataaa ataattgtac atatttatgg gatgcatgtg atattttgat acatgcatac  21600
aatgtggatc aaatcaaggt aattagagta ttacctcaaa catttgtcat ttctttatgt  21660
tgggaacatt tcaaaatgtc tagctatttt gaaatataca ataaattatt atctataagt  21720
cacctcattg tgctgtcaaa cattagaact tattctttct acctggcttt atttttttta  21780
ccccttaacc aaccattctt catcagctcc ccgtctcccc tactcttttt tttttttttt  21840
ttttttgata cggagtcgct ctgttaccca ggctagagta cagtggcaca atctcgactc  21900
actgcagctt ccgcctccca ggtttaagca attctctgcc tcagcctccc gagtagctgg  21960
gattacaggc gaatgctacc acacccgact aatttttata tttttagtag agatggggtt  22020
tcaccatctt agccagactg gtcttgaact cttgacctcc tgatccaccc gcctcagcct  22080
cccaaagtgc cgggattaca ggggtgagcc accatgcctg gcccctctta ctcttttctt  22140
agcctctggt atctatcatt ctactctcta cttctatgag atcaactttt ttttagctcc  22200
cacatatgag taagaacatg taatatttct ctttctgggt ctggcttctt tgtatatttt  22260
ggataataag tcttttatta gatacgtgtt ttgcaaatat tttttccgag tccgtgactt  22320
atcttttcat tctcttaaat agtgtctttt gcagagcaca cattatacat tttagtgcag  22380
tccagtttac caattctttc tttgatggat tttgcttttg gtattgtgtc tagaaagtct  22440
tcgccaaacc acagtcatct agagttcccc ttatattatc ttacaggagt tttatagttt  22500
ttgttttaca tttaggtctg tgatctattt taagttaatt tttatgtgaa agatataaga  22560
tctatgtctg gattctctct ttttttgaga tggagtctcg ctttgtcgcc aggctgaagt  22620
gcagtggcgc gatctcggct cactgcaacc tctgactccc tggttcaagg gattctcctg  22680
cctcagcctc ccgagtagca catgacacca cgcccagcta atttttgtat tttgagtaga  22740
gacggggttg caccatgttg gccaggatgg tcttgatctc ttgacctcgt gatccgcccg  22800
```

-continued cctcagcctc ccaaagtgct gagattacag gcatgagcca ccacgtccgg ccagtttttt 22860
tgttttattt atttatttat ttgaaacagg gtcttgttct gttgcccagg ctgcagtata 22920
gtgacaccat caaggcttcg ttgcagcctt gacctcctag ggtcaagtta tcttcttgct 22980
tcagcctcct gagtagctgg gactacaggt gagcaccact ctgaccaggt actttttaaa 23040
tttattttag agacagggtt ttaccatgtt gcccaggctg gtcttgaact cctgggctga 23100
aatgcccctc ctaccttggc ctcccaaagt gttgggatta cagacatgag gcactcagcc 23160
cagccaatat aattcttttt tttttttttg agacagtctt actctgttgc ccaggctgga 23220
gtgcagtggc atgatcacag ctcactgcaa cctctgcctc ctggactcaa gctgtcctcc 23280
cacctcagcc tcccaagcag ctgggattat gggtgcccat gaccacaccc agctaagttt 23340
ttaaattttt ttagagattg aatctttctt tttctcagcc tggtctcaaa ctcctgagct 23400
catatgatct gcccgcctcc gtctcccaaa gtgctgcgat tacaggcatg aaccactacg 23460
cccagcctac aatttatttg taatccaagt tttattgaaa aaaaaatcca catataagtg 23520
gacatatgta gatccaacct gtgttgttcc agtgtcaacc atatatacca ataattcttt 23580
tttttttttt tttttttttt tttttttgag atggagtctt gctctgtcgc ccaggctgga 23640
gtgcagcggt gcaatctcat ctcactgcaa cctctgcctc ccgggttcaa gtaattctcc 23700
tgcctcagcc tcctgagcag ctgggactac aggcatgcac caccacgccc agataatttt 23760
tgtattttta gtagagatgg ggtttcacca tattggccag gctggtctca aactcctgac 23820
ctcaagtgat ccacccgcct tggcctccca aagtgttggg attacaggag tgagccactg 23880
tgcctggcct ataattcttt acgtatattg ttagattcag tttgctagta ttttatttag 23940
catttgtgta tctgtgttca tgagaggtat tgttctgtag ttttctttgg tttcttttct 24000
gtctggttta gggtaatgct ggcctcatag aataggttag gaaatatttc ctctgcttct 24060
gtttctgaaa gagaattgag gtaatatcta tttttttttt tttgagatgg aatcttgctc 24120
tgtcgcctag gctggagtgt agtggcgcaa tcttggttca ctgcaacctc tgcctcccag 24180
gttcaagtga ttctcctgcc tcagtctcct gagtagctag aattacaggc atgcaccacc 24240
atgcctggct aatttttgta tttttagtag agatggggtt tcactatgtg ggccaggctg 24300
gtcttgaact tctgatctca ggtgatccac ctgtcttgtc ctcccaatgt gctgggatta 24360
caggcgtgag tcactgtgcc tggcccgaga taatatctaa tttaacagtt tggtagaatt 24420
caccagtgaa cccatctggg cctggtgcct tttgctttag aaggttattg attattgatt 24480
caatttcctt aatagataaa ggtgcattga gattgtcttt tcttcttggg taagttttaa 24540
tacattgtgt ctttcaagaa attgttccat ttcatctagg ttatcaaatt tgtgggatta 24600
gagtccttca taatatttct ttgttttgct tttggtgtcc ataggttcag aagtgatggc 24660
cctttttcat tttttctatt agtaatttgt gtctttgccc tttttttttct ttgttaatct 24720 ggctagaagc ttatcaattt tgttgatctt ttcaaagaac cagtttttgg tttcactgat 24780
ttttctctat taattttgtt ttcaatttaa ttgatttctg ctctaattgg ttttcttctg 24840
ctcactttgg atttaatttt ttttagtttt tctagaaaac taagttttta agtgaaaact 24900
gagattattg atttttagat cttttttcta atgtttacag ttaacactgt acaatttcct 24960
gtaagcactg ctttctctat atcttacaaa ttttgatgtc atattttcat tttcatttag 25020
ttagaaatat ctcttgagac ttctttgacc catctgttat ttagaagtgt attgtttaat 25080
ctccaagtat gtattttggg atttttctgg ctatctttct gctgttgatt tctagtttaa 25140

```
ttacatgtgg tctgagagca taccttgtat gctttctatt cttttcaatt tgttaaggtg  25200
ctctttgtgg ctcaaggtgg tctacttttt tttttttttt tttttaaag aaaagctggc  25260
caggtgcagt ggcttatgcc tgtactccag cactttggga ggcgtaagtg ggaggatcac  25320
ttgaggtcag gagtttgaga ccagcctggg caacatatag agacttcact tgcacaacaa  25380
atttttaaaa tattagttgg gtatggtggc atatacctgt atatggctga agtgggagga  25440
ttgcttgagc cctggaggtt gaggctacat gagccatgat cgcaccactg tactccagcc  25500
tgggcaacag agtgaaattt tgttctctct tgaaaagaaa aaaaaagttg atgacataaa  25560
gttcattcat ctttttgta tgtgacttca aaataactac tgatggttaa aaaaaaaatc  25620
agaatgatgc aacccaagtg tccatcaatg gatgaataga taatatgtgg tgtatgaata  25680
caatgggcta ctattattca gcctttaaaa ataagaaaat gctgacactg ctgtaacatg  25740
gatgaacgtt cagatcatta tgctaaatga gaaaagccag acacaaaagg acaaatattg  25800
catgattgca cttatatgag gtatctggaa tataagagtc atagaaacag taattcagta  25860
attagaataa tgcttgccag ggcctgtggg gaggagggaa tgaggaattc atgtttaatg  25920
ggtacagagt ttcatttgga aaagattaaa aagttatgga ggtggatggt ggtgaggatt  25980
gcacaacagt gtgaatgtac ttaataccac tgaactgtac acctaaaaat gattaaaatg  26040
gtacatttta tgttacatat gttttacaac aatttttaca gatggaaaaa aattataaaa  26100
aacatcagga tggtgttgac agtgaaaagg ttaaagagtt actttaaaaa tttactttat  26160
tccagccggg tgcggtggct cacacctgta atcccagcac tttgggagac cgaggcgggt  26220
ggatcacctg aggtcaggag tttgagacca gcctgaccaa catggagaaa ccccgtctct  26280
actaaaaata caaaattagc caggtgtggt ggcgcatgcc tgtaatccca gctacttggg  26340
aggctgaggc aggagaatcg cttgaacccg ggtggtggag gttgcagtga gccgagatct  26400
tgccattgca ctccagcctg ggcaacaaag cgcaactccg tctcaaaaga aaattttttt  26460
tttttacttt atcccaaatg tttatattta ctttggggct tatgtgacca gtttaatttt  26520
catttgtaat tgacttgata gaacacacta atgttcagtt aagatttctt atggtgtggt  26580
gaggagtagg atttttatgt aaataagccc aaaattgtat atatgaggtt aatctgatat  26640
ttgcagaaga tattcatgca ttactgtaag gaccactctg cttattcatt tgaccgattt  26700
gttacaacat ggttagaaat catcaaggtg tttgagatca aaggatcttc agaggtgatt  26760
tactccaatc ctttttttaaa aaattaataa cttgagcctc agagaagtta agtgacatta  26820
ccaagttctg ctgttagtat agtgacttta tctttacctg aatccagggt ttcttagccc  26880
tagtctgtaa tgtgtcctag tgtgcctcta gaatctggtc ctgtcagccc aagtctgtta  26940
aatcaaataa aaccagggct tggtgcttca ccttgtcttc tgccataccg ttgggtttcc  27000
tgtggaccat gcagataatg atgatgggct cagtgggctt gatagtgata actcctaaag  27060
cagctccttc taagtgcggt tctcaatctg aggaagttaa aaaaaaaatt agtgactaga  27120
acccacttct caggtactct gataaaatac atttgtaggg gagtgatagt tttcactttc  27180
tttttttctt tttcttttt ttttgagatg gcgtctcgct cttttgccca ggctggagtg  27240
caatggtgcg atctcagctt actgcaacct ctgcctccca gtttcaagtg attcttctgc  27300
cttagcttcc tgagtagctg agattacagg tgtgtgccac catgcctggc taatttttgt  27360
atttttatta gagacgggat ttcaccatgg ttggtcaggt tggtctcgaa ctcctaacct  27420
tgtgatctgc ctgcctcagc ctcccagagt gctgggatta caggcatgag ccactgtgcc  27480
cagccttcac atatttttg aaataatagg ccagttgcgg tggttcatgc ctgtaatctc  27540
```

```
acactttggg aggccgaggt gggcagatca cttgaggcca ggagttcaag gccaccctgg  27600
ccaacatggc gaaaccctgt ttctactaaa aatacaaaaa aattagccgg gtatgatggc  27660
atgtgcctgt ggtcccagct actctggaag ttgaggcatg agaatcgctt taacttagga  27720
ggtggaggtt gcagtgaggc aagatcgtgc ccctgcactc cagcctgggt gacagagcga  27780
gactccatct caaaaaaaaa aaaaaaaatc gtatgcagta aaggttgaaa actgctgccc  27840
aaaggcgcta ttaaactata ggttcccaaa cctggccaat tgtcaaaatc cctcaagaag  27900
gggcagtggg gtctaaggga ccccattgct gtagaggaga ttagtagtcc aagagtgaga  27960
tgaactgttg gaagtcctca aacttccaaa ctattaaaat agaatagttt tgcttcctta  28020
aaatagaata gttttcttcc tcactgattt ttctgtattg attagaacca taacaagtga  28080
attaaacaac tacaaaatag ttatgtgggc cacagacatt attgtaatga agtgaagttt  28140
ggctcaggcc ttgtaacaca attgcttttt ggattaaaag taaaaatatt aaattgtgaa  28200
attatgtgta agttttaaaa aattggtctt gtacaaaagt gttgggtttt tctttgtttt  28260
taactggatt tgtttttaag caagacagaa tatttatatt gttggagagt cacaaaggag  28320
gtgtgtttgt ggatttaaat gtggagacag tgtgccttga aatgcccttt atcagtctga  28380
ttcaagccac ctgcaatcat ggatttgaac tttttttttt ttttcccctg agatagggtt  28440
gcctaggctg gggtgcagtg gtgtgatctt ggctcactgc aacctctggc tcagcctctt  28500
ggagtacctg ggactatagg cacacaacat catatccagc tattgtattt tttttttttt  28560
ttttttttat agagacagag tttcaccatg ttgtccaggc tggtcttgaa ctcctgagct  28620
caagcaactc acctgcctcg gccttccaga gtgctgagat tataggtgtg agccaccatg  28680
cccagccttc actttattta aaaaccatag tttttaaaag ccacattcct actgatgaac  28740
acagaggttg tttccagtgt tttcatttgc agggctgtag tgattgtttt tgcacatgcc  28800
tctttatgta catgtgctgt gtcttctggg acagagagtg gacattttaa gtgttttatt  28860
ggtcctgcta aattgtcttt cagccaaact gctgcagagg tgatggagat gaggtgggta  28920
ctcaggagaa ttatgctcag tgcttgtgtg ctagtcactg acctggaaac attttattaa  28980
aaatgctaga ttaggttagt gatgtaaata ccaggtgata gtaaccagaa taattgtgtc  29040
aaaacatcaa gaatcatcaa gagatgccag gcatggtggc tcatgcctgt aatctcagcc  29100
ctttagtagg aggccgaggt gggcagattg cttgagctca ggagttcaag accagcctag  29160
gcaacatggt gaaaccctgt ctctaccaaa aatacaaaaa tttgctggat gcagtggtac  29220
gtgcatgtgg tcccagctac tcagtaggct gaggcgggag gatcgcttga gcctgggagg  29280
cagaggttgc agtgagccaa gactacacta cagcccgggc aacagagtga aaccctgcca  29340
taaaaaaagg agaaaaagaa tcatcaagag aaaacttaat ttgatgtgct ctgcgttttc  29400
tttggtgctt catgtcagtg ttagaaacta taggttgtat atttattaat ttttctccta  29460
catttgttca acttgactaa aatattaact ccaaatgcct agaatttcaa aatacctctt  29520
cgttataaag tatcaactat ttcttagtcc ccttaagctg atagtattgt gtcattgtaa  29580
aagatccctt gtgaaaaata atttttgtca acatgaaagg tcttaatgtg tctcctagtt  29640
tacattttac atggtctttt ccatgtattt atatagttga catatatagc ttttttttgta  29700
aatacacttt cctatgtgaa catgccaagg tttacttaag cattctctta ttcttggaca  29760
tctaaattgc ttcttatttt ctattgtaaa taaagtgcta gaagcttctt tcctgaaaag  29820
ttatttactt ttcacctagt atttccatct gtgttcctca aaataagatt gctgagattc  29880
```

atgtatgttg ccagaaagat tgtgaggttt aacagtgaat gaggaaaact tttaacactc 29940
aaggtctacc aagtacagca agttttattt tacctttttt tttttttttt tttttttttt 30000
tttttgagtt aggccaagtt gcctaggctg ggctcaagca atccttctgc ctcagcctcc 30060
ggagtagctg ggattatagg tgtgcagcac cacacccggc tttcttgtat ttttttttta 30120
tttttattta tttatttatt tttgagatgg agtttcactc ttgtcaccca ggctggagtg 30180
caatggccca atctcgactc accgcaacct ctgcctccca ggttcaagcg attcttctgc 30240
ctcagcctcc caagtagctg ggattacagg catgtgccac cacacccggc taatttttct 30300
atttttagta gagacggggt tcctccatgt tggtcaggct ggtctcaaac tcccgacctc 30360
aggtgatcca cccacctgag cctcccaaag tgctgggatt acaggtgtga gccaccgtgc 30420
ctggctgctt tcttgtattt tatcttgctg tagcggttgt gggatttttg cctggtgtgt 30480
tcattggagt gtgtgtgtgt gttttgagat gtatgactgt gttggttgtg ttgtcatact 30540
ttgaaggttc attaatgtgc tggtctttct atttttcttg ttatacttag tcacttaaaa 30600
acccttttttt tttttttttt ggaattctta tttttacagt actttgaatt cctgttttat 30660
taatcacctt cttatctgaa agtgaagtaa tagtgtactt ggcaccattg aattagaaaa 30720
ttgtgtgtcc ttggccagaa gatcacatac acaggaactc gataagttga gagatttagc 30780
cgtttcagaa atgggcattt gtgtcttcca gtggagaagc atctgcaaaa gaattgggca 30840
gatttggcca ggcgcggtag ctcatgcctg taatcccagc actttgggag gccgaggtgg 30900
gcagatcacc tgaggtcagg agtttgagac cagcctggcc aacatggtga aaccccgtct 30960
ctactaaaaa tacaaaatta gccaggcgtg gtggctaacc catttaaagt gggtgaatta 31020
tatcttttat gttttaatgt attcctagag ttgtgcaacc atcaccagaa taagttgtag 31080
aacattttca tcaacccaaa aagaaacttt gtattcatta gtcgttcctc ctcatttctc 31140
ccctaacctc ccagcactag gcaaccatca gaatactttt tgtctccacg gatttgactg 31200
ttttggacat ttcatattaa tggaatgcac aatacagtag tataatacat taattttgga 31260
aggccaaaat taatggcttt tgatgtctgc cttttttcac ttagaataat gtcttccagg 31320
tccatctgtg ttatagcatg tatcattact ttatccttta tgtggctggg taatattcca 31380
ttgtatggtt ataccatgtt ttgtttatct attcatcagt tgatggacat ttaggttgtt 31440
ttccattgac tattaagagt aatgctgccg gccgggcgcg gtggctcacg cctgtaatcc 31500
cagcactttg ggaggctgag gcgggtggat acgagggtca ggagatcgag accatcctgg 31560
ctaacacggt gaaaccccgt ctctactaaa aaacaaaaaa ttagccgggc gtggtggcgg 31620
gcgcctatag tcccagctac gcaggaggct gaggcaggag aatggcgtaa acccgggagg 31680
cggagctggc agtgagccga gatggcgcca ctgcactcca gcctgggcga cagagcgaga 31740
ctccatctca aaaagaaaaa aaaaagagaa taatgctgcc atcatgcttg agggtttttt 31800
tttattttgt tttgttttgt ttgtgggggg agcggagggc acagtctcac tctgttacgc 31860
aggctggagt gtagtaggct tactgcagcc tcctccgccc cctggttcta gtgattcttg 31920
tgcctcaggc tcctgagtat catgctgcaa tttttgtgtg agcatacatt tttcatttct 31980
cttgggtcaa tatctaggag tatccccact tttggttctg agtgttaatt gagcctgttg 32040
tgttctcaca ttccctgtac ttagatggaa atagtgcttt gcctaaaaag aaaataaaag 32100
acctgattgt gcaggcgagt gagaaagaga gagaggcgct agggttattt ccaccctgat 32160
actctttggg tagtcttggt atgactagca aagaagcaag ctccaagttg tagtttgctt 32220
ccaagtttct ggcttctgtg ggaatttctg catctaagta atgacaattt tcagttactt 32280
gcagtaagta aattatcaac caatcttact gtgtattact agcctagtag gaatttactt 32340
gtatatcgag aggaatgctg cagctttcac cttacttcta atggggatta atgcttactt 32400
aacttgcagt tttggaggca agtacaaagt acaggaccaa ttatggtcat gaagtgagag 32460
agaagtctgg ctagtgaatg gtgattggca actccagttg actgttcatg gcatcttaga 32520
tctgtgagga gggaggaggg aaggaaagtt caagctggtc tttatggtaa gttctggaac 32580
atttccctgt gtcaatgggt catctgttca ttcactgtgt aaaatggttg agggaagttt 32640
taatttacat gcttccttat tgtgtaaacc tttgattttt agtgatttca gagtttgttt 32700
ttataattac ttaacacgtg aagaggatgc agagtaacgt atcgaagctc tggttacctt 32760
ccactgggat ttgacacatt tgatttcctt tattccctcc ttccttccct tcctccctct 32820
ctcttttctt aaggaatgca actactcaga ttcacctgca caccccttggc atacctctca 32880
ctccccctta cccccacttc ctcagaggtg acctgtcctc agaggcaaat gtgtgccctt 32940
tccatccgta cttttatgct ctcatctatg tttacatcta ttagtacact attgtctgta 33000
tttttaaaca ttacataaat ggtgtaattt ttacttttaa ttctgtagtg gtgtttctca 33060
aattaagttc tgcacaaaac atttttatag atatccagtg ttagcttaac gtttttctta 33120
ttgtggtaaa atatacataa gataaaattt accattttag ccatttttaa gtttacaagt 33180
cagtggcatt aagtacattc acagtgttgt ataaccatca ccattgtcca ttgccagaac 33240
ttttcatcat cctaaacaga aactctgtac tcattaaaca atagtttatc actccttccc 33300
tgcaactaga tgctggcaat caccattcta ctttctatct ctatcaattt gcctcttcca 33360
tctaagtgga atcctacata tttgtcgctt tgtttctggc ttttttttct tcttgtgatg 33420
ctttgtttta attatgttcc tggctttcat catctagcag gctgattcca aggtttgtcc 33480
atgtggtagc ttgtatcact ttaatgtttt tagagatagt taatattaca ttgtttatat 33540
ataccacatt ttgtttttttc attcaacctt gatggacatt tgaattgttt ccccctttac 33600
ctgttgtgaa taatgctgcc gtgaacattg ataaccaaat atttgtttga atctctgatt 33660
tcagttcttt tggttccata cctaggagtg gaattgctgg atcatatgat aattctatgt 33720
ttaactcttt gagggatggc cagacttttc caccatagct aaatcatttt accttcccac 33780
aagcaaagtt caagggctcc agtctctccc cataaggtcc tttgcacttt tttttttgag 33840
acggaatctc actctgttgc ccaggctgga gaacagtggc accatcttgc ctgacctcaa 33900
gtggcacctg ccttggcctc ccaaagtgct aggattgtag gcgtgggcca ctgcactctg 33960
ccaatttttt aatttttatt ttcatttatt tttctttttt taattttttaa ttttttttatt 34020
ttttgaaggg ataaggtctc actttgttgc ccaggctggt cttgaactcc tggcttcaag 34080
caatcctcct acctcggctt ctcagagtgc tgagattata ggtgtaagcc cctgcacatg 34140
gcctttactc tcttgatagt gtcctttgat gcacaaaagc tttcaatttt gatgaagttt 34200
attttttatc ttgttacctg tacatttggt gtcatatatc taagagacca ttgccaaatg 34260
cagtgtcatg aagctttccc tcagtgtttt ctttctgcag ttttatgatt ttagctccta 34320
agtttaggtc tttgatccat tttgagttaa tttttgtata cagtttgaga gtcacacttg 34380
aggctctggg cgcagtggct cacgcctgta atcccactac ttggggaggc cgaggcggat 34440
ggatcacctg aggtcaggag tttgagacca gcctggccaa catgccgaaa ccctgtctct 34500
actaaaaata caaaaattag ccaggcatgg tgatgcatac ctgtggtccc agctacttgg 34560
gaggctgagg caggagaatt gcttgaacac aggaggcgga ggttgcagtg agccgagatt 34620

-continued

```
gtgccactgc actccagcct gggcgacaga gcgagactcc atcgtgcggg gtggggggta  34680
aaagtcaaac ttgagtcttt tgcctgtgga tatccagttt tcccatcact atttgttgaa  34740
aagactatcc tttctcaact gtgaatggtc ttggtaccct agctgaagtt atttttatta  34800
ttatgttact taggaatgca cataaggcct ggcacggtgg ctcatgcttg taattgcagc  34860
actttgagag gtcaaggtgg gaggattcct tgagccgagg agtttgagac cagcctgggc  34920
aatatagcag caagacccca tctctatatt ttaaaaaaag aagaaaaaaa aacctctgat  34980
gcataaaata tttaaacttg tatgcattct tttctttctt tattttttaa aaattgagac  35040
agcagcttac tctgttgtcc aggctggtct tgaactcctg ggctcaagca gttcctctca  35100
ccttggcctg cagtgctgag atgacaggtg tgaaccacta cacctggcct gcttacagat  35160
tataaaaaga aaataagttt acaagttaaa gacagataaa atgacaaaat cagtaaaatt  35220
aaaattactt ttatggagcc gatgatgttt attccagttg ctcctctcat tgtgaatatg  35280
gtattgttgc tgtggcagat ttggaggccg tggcagattt ggaggctttg gcaatggctt  35340
ctgttacctt gccatgaggt aactcagttc cctcatcact tttctctgag aactataaaa  35400
ccttggaggg gtgccttctg cccttcgctt ggcatgtata ttatgcaggg atcaggtctt  35460
actccgttct tgattgttag tacaaattag ttaaaattgt attgtttggc cttagcctga  35520
tggtaaacac aacagcacac gtgggctgtg aaatctctgg gcagctctgt gtttctaggg  35580
aagcatctcg atgatccaga acaggcttat actaatgttt tagtgtaatt ttgaaatgaa  35640
aacacagcat ttaaaaattc ttatagagaa tgtatagacc ttgagaagtg ttagcagacc  35700
cagtttacga catgtctcaa tattatgaaa cattgcttta ttccctatcc tgcttgtaca  35760
tttaattttt tcatccagtt ttaaacaact tgggtactgt ggcctgtgcc tgtattccca  35820
gctactaggg aggctgaggc aggaggattg cttgagcaca ggactttgag ggctgtagtg  35880
agctgtgatt gtgcctgtga atagccattg tgctccagcc tgggcaacat agcaagaccc  35940
tgataccttg ggtttttaaa aaacaaaaca agatacatgc tgacatttct ggtttggcag  36000
gcagagcttg ttctgctccc caccctccct tttcccatag taaccattta taggacatct  36060
cactgttgtc tactctgtgt tgcctctgct tccctgcgtg gtagatctag gaatcttagg  36120
atttcttagt tttagctggt gatccgtatc tttttcttaa ttccattgta acttcagctt  36180
ttcttattgc ttgtaggaag gctgtttcca ttgaatacaa acaaaataaa agcttttatt  36240
cttaatctta gagataggat gtttgtattt aaaaataatt gtgctgtcaa aattctgtca  36300
agttggcttt taccacatta gtttttttta atgtggttta tatgaccctg gagtaccttg  36360
tcttctcact gttaaattct caactgagtt gtccctattt aaagtgtgag actgtgccag  36420
tttgatttta aaatattgca agtgcgttat ggcaagataa aactgcaaag aaagaacctt  36480
catgtccctt tgattataaa tgcttttggc acttgtttct actttttcct aatgtttttt  36540
gaggaaagaa cctccaactc tccagacagg tctgggggca aatgactaaa acatgaactg  36600
aggccctggg ctgtctctgt gaggatatcc cctctattct ctctgaaatg tcccagcatg  36660
tggtgcattt cttgttagtg tggactcctc tgtatataac acatcttatt tatcttctgt  36720
gcataacatg aagtagtgcc ctaatgcaat tccaggatgt aattcagcat ttctataaaa  36780
atacagtgtt tttctacatt tgcatcaaaa aataaccaga taattatatt tattaagaaa  36840
atagcatttt tggctgggtg tggtagctca cgtaatccca gcactttggg aggccgaggc  36900
aggcagatca cttgaggtca ggagtgaggc aggcagatca cttgagatca ggagttcgag  36960
accagcctgg ccaacatggt gaaaccccat ctctactaaa aatgcaaaat tagcctggcg  37020
```

tagtggtgca tgcctgtaat cctagctact caggagactg aggcaggaga atcacttgaa 37080
cttgggaagg ggagattgca gtgagctgag attgtgccac tgcactccag cctaggcaac 37140
agagtgagac tctgtttcaa aaaaaaaaaa aaaaaacaaa gaaaagaaaa gaaagaaaga 37200
aatgtatttt tggtatttgt tttcacaaac tagagcattt atgtgaaata acattgctag 37260
tattgatatt ataccatagt ataatactta gttcttcagc gatgtatctc tgctgatcag 37320
ctacatgata tctacttgag ctgttggatt ttttttaaga acagtgcatt tttgaatgct 37380
tttgaaaaat tgtagtaaaa tacataaaac aacatttacc ttgtaagcat tttaattggt 37440
acaattcagt gacattaagt acagtcccag tttagtgcaa ccactgttac tgtctagttt 37500
cagaacgttt ttgccccaga tggatactct gtacctgttg aacattcagt cctcatggcc 37560
caataatctt tatgtctgta tagatttgcc tattctgcat attttatata aatggaatca 37620
tgtcttttgt gtctggcttc ttttacctag catagtattt tcaaggttca tccatgttgc 37680
agcatgtttc aatactttgt tcctttttat gtccattgta tggatatgcc acatttcgtt 37740
aatgacaatt cttttgggta gctacatttt aaaacattat agtagaatac atatagcata 37800
caatttacta tcttaaccat ttaagcctgc agttcagtgg cattaaatac attcacgtta 37860
ctgtgcaatt atcaccacca tctgtttgca gaaacttttc atctcctcca tttgaaactc 37920
tgtatacatt aaacatgaac tctcccttct ccccttcctc cagccctggc agccaccgtt 37980
ctacattttt atctttctga cagagatttt actactctag gtacctcaca taagtgaaat 38040
caaccagtat ttatcctttt gtgaccagct tatttcatta gcttaatgtc ctcaaggttc 38100
atccatgttg tagcatatgt caacatgact ttccttttaa ggttgaataa tattccattg 38160
tatgtatatg tcacaatttg tttctccatt tatccatcac tggacatttg ggttgctttt 38220
acctatcggc tgtcttgaat catgttgcta tagctgtaca agtatctatt tgagtttctg 38280
ctatcaattc tttaagtata tgcccagaag tggaattgct ggatcatatg gtaattccgt 38340
gtctggtttt ttttttgagg aagtgccatg ctgttttcca cacagctgta ccattgtaca 38400
ttccccccag caatgtacga gggctctgat ttcttcacat ccttgctaac acttagtatt 38460
tttttgata gaatagccat cctaatggct acttttaaag tatgtttaac attatttatt 38520
tatttttaat tttttttgta gagatggcat cttactgtgt tgcccaggct ggtcatgaac 38580
tcctgggctc aagcagtcct cctgcttcag cctcccaaag tgttcggatt ataggcgtga 38640
gccaccatgc ccagcccaaa tttaaatata taactaaaca catagcagct aacaccaagc 38700
ctttaaaaat atcattaata ggccaggcgc agtggctcat gcctgtaatc ccagcacttt 38760
gggaggccga ggcgggcaga tcacctgagg tcgcgagttc gagaccagcc tgaccaacat 38820
ggagaaaccc tgtctctact aaaaatacaa aattagccgg gcatggtggc acatgcctgt 38880
aatcccagct actggggagg ctgaggcagg agaatcactt gaacctggga ggcggaggtt 38940
gcggtgagtc gagatcgcac cattgccctc cagcctgggc aacaagagca aaactccatc 39000
tcaaaaaaac aaacaaacaa acaaaatata tatatcatta ataggccggg catggtgtct 39060
cacgcttgta atcccagtgc tttgagaggc cgaggtgggc agatcactgg ggtcaggagt 39120
tcgataccag cctgggcaac atggtgaaac cctgtctctg ctaaaaatac aaaaattagc 39180
cacgcatggt ggtaagcacc tgtaatccca gctactcagg aggctgaggc tggagaatgc 39240
ttggacctgg gaggtggagg ctacagtgag ctgagatcac actccagcct gggtgacaga 39300
gcaagactct gtctcaaaaa aaaaaaaaaa aatcattaat aaatgtgatc tttttcttc 39360

-continued

```
ctatacaaca agttgtcaag caagtatgac cttcttaatt gaccctttga catgaactgg  39420
gatgagatcg tggaggatgt tgaggagaca gttgttacca tagtgcactt ctaaaaactt  39480
taattctata gatttcttta aaattttttt taaaattatt atgagtacac aataggtgca  39540
tctatagatt tcattaccct caaataaatg tacaaggcaa tgcagagaaa tgcacagtgt  39600
aacttggtag acttgaccta tcaagttact gttgaatata ttatggagcc tgtgtattac  39660
caggggcagc agacttttcc tgtaaagata gttgttttca gctttgttga atctgtggtc  39720
tctgtcttaa ctacaactga gaaagccatt gacaatatat agatgaatgt acatgactat  39780
tctaataaaa ctgtgtacac tgtaatttga attgcacata attttcatgt gtctcctgta  39840
taattcttct tttgacttct tttcaaccat taaaaaatgt aaaaacaggc caggcgtggt  39900
ggctcatgct tgtaatccca gcactttggg aggctgggtg gattgctgga gcccaggagc  39960
ttgagatcag cctgagcaat gtgatgaaac cctgtctcta caaaaaatta gctgggcatg  40020
gtgttatgtg cctgtggtcc cagctacttg ggaggctgag gtaggaggat tgcctgaacc  40080
cgaggaagtc aaggctacag tggtttgtgc cactgcactc tagcctaggt gacagagtga  40140
gaccctgtct cagtgaatga atgaatacat tattagcttg tggactatac aaaaatcaga  40200
ggctggaggt gagctgggta tggccattgg gtgtggtttg ctgacttctg gtagagagga  40260
attaggagat gttaaaggtg gtggaactgt cagatacttg cattctttta gaaatacttt  40320
ggagttagct ttttggttca ggcaaaggac caaagggtta ggagagtcag gccggtaaag  40380
aggagtggtg ggcccatagc agcagttcct ggagtttttt tttttttttt ttttttgtga  40440
gacggagttt tgctctgtcg cccaggctgg agtgcagtgg cacgatctcg gctcactgca  40500
acctctgcct cctgggctca agcaattctc ctgcctcagc ctcccgagta gctgggacta  40560
caggtgccca ccgccacgcc cggccaattt ttttctattt ttagtagaga tgggatttca  40620
ccgtgtttgc taggatggtc tcgatctcct gacctcgtga tccacctgcc tcggcctccc  40680
aaagtgttgg gattacaggt gtgagtcacc gcgcctggcc aggtcctgga gtctttaaga  40740
ggaggtttgt ctgatggttg gttggacaaa agcctgggca tgttgtcacc ttccataagt  40800
gtttgtggga atgtaggtaa tgaggaggag taaaggattc ctgaaggatg aggaggaggg  40860
ctggtggctg ccataggaag tgatcactgt tttggcagac ctgtcttaga gtaatgaccg  40920
tcatactctc tcattgccct tgtgaactca tgaaatccca tggctgctaa agctgaaggt  40980
caagtgggga cttcccggcc actgggctta gcaccccaca gagctgtgga gtgggcatta  41040
atgtcccttt tttatagatg cggagactga gaatgaggac tgttggtaac ttttgaaagg  41100
gcactcagct agaaaagtct gagccaggat ttcaagtccc atggctttac ctctgtggtc  41160
ctaatatttg gtgtgttcaa gtgagatctg tttttttcct atttcatttt gattattgat  41220
tttcataaat ttttttctct tttgagatag tatcttctct ctcttttctt ttttctgttc  41280
tttctttctc ttttctttct tttttttttt ttctctgaga cggagtcttg ctctgtcgcc  41340
caggctggag tgcaatggtg caatctcagt tcactgcaac ctctgcctct cgggttcaag  41400
cgattctccc atctcagcct cctgagttgc tgagattaca ggcacctgcc atcttgcctg  41460
gctagttttt gtatttttgt agagacgggg tttcatcacg ttggccaggc tggtcttgaa  41520
cttctgacct caggcgatcc acccgcctct gcctcccaaa gcgctgtgat tatatgcatg  41580
agccaccatg cctggccatt atttctttct ttctttcttt ttcttttttt caggttcatt  41640
gaatttgctt tgagacaggg tcttgctctg ttgcccaggc tgaagcgcag tggtgcagtc  41700
atggctcact ggagcatcaa tttcctgggc tcaagcgata cttgcacttc agcacccctc  41760
```

caccccccacc cgctcctttc ccccacagta gctggaacta caggcgctag ccaccgtgct 41820
tggctaattt tttttttttt tttttttttg agacggagtc tcgctctgtc acccaggctg 41880
gagtgcagtg gcgcgatctc ggctcactgc aagctctgcc tcccaggttc acatcattct 41940
cctgcctcag cctcccaagt agctgggact acaggcgccc gccaccatgc ccggctaatt 42000
ttttgtattt tttagtagag acggggtttc accgtgttag ccaggatggt ctcgatctcc 42060
tgaccttgtg atccgcctgc ctcggcctcc caaagtgctg ggattacagg catgagccac 42120
tgcacccggc ctggctaatt tttaaatttt tttttgtaga ctgcccaggc ttgtttaatt 42180
gattttctat gtgatcttag ggaaatcgat tatttcccat aaacattttt ttaattagaa 42240
gttaaattct gcctagtttg attcacagga ttattgtgga tgactgaaac agagaatagg 42300
taagagcttc tttgaaaaat atgaggtacc atacagaagt tagatgcttt gtcctggtga 42360
taccccctcc aaagcacagc taaggaaatg tggaaggcac tcttatctca tcatatagct 42420
ttgaaagcct agcattgaaa gtacgaactt gattcttttg gagaaatcct ttggctctca 42480
gtgagtttac tttctattaa tgactgtgtt aagcggaatg aaaactgaaa gaggaaaggg 42540
gaggaagtca gaattaagca ggaagagtga gcccatagca gagtccagat ttagacccca 42600
agctacttgg aatgatactg gacaattatg ggtgtgttta atgatggtcc tgagtcatga 42660
aaacaaaagg aggctttaaa ttatgtctgg cttagtgtac agcatatttt tgtcattatt 42720
caagttttag catgtaaaga ggaaagtgtg cagtacttat gcatatcatt ttcattaatg 42780
aaactaaatg aggcctcttt aaaattatca gtgttcacag tatcttccaa aagacatgta 42840
aatgtataaa ggtataaaaa atatacatat aaattttaca attttgtgag ctatatagta 42900
gatctcttat tttgtccata ggtcttaaag atcttatact gtattcagga ataaagataa 42960
cttcagtggg aggcctttac agggctaatg agtaagcatt attttgataa agttctgtgt 43020
tgtctacaat agatatagta gaaatactct tggaatggta atcatcccag gccctgcttt 43080
ggagcggaag aaatagtcaa tgtagaactt tacagtatat tgtacacaga tgtgcctgct 43140
aataacttct gtagacagca aagtttaaga gaaattaggt ggtaaatgca acatatgtat 43200
ctaaataaat ttggtctgag ggatttgata agatgaaaca gtacatagtc cagaaaattt 43260
ttatactcaa agaattatag aaaatatctg aaatgttttc agttttgtgc atatccagaa 43320
aatgtcatcc tgtgatctgc tggttggcag cccaatggca gtattagatg tattgttttt 43380
attttgtttt gtttgctatt tatttggtta agagagttac ctaattagga gtgtgaaaaa 43440
aaagatttat tatagtagtg ggcttttgtt tgacttaaaa catttttgtt gttaccacag 43500
tatgagtgcc ttgtttgtga aatttgttta ccgggaagcc atatacttag agtagctttt 43560
agtttatcat tatcatcatc atcatcatca tcatcatcat catcatcatc tccttcatca 43620
tgaaaggaag aagctaccaa tgttgcttta ttctgcaaaa aatacaatag atgcttgttg 43680
aaagtatgga gtgaaatctt aaatatgtct gttaaaaaga gtacaactgg ccaggggtag 43740
tgcctcatgc ctgtaatccc agcactttgg gaggccaagg cgggcagatc gcttgagcca 43800
ggagtttgag accagcctgg gcaacatggt gaaatcctgt ctctacaaaa aaaaaaaaaa 43860
tagacaaaaa ttagctgggt gtgatggcat gcagctgtag tcccagctac agtggggctg 43920
aggcaggggg attgcttgag cccaggaagt aaaggctgca gtgagctatg gttgtgccac 43980
tgcattccag tgtgggtaac agaacgaaac cctgtctcaa aaaaaaaaaa atagtacaac 44040
tttaagcagg atgtgggcac atgcctgtag tctcagctac ttgggaggct aagtcaggag 44100

-continued

```
agtcacttga gcccaggagc ttgatgctgc agtgagatgt gattgtgcca ctgccttcca  44160
gcctggggat gatagcaaga ccccatctct aaaaaaaaaa caaaaaacaa aaaaaaaaca  44220
gagtacaaca acctttggta aacttggaat ataaaggtgt ttccttaacc tgttaaagag  44280
ctgataaaga gtggtacttt caaaccagta cacattatgt gaaacactag agacacttcc  44340
catttgttaa aagaaaaacc ttagccaaat taaatttaag ttttttttgg agacagagtc  44400
ttgctttgtc acccaggctg gagtgcagtg gtgcaagcac agctcactgc aacctccgcc  44460
ttctgggttc aagtgatttt cctgcctcag cctcctgcgt agctgggact acaggtgtgc  44520
accaccacgc ctgggtgatt tttgtatttt ttgtagacat ggggttttgc catgttgccc  44580
agtctggtct tgaactcctg ggctcaagca atctgcctgc ctgggcctct gaaagtgctg  44640
ggattacagg cgtgagccac catgccattt aatggtttaa ttgagcaaag aatgatttgc  44700
aaattgggca gcctcccgag ccagagtagg ttcagagact ccagcacagc catgtcgtgg  44760
aaaaagattt atgaatggaa agaggaaagt gatgtaccga aaacggaagt gaggtacaga  44820
aacagccgga ttggttacag ctctgaattt gccttatttg aacacaagtt gaggtttgta  44880
cagttggcca cctttgattg gccaaaactc ggtgattggc acaagagcag gttatagtct  44940
gtttacatct ccattttggt tatagttcat tatggacaga aaaacctgta ggtcaaactt  45000
aaaatatgta aggagacagt tttaggctaa acttgattta acacattaaa tccgtaacaa  45060
gacaggatgc ctgccctcac catgttattt gatcttattt tagtaattct agccaatgta  45120
gtagggcaag aaaactgcct gcttggctac aaaataaaca cacaaaagtc agtatctgta  45180
atatgtgaca gaaaatataa ttaaaaaaaa aaaaaaaagc cgggcacagt ggcccatgac  45240
tgtaatccta gcactttggg aggccaacgt gggtggatct cttgagctca ggagttcaag  45300
accatcctag gcaacatggc aaaaccccgt ctctacaaaa aatacaaaaa aattagccac  45360
gtgtggtggt gagctcctat agtcccagct actttggagg ctgaggttgg aggatcattt  45420
gaacctgaga agcacaggtt atagtgagct gagatcacgc cactgcactc cagcctgggt  45480
gacaaagtga gactctgtct aaaaaaaaaa aaaaaagaag aaaaggaaag gaaagtaaaa  45540
gaaaaaataa tttcacttac tagagcatca aatccctaag ataatttaga gcaaagccag  45600
aaaagtgaag aaaatataaa aatctttaca gtgggttgca ttttaaaaaa aaacttgaag  45660
atatcagatc aactcactaa tgtattaatt aatataattt aaattaaaat cccactgatt  45720
tttttgtggg gagggtggga gagtcatttg ttaaaatgat tctaaagagc atctggaaga  45780
ataagcaggc aagaatagcc aagaacattt tgaaaactaa agatgagttt ggaagacgat  45840
tggttttgta ctgtcaacta cttatagatt ttacatgaat tttaaagggt aatctgagcc  45900
ctcgaataga cagaaatagc catagatctg aaagaacact taagacctga tccagctatc  45960
catgagagta tatataatca aagtctttgt gtgtgaatca ggagtctttc aggtgcaagg  46020
taaataaact cataattgct tacgcaaagg tggtatttgc tttagtgact ccagagaaag  46080
ctcaagtgcc tatctctccc ctgactttga ttctttttgg ggttggctcc attctctcct  46140
gttgctaatg gcttcctttg tgcagccaga ggaaaggagg tgtggttttt tgatacttcc  46200
aggcttctat ttttatagct tgagatcaaa gagggaagtg accttcctta gagtcagtgt  46260
gtaaagtcct aaggaagata ccacgtgggg tgctggggcc atgtgcccat ccctggccca  46320
tgaccatggg gatgctacac taactggggg ccacgcatgg ctgttcctgc cctgaactgc  46380
cagctggctt tgcagtgcag cctcaccaga atcacatgga atagtaggga tatgaattgt  46440
ttcccaaaga aagtgtgtgg ggtggtagaa ttactagtgg gggagtaagg ggacaggcca  46500
```

-continued

```
ttgggcatac tggagcagca tttactcagt cattgagaaa aggatggaac attcaataaa  46560
gggtgctgga cacatttgtg ctctaaaaat tttgtgtttc acctattaat ttatccctcc  46620
ccttagcccc tggcaaacac tgatctgttt actgtctcca tagttttgcc tttcccagaa  46680
tgtcacaccc ttggaatcat acagcatgta accttttcag attggcttct tttacgtagt  46740
aatatgcatt taggattcct tcatgccttt tcctggattg atagctcatt tctttttagt  46800
cctgaataat attccattct atggatatac cacaattgat ccattcacct actgaaggtc  46860
attttgattg cttccaagtt ttgataattt aaaaaatttt ttaagacagg gtgtcattgt  46920
gttttccata ctggtctcct gaacacctgg gctgatgtga acccctctcc tcagcctcct  46980
gggtaactgg gattacagct atacaccact gtgcccagtg tgacaattat gaataaggct  47040
gctgtaaact tctgtgtagg tttttttgtg tgtggacatt ggttttcagt tcattatggt  47100
aaataccaag gagtgcagtt gctggattgt atggtaaaag tatgtttagt ttgctaagga  47160
actgccagct gggtgtggtg gctcatgcct gtaatcctag cataatggga ggctgagaca  47220
ggaggatccc ttgaagccag gagttcgaga ctagcctggg caacatagtg agacctcatc  47280
tctacaaaaa atttaaaaat tagctgggcg tggtcttatg tgcctatagt cctaactgct  47340
tgggagactg aggtgggagg atcacttgag cccaggagct ggaggtggca gtaaactgtg  47400
atcataccac tgcactgctg cctgggtgac aaagcaagac cctgacttaa aaaaaaaaag  47460
agaaaagaaa aaaagatgag tcagagggta aggaagcaaa aataagtaaa taaataaata  47520
gaagagaaaa gaaaaaagaa aaaactgtct ttcaaagtgg ctgcgccatt ttgcattcct  47580
accagcaatg aatgagagtc tgttgttgca catcctcacc agcatttggt gttgtcagtg  47640
ttctggattt tgaatattct attaggtata taatgctgtc tcacttgttt taatcaatga  47700
tatatgacat tgagcatctt tttaatatgt ttacttctca tctatgtatc ttctttagtg  47760
aggcctttgt ttaggtcttc tgcccatttt aaaaaatggg ttcattttct tattgttgaa  47820
tatcatgagt tctttgtcta ttttgaatac ctgccttttg ctttattttt gtgtttttta  47880
tttttttttt ttattgagac aagttctcac tctgttgccc aggctagagt gcagtggcat  47940
gaacatggct cactgcagcc tcaacttctc ccagcctcaa gcaatcctct tgcctcagcc  48000
ttccgagtag ctgggactat aggcacacac caccatgccc tgctaattta aaagagtttt  48060
tttttgtaga ggtgggatct cgccatgtta cccaggtggt cttgaactcc tggcctcagg  48120
caatcttcca gccctcagcc tcccaaagtg ctgattatag gcctgagcca cttagcctag  48180
ctcagaattt atttttattt tgttaatttt gaaaaaatat aggacctcat aaaagtcagt  48240
ctacatttgt acacattatg tttttggtga atatgtaaat ggattctttg tgaatcaatt  48300
tggttttgtt tttttgcttt taaaaatacc agccctgggc tggatgcggt ggctcacgcc  48360
tgtaatccta gcactttggg aggctgaggc aggtggatct cctgaggtca ggagtttgag  48420
accagcctgg ccaacatggt gaaacgctgt ctctactaaa aatacaaaaa ttagctgggc  48480
gtggtggcgc atgtcagtaa tcccagctac ttaggaggct gaggcatgag aatcgattga  48540
acctgggagg cagaggttgc agtgagccga gatcgcgcca ctgcactcca accttggcga  48600
tagagcaaga ctctgtctca agaaaaaaaa aaatgccagc agtggctggc tgaggtggct  48660
cacacctata atcccagcac tttgggaagc caaggcaggt agatctcttg tggtcaggag  48720
ttcaagacca gcctggcgaa catggcgaaa ccccatctct accaaaaata caaaaattag  48780
ctggatgtgg tagtgcgcac ctgtaatttc agctgctggg gaggctgaga catgagaatc  48840
```

-continued

```
acttggaccc tggaggcaga ggttggagtg agccactgta ttccagcctg ggtgaaagag  48900
ggatactcta tttaaaaaaa aaaaaaaaaa aagcgggctg gatacagtgg tgcacacctg  48960
taaccctagc actttgggag gctgaggtgc tcagattgct tgagctcagg agtttgagac  49020
cagcctagac aacatagtga gacatcgtcc ctaaagaaaa aaaaaaaata ccagcactta  49080
gccaaaagat ttcaacagtg cagaaaaaga aagttgtgat atcttttctc caaattagtc  49140
ttgttttcag tttcattatc caagtaacca ctactaatag ttaaaacatt tgaaatacgt  49200
gtgggagctt gtcctattta atataaatta tttattgagc aaataatcac cactagtatg  49260
ttttggatac tggaattttc atatgtagga gtccttgaat gtaaggtgcc cctttggtag  49320
ttctgtgctt cttttacctg tactgtaaca tagggaaaga tgttacaaat ggttgtattt  49380
ttaacagagc agtatctatt cttaaacacc agcccttcca ctaaaggtaa acaacaaatg  49440
aatacataaa tgaagttttg gtattgggat tatgtgggtt aaacacatcc atatttcatt  49500
attaatattt aagaatataa caaacttttt attggcattt ggaccttgta gctaaggaaa  49560
gattaaactt tgtttatttg tgctttgttt tttttcttca ctcagatatt tgaggatttc  49620
ccatttgagg aatacattta ttaatcaagc tttagtttca agatccttga tcttagggaa  49680
taccatcaac cgttcttctt taagcttcct aactttgccc aaatttggtt agaactactc  49740
aagagtagtt tgggtaattc agaaatttta ttggaagggg aaagaatttt tgacccaaat  49800
tagataaagc aactcttggg taatgatttc ttttcttgtt ctctctttat aatcaattga  49860
aagtagtagt aaggctgggt ggcaaaagaa agaggcctgg ggagaatcgc gtggttttca  49920
ttatctcttt tcatagcagc aaagtgggaa gggaccaaga ggaaatcaac tgaaaaacca  49980
tccttctgaa acattggcct aaaaaactgt agtccagaaa ttgagtgcaa ctggcagtgg  50040
catttaaaag gaatgctcta atttctagga aagcaggcac gagtacctct taaaagaaga  50100
aaaaaatgaa aactgtaatt taggacacat agacgagtat ccattccctg tacttttact  50160
ctcatgtcct aaccaaggaa gggttgccat agcaaatatg gcattcctta gccatgattc  50220
actgttgtaa atgcctgcag cattcataaa agtaagatat atgggctctt ctttttcctt  50280
ttaaatcttt atttctgtat ttaaatctgt atgtcatcat ctgtattttc tctcttgttt  50340
tttttaaatc ttgggagatg gtacaaatta tttaggggag ggaatgagtt tcttgtccac  50400
aaatagagga gagagagggc tttttgtctt tctgctttgg aactggagag cttcctattt  50460
aggcatggcc tttttcaagt gaccttgtat tgttatcagt actgtagaag gtaggcacgt  50520
tgtgtaaact ttaaaattga aagccattag gcattccact tgtaaacctt ggctttttaa  50580
agaaaattac atgttcattg tgaatatttt cttatcgacc tatctctgtg cacatgcaga  50640
cttcctttgc ctacattctg aaaggtgtaa ttgccttctt taaggacagc ggacatctat  50700
agttcttggg tcaaattgtc ctccttctgg ttttgtcagt tctcagccac actgtgtgag  50760
catccatttt cttggattct ggttcggagc tcattttaag gaacatcatg tccctttttga  50820
gactctgtgg acattggggt gggtagatgt ccccctgtga acagaaggtc cctccctaag  50880
gaggtgcttc tctgtgttga gtcctgcatc tgggcacaca gagcccgaag caggaagagt  50940
tgagtctgaa tagggaggcc tgtaagcctg actgctctgc cacgggtagg cctggtctgc  51000
catgctccag gagcccccag gaggctctga agtcattctg cctctgggaa ttttacagag  51060
gagctaatat ttgagctgag tgagaaggtg attcttgaaa aagcaaggcg tgccctggtc  51120
cagttctgtg gggctgtcgt agaagagggc tcggaagctc ttgggagtga ggctagaaag  51180
gtaggcagtg ttaccataag gaggttggaa gtgacacaga taggctaagg aaggggactt  51240
```

cagtaatcat gcagcaatgg cctggaaaag ggagaggctc atagtaggga gaccagtttg 51300
gaggctgcca tagtgttcta ctgagagaga aaaagacttg aactcagagc acggtcaggg 51360
aaggtggagg ggcagggtct gatttggaag tgttttgttt tttggttttg ggaacaagga 51420
tttggaaacc tcttggctcc gtagatgaag aaaggtgaac caaggaagac tgaagtttcc 51480
actcaaggaa acagtaactc agggaagaaa acacaggagt aggaataggt ttaagagaat 51540
gacaagcagt tgtgttttgg acttgtttag ttcgaggtga catctttgta gggatgtcta 51600
gctggtagct gcaagtatag gaggaggctg gatgtgtgca tgagtttctt ggtaaagatc 51660
catctgcagt ctcctgaaga tgtcacccag attgccctgc catcacccca gggccttgag 51720
tcactcgctt ctcttggtgt ctaggcaggc ttgaagaaaa tcaaacagta caaaatcatg 51780
caaattcaga cctctattcc accccagagg aaagtcctgc tagcagtttt tgtgtattct 51840
tccagaaatt tgccttgcaa cgcgtttgag tatataaata atcccagaaa ggatgggcca 51900
gacactagca gaaactcacc acacacactg cactgggcat gcagaaactt tgcaaaatgt 51960
actggtgtgt gctgtcactg cattcctggg tttggaggtc ttctgtgtcc ccagctgtca 52020
gtattgccca caggctgacc actgagctcc ttccacagcc ggcccatatc accctctttc 52080
gaagtgtgtc tgcaaggcta gattattaga gtaatttaag tgtttctgct ttgtgttttc 52140
tttaatgaat ttttttatga tgaagttctt gttttaaaaa tatacagtgg taattaacat 52200
gtatgcattt ttcttaaaat gacccccccca gtccctcttc ggatgtgatc actgttaaca 52260
gtatcgtata tagaccctgt tctgtgtggg gcgggcagag ggctggttag tgggtggaac 52320
atgcatactc acaaccatat ttttcacatg ggaaaatata aaggtgacaa caaatctcct 52380
ggactataat ctcatcaagc agacaataat ctctgtttca aaagtggaca aatacatgct 52440
gattttttaa aaaaaattat aatagtacag aaagatacaa aaataagtta aagtcttcct 52500
aactctcctg cctgtgccct ccactgggca aaagtccctg tccctaaggt aatatctgtt 52560
aacagttctc cttccagaaa acttgcaatg caaataggaa cattttgtgt gtctgcctct 52620
gtgtgtatgt gtttacatgt cttttttttt tttttttttt tttttttttt tttttttttt 52680
tttttttttt tgagacagag tcttgctctg ttatccaggc tggagtgcag tggcatgatc 52740
tcagcttgct gtgatctctg cctcctgggt tcaagtgatt ctcatgcctc agcctcccga 52800
gtagctggaa ttacaggcgc ctgccaccac acccagctaa tttttgtatt tttagtagag 52860
atggggtttc gccatgttgg ccaggctggt ctgaaactcc tgacatcaag tgatctaccc 52920
gcctcagcct cccaaagtgc tgggattaca ggtgtgagcc actgcttctg cccctgcaca 52980
tgtctaacgc acacaaaaga gattctgctg aacacatttt ttatgctttt tctttccaat 53040
ttaacatatt tgacatcttt atcagcttat atagctttat ttttttaaga ggttattggc 53100
tataaaggga aagtgcttta tgggtgcttc tgttgttatt taattggatc ctgttgatgg 53160
acattgatat catttctaaa ttttttagta tcctaattaa tcctgtggtg agcatcctta 53220
tacagatatc cttgttccct catgaaaata tttctggagg atggaaagaa gggaaatttt 53280
aaaaattatt tgtgtaaaca ttatcgtttg ttagtagaat gacctcagga gagattgtag 53340
taatttatac ttccccacat gcatatgaat gccttttcaa tatattgttt caaaattgga 53400
tatcatgaac cttaagagat aaatatatat gtatgtattt tttttttttt tttttttttg 53460
gtgggggcat gtcctgttat tgacagtttg ttttggtgga gggatgtcct gttattgaca 53520
gttatcgaat agaactttgt cagttccttc atgtaaggga tgaatttggt aataaaacag 53580

-continued gtctgacttc agttatggaa ctgggaaagc tggaccttga tgtggaggtg ggctcagaca 53640
tgctgtgtct gggcaggtat ctcttgggaa gcagtgtcat ccctgaacag aaacatggat 53700
gagccgcagg ggacggtgct gagcagaggg gctggccgtg ggtcatctgc ctcccttggc 53760
ctagaaggca caagggagct ttccaccttg cctttggttt tgagaatgca gaagctacta 53820
agcaactcac agtgtgccca gggtggtcca gctgaaggat gcgaaatggt tcttcctttt 53880
ccagccaaag atcttgaacc tcccacccca tgacaagcat tataaaattc acataatttt 53940
gataggctgg attccttttc tgtagcagat ctttcctcag aacagaagtt tgtttttttt 54000
ttttaaccta aattacctgt gagttttatt ttttaaatat ggaatctgtt ttttggacac 54060
ctccttgtca tattaaatgt tctgttatta attttgagat tttaatgtaa attttacccc 54120
agcaaattaa ttttgtttct cttgctctct cttttttttt ttttggcatc ctttcccgtt 54180
gtatagtggt gctcatttta tcatactgct tttatatgac ttttcttttg tgaacaggga 54240
tcttgttcac ttttcctttt ttaaaaattt ttttattttt ttgagacgga gtcttgctct 54300
gttgcccagg ctggagaaca gaggcacaat ctcagcccac tgcaagtttt gtcttccggg 54360
ctcaagcgat tctcccacct tagcctcttg agtagctggg attacaggcg tgcaccatca 54420
cgcctggcta atttttttgt atttttgtag agatggggtt tcactatgtc atccaggctg 54480
gtctcgaact cctggactca agcgatccac ccgcctcagc ctcacaaaat gctagggtta 54540
caggcgtgag ccactgtgcc cgagccactt ttccttttaa cataaaaaca ttgatatcct 54600
agagagggca ctgtattttg ggtacataca ggttcagatc acggaagagt tgtattctat 54660
acttttttttc atcattctta gttcagtatg atgtatttta taatttcata tgagaaactg 54720
taacaatggg catgtgtcat ccagcaatac ctactcataa atcatattaa attttgatcc 54780
aaacatggga gaaactgaag ttttctctgt gtacttggat gctttcagag gcataaaatt 54840
atattaccat gtgaaagcaa gcctacaaaa ttcctcaggt ggtccactct gccactcaaa 54900
tgagagccag acttacagtg cacactctac aaacggactt ccagctcgtc agggtatttt 54960
aagtgcctga atatgcaagg cactgtgcca gtaaaattac tcagtcctga ggatagagcc 55020
tgttagaatt attttaaaat ctgtacttga agtttatttc ctcagtattc caagatattt 55080
tatctggttg ttctctgagt atttcacacg tagctagtta catataggtg agatggtgat 55140
gcttgtgcct ggtgtggatg agaaactgag cctggcagac ccgagattgg atttcctctt 55200
ctgactttgc aagtgtggct ttgctttaat aatagccctc ctctttttct gtattcctct 55260
tttctccttc cagtgtggca aatatgcatc aatcaaaata caataacctg tggaaccatt 55320
ttttctaaaa taggaaggtg gtgccatggg ctattgattg ttgagggtag tcttcagagc 55380
ctgtcttata aatctataat aattcccccc aaattaatgt gctagttaga accctagaat 55440
tgcagcactg aaagtgaatt ttagaatctt ttccaacttt ttaccaagct cagaaagccc 55500
ttttattgga cctttgtttg cctcatggtc atctggtttc tttatgctgg tagtaacagg 55560
aaccttacta acctacaagg tgacccagtc catcctgggc agctgtgatc attggaaagc 55620
tctgaatcat tcatctggaa gctgcctgtg gcagaatagt acagaacata tgcattgcac 55680
acactacaaa actgctttaa ataagtgttc cttttcattg ttagatggaa gtgacccagg 55740
gcaaggatca tgttttatga gccagttttc tcctagtgcc ttgaacatag gcacttggta 55800
gtgtttagag aatgaattgt cttttttttt tttgagacaa agtctcactc cattgcccag 55860
gctggattgc agtggcacgg tgtcagctca ctgcagcctc cacctcccaa gttgaagtga 55920
tttttgtgcc tcatcctccc gaggagctgg aattacaggc atgcgccacc acacccagct 55980
aatttttata tttttagtag agatggggtt ttgcgtgttg gccagatggt ctccaactcc 56040
tggcctcagg cgatctgcct gcctcagcct cccaaagtgc tgggattaca ggcgtgagcc 56100
actgcgcctg gccagagaat gaattcttaa taagtttctt atgacttcag attgactggc 56160
agttgtgcta aatatttttt gcctttattt gaattagaaa attcgtaagg gggccttgag 56220
agtagatgca gtcacattta ggagattttt cccccccatt ggttaaaatg cagtttttct 56280
atggatctgc tttagaacta caaataaact ccgatcactc acagcagact acgcaatgag 56340
ataagaagca gtccatttgt tctgtcgttt attcatggcc ctcatctttg ccagccaacc 56400
tgtgcagaag agcacagcaa agcataagct tcctaacagc tattcccatt cagctgctgt 56460
cttcaagaag cagaagggtt tagataacct tagagaacat aatcaaacct gggaaactca 56520
aatcaaaaca aaacttcgaa acggaagttg aaggtcctga ggtacccaga ggcatagcaa 56580
ggaaaacgtc cccactggga tatcttctgg attcacctac agacctctct ggagttttaa 56640
gatccacgtt ttatgacata ttgcatagca aacaggccga acgctgttgt aaatcatcct 56700
ctacgaaagg cccaggtttt gaaactgaag gcctgaaaag gctcctgctt accagctgtg 56760
tgctgtacct gacacactga agcctgagag tgccagtcac ctgtcagagg gaacacagct 56820
gccctcaggc agaacctgag tctagaactc aaggtttttg actcttaggc taaaaataaa 56880
aaatcagaag gaggaactat ggattgctta atcagtcaca ttttcacttt ctaaggtttc 56940
ttgtagcaaa agttatagtc tttggggatt gggatgtaga cacttttttt tccttcccta 57000
aaacaatttt tggcctgcca gtttttcgag cttcctgctc tggaccctga agttgccatg 57060
cagttgcaga catgctcctc cttcaaggct ctgttaagct gtggctgccc ttccttacca 57120
ctgctgtgcc ccaggccaaa ccccctgccc ctccttcccc taaggcactt tgcacctgtt 57180
gctccgagcc ttctggtcta tcccagttgg tagagtccct gtgcttacct ctgtggctca 57240
gtcctcgtgg gtggtcagtg ctctagggaa ggtgagctga ccacttcact ttcccttccc 57300
agccatagct cttcacagcc tcaccaactt agaaaggaat gctgcttttc tctctgtccc 57360
ccgtcctgac tatgttcaag tcattgctca gcccagtgag tttgtccttt cttccagacc 57420
agtagttttc ccccagtccc tcaggcttca gcccttgaag gcatccttag ccccccacca 57480
ccatgatagt caggcgctgc gcctatccgc agggtgtggg tatgtgtgtg tcttttgttt 57540
ctggagccca ttcctttcct tccaccagcc tctaggcctt catccaatcc ttttgcaact 57600
cagtgattca tgacttttcc ctgcatccag tctagtctct ttgctggtcc attgtttcca 57660
tagttgccag tttaatcttc ttaaaatgct gcatttttga agtcagtctc ttttggtccc 57720
tctcagaaac atttaaatag ctatctgttg ccacaggggg aaagcttgaa cctcttagcc 57780
agtcattcag agcctgccct ctgctggggc ctgctttcct ctacagatgc ttctcccact 57840
ctgcctgcca cagcccttgt agctggctga ttgccctgta cctcgcaggc tctggaagtc 57900
ttcagctcct tcatggagcc tttgccagcc attcttttca agactttgct gttgttcact 57960
gcctgatttg ttcatttgac acttaattca ctgagcaaac attatgaaag atgtactgtt 58020
tgctactgtg aggaatggat ccccaagaga taagagggtc agtccctact gccaggaaac 58080
ttgcctgtgt cacctgggtt cagtatcttg tgtctattag atcagaagtg gaaaggcaga 58140
ggccagcccg tatgcttgtt ttattttatt taaatcacca gcaccccagc aagtgttttg 58200
cacaggaaat ttctcattat ttaattattt tgggtttttt gattaaattc tgtacattcc 58260
cattttagct tatcttgagt tataacatta aaattaaggt agtcatcagc tgaattataa 58320

-continued

```
gacttaatta gataagatta tttaagatag tgatttctca ttagattggc cctgttcata  58380
ttaacttttc tgtttttttc ttcagtctgc atgaagaaat cagtgatttt tatgaataca  58440
tgtctccaag acctgaggag gagaagatgc ggatggaggt ggtgaacagg atcgagagtg  58500
taattaagga gctctggccc agcgctgacg tgagtccctt cctgggtagc ttatgcttcg  58560
gacagtcctt gtccacgggc tagaagccta tctgctggta tctcatgcta gtcctcacat  58620
gcaagtagaa gtgctctgta gagttgtggt ctaattaaat tttaaaggca aacaattttc  58680
tgcagtcttt agaattgagg cttcctaact attttcattg gattggatga ctaacaacta  58740
ttttttttt gtagtgctaa tagcaactac taaaggcaag ctatccttag aaattattag  58800
tgtaaagaga agaaagacaa atcaaacctc attgttgtag tggtctgtta ttggatatga  58860
tatatcaaaa cctcattact acttagttcc agcctgccag ggtaaacatt atataattgt  58920
ttacagctaa atgaaaatgt caagtaagaa cttttgtcac ttgaagttca tttcctttgg  58980
ctaatgcacg cataagtctt ttcttatttc tttcctgaaa ttgccatttt tcatctctct  59040
cagaccagct aattgccttt tagacagctc ccagtcagtg aacaaaatga ttactcagga  59100
tttcttcttg gcttatttgt cgtttttgtt actggtacta agtcttttgt tttttgtttt  59160
tgagatgggg tctcactctg ttgctgaggc tggagtgcaa tagtgcgatc acgacttact  59220
gcagcctcga tttcctgggc tcaggtgatc cacctcagca tcccgagtag ctgggactgc  59280
aggtgcacgc caccacactt agctaatttt tgtatttttt tgtagagact gagtctcact  59340
atgttgccca ggttggtctt gaactcctgg gttcaagcaa tgtgcccgcc ttggcctccc  59400
aaagtgctag gattacaggt gtgagccacc acacttggcc tgttactggt actaagttaa  59460
tacgtcactt tttagggcac tttgagggcc tgttctacaa ttttgtgtat gcaaagaagt  59520
acacaaaata atactaataa aatccattac tttgtgtttg tagcttttct tcaggcactg  59580
tcctgggtgg tggtgggaag ctagggaagg ttttttttcca attggcaaaa caaagaagtt  59640
tcattgtatg taaaacttgc aagtatatga cagtatgtat atgacactgt aggtaaaggg  59700
aaaaggcaag ggtactaatg ttttatgagc aatgaccata catcgcattc tttctcctat  59760
gtgatccaaa tcagtggttc tcagctagtg gctattttgt tctccagggg gcatttggca  59820
atgtccgaga catatttgat tgtcctgact gggtacgcac tgctagtacc tagtgggtag  59880
aggccatgga tgccatcagc cattctatga tgaacagtat aggcccttac aacaaagaat  59940
tatccacccc caaatgccaa tgttgagaag ccgtgatcta acttaaccct tatctttctt  60000
aggtggaggt tgattatcta tctatctctt tctctccagc cagccaggca gccatcatct  60060
gtctacctac agatgaggaa catgagcttg tggttaggtt cccaggtcca tctcgcctca  60120
gaggttgaac tggtttcact gtttatcatt tttttccccc gagatggagt ctcgctctgt  60180
cgcccaggct ggagtgcagt gacatgatct cagctcactg cagcctttgc ctcccaggtt  60240
caagaaattt tcctgtctca gcctcccaag tagctggggt tcaggcgccc gtcaccacac  60300
ctggctgatt tttgtaattt tagtagaggt gggatttcat catgttggcc aggctggtct  60360
tgaactcctg acatcaggtg acccacctgc cttggcctcc caaagtgctg ggattacagg  60420
cgtgagccac tgtgcccggc ctatcctttt tttattacaa ttacctgcat acatatttct  60480
gcctgagttc caccgttctc catgggttga gatggaatgc atcccagttt tatgccacag  60540
catgatgtta cctgatgttc tttgtggaat tgacctaaag gccctcactt gccctacagt  60600
taaagtagtc tgatcccaat ttagtaatct attcgaagac tcctgcttag agaacaaaaa  60660
tgaaggattt gtgattgtgt ctctggataa tgagggaaca ttagtgatct gaactgcttc  60720
```

-continued tgaaagtttc ctgtggttgg ctttctgtat ccacaggtac cacacctcca tattaaacca 60780
acaatggatt gaaaatattc agaaaaaact ataaaaataa caatgtacca ataaaaacaa 60840
tacaaattat tttaaaaata cagtataaca actatttagg tagcatttac atcatacttg 60900
gtattatagg tattataagt aatctaaaga tgatgtaaag tacatgggag gactagcata 60960
ggttgcatgc aaatactcta ccattttata gcagggactc aagcatcttc agattttggc 61020
atggtgggac tggaaccaat ctcctgccga taccaaggga caactgtatt ttggtctatg 61080
tgtttcatat tgaaccagat aagtttaaat tatattcaga atgtctgctt gtgaaacaga 61140
atccccgctt catgaagctt ggggttagaa aaaaatgctc ttgtcatacc aaaaagtacc 61200
agtagagggt agcaaaaact gacatttctc catatcttgg tgactcaata tgataacaac 61260
ttctgataac tcaatataat aacaacttct ttttctgttt caggtccaga tatttggaag 61320
ttttaaaact ggactttatt tacctactag gttagtacac tcatgaatct ttcaaaggac 61380
ttttcttaga gtgtattcat tttggctgtc aaatttgtaa ggagtagaaa caaaacaaat 61440
ttataaaaca aaatggggct gggcatggtg gctcatgcct gtaatcctag cacttcggga 61500
ggccaaggag ggtggatcat ttgaggtcag gagttcaaga ccagcctggc caacatggta 61560
aaaccccatc tctactagaa atacaagaat tagccaggcg tagcagtgcg cacctgtaat 61620
cccagctact caggaggctg aggcaggaga attgcttgaa cccgggaggt gaaggttgca 61680
gtgagccgag atcgcgccac tgcactccag cctgggcgac agagcaagac tctgtctcaa 61740
aaaataagta agtaaataaa taaaggattt accagcattt aatttgattt accttgaagt 61800
agaatatcac ttcacatcat cttaccaaga catagatggt acagagagat ggaaaaggga 61860
tcatgttgca atggaatcaa ttagttacta attttagaaa ttgactgcct ggcagagtat 61920
tgctcagtcc cataacttaa cccactgaca cagatgttaa tgtagtatca tgataaaatg 61980
tctgattata tatcctcttg aatgtgagtt cccgctgtct tgctcactca ctcttacact 62040
caccctcgct ttcaaattaa gaactcattc tactagttat ggctccagca tcctgatcca 62100
gaaattcagg gtacagatct cttctctgag aaagatcttg gcctttcagg actgttgttc 62160
agtttcagtc ttctcaaatg agacctcttg tgacgcacag ccttggaggc tctcttttgg 62220
gaaatgataa tgtttctcca aagggtgaat acttgctctc taagaattga aattgtttga 62280
acattccatc atggttatta ttattattac cttaaatttt aatctctcca gaataaagtc 62340
agcatcatgt ttttccattt gagcttgatt tggtatactt taccccaact taaagtgtgc 62400
tgaagtggat ggaccctggc aatttccgtt cttctcatag atgcccttgg cctgcaaaag 62460
tcataaaata ctcaacttcg agttaatatt tcttatttag gttgtcagca tcagtaaaac 62520
atgaaaaatc acctttctta aaaaatttaa ttaaatttta tgaataggta gtacattcac 62580
atagttcaca tttggaaaag gcacaaaaat caatacaggg aaaagtctca gtcccacctc 62640
tgccccctgg ttctccttgg aacagccgct tttaccagtt tctcacatat cctttcagag 62700
atatctgtgc atataaaagg acatgtgtgt atattaacac aaatggtagc atgctggata 62760
cctgttctgc atccagctta aagcacttca taatatttct gagttgcaat taatctcatc 62820
cggataggaa aatcattatg tctagtacca caagcgttta ttaaagaaaa tacatgaagt 62880
gctttttgtt tttttttctt tgaggtttta cttctttcaa aatcacccta tttcctgagg 62940
cctgaattct gtgaaatgac tgagaggagg agtttgttaa aatcaacaac tactatttcc 63000
cttctccaca aaaccattat caccaacaca tttagtcttc gttggccagg gtgggaaata 63060
ggttttaatt gtactaatga agtctataag catgagtgtc agttaaaaca agtttccaac 63120
ttcttccgac cctcttgtat atgtattctg tgttcagtga catcgaccta gtggtgtttg 63180
ggaagtggga gaacctaccc ctctggactc tggaagaagc tcttcggaaa cacaaagtcg 63240
cagatgagga ttcggtgaaa gttttagaca aagcaactgt aagttctgca gcatttcata 63300
ttaaaatcct tagttattta cctatgaaac ttgaattaaa attaaagttt ggtgagcaca 63360
gttgcattgc aagtgagtga ttctttcatt ttgttaatgt caccgtgctt gcacataaaa 63420
agttttctgg ttgtccacac tggagtgtga ccatacaatc tcggctcact acaacctgtg 63480
cctcctcggc tcaagtgatc cttctacctc agcctcttgg ggagctgtac tacaaacaca 63540
acctgccatg cctggctaat tttgttgtat tttttgtaga gacggggttt caccgtgtta 63600
cccagactga tctccaactc ctgggctcaa gtgatccacc cacctctgcc tcccaaaatg 63660
ctgggattac aggcgtgagc cactgcacct ggtctgcatt tcttttcaca gcagcaaaat 63720
atgcaatttt attatacaca gtactcactg tagagatttt tgtttgtttt attcattttt 63780
tttagagaga tacagtctca ctatgttgcc caggctggtc tctaactcct ggactcaagt 63840
gatcctccca cctcagcctt atgtgtatct gggactaagg cgcaccctac cacgccctgc 63900
ttatttaaaa aattttttt tgtagagata gggtctccct gtgttgccca agttaggcca 63960
ttttttgaaa agaactgctg atagctcatg taaataatcc tgtcagcttt ttagaataat 64020
ttttatattt tatcttgtca ggttgttttt tgggctattt gcaaaactga ccagtaatgc 64080
aagtgggttg tagtgtacac cttaagaatc cagcaatttt cttattagaa acagtttgat 64140
gatacaaaac atttaatacc tggcattcct agttcttcat cttatactca gaaagtgttc 64200
tccaaattat tgaggaaggt ttttgttcat tttaaaatta tcattataac tatatgtcaa 64260
ctaataaatg agatgatggg catattaatt tatttaactg tagtaatcac ttcagtatgt 64320
atatcaagat aagtatatca aaacatgtac accttaaata taaacaataa aaataaataa 64380
taaaaaattg gacaccaaac aaaattctcg gttgatagaa attatactgt aatatactgt 64440
atgggaccca gtgctaaata tgcagcatat agtatttgta gcagaccagg tttactgggg 64500
tgtgccatat ttagaatact cagtgttctt atgctctcat gagatgatgg agacctcatg 64560
tctagtaggc ttccatcccc tgattttatc atttaatctg gttaaagcat ttacatttta 64620
cctttcttct ctttataggt acctattatt aaattaacag attcttttac tgaagtgaaa 64680
gttgatatca gctttaatgt acagaatggc gtgagagcag ctgacctcat caaagatttt 64740
accaaggtca gagaatttag cgtttataca acaaaactat tagaaacgta attttaagat 64800
tctgttgtgg tggtgttcta atatttttat atgcatgttg ctgtctctct ctctctcttt 64860
taaatagagc tagggtctca ctctgtcacc taggctggag tgcagtggct ggatcatggc 64920
ccgctgcagc ctcaaactcc tgggttcaag tggtcatctc acctcagcct cccaagtagc 64980
tgggactaca gacgtgagcc actacacctg gctatttttt gtattttttt ttttttttta 65040
gtgttggggt ctcgctgtgt tggccaggct ggtctcttaa ctcctggcct tagcctccca 65100
aagcactggg attacaggca tgagccacca tgctcagcct gcaccttact tttgtatgca 65160
acggttttgc tttctttgaa tctgcttgta atgatcagtg attaacttat aatgtgacct 65220
caagtaagaa ttaaaagttg agaaagcttt tgaagaaatt gtctgctcta gatccttcct 65280
tgtagagaca gaagagatgg aattctacta cacagttgat tccatctgtt tttaaccttc 65340
aggagttcag attaagaacc tttcctttaa cccatttccc atatgcccca agaatactgt 65400
gcgggcagtg agctgcactt ttttttttc ttttttcgag gcagagtctc tctctgtcac 65460
ccgggctgga gtgcagtggc acgatcttgg ttcactgcca cctccgcctc ccgggttcaa 65520
gcaattcttc tgcctcagtc tcatgagtac ctgggactcg tgcctgggac gagtaccagg 65580
cacctgccac catgcctggc taatttttgt atttttatta gagatggggt ttcaccatat 65640
tggccaggct ggtctcgaac tcctgacctt gtgatccgcc tacctcggcc tcccaaagtg 65700
cccggattac aggcgtgagc caccgtgccc agctgtactt tttttttcc taaacaggaa 65760
ataggttaag agttttaaga gccttttcta gatttcaatc cctaaattac ctttaaggtg 65820
tttcctacag gcttccttac ttctgttttg aaattattta agtttatttc tattctgttt 65880
tcttccaaga tagagaataa tttgtcacca tcatctgtgg aacattttac atacttaggt 65940
agttgtcagc tttctcacct ctaacctaag ccattaactc ctttggcttc tgttagaata 66000
ttcacaattt tttttttctg tagcagctct aaagtttcta tttcttcttt tttgtttttt 66060
aagaaaaaaa tgttaactac ttgatgttac aagcattatc atcttgcata aatgtatgga 66120
agacagaaaa gcagaaaaat aaaagaaaga ttatccataa tcgcactata ttgggggtgt 66180
gtgtgtgtgt gtctgtctaa tattttcttt ttctggaaaa aacttttaaa aattgaaatt 66240
catatgcatg ataacattca tcagtataaa gagacagtgt aaagtgagtc acccttacac 66300
catagatact tagatcattt ttacagaatt tctcattgcc aattattgtt ttttgcgttg 66360
ctttttttatg ttctttaaaa ttataagcaa aaggagtagc acattataca cacattgtct 66420
tataacttca taaaaactta atgttttgga ggtttcttcc atattagcac atacaggctt 66480
gctttattct ttttgttggt tacacaggca gtagtctttt ataaggctgt gactgcttga 66540
tttagcagtt cttcagtatt gttccagttt tcttttgcta ttagaaaaag ggattgatga 66600
atatacttcc atacatgcat cttgctttac acatgcaaaa tgtttgtaga aagattccca 66660
aaagcaaaat tttgaggtcg aagggtatat ccagataaaa ttctgttgga tatttcccta 66720
attatttatt ctttcatatt ctcattttct ctctctccct ccccctttttc ttctccctcc 66780
ccctcttcct ctatccctcc ctttcccttt tctctctttt tctttccctc ccttttcttt 66840
tctcttttct cttcttcctt tttcttcctt cccctttccc ttttccttcc ttctgcttcc 66900
ttttttttcct ttctttcatt ttttgacacc gagtctcact ctgttaccca ggctagagcg 66960
cagtgatcat ggctcactgc agcctcggct tcttgggctc aagtgatcct cccaccttgg 67020
cctgagtatc tgggatcaca ggcttgccca ccacacctgg ctaacttttt ttttaatttt 67080
tttttttttg agatggagtc tcactctgtt gcccaggctg gagtgcagtg gcgcgatctt 67140
ggctcactgc aacctccgtc tcccaggttc aagcgattct cctgccttag cctcctgagt 67200
agctgggatt agaggcgcac accaccacgc tcagctaatt tttgtatttg tagtagagat 67260
gtggttgcac catgttggcc agggtggtct caaaccctga cctcaggtga tccgccctcc 67320
tcagcctccc gcagtgctgg gattacaggc gtgagccact gagcccggcc acttttttat 67380
tttatttttt aagtagagat gaggtcttgc tatgtggcca cttttttttt tcttttttttt 67440
taagtagaga taaggtcttg ctatgttgcc caagctgttc ttaaactcct gggctcaagc 67500
agtcctcctt ccttgacctc ccaaagtgtt gggattacag gcatgaacca ccacacctga 67560
cccctaattg ttctttgaaa gggaactgta tctagactga cttaaccacc atgttttgtt 67620
ttgttttttg agacagagtc ttgctctgtc actcaggctg gagtgcaatg gtgcgatcat 67680
ggctcattgt accctccgcc tcctgagttc aaacgattct tgtgcctcag cctccagaat 67740
agctgggact acatatgtgt gccaccacgc tgggctaatt tttgtatttt tagtagagat 67800
ggggtttctc catgttggcc aggctggtct tgaactcctg acctcaagag atccacccgc 67860
ctcagcctcc cagagtgctg ggattacaga tatgagccac cgtgcccagc ccacaatgtt 67920
taaaaatact tatttctcca tatttttgtt ctttcctatg cttgcttagt ttgatacaat 67980
ttgcaaaagt ataagctttt ttttcttttt tatagaagcc atgcgtgttc attgtaggac 68040
atctagaaaa cagagataag agtaaagaaa aaaaaatgga aatcaccggc caggtgctat 68100
gtttcacacc tgtaatccca acactttggg aggcccagac aggcagatca tttgagctta 68160
ggagttcaag accagcccgg gcaatgtggt gaaaccctgt ctctacaaaa atacaaaaat 68220
tagctgggca tggtgggctg aggtcggagg atcacttgag cccaggagct ggagattgca 68280
atgagccaag attgtgctac tgtactccag cctgggtgac agaatgaggg ggaaaaaaat 68340
ggaaatcact agtaatttta ccaccctaag taataatagc tgttaagact tctttgaaga 68400
tgttgtgcct gctttgtttc cctccgtggc cccagcctat ggcatggttt acagaggagt 68460
gaatgaatat gtgcacagca aaaggtggac tcattctgta catacttgcc cactcaggtg 68520
ttctctcggg tagccctgcc tcattccctg tgaagcgtgg aagggagggg tggtctgtgt 68580
gtagtcatca gcccatgtgc aagtcagcag gcaggactct tgtttgcccc agggctgtgg 68640
cagaataatc taaaggtcgc tagtctacag tggtacatca ccaagaaaag tgattcttaa 68700
aaatctcact gatttagtgc tttaagatgt tggttacttt gtccttgtac tctttctatt 68760
ctctgtttac aaatgaatat tagagggtca tggtcacaaa tgagcatcat cagttacatg 68820
ctgttagtgt ttctatccta tagcaagtac tttttttttt ttttgagatg gagtcttgct 68880
ctgtcaccca ggctggggtg caatggcacg atctcgcctc actacatcct ctgcctcccg 68940
ggttcaagtg attctcctgc ctcagcctcc caagtagctg ggattacagg ctcccaccac 69000
cactcctggc tatttttttgt atttttagta gagataggcg tttcaccatg ttggccaggc 69060
tggtctcgaa ctcctgacct caggtgatct gcccgccttg gtctcccaaa gtgctaggat 69120
tacaggcatg agccaccatg cccagccctg tagcaagtac ttagatacta ttattcattt 69180
gtacatgtct tacaatttaa gtataagggg agaaccattc attacctata gtttactttt 69240
ttttaatagc ttactcttaa aatagaaaat taagtatgtt gtatatctct accaaatttt 69300
ataatgtaag gaccaattta tgcccctctt aatgcttaga tctgttgctg atacaggaat 69360
tcattgaaaa tacaatttttc tttttcagaa atatcctgta ttgccatact tggttttagt 69420
attgaaacaa ttcctattgc agagggacct taatgaagta tttacaggtg gaattggttc 69480
ttatagtctc tttttaatgg cagtcagttt ccttcaggta agtcatatgg gtatagcatg 69540
ctagtgcaca ctaaaagcaa aagtgatcaa tcagctggga aacattttgg aaaaaatcga 69600
aatcaacctg taattgcatt gctttccttg attacttaac ggcttttccc tttaaactgg 69660
gtacatttta tcatttagca aatatgtatt tttaaattcc tatgaaagaa tatttttggt 69720
tttaaatccc atacattcta gtatttttga gacttttcac tgcaaatttt aacatgcaaa 69780
atgtacggcc tggtttccat aagcataaat agtataaatg ccaacaataa gaatgtcttc 69840
taagcagcta aatcttgtaa gtttagttgg aattgagacc agctatttgg gtaagcgaat 69900
tagagtctta gtattgtaag tgggtatgtt tatgtggcac agggttgcca actgcctgag 69960
tctattcgtg agtcagaacg actttgctga tgtgttgggc caagccagcc ctggttggca 70020
gcctggtgca gccgtaaaat tcagccttac aaacagtctc ccgccattcc cgcaccatgg 70080
gactttagtg ttgtgtgtaa caacagtata acctgctgtt agcccattat caactgactg 70140
ctatgctaaa ccaaaattat aataatattg cttgtagaag ttagaatata atttattccc 70200

```
cctctccttg ataatttagc aaaaatccaa tataatttct tcttttctgc ttttagttac  70260
atcccaggga agatgcttgc atccccaata caaactatgg tgttctctta atagaatttt  70320
ttgaattata tggacgacac ttcaattatt taaagactgg catccggata aaggatggtg  70380
gttcatatgt ggccaaagat gaagtacaga aaaatatgct agatggctac aggccatcaa  70440
tgctttatat cgaagatcct ttacaaccag gtattgaaat taggtaaatt tgtgggcatt  70500
caaagagagg gcactgtcag tcaccttatt atactttaaa ttctctttag atgaaaaatg  70560
aaggaacaac ttctaattgt tattcttttt tcatcgaaat atttcatgag caaacatact  70620
aaaataaaca gacacagaca atagaaaaac accttggaga cttccagata agtagggagt  70680
agaatctgtt taaccctaaa agcatagtag aaaaggcatt cacttatttg gatgggttca  70740
tgtttggtgg ctgtttctcc ttcttgggtc cttattgcct tgattacaac caattgtcag  70800
caattaatga ggctttaatg agatgattct gaagtcctga gaggcagcaa gcatagtaat  70860
atatctttga attcatgagc agaagggtgc aaggagacaa tgtattttct ttttgaattt  70920
ctcctttcct gtttgatttt gcatgtctct ttgtgctttt tccagcttca tgtgggcttg  70980
aaagtaagca gaaagtaaat tccttccatg cttttctgaa gttctgtttg cttgcttgtg  71040
tcctgatttt tgtgagcaat attttttctt gatataattg taaaatagat tctgcgttat  71100
tggacttcag tggaagtgct tttagtcatt tgctttaatg tgtaaacttt gaaaatgagt  71160
aaggaaaggg ggtgaagaga tagagtagtt gcctaggaac cattttctgg cttattgagc  71220
tgccttataa acattaatag ttctatgtgt ttattcattg aggaaacatt acattgattg  71280
ggagcctgct ctgttcaaaa gtattgggcc aaaggacacg aagactttttc agcaagacga  71340
tccttgcttt ttaggggctc ataatttaga gtgagaaata gatatatagc taatataaac  71400
ccaaaaaata tagaagtatt tctgatgtaa cttggggttt cactcttagg agtgaacagg  71460
gcactatttc ttttgtttgc ataactgttt atgtatggaa tgggataatt cttgatgggc  71520
cagaatacat tccggcaact gatacaccat aatgaagtac caactgcatg attcacatat  71580
tcagagactg gggagctttg gggacagctc acagctcagc ttccaggcac aactctggtg  71640
ggataactat ggcccttgct ctcctggaag agagtcatca acatttagtg catattaagc  71700
acagtcaggc ttactatgtt acgtatattt cttttaaagg taacgatgtt ggaaggagtt  71760
catatggggc catgcaagtg aagcaggcct ttgattatgc ctacgttgtt ttgagtcatg  71820
ctgtatcacc aatagcaaag tactatccca acaatgaaac agaaaggtaa aagttcatct  71880
ataaccagcc cattgtgtca aaattagttg tggcttctta tcttcaaatt aatgttattc  71940
cctccctctc cctttctttt taaacacatg cagcatacta ggtagaataa ttagagtaac  72000
agatgaagtt gccacatata gagattggat atcaaagcag tggggcttga agaatagacc  72060
tgagccttca tgcaatggta agatattttc cttggtcgat tgactgagta ttagaggctt  72120
ttctgtgttg tgtgcgttta atgggaagaa acgttttcca atcttttgcc actctttcag  72180
gaaatggtgt taccttgata gtagatactc agcagttaga taaatgtaat aataatctat  72240
ctgaagaaaa tgaagccctt ggaaaatgta gaagtaaaac ctcggaatct cttagtaaac  72300
actcttcaaa ctcttcatca ggtccagtgt cgtcctcttc tgccacacag tccagctcta  72360
gtgatgtagt aagtatgaaa gcctcggctc ttctgaactc agatgcatgc acgttctctt  72420
gctggggtta acactgtctc gaaggctaag gctacttcct ttgcttacat gttactggga  72480
tattttaata actttcatgc ttgtacattt tctcaacatt ttgttatgaa aaagttcaag  72540
```

-continued

```
catatagtaa aagtgaacaa attttagtga gcattcatgt actcaccagt agattctgct  72600
attaaccttt tacttgctta tgtcatacct gtctatccat cactctatcc attaattcat  72660
cttattcttt gatccatttc aaagtagatt acagacatca gttcccctag agtactgtag  72720
cttgtgcatc cttgtagcca gactccagta tttgtttatt gttttttcct ttttttttt  72780
tttgagacgg gatctccctc tgtcacccag gctggagtgc agtggtatga tctcggctca  72840
ctgcaacctc cgcctcccat gttcaaacga ttctcctgcc tcaacctcct gagtagctgg  72900
gattacaggt gcgtaccacc atacccagct aattttttgt atttttagta gagacggggt  72960
ttcaccatgt tggtcaggct ggtcctgaac tcctgatctt gtgatccacc cgcctcaacc  73020
tcctaaattg ctgggattac aggcatgagc caccacacct ggcctttaac gtttttcttt  73080
tcttttcttt tcttttttt gagacggagt cttgctctgt cacccaggct ggaatgtaat  73140
ggcatgatct tcactcacct caaccttcgc ctcctgggtt caagcgattc tcctgcctca  73200
gcctcctgag tatctaggat tacaggcatg tgccaccaca cccagctaat tttttgtatt  73260
tttagtagag atggggtttc accatgttgg ccaggctggt ctcgaattcc tgacctcaag  73320
agatccaccc gcctcagcct cccaaagtgc tgggattaca ggcgtgagcc cagctgttat  73380
gactttttaa caccatagtt agttttgcct gtttcagaat ttcatacaaa tggaaccaca  73440
tagaatatag tcttgtgtaa ggcttctttc actcaatttt ttttcagctt tctggttgaa  73500
tttttgttg ttgttgtttt gttttgtttt ttgagacgga gtctcgctct gtcgcccagg  73560
ctggagtgca gtggcgcgat cttggctcac tgcaagctcc gcctcccggg ttcatgccat  73620
tctgcctcag cctcccaagt agctgggact acaggtgccc gccaccacac ccggctaatt  73680
ttttgtattt ttagtagagc cagggtttca ccgtggtctt gatcgcctga cctcatgatc  73740
cgactgcctc ggcctcccaa agtgctggga ttacaggcgt gagccaccac gcctggccaa  73800
attttttttt agttgagata tagttaacat aaaattcagc attaaaaatg tacaattcag  73860
tggtttttag aacatattca caatgttgtg cagccatctc cagtaattct agaacatttc  73920
catcacccca agaagaaacc ctgcatttag cagtagtttc ttctaattct tccttccctc  73980
ccttaacctc tggtaacctc taatctactt tctctttcta tcctgataga atttttttg  74040
ttcccccatc ctgatagaat ttatgtgtca attataatgt aagttacctt ttaaaatcaa  74100
agtgaatttg tagtgtactg atttgagatc taaagcaggc ttacctgttt gagtttaact  74160
ttattaagtg taggacatga aaagtaatct aaatattgta tgttgttgat gatgaccatg  74220
tgtcaatatg gaatcataaa tcctcctgtg cagaatctcc ctgtgtgctt ttttggttcc  74280
tagagcagta tgctttggag gacagaagcc aagctagatg tcacagacac agggagatgg  74340
agtgttgggg actgagagaa tgtgactctg acatgctggg tagagtgcca gggccagggt  74400
ggagacctgc agagagacgt agcattgtca tggcccatgc agcccagaaa taggtggagc  74460
tcagcccact gtcgcgggaa gtccaccccc acccacacca gtatgtttgg ttagaatgat  74520
cactgatttg tcatcacaga ctctcagaga ttgaacccct taaacccatc atcttgtgtc  74580
tggctgaagc cagggactag gacctaggtt cctcactctt taccatactc tttcattttc  74640
tataaataaa aaaacaaata aacttagacc tctgtgagct ccttcaaggt cagatgtggg  74700
cagtggattt aacaatgaac agaagctctc tgataaaatc agtcatttta aatgtttgga  74760
ggaaaattta aacaaacagt taatttttttg tgtgcttctt ttaactccca aatgtttaaa  74820
tttagtccag agagtacttt aaccaaaatt gtttttcttt ctgaatattg agtatctaaa  74880
ttactaatat gtcacattat aactcacgtg acttgtgtta ggattccgat gcaacaccat  74940
```

gcaaaacccc gaaacagctg ctttgccgtc cgtccactgg gaaccgagta gggtcgcaag 75000
atgtatcctt ggagtcctct caggcagttg ggaaaatgca aagcacccaa accactaaca 75060
catccaacag caccaacaaa tctcaggtgt gtggaacgtg ggtttttaat tgttagtatt 75120
tgatacaaaa tatttagaat ttcccacatg taaataatat gcagcatggg tttgaagaaa 75180
acgctagatt gaagaacaaa cttattttat tctaagaggt tccaacacat gacagtgctt 75240
ctaggaacag gatgtcctaa ggatccttgt gagacaccat tgtaacataa atctcttcag 75300
gaatctattg actggtcctt ataagatgtt ccagccaaac taccatataa aaagtgtctc 75360
agttgtacat gaaataagct ggcatgaagg ttttgtgagg cctcatggca gtgtgcatat 75420
ctgggaataa tgtatccttt tctaatattt taatgttcaa taccttgttg ctggtgttga 75480
aatgatcagc tggctgtcag gcgtggtcag ttgattaaca ttagcttgga cttaaaaggc 75540
cacagagata ctctagttta agttttttttg ttgcctagaa ttgtcattaa ctgagtaatg 75600
actcagagtg aggggaggaa gccattgata tggggctctg gcctaaggct gggtcactcc 75660
tcactatagc tgggaacctg ggaataggcc tcttggctgt aaccttgtgt ctgatttgac 75720
tcactgagtt cactttacct acgcggcctt agccatgtat gccagacaca gacttatcac 75780
aaaataccag ttcaagtgac agggttgaca gaagggactg aggtcacgag aaagccacag 75840
gccatgagta gcaggaaggg agtagccacc tgtgctgacc caaacctacc agtgtgcctg 75900
tcatgcccaa gagcctcttc ccgctctgtc acttatgatg tggtgtttgg gttggtaagt 75960
ttcttaagaa aacctttgca tcccacacac tgttaagaag gcgggcgagt ggtctatgct 76020
tttcattatt tccattaaaa taaagtaagg gttttagagc taaaaagaac ccctgtaaca 76080
gctttttctg cccactagat aagtcagtga tcagtaaggt aacaatctag ccagcatatt 76140
cctagttttg aaagcttccc caaatccagg tgtttgagaa cactctgctt ttctgcaata 76200
ctgatgtctt tgtggtcgtt ttctgtttct gcagcatgga tcagcaaggc tctttcgttc 76260
ttccagcaaa ggcttccaag gtacaactca aacaagccat ggttccttga tgacaaacaa 76320
acaacatcaa ggcaaatcca ataatcagta ttaccatggc aaaaagagga aacacaagag 76380
ggacgcgccc ctctcagacc tctgtagata gtcagcgctg cgcggtggac tgtcttctct 76440
gtgcaatgat ctcatgctca ggacagttgc gcagggactc ctgggagata ttcaggagcc 76500
tcacactgtt cagacgttga cttagcaact gcgttttttc ccagctcgcc acagaatgga 76560
tcatgaagac tgacaactgc aaaaaaaaca aaacaaaaca aaaaaaaaag caagcaaaaa 76620
agagggaaaa aaaaggctgc ttatttgata agtcatatgc tacaacaggg tcattttaag 76680
atttaaagct tgaatgtaaa ataaatatat ttctcattgg ctttatgcag agttataggg 76740
aatagtattc agtgttggta gggtgataga aacaaaaaac agtatcagag gatgaggtgg 76800
ggaaggaaaa caaaggtatc tgataggaag tccagattcc aaaggggaaa gtgatctgtg 76860
catgtttttt ttttaaatat ttttgcatat atttaccatt ttattgtgtg tatatataga 76920
agaccatata ggagattgat atttgtaata gtggatttgt taataatact ttttacataa 76980
cattactgtt taaattgtaa acagattttt tctcaggatt agtttgaaaa ataatctaaa 77040
ttgtcatctt aacatccata tatagggaag tgattagttc tattactcaa tttgtttttc 77100
tcagcattga aatgacttaa tagaaccctt gtgtcctgct gcaaaaattt ttcctctcta 77160
aagaaaaggt ttatggtggc aaatgatgtt tattttattt tgtaaaaaaa aaaaaatgta 77220
ctatgtactt ttgtgtaaac actgaaaaat ctctggtcat ctccgagaat taacttgcaa 77280
ctgttttcta tagtgctgtc gtcttgggca atgggcaatt acatgacttt gtgtttgctt 77340
cctttgcagt cttttttttt tccccccatt tcttcctaat aggaaaaaaa aaaaaaaaaa 77400
ggtcacccat gtctggtctc attcctgttg cagtgaaact tcgagttcca cagactttgc 77460
atgctggctt ctctaaccct gtgtgctgcg tgtgcctgtt tctcatctct tattcttttt 77520
aaaattcatg cttaactact gtgggagaat aactgtaaac agctttaatt aaatcatact 77580
tataaaaaac tattttctta tattccactc tatgcttttg gtattgttga tctttacaaa 77640
ttaaatggtc tttgataatg gatctatttt gtattgcctt attaagacca aatacttctt 77700
gtcatcccat tctttatcct cttctttcat ggaattgtta tcgttaatta aaactttttt 77760
aaacattggc ttgtttcaat catactgtaa attttggttg tagtcagctt tgagtgcaat 77820
gagatgtata attctgttat cattacctgt tgagtttgaa actcagttgg gaatatttaa 77880
tataatagaa tgtaagtgac atttctgaaa atgctttctt tcagggtgaa agctcttatg 77940
tttagcatca atgtgtatgg ctctgttaaa tgcagccatt tctgagacga gattctttta 78000
tatatatata catataaagt actattggct tttaggagtt tcttttatat acatttatga 78060
aatactgaag accaatcaga ccattaatgg acacttagtg taacttttta taaagaaaat 78120
aatgctaaag taagaccaaa actgatgtca tcactgaaat taacaatttt caatatgttc 78180
atattttaat tcacaatgga aaaatgtgtt ccaaaactgg aaactcatag tactcgtgta 78240
aactgtggaa gatttcaaat gtgatgttat tttgacaatg ttttaaattt tagagtcaca 78300
ttttattctg atcagaattt ttattgagat gttgagcttt tgtttttgaa actagtttgt 78360
cataacattg tgcataatca cagtatttat tttctaggac aattgtgaat gtgtagactt 78420
atgtttactg ctaagggaac aattatttat aaaataatat taaatccagt attagctgcc 78480
tatttcagac acttaatact tgcagagatc tatgttacat ttaccacact gaagtttttt 78540
ttgttgtttt ttgtttgttt ttaaagaatc accctcattg ttgaaagtaa atgtactctt 78600
agggtgcgaa tattagtgtt ccaataagca tgtgattata ttaaggtggt ggtagcggga 78660
agataattct gattccattg ggaatcttag gttttcgtaa atttattggg aaaatagttt 78720
ttcctgtact gctgaagttt ctttttggta aacagtatct ttctaaaaga aaaaagcatg 78780
aaggagaaat tgaggtgtgt atacatttcc tcaaatgacc agcattgtat tcgtgaatac 78840
tgtgtatctt gcagtgaaca gtgtggaagc tgttcatttt tcaatctgaa gtaaaatact 78900
ttcaagaact tttagtttgc ctgctcattt gttttataca tttcatctat ttgactccta 78960
tcttatttct tttttgagtt ttaatacttc ctatattttg tgaatatatc agaaatgtgt 79020
catttatata ttagagtcca ttcatatcca tgaatcataa ccttcctttg ctaatacttg 79080
ttgaatggga ttttacaaat tctccctcac tctggtgaca tttctcaggc agtcatgtat 79140
gtgtacctgg ccattagaaa tattaatatt taaagactgt tttttagagg agctgatggg 79200
ttggtgaggt gtcagcacaa aatcttactg gttatgtttt gatgataaaa gtatatccat 79260
tttttccctc cagctttaag gtgactgtga aggtgcctgg ttttgaatgt ctttgtttgg 79320
tttggagatg tcgcactcag ttttcaaatc tagcttggat ctgtaggacc tatgtttttt 79380
acaagtaatt gccctccagt cttcaacagt tgattctgtt ttatttttat cctgttttga 79440
gtgtacttta cctttacttg cattttgagc ctcattaata tttaggttat ttgatttggc 79500
tccagatatt cctagatctg cacagggcaa aacatgggct atagggtgag catttttaat 79560
tgtctttttc tgctggaacc ttatatctct ccatgtgttt tctgctcctt ccctccccca 79620
tgaaatggta agtgtgactt gtgtttgcct gaacctgtgg actagtgttt ggggtttctg 79680
gaaacactag agggtcagaa aagagtaatg accaccgtga cgtgcaggat tctcttgctg 79740
tgacatgttc attgcaaagc cctctccagt gactaggagg tgtagttatt aaggttgatc 79800
tgttagaaat caccattatt aggtattagt ggtagatgtt gctgatactt ttattggtca 79860
tgactacatc tcagttttac tttaatattg atctatagtt tgatcagttc cttgaattct 79920
aatatgttga tttctcagtg tttctgtcac taaccaagaa tgtttctagg cagttggttg 79980
cttcacagtc aaaactaaat ggtaaactat caaaaataca ttcccaattt tgctgtgata 80040
aatattgaaa tgttaaaatt aatgaacaga agaatttatt cttacccatc tattcttgtt 80100
ctcctagttc attaaacttt cagttattgg aaaggcacat tctcaaagta ttttatgagc 80160
aaaatattct ataaatgcgt ctaacaaacc taattgaata taaaagttat atttagtagt 80220
tactgttgat agtaattttc atcagggtca tagttcatct agtaaaatat ttagagaatg 80280
atgttaacat tccagcatta aagtgggaac aaagatttat atatgaaatt ccttaaaaga 80340
gttcatcttg ccttggtttc tgaccctcaa gactctagct acctgccatc ttgtcaaaac 80400
atttgtgggt agaataagtg ttaaagatca aattttaata tgcttctcga tatttaacat 80460
agctaagaag ccagatttta ctgtagaagt tatttacatg atttgaaaac ttgacctaac 80520
tggaagcctt tttctcagtc atcttgttct aagccatctt gacttcacac ccttagcgac 80580
ttttcttttt tttttggtca aagataatga gctaaatata tatagacgtt gaatgttgac 80640
aaaattatta accagaaaaa ttgcttataa aggctgctga tctatttgat acctagaatt 80700
aaatatttga ggacagtttt tagttaataa actgctaatg tttattttac tgtctctcag 80760
gtttttggtt tttttaaaaa aaatgtgttt ggcctttaca ttttctactt aagtgtgtac 80820
tttattgagt ttaaccttgt ctgtagccta gtagcctgaa agaaaaggag acagaaccag 80880
agagatggat gtagtgcatt ccctttggtt attacacatt tgtggtagct cctggattta 80940
ctgagagata ttttagctat gtcaataaga acagctaatg atgtggaaat caggtgttct 81000
cttgtgtatt tcagtgaaca tttttattag tagttgcata tcatctctag ttccacattt 81060
taacttaacg tctttgtggc ttcaccactg agctaccttt cactacacca gcttctgtgt 81120
ggcctggtaa catggaaggt ctctcctaag gacagtctgg acgtattttg ggggaatgtt 81180
atttatctta aagatgccta gaaacaaaac gcatatagta ccagtgagaa actatgaagt 81240
aaacaagttg ctcaggccgg gcatggtggc tcacgcctgt aatcccagca ctttgggagg 81300
ccgaagcggg aggatggctt gaggctggga gtttgagacc ttcatctctt aaaaaaacaa 81360
acaaaaacct gaatggtgag gtgtggtgga attgggtagg ggagggaaag gaggacttgg 81420
aaaagcattc tccaaagcca gcaacttggt gaagttcagt acttgcctct tagaggttag 81480
gccatgcctt tcaaagagag tgaaatgatg ggttatcagc cacattcttg gagttaatat 81540
ttttcttcat ctttcagttt gggttctgtg ctattcatag ttcttcccta agaccatttc 81600
attattacct tttatattta gttgcaattt attataatat gttgttttgt ccctgaactt 81660
aatctcctaa ttttaagatc ctctctgatt tttgcatatt gaaacttaca gaagtcactt 81720
taaaaaagtc ttttgaaagt cctacaatcc taaaataaat cacaagcttg tttgttagac 81780
gtgtcaagag tctccagtct ttactactaa aaagcagcac tgccttaaca cacattgtta 81840
tgggtgaaaa gtgagggacg accagtgtag tttctggata taaagtgtga aggactgttg 81900
agttaaacat ttttagtgga atatacatag ataacgtgta tttagaaact ttggtgaagc 81960
cagtatttgt ttttagtaac ctttttatgt atttccttct ttgattagca ttgtcttcag 82020

-continued

```
tgttaagaaa tgtggactcc tgtgaggtgc tggaggtttg aatcatcttg aaaactttcc  82080

aatcttgtct agttaccact gcagagacac taaggaattt accagaaaaa gatatttgat  82140

acaagtgatt taagaaatct caacatttcc tgaggccgta tcactgggca accagtgatg  82200

aaaactatga atgaattgca cacctggaag attttttaag ctaatgacag tttcttcaaa  82260

gatgtcaatt atttgccttg gaaattttat aaattgcatt tctatgcaca tcggcctcta  82320

gtgcttacca ctcggtttat tattcataat ctgcaattca ataaaggctt tgtgttttca  82380

tttatcttca aaa                                                     82393
```

<210> SEQ ID NO 11
<211> LENGTH: 44042
<212> TYPE: DNA
<213> ORGANISM: macaca fascicularis

<400> SEQUENCE: 11

```
ccacgctgcc ctgcgcacgc gcagcgcggc tcaggcggca gcccggtgac accggcccta     60

gcgcgcatgt ctgcacgccg gggtctgcgc gccgcggcgg gccgagggcg gcgtgcgggc    120

cttccagccg ctgcctattc cacccaacgc cggcctagtc agtaatggct caacgccacc    180

gcctctccct ccagcccctc ccagtcgcgt agcttctgac gccgtcctca ccccgcccgc    240

ggccgacggg gccccaacgc gcaggcgcgg taaccacggc ggcagtgtct agtgaggatt    300

tgaaatcggt cgcgcgtgcg caccggcgac acggcccggc gaccgaggcc gcgcttcctc    360

ctgccgcccc cgtccccgcc ccctccccccg ccccctcattg gagcggacgc ggcggcggcc    420

ccctccttcc cccgcgctgt cgccgccgag agtgtctttt caccgccgcc gccgccgccg    480

ccgcaggagc gccgagccag cggcgcgagc gtgactgagg gctagccgca cgggcggcgg    540

cgcctcccgc gggtccttca gccgctcggc gcctgggccc gccccctcgg ccccgccgcc    600

cgcccttctc cgatggcctc tccccgcggc ccgagtggaa cgccgccgcc gccgcggccc    660

ccgcgcccgc cccgcgccgc gtgaagcggg agcccggaga ccgcagccgc ccgctgggac    720

gcgccaagcg ccggagccgc ccgccgcggc ctgccggggc ccatcaccgc cgccgccgcc    780

ccacgccgga gcccgacggg agcgcggcta gagcaggagg ccggggctcg gcccgcccgc    840

cgccgccgcc gccgccgccg ccaccggccc aggcccgtcc gtccgtccgt gcgcgcgcgg    900

ccgggcctcg gggcgcggcg ggggcggggc cgcgtcgggg cgggcgggcg cgcgggcccc    960

gcgggggcgg cgcgtggatg gatccgcgcg tggcctggat ccagcccgag cagaaggggc   1020

cggccaatgc cctgtggatg cagatctggg agacctcgca gggcgtgggc cgcggcggct   1080

cgggcttcgc gtcctatttc tgcctcaact cgccggcgct ggacacggcg gccgcggcgg   1140

gggcggccgg gcggggcagt ggcggcctgg gccccgcgct gcccgccgcg tcgcccccgc   1200

cgcccggccc caccgcgccc gccgcgctgc cccccgcgct gctgacggcg ctggggcccg   1260

cggccgaggg cgcgcggcgc ttgcacaagt cgccgtcgct gtcgtcctcg tcgtcgtcct   1320

cctcgtccaa cgcggagtcg ggcaccgaga gccccggctg ctcgtcgtcg tcctccagca   1380

gcgcctcgct gggccggccg ggcggcggcc gcggcggcgc cttcttcaac ttcgccgacg   1440

gcgcgcccag cgcccctggc acagccaacg ggcaccccgg gccgcgcggc cccgcgcccg   1500

ccggctcccc gtcgcagcac cagttccacc cgggtcgccg gaaacgcgag aacaaggcca   1560

gcacctacgg cctcaactac ctgctgtccg gcagccgcgc ggccgctctc agcggagggg   1620

gcggccccgg ggcccaggcg ccgcggcccg gcaccccgtg gaagagccgc gcgtacagcc   1680

cgggcatcca ggggtgagtg cgcggggagg ccgcgggggc gggggcgggg cccatggtcc   1740
```

tggccggcgc ccgcggtgca gacacccgtc ccaggcgccc gggcttttgg aggatggatg 1800
ttgaaggcta aggccaaggc ccgactctgc actgaaagtt tttttttaa acatcagact 1860
catttatcgt ggagtgactt gcccagatcc tacaagtaac agtccaagaa aaggggctgc 1920
tgggtaggac ctgcaggtat ttgtcttttt tactcttgag attggaacgg gaaatcgact 1980
ctctacccct ccaccccgcc tccgggcaag tgaggaaccc cttgtcaaag tggggcgtag 2040
ataagtgtgg agtttcacgt aagttaagtt gcagaataat ttagcattgc caggaactcg 2100
aatcacgtcg aaggtaaata ttaacctttt taatttcatt ttttaaaaaa atttaactgt 2160
caacttagag gtgattcatt ttttgggggg tgttgtgtcc tttaattttg tgctgcaatt 2220
accataagca tcgcctatgg tttataaaca ttggcttaat tcaaagaaaa aaccagattt 2280
gtcatatatg tctattcttt ggaaggtgcc atttttattt taaatatttc tacatccgcc 2340
tagagggaat tagaggctct acttaaattt agtgcactta cagacggcaa ggaatgaaac 2400
gaaaggtggt gtgtgtttcg gggttggaat tgtcccaggt gaggctgttc aggtgtgatg 2460
ctgttgacgc agcccctttg ccattttggg cttttctgag cgtctggaag caatttatgt 2520
gtaggttgta tgtcagtatt ttaagactta aatgataatt tttccttgca caatttttcc 2580
ccccaattta aaaaacaatt aaggatttgc tggggtatga gggttgttgc atgcagtaga 2640
gtcctacaaa taaccacaat tgctaggtgt tgggagttct tatagtaaac ttttgcttgt 2700
aactcttttt ctcatttgaa gtatgttggg aaacacgagt tgatacttct ttaaagcgtg 2760
tgatacactg taatagctgc atgttctgta acttatttca cctggcttgg gctacaagcg 2820
ataccttcta aatttcccga agtgtaaaca tgcagtgcag acgccggcag gagcgcagac 2880
tcctcttctc tccctccagt tcttacctgt agaactttct gagagcaggt ggttgggagc 2940
agtttcttct tgatgaatag caatatatac ctaagggctc gcttggggag gacctttagg 3000
tttccagcct gttatgtaac tggaatggac tccgtttctc ttagcactag aaaaaacagg 3060
aagacacgtg gtctctgcca gtcttgggtt gtacctctgc tcttagaaag tggtagcgca 3120
tcaggtccca tgcacctcac ttgggctccc cgagctgttt cctccaggta actctagtca 3180
ggctcagtag gtggtgttgc ttttgttagt gaatgagccc actaggatca ggtgctgtgc 3240
taggatctgg ggatctgggg cagggacggc atgggagaca cagtctcatg atcttgaccc 3300
accctgaaac ctgcctgcaa gtgccccctg cctagagcac aagagtaccc tgctcagttg 3360
tgcaggtccc ctctcacgct cttcgtcacc cacgtccagt ctctcatcac atgctgttcg 3420
tttggccctt ttaatctctc cacacctcat cctccctcat gcaggctctt gttacttctg 3480
tggagattgc tcaagcagcc ggaggtgcct ttgatgcact ctggtcctgc ttgagtcctt 3540
tcccatcaca ggtaatgggg caatcttctc tgccagcagg tctggtcaga ttccccttca 3600
ccctgtgatg tcacctcccc catctccaat cccccacatt aaagactaaa gcctaaaact 3660
cagcaacacc tccagggctc tgctgctcag atgcccctag gtcctggctc ctggccccac 3720
cccttgccaa cccgttagaa cctagctgta aggcagtatg gtgtagggca tgagagggct 3780
ctgaagccca ccaggaggtc tggtttgata ctgcagtcat gctcttggaa ctttcctttt 3840
ccccttgct ggagacctct ccttgcctgt ctctgggtgg tgtgtaccat gcctccagta 3900
tggccttggg tgcatccgct tcctgccgtc tctgcccaaa ggggcctgtg aggaccacct 3960
gctctgtgcc cagaagggca cggtgacctc tgcttgggct gctattccag ctactctttc 4020
agaagcaaac ctaagctgtg gtagagttgg gcctgtggct agaggaggta aggtcccccc 4080

-continued

```
tgtgatcatt tccacatggc ctgttggtcc tatataaact aacctttttg tatcaataaa   4140
tagttctgtc tagaacttgc ttctggccat cagcttaccc agagtgttga gaaaggccac   4200
caaaaagtct ttcggttgtg gcttagctaa ggaaataact gagttttaaa ggctcacctg   4260
ggctggccaa tagtaaagga ccttgttgct gagaagctgc ttggggttgt gatatagtcc   4320
caggacatgc acttctgaaa atgcagtgtg tattcctcat gggaggatga gcctgctgtg   4380
gagcattggc tgaacccagt tgggtctttg cctggtagcc catgtggcaa ccctcactgt   4440
ttgtcctttt ctggggagga gttttctgcc cttggacact ttgcctggtg gcttggcctt   4500
gtgagactgc cagtctgcct tctgcttcaa gtaggatgaa gaaaaagcag gtgaaagagg   4560
acagggattg gtgcaagaac cttcagagga gaggaggtga aatgcttctt ttggctctgg   4620
ttcttgaatc attgtttgat tgaaatctca agcctttgtt ttgggagtgg tgtgcttagc   4680
gtgagctgtg ctatctacct gggcttctga cctagagatg ttgggcaggt gtttggacag   4740
gccctgggcc ctttgcatcc cagcctctgg ctgctgtcac ttgcaagtgc tctcatcccc   4800
tgacccagca gggctttggg ctgttgttac tttgtcatgg tcgttctagc agctttggaa   4860
acctcttcag gttaagagtc ttgcataagt gagagtggga gcatggccct cagatatttg   4920
gccacatcct tactggtgtg ttacagagac ccaggaagaa tgtagttgaa cgaggacaca   4980
tgcaggtgtc ccgggccctg aacagcttct attcagagtt tggcctttcg aaggctgtgc   5040
catctcaggt gtgcctgcag tgtgcagcag gtgtatgcag cttcctcttt gcaggtttct   5100
tggtatttaa tctcatcctt taatatcttc tattaactca aaggaaattc tgttcttagt   5160
ttgaagtctg agagagaccg acgactgtcg gcataggaca tggtcagcca tgccccgcaa   5220
ggcgtctggt gagagtcgtt tccaacttgg tgcatgtttt tctcaattct ttcttgcgaa   5280
ggagtcacag cttggaggcg caaccaggat ccccccctctc cctctagcct gacctcactg   5340
acataaagta gagcaggtgt gacctgtccg gaacatcctt gtgatgctca gcagggcctg   5400
ctgcagagca cgggaggcat cactctaggg gcctttccct cccatacttt cctgtgagtg   5460
tccaggatgc atgagagagg ttgttgtgag acctgcctta aagggtggcg gtggcacgtg   5520
tggaccttgc tttctgagtt tcactctccg agtcccagag gtataagctt gtgaagagaa   5580
gcgtgtatgt atgatcacac taagcagata cttgctcctg cactgttgga ggaggaagag   5640
gagttaattt catcaattaa ctcttccaac actccttcca tttagtaata gcatcacttg   5700
ttcctgtctt ttgttccatg gccaagctcc acaaggtgaa attgaaaatc gagtgcaaga   5760
cactggctgt gctggagttg aggaaagttt tgctggagac ctgcttgcac catatgtctg   5820
gtcactgata gatgaggact ggccaggtca ggacagctga cacttggaga aggggctgcc   5880
caggagggca tgacagactc tggaaaagga gggtcggagt attaaactgg ctgggaatga   5940
gaggcctcca atcttttcgc aggaaaaaaa aaaaaaggct taatgctcgt gctgtggaag   6000
tcagaatgga gcaaagtggg ttctgtctgt cttgctgctg tgagcgtgtg atggaacaac   6060
agtgtcattt gctttttctc agaaatattt aatgcatgtt tgtgacataa tttttcaaag   6120
taattttaag taaatatttt aaagtaaaaa gttctaagat ttgtgtctca aggtaaagtc   6180
tcaaacgttc tttggtcact atttaatatg agattttgtc ctcattttaa atggattcat   6240
gtaagcgtcc tgtggaagaa gagttaatag ttatccttgg aaaataagaa ctttttatgc   6300
ctcagttagg tcatatggtt taggatctga ttttgtagtt gtggagtaaa ggttaagaaa   6360
aaaaaacagc aaaccttgat attcaaattc agaaacttga tttttgagga tgcaaccaga   6420
atttggacta aaggtacaga ggggtggcag agtcagacca cccagacttg cagaagattg   6480
```

-continued aagaagccgc agtgctgcca tgaagaggcc ctttctagga ggtgtggctg gcttgtcagt 6540
gctttgtctt ctctgcagtg aattggatgg caagcctcgc cctcttcgaa agctgccact 6600
ctgaacctgc cttgagaagc acctcaggga gggcaggcag gtggtctcag tcagcgctga 6660
caggtgtcca agttacctga cctgttggga acatgtgcct gagtgaggtg gccaggatgc 6720
cttttctccc aacactgggg atgcacactc gtcagcatcc tatttttgag atttctatgt 6780
tgtggtagtt ctctgttgct gtgtagcaaa ttaacataaa ctcagaggct tagaagaaca 6840
ctcacttatg gtcttaagga ttttgtgtgt cagatcaggg atggcggggc tgggttctct 6900
gcttaggctt ttgcaaggct gaagtcaagg tgttggccag ctgtgttctc agctggcact 6960
cagggtcctc ttaccagcac attcctgtta ttgtcagaat tcagttcctt gcaggatgga 7020
agtccttgat tgcttgctag ctgccagcag gggaattggg tagggcgctg tcagcttctt 7080
aaggccacct gcattccatc tgcaaagcaa ggtactttga atttctctga tgttttccgc 7140
cagctggagg aagccccctg tttctatggg cttgtgttat tgagtcaggc tcctgcagat 7200
aacctgccta cctgaaggtc atgtagtagt acaacatgat catggtgtga taacctcatc 7260
agagccacag gttccaagga gtagggtgta ggaccttgag gggaggaggt tcttctgtgg 7320
gtagacttcc cctggcatag aatccgttga tgagcaggtt gtggttcttc ttgtccaaca 7380
cttttcccct gactggactc cagcccatcg caatgactct tgcagattgc cagttccgtc 7440
ctctggcttg gtggttacta ctgaactcag gcagccacta taaccaggag aacctttctg 7500
tgctgcactc agatgaacat tctttaaaat atgtcattta agaaaagttt gcaggactac 7560
tcgggaggca gaggcaggag aatcctttga actggagagt tggaggttgc agtgagccga 7620
gatcgcacca cagcactcta gcctggtgac agagcgagac tctgtctcaa aataaataaa 7680
taaataaata aataaataaa taaataaata aataaaagtt tgcaggaaag ccgtgtgaat 7740
atatgaaaat acagtgattg aaaagtcctg ttcacgaggt gtcctgcatt ggctagttta 7800
ggaaaggggt ctttcctatg caggtggggg ttgatgactt acccaagagt cacctctgga 7860
acccagttct cttaagttga tagcagtcta tctttgcttt gcagaagatg tggggaacac 7920
ttgtcctgca agcccaggtt cgtagcaatg ttggcttccc cagaaccttg gcttcagagc 7980
actgtgcctc ctttaggagg cacaagaaaa ctcccacacg gttcttccct ctgtcccttc 8040
ctgagccccc tgagtgtttg gctcttgtgg agttgctgct attactaagt tgatcccact 8100
gccctcctga gtctcctcag ggaaggaggg gctgtattgt agcccgcatt cttagtgcca 8160
agcacacggt agccactaag taagtatctc ccaagaaaga agagcaggag gaggatctgc 8220
caactcagga gagcaggtgg gggatggcaa gtcttcggag tattcataaa ccaaatgcta 8280
agggaaactt ttgttgtttg tcttagaatt ttaaaaaata aagtctgttg cagtttatct 8340
gctttccttc ctggagagtg gctaaactag tgttctgttt tacaatgtag aatgcaaaag 8400
cagaaaacat tcaagaaaat tctatactgt atttgaaaaa catcaccatt tagttttaac 8460
tgctctttgt ttcttattat aaaaattaat acctaactat gaaaagttag aaagcctgga 8520
gaagtatgga ggtgagttgt ccaccattgg gccactagag agtgccctat gagcctgtcc 8580
ctggtgtcct ggactctggt ggtgtgcact gcatttgctg gcagtgagcc agggggtggg 8640
ccacatctgg gcccgggcgg ggtggatctc tgcagaagtt tatccatctc ttggctgaca 8700
gggtgggcga gatgggagca gctctgaggg tccctgttgg cagagaatgt ctttgattat 8760
caacaacatg cctttttgtt gtgggcttgt gatccttttc tttcctaaat cagctgccgt 8820

-continued

```
gcataaccag ttaggctctc ctgtggcttc agattggagt tagtttccca agtgctagga   8880
tgtgggtgtt aggtgatttc tgtctttccg tttgaaagag atttcagatc attgtaacat   8940
ttctggaatc ctgtcgatct gaaggaatgg ctaggatgta gtagtttaag ggaaatgaaa   9000
agtcgaatgt attttgatgt ttctgcatca gacctgctcg gtggagtcca tttctcagct   9060
tcgggagcca cgtgcttggc tcttgagagc ctagctccat cagcccatgt cacacactca   9120
caggtctggc tttagctggt ttcgccatgg tttctaactt gagcctcagt ttcccccct   9180
gtgaagcaga gcctgtggca cccacctcag agagtacatg aaagacttgg aagcactctg   9240
tgagttgtca tgcgagagat taaaaaggcc accgctgccc ttttctcctc tctttaagga   9300
aattgaaacc aaaaattaag tccttcttgc cagctggaca ggaaaagcct ttttcttggt   9360
ttttgaaaat acaacttcca ctttcagacc aaagtgaaaa ctgctaaaga ctgaatattc   9420
tgagtcttgg gagtgggggg ctagaggggt gttgtgaatt gaaagatacc tttctatttt   9480
taaaacattt taacaatgcc ttaatgatga ataatgtctg ttctagtttt gcatttgtta   9540
gttttttttt tttttttttt ttaactgttc tgaaggtaca tcagcactgt tctacagctt   9600
taaataagaa tctcatctcc ccagaggcaa gggtactctt gatgtatttg ctcagggctg   9660
tatgtgctgc tccgtgtaac tcatttaaag ttggttaagg tttttttatt tcttgcacat   9720
agtagaagga gtggatgaag tgttttctga actctttgca gcttctaaca tagtgttctg   9780
tgtatagtga aggaaaacaa aattaagggc cagggaacat taagtaggca actagaacag   9840
cactgtccag tagaacttcc tgtggagatg gaataattct atttttgcac taatacagta   9900
gccactggcc atatgtgact tttgagcact tgaaatgtga caaatgcaac tgaggagctg   9960
aattttaatt ttatttactt ttaattaaaa tttaaatggc catgtattta gacagctctg  10020
aactgcagta actttaggct ctatttgaaa cagtgtttga ttcagtaact gttgctgaaa  10080
taaattgaaa ctcatacaac agtaaaagct gtgttactca gcaagttatc actgtgaaag  10140
ctctagaaat tgtttgagtt tccaatgcaa atccttttca aaaagccgct gttttaatag  10200
cacatgaagc ataaaatagg ttcatagcag agcgcagcac agagcaacat ggagcaactg  10260
ttatgacctg gagtgtctcc agtccagcat gcaggtgata ggtctcagca tttttgcacg  10320
caggttaatg atggtgcaga cggtcacttc cttctctcaa cagtcttcct ggtcacgagc  10380
accattgtgg ctcgtgtgtg gggctctttt ggcttagctc tctgcacgag tttgctcctt  10440
tagttcccag agctgaccct tgaaatgagt gatattactc ctgttttgta gacagaaaac  10500
tgaagccttg acagtctgac gtgacctggc aagaggtgct gcagttggaa atgtgaattc  10560
acggctgaca tctgggcact ttactcctaa cagtgttcag tgaacaagac gtcgctaaca  10620
tgcgggggat ggaacctagc aactcattct acaaacatgg ttcaaatatg ttggtgcagg  10680
gccttttgct ttgttttcct aaagagatta gattcagatg tggtggggtg ctttgacagc  10740
caccgcagga caaagttgat agctgtgggg ttgcggagtg ttgaggattt catagggaag  10800
ccagtcctgc gcagtagtac gctcaggttc gtgctttctt gaggtgttcc agaactggcc  10860
tggagggagg ctgcagtgtg gaagcgggat ttctgtcacc tggagtattc ttagaagttg  10920
cattctatga agagtggagc atctgatgag ctgtttactc gctgtttcat ctgacggcag  10980
ttgaaagaca aggcaggact ggcagcgcag ctgcctcagt cagcactgct gcactggggg  11040
cttgacctgc agtctcgcaa tcctggacta taactcattt tgaagagaga aaaattaagc  11100
attaagtgat tcaagcgtct tgcccaaggc gctactagaa aataaaggca ctggtgccca  11160
gatgcaggtc tgcatggtat gcaagcctgg gcttcttccc acctccccca cagagagggc  11220
```

-continued

```
actggtatgt tggagtgaag agccacgcaa gacctctgtg aatgggcaga gatgggccag  11280
tgacgcaaca cagtaaagtg tattttggtt ataggcatcg tctctaaact tatgtaaaac  11340
attattaaaa aatggaagga caacgatgaa atgatggcca aaaatataga aaaggatacc  11400
ttgcatgtcc tgtgaaatgc aaaggaattc taaagtgtca ttatgagtta cctcatggaa  11460
gaaagcaaaa ggtgaatcta tctagagttt gtggttctga ctcacaagag actgatgttc  11520
atgctgaagg acgagtgtga caggtggaag gatagagcac cgagaccaca ctctaaaggg  11580
taggaatcta tgggaactat tcagggagat gaaagcatgg aatgaactga agcttgcaga  11640
ctcgttgagt aaaaagcgcg ttttaggatt ggttttagaa taaaataaca aggcctgtgg  11700
ttggggaaga tgacttgctg ttcacagagc ctcccttaat aggtggggac ctcagctttt  11760
cctctgctgc catcaggtga gtggtgtaca gtcctagcca cagtagtaat caccactggc  11820
ctgactgagc cctcaccctt tatacagtgt ctcctgccac cctcctggga gaggctgttc  11880
tcggcacagc tggcctgggg tcacacagct ggtaggtgta aagcaggcat tggagtccag  11940
gtagtctcac tccgtagcct gtctctttag ccactggaaa tgtagagcaa agcgagaatt  12000
gtccaaagag ataagctaat aaagaggaaa acaggctggg tgcaatggct cacgcctgta  12060
atcccagcac tttgggaggc caaggagggc ggatcacaag ttcaggagat cgagaccatc  12120
ctggctaaca cagtaaaacc ccatctctac taaaaataca aaaaattatc cgggcgtgat  12180
ggcacgcacc tgtagtccca gctacttggg aggctgaggc aggagaatct cttgaatcca  12240
ggaggcggag gttgcagtga gccgagatca cactactgca ctccagcctg cgtgacagag  12300
cgagactccg tctcaaaaaa agaaaaaaaa aagaaaacaa ttatgctgag ttccagagaa  12360
gtgatgtctg tcttctcagg agagatgccg atgctgtctg agggcctgcc cagtctccac  12420
atgattcaga gactccagag atggacagct agtgccctga ttttcccaag aggattctga  12480
gggtgacttc tgtcaaccaa acaggaggac ctggtgctgt catcaccagt tgtagagagg  12540
ctgcggacca cctgctgtgt gtgccatctt acactgccat ttgctgattg cttcaaagct  12600
agaggttgtt tctaagagtg cttcgtgcta actaactaaa acataatgac attgtttttg  12660
taaaactgat ccgtggtttg ttttttaaag cagaaagctc taaagtcact cagtcccacc  12720
acccagaagc acaagcaggt ggctgccact gtaggacctc tctctctagg ctcgtgtaga  12780
tggacacatg gattggtcag tagaaatact tttattaaaa gtcttatctt tacataaatt  12840
tgccaaatta ttaattttgc ttgaaaggga aaggtgtcca acttcagttg gaaatactag  12900
tttctaagag atactgctga gactaagagc ataaaacatg atgaaaacct taagtggcta  12960
agtgcagcaa cgtcagagta aaagctttga tgaagtcttg gtttgcttgg gctgtgtagg  13020
ttggaggctc agcctttgtt tctccctcct ctggtgccca gtggtggtgt ttgtgtccgt  13080
gaattttcaa cctctgtagt ttgtttgtag ttatgaccac tgttgcaccg aacccttacc  13140
gagggccagg ccctgtgcta agcacttgcc agtgtggatt tattaagtct tcatgacagc  13200
accatgtagg gggagctgcg tccctgtgtt gtacttggga cgcgatctga cctcaggcac  13260
ttcaggctcc tgaagggtct gcagtctcgt ctctgcctgg gaaaccacga tttgcagcat  13320
attccacaga cctcatgctc atcatcagga ggcttcccgg gactgctgcc tgagatttct  13380
aagttcctaa tgtggttcat gcttctggtg agtttctttg aggcgacgcc ccctgcgttg  13440
cctctggtca gctcagtcct gtggtcctgc agggcatcct acagtgtcct ctgtctgtga  13500
cttgtgccgt gccaccttga cctggcatcc actgtcctct accgcgtttg cagataggag  13560
```

-continued

```
ccactgttgg tgcctttttg tcgtgtgtgt tgaatggtca gggtcccaaa tagctgattg  13620
ggagcactct ccttgaatct gccatgtgcc tgggtctcag gtgactgggc ccctccttgc  13680
ttcagaaccc acgtgcgttg cctgtcctct ctggcttgga gggttgtgtg gaatcagagg  13740
tgagacccag tccccaggga tgggcagttg cctttgattg cccagctgtc ctcagcgccc  13800
tccctcctgc gcccaactgc tgtctcagtt gcttgcttga ggatccggat atagactgag  13860
gtcggcctta gcgtggcggg gggtttttctc ttgagtcttg gatactttgt taccggtccc  13920
atcttcctgt gggtgggagt gtctgtcttg cttggcccag cctcccagag accttagctc  13980
tcttagtaca tgggctctgc ctaccttgat ccccagctca ccaccctagt gcagttgctt  14040
cttcgctctt gttccactcc ttgtcgccat ccaccctgtg ctttctcgat gtgtccttac  14100
tcggtgtttc tgtggagcag ggcatcctgg gcttcctttc tgatccctgg ctcctgtgat  14160
cttccgtgct gggctccctc ttcccttccc ttttccactg tgttgccctc acacagctgg  14220
catgccatgg atgtcgctca cccaagccct tcctaatgtt gctcaccaaa acccctccca  14280
ccttgcccct gggaccttct ccccttccag gctgcatgca ggccgagggc ctggcgtctc  14340
agcaggaggc agtggggcct ttgctggcac ctgggctctg catcctgacc ttctgagggc  14400
ttggtccttt aggtccatct tgaatctcct ccaggcttcg gactctctgc tctgtagctg  14460
gcccatggag acgggtacac tcaggcctgg tcttagactc cgctgcttgg gctgtgctgg  14520
tgcctttggt gccctcttag tccatcccac ctggggggccc tgtcctgctg tccattgtgc  14580
cagagtgctg tccccttgtc tttccgtaac tggctgctcg ttacctttcc catctcagcc  14640
tcagtaccag ccacttggta tcagggaggc tctccctgac caacctaaag ttcacagccg  14700
tggttgccag tttaaatttc tgcatagcaa ctttttggtt tattttggct acttatcttc  14760
cccatcatgc cccctgtccc tcccatataa actcagtgag agtaggggcc acatctcatc  14820
atcctgccca cagctctgct gtctgtatca gccagggtat gctgtgcaga ggctcacggt  14880
aaatagctgc agaccacgaa tcccatctgc ttgctgtgct ttaatattgg cttacatctt  14940
tggatccagt gagttctttt ctctgtctcc ctctctctca ctcgctcata cttactttgt  15000
gtaattggtg atttccagcc ttttgtatag tcctttctcg aatagttgtt ttctgtcatc  15060
ttggcggggg cctcaagggg ttgactgtac ggagggcagg ggctgcagag ctgcagctgc  15120
tgcctggggt ctcacggcgc ccgtgaggtg taggcaggtg ctttgcctct gagctgtctg  15180
tagaatgggg tgacggcggt ttcatcagac tcagtgaagc atgtcataca gtgagtgtct  15240
ggtcacagca ggaagatggt gaatgtcagc taatgagtat tcatcaccaa tgaatagtaa  15300
cagttttttt tactaaggct atgtaatgta gcctcagaat tccactcagc acagcccccct  15360
ggcagcggtg cctctgagag ctggcatgat ggagagagcc tggttggcct tactggtgtg  15420
gttggggcac ttgggagaac gccttcctca caaagctcat ctggagggtt ttcggacttg  15480
taggatagct ttttcagggg ccttgccttt ggcagggcag ggacgtgtac tgctgcagtc  15540
tagggtatgg gataactttc taaaccagac ccagaacttc atggccgcag gggcctttta  15600
gccatgcggg gctaggagct gacacagcgt cagcagcatg agggcctgtg gtgctgggcg  15660
gcagagccca gagggagccc ctgctggtgt gactttagtg taaaggctgg gggataccag  15720
attcttacag aagacttaag acgggcacag tgatgtctgc tctttgaccc ttgcagtatg  15780
aattagtaaa actgaaatta ttacatttcc tttattagga ttataaaagc aatgatgact  15840
tattgaagaa aatttggaaa atacagaaac tacctataat ttttccattg ttaacatttg  15900
agcatatttc ttgtcacttt taatggtgct ttaaatatgt agcaaatgta tcatttcgta  15960
```

ttttaaaaaa atgctaggta agcatttcct cctgtcctta aaaagctctt ttaaacaact 16020
ttaaaatatt gtatagatag atgtacacaa ttttctgaat aattggagtt atatttacat 16080
cttttcactc tttaggaaag gactggcctg tttctgtgtt gggttccttc ctgagtgtgg 16140
cttccagctc agtggctcag acttcaagat gaagacttca gtcctggttg tgtatggtct 16200
tgggccagtt accatatgtc taatgaatac ttagttttgt catctacaaa atgaaaatag 16260
taatatttgc ctcaaagact attatttggg aggatctagt gcaaatgtta gtaatgtgga 16320
tattgtgtag tgtcccagga tattaatgtt tttagcctct tggcttttat tctgtattgt 16380
tgccccaaaa gatgatgctc acttatcttt catccagtgt aaggatatct ggaaagacaa 16440
cagaaagtat agctgttttc atttcaaaag tgatcagctg cttgagctag caagcaaggc 16500
ttgcactagc ttccaggcgc agtcacgcag tttcacagca ggcgcggttc cctcggagca 16560
cccagagctg ccctgcggta gtcagcagtt gtgctgtggc tgcactgcca ggctgggtgg 16620
caggtggatc ggagccagca gatgtggctc aggaagtgcc ttcttggcct ctccttaatc 16680
tctttcagag tctgtgggcc cttgattgca ctgtgggttg tttcagactc cagtattagg 16740
agactgaacc ccttggtggt ttttttgtgt gtgtgtgctg agctgggttg aggacatgtt 16800
aagcaggtgg ggtgcctccc ctgggtttgc tccgggtggt acctgtggtg tggggtggtt 16860
ctgagtagtt ctggccccac tgctggagta tctgcccact cagtttgtga gatggcaggg 16920
cttcatcctg gtctggtgcc tcatttttctt ctttagcagt gggcttagaa ccaatgcaga 16980
ttcccaagtt aagtattttt tctgtagctt aattattaca ggcttctggt acctaagccc 17040
tttcttactt tctgttctga ggggaagaga agataatgtt gtttctccgc cccccccccgg 17100
agtggcccca ggaccttgca tggcatttgc agcatttgca gcgtgcttgg gtttgcttta 17160
ctagggtgaa agtgttgcac cccccagcac ccacaaaggc acctctgctc acactccggt 17220
gaggttctga ctggccctgg gacatcacct gctccaggat cctatgtggc tcatcccagg 17280
agagatgtgg gagggaaggg gaaaaaaggc ttacatttgc tgagtggaat tcatgtagat 17340
ctgagttccg cattgattcc taagctgcag agcccttatg ccttggctgt tttgtgaatg 17400
ttagtcggtc ttaacctttt tcaccgagtt agcattggct gtctcaggag gctcacagct 17460
cctgctcctc ctccagggga gtgcgccctc ctcctctgtc ggtagctgtc aggtgcccct 17520
ttcctctgca gcagactgtc ctgggtcctt gcctggcctt cccctacac gtgagcctgc 17580
agcttcattc acagcccctg tgtagaaaga taggcacatc gataggtccc tccctgccca 17640
gagtgggcgg aactgaggca ggcactaaaa gcagctgact ggcagcccta gaaacatgaa 17700
gggtttcatt tatagtttca gtccttttcc ttctttcgag ccttaattta aaaaaaaaaa 17760
aaaaaaaagc cttgaagtcc tgcttctgag ttttctaatt tgtgcaggta ttagttgcct 17820
tgtaacataa tcaaaaataa ataaaaatga tttataatta gcttattaac tgtatcagta 17880
aatggatact ttaaagagga tcattgatcc ctcaaaatag aagcaatgca gtcattccct 17940
cattatgctt tacttgtgat ttgcttacaa cccactcttc ctagttaaag ttaaatatta 18000
atccagaccc tatcagtgcg atgtagtagt gtctgaatca gttgttgttt tggtgtaatc 18060
gtatcaaagc atgttataaa atctacaaaa ttgcagggtt aactccaaat attttcacta 18120
aggtattgtt tttttgggca aaaatgcata gtgaacattg tggagctgaa gtgagggaac 18180
ttcgatttct gagaaaccac tagttttaag ggttttgaag gaagagttgg aggaggagag 18240
gaagagaata aattcacagt taatgagttt ccagtatttt ctgtcgcatt ttacgttgta 18300

-continued

```
atggaaaaga ctgggaactg aactcacatg cagtttgtca aatcactttt tccctagaat  18360
tcaggattga tgagattaac ggggtgttaa aggtaaactg aggcacataa ttaacatgga  18420
cagaactgta gacctgagtg ttgagagttg ggaaatttca gtgagttggg aagactggaa  18480
gcacctgttc ttcagagtgc aggtcctcat attcagtggg tttaaggtgc tgaaactttt  18540
tttttttttt tgagatgggg tcttgcactg ttgcccagac tagagtgcag tggtgtaatc  18600
accactcact gtagcttcga atcctgggct gtcagcctat cctcccacat cagcctcctg  18660
actagctgga ctgcaggcct gggccaaaac tcctggcttg aaacttcttg taaccagatt  18720
ggaggaggag ggcatgttca ttttcgtgac gtttcctttc ccttaaacat ccagtgaaat  18780
ctgacctttg accatcactt tgcttaaaag aagctactgg atttaaagtc taggagaatg  18840
tcctagacaa gcccatagta tgttcctgta tgttccccac ccagagacct gcgttatgaa  18900
gtgtttggtg tgcttcttcc agccccactg ttctttctaa agtgttttat tttacatacg  18960
ctgtcctggc ttctgggcta tgacctttgc ctttttttgcc ctttagttcc tttgcccttt  19020
acctactgca gtgcagctgc ctgtccttgg gttgactaca aagaagtcac ctttgaacaa  19080
cttagaaatt gtgacttttg gggaaggcag ggcagagcct tggggctgag atgggggagg  19140
agccagctct gccctgggag agatacaaag cgcctgcctg ggtgaggcag tgcacgggtg  19200
ggcttgcttc acctctttgg ccccagcttc aaaaccagcc agtcctccct ggctttggct  19260
ttaattcaca tttacaagct tgaaaaccag ttaatcccat tagctcagct tctaaagctg  19320
aaaatcgtcc cctaaatggg tcacctgttg tcatcaatag ctttattagc tatggaataa  19380
tatagttttg ttctctaact gtaggatcct tcttttgctc ttaaaatagc tcagtaagtt  19440
gggtctcata aatacataca gcaagcatat accagatact aaaatacaaa aacattgctg  19500
atcttgcttt tcagtactaa aagcagaaaa tcgggaattt actaaattga gaagtcagtc  19560
attacctttc gatgggtttg gactcttgca aggcagtgat tgtaaacgag agtgatcttt  19620
tgttgttttt caatgaactt tattctctaa tttttagtaa agcacactag gaaataatgc  19680
ttcagaattc tgttttcgag tagtttcctg actaaaataa aaattcacta aaaaaaacct  19740
ctgctgtcac catttccttt tttcttaaga taactaggaa atgaatcatt aagagtttgc  19800
tccgtggcaa tggatcggga agctgaccct gctctctgtg ggctggagc cttgctaatg  19860
tcccaggatt tcacttcaca gagacaagca tcagaggctt gcttcattta tagatcctac  19920
ttcttttcta caccacagcc aactcaaaat ggtgacagaa tctaagacga ggctagaagt  19980
caccacggag cagttggaag ctctgcttcc ggttctgggg gcagtgttcc tggcgttgtg  20040
tcctttggcc ccacctcagt ttgtccgttt agctcctcag ctgagaatga gatgtgtatc  20100
atataggagt ttcctgggcc actcacagcc ccaagctgga gagtgccagc ctaatgtgtc  20160
aggagtaggg ggtgaggcca gagggctgtg tgccaactcc tccctaagaa gcctcctggg  20220
aaagccctcc caggcacttc ccaggtctca ctggccgcct gaggctgcag gggaggatgg  20280
tcaggccgcc tcttggctgg cactgcttcc cggcgtgccg ccagcctttc tcatggggag  20340
gggaatgatg gcatgcctgg ggggcagcag ggccccaggg ctgcctaggg ctctcactgt  20400
gtcctcctgg ttctgagatg ccacctttgt gatccactgt agagggattt attctattat  20460
gatcaatgca tagaaatttc ttcgatttgg agactgaaca ctagtgagca gaactgaaat  20520
tgagctttaa aagatattga tgacgggtct gtggatagga gactttagtg tggtttttat  20580
gcagacgtcc tgccagctgt aaattccctg gaggtttggt atgtgagaac ataagactaa  20640
acttatttct attttgttga ggagaaatga ttaaaacttt tcattgatgt acttctgtgg  20700
```

```
cagacttttt ggagaattga accagcgggc atattcagta tttgaagtca tagatgagta  20760
aaggaggtat gttgtagttt gcgctggcgg cgtggcctgt ggtcggcagg gcttatctgt  20820
gaaggtatgt gcacagcttc ctaaggcagt gaaaagtcct ggcagtgtta gtattgaatg  20880
agataatcca aaaaatgtaa aaatgtttac atttttaaag ggatagttgg cgatttaaat  20940
ggtttctgct aacaaatcaa attattcatt gcagaggtaa aatattttca gaatgttaat  21000
tttagatgtc gtagagagtg tacatcagca atgacaaggt cagcaaaata tcttagcaaa  21060
acttgattga ttgattccat gcacaggcaa gcgctgttct gggcaccgga gacggagcag  21120
tgcgctgttg cgtccatcca cagatggcct ccagagtcat gcggttgcag ggaggccgaa  21180
gggccaggga ggccgctggg tgggcacggc tgggcggtgc cctcacgtgg gttttgttgg  21240
gctactctta ctgtgcactt tttctcagtt tggtcagtgt tccgccttgc tgcctggccc  21300
ccaaccctcg ccctctgagg gcctcacaaa gagccaagca gaaggcaggc tgggggcttt  21360
tcaggccagc ccagaggatg taatgatgat ggttggcact gtcccacggc cgccaccagt  21420
ctcacactgc ctcgtgggca gtcctggagt cgtgcggcac cttgctggtc cctgctctcc  21480
ttgaagaagg gccagtgggg cacttcgcca gagccttctt gtctgactcc gtcatccaag  21540
aggcatggat ggccgggccc ccggcagttt ccattctatt ctgagaaggc aaaacaaaat  21600
tattcctgtc tcttattatc taatatttgt tacagcagtt gctcactttt aggtgcattt  21660
tattacagat ttcagacagg tgtggttatt agtgcagctt actgtttgga cacaatgcca  21720
aggtcaggag gacagtgttc ccctgagcac cacttctgct aggagcatgg gcaggccatg  21780
cctcgccatt aatctctcct gatttagggg aggaatacca ggccaccccc tcttctccct  21840
gtgcaaggga acagacattt gacaaaaacg gatgccatgt tacgctgatt ttgtgtgtct  21900
aaggcagact gcagcaggtg ttatctccgt gctcttcctt tcctggagtg ttgagcatct  21960
cttgatagta ggggatgccc ctgagggtgg tgaatgtggc tgcacaggtc ctgaaagcta  22020
tttgatgttg ccgttacttc aggtagaact taaagttgac agtacattct actctgcagg  22080
tggaaatgtg gagtgccatt ttgacaaatt ggaatgccct gtttacaata tgctttaatg  22140
agttaaatct gggggatgtg gatagaattt tagtatccta gctttggcat tcttccatga  22200
ctttgggcca attatttaat aattccaagc ctgcatcttt gttagaatct ctaaatttct  22260
ctactcctgt tattatcctc agaacaggac tgtgaggtgc agtaggccac atggtgtagt  22320
ggtttaggtg gacagacttg ccagtgctgt tctcatggat agcctaggac tgtccctagc  22380
tctctgcagt gacagtgata gtgactggtg aaggtgaagg gatccaccca gacgttcttc  22440
ctgatggaga gaggctggcc tgtggctctt ccctggggtg gatgttaacc tgctaacgtg  22500
acatatctag tcctgcttac attactaagt ggtaggaaat tttaggtaac acctcagact  22560
ttaaagtggc ctactgagct ggtagaaaag tgtgtagttg gtgctcagta attgttgaaa  22620
agatagaagc tttacttcaa agctcttgta gtttgatcag tttggaaaaa atattttaat  22680
gttgggctct gttaacagct ggactggtgg ctgtctgaat tgggaccatg cttggggtga  22740
ggttttttct tacttttttt tttttttttg gtgagacaga gtcttgctct gtcgcccagg  22800
ctggagtaca gtggtgcaat ctcggcccac tgcagcctct gcctcctggg ttcaagcgat  22860
tctcctgcct cagttttctg agtagctggg actacaagca tgtgccacca cgcctggcta  22920
atttttttct atttttagca gagatggggt ttcaccattt tagtcaggat ggtcttgatc  22980
tcctgaactt gtgatccatc cacctcagcc tcccaaagtg ctgggattac aggcgtgagc  23040
```

-continued

```
caccgcatct ggccacatat ttttttaaat taaatgtgat acataaaatt aggctgcagg  23100
catggcctga tttgcaggtg cttcatgagc aagcgtgcac agcatttatt tgctgctcct  23160
ggagtctctc gtgtgtgctt gtagcctagc cttaagccct ctgtggacgg cttggaatgc  23220
gtactccaaa tgactctttt ggcggggtgg gaagtggcaa tactttaggt gactgacagt  23280
tgaaattaac cttacacaag agccaaactg taggctgatg cagggccact cacctttgta  23340
ctcaccccctg gcaggtcctg taagaggtgc tacttgcttc cactttgcca gctgttcgtt  23400
ggccctgttt tgtcttctgc tgtttgcctt atttatgaaa cagaatggaa acaggcgagt  23460
ttgatttgtt ataattccta ggagtcatag aatggaagca ggtgagtttg atttgttata  23520
attcctagga ttggataatt tgccttcccc tctctccatc tttaattaat cccttaaagg  23580
aaaagaggac gacagcactt ttcctgcagt catctgtgta ggcctcagcc ttaactcatg  23640
acataggctg gtgccactgg ccacagggct gacctcagct cttggagccc atggggtgac  23700
aggagatcag cacctttgag gtggcggcgt gaggcgtctt ccaggccttg ctcatggtgc  23760
ttgaaaacac tgctttagag ctttgttaag agagagaggc cctacttact cctgtcccac  23820
aggcatttgg gtgttgacct ccttgttggc ctcttaagga gagaatactt gagtattgaa  23880
ttcgatcagc ttttctgcct ccagggaccc tgtttctctc tgctgagact gtggcggatg  23940
aaaccaggat ttagtggatg gtcaccaggt agcttgggca gacctgggcc gcggggcccc  24000
tgaggactca tacgtctttt tcctgttcac atgttccttc cccacacctt ggcccattct  24060
cagtccctcc catgctcctt agcgtgaggc actcagggag gtgcccatgg ggccttgggg  24120
cctgtgctgg agctggttcc cagcctcaga agtgtgccta actgtgccac attcattgga  24180
aagctgcttt cacacttcct ggatggaatt ctctcatttt ttcaatataa agtcactgag  24240
atgatttttt tggagaagtc tttaaaggcc agttatacat ttattgatac ttggtattga  24300
caaagttcag ttgtttagtg ttgctaagtc atactgtgta agtttgttga gcacagagtt  24360
ttcattttat actttcagag gagaaatgaa actgaatttc gtggccagaa atatgtttga  24420
gcgtcatcct gatgtaagaa cagaacagaa aatgtggtga catttcattg taactctagt  24480
atgttttctt ttttgtccat tagactacat gaggaaataa ttgactttta taacttcatg  24540
tccccttgtc ctgaagaagc agctatgaga agagaggtgg tgaaacggat cgaaactgtg  24600
gtgaaagacc tttggccgac ggctgatgtg agtatgttct ttggagttct gtgtcgcacg  24660
tcacgtgcga gtaaatttaa ataccctgtg atgatgatgt gtcggctaga tccacacaga  24720
ccttttctcg ttggcccgag gcagcagttc tccaagtgtg ctttgagaag gcctccgttg  24780
cctggaatgc atggcccccg gcgcacctgc acctgctgtc ttagacacct gcggtggccg  24840
cacatcttcg tgatgctggc gcgcactcaa gtgcgaagac catcggctga gggatttgtt  24900
gggttttttt tttttttttt tggaaggggg agaatggtgt gattgtttct cttaagttca  24960
ccttaaaatt tagaaatttc accctgtcac ccacccctgc ttccccacca ccacacatag  25020
tagcatataa tgtgctcatt tttgtaaaac ttggaagtgt tccctcatca cacaccactc  25080
ttgcagtgaa ggaacaagtg ttttttgaca tgtggagtgg ggccttctgg aatgcttggt  25140
gcaggtggcg tgaagcctgc ccctggccgg ctctattcag cagccttccc tactgctgac  25200
tgggctcagt ggaccagcag ggctggccgt gccccagctg tgaggggcat gtgtgctctt  25260
ggtgggcaag ggcaacccag ttttctgcgc ctcttttaaa atgatacaga tttttggctt  25320
taaacttcag agtcctagga caaagccctg ccccagtgcc ttagctgtgg gtttaagaag  25380
aggttgaagg gtttgaagct agctctgaaa agtcctcagc tttgaagggt tatagggtga  25440
```

ggacaaaact tgtttcacct cttaattttg agtttttaaa cattcctttt ttgggcatgt 25500
ctttaactta aagggaattt tctggttgat tgttatacgg tcccctccat cagtttccaa 25560
ggtagtttta tttttaccc aagggtatag tgagggcttt cttttagtaa gaaataatgg 25620
tagtgtgact gcttggtttg tggtatacat tttaaggcaa ccactctttc tttcaggtac 25680
agatatttgg cagctttagt acaggtcttt atcttccaac taggtgagta ccagactgca 25740
tggcatgggc tagtgggggg ctgggatggt gtctatgcaa tattaagggc tacaaataga 25800
ttctttgtaa ttgagtctaa ggcgagaaat gccagctaaa ggaaaagact gtggttacag 25860
agggaaattg gcagaaagat ttaatttagt gttatgatga attcattgct ttgcattttt 25920
cctctcacac ttaatttgtt ggggtgcaaa aatgcttcat gctggaaata tgaagaagac 25980
aggtgggagg actgtgggaa gtaaacgcaa tagaagacat tctgctgata ttttaggaca 26040
tgtgtttgaa aaattgatct tatgttttga tgaagattca agcaaaattc tctttaaata 26100
gtattttcta agtattttta cctgatagga aaatgtcaaa caagtttgca ttctaaaata 26160
caaactagta ttttctcatt aaggattctt gatagccaaa taaatttcct gtgcactgtc 26220
tcattaaaag cttaccttct attaacccac tgctagttag catttggagg ccgaagaggc 26280
tataatctca ggatttgggg gttgacatta gcagggccag tgggtaattg aacaggtttg 26340
ggtatccagg aatctctggg tccgcaggag tgatccagcg taggcagtgc cggagtaggt 26400
gctgggagag cggggcctca gcctggtttg ggggcaggca ttttcatttg aatcccctca 26460
catacctagt gctgttggga gaatgattta accttcttgc tttccatctt atgctacaaa 26520
tatggaagtc ttcccttaag ttcagcgagg acttgctgta gttcatgaac tgcacttcac 26580
ctccttaggg gccataggct agtgggattg tgtcttggcc tttgtgggag acacaggcac 26640
atgtgccttg gtgcttatcc tccccacacg agtgtgtagg ctgtggcgag gggagcagtg 26700
gctgacgtgc gttttcttct gtcagcgaca tagacctggt ggtcttcggg aaatgggagc 26760
gtcctccttt acagctgctg gagcaagccc tgcggaagca caacgtggct gagccgtgtt 26820
ccatcaaagt ccttgacaag gctacggtga gtgcctggct ttggcccctc tgaccgggca 26880
ggagccttgt cacatcccag gtggtcacag gatacgcctg cgtcacgagc ttgtggtatt 26940
ttacacagtt attggctaca gttttgaaga ttaatctgct tctggtatag acatgtgttt 27000
tatgtttttg tttcatagtc gtgatcacca actgagaaca tgtttagtga cagtctgaac 27060
ttttgggact tgtgagccca ttaaactgtt cttggaatga aaatatatga ttgtgtctac 27120
ttgtgttagg atgaatagga aaggagagtc atctgaaacc ggacactgac attcaggtgc 27180
tgcccattat ggagagtgtg gctcaatgat taaaccatgg tttttatgat taccatttgc 27240
tatgttatgt taaagaggaa caacttagct gttcctttcg tggttccaaa aaatatacat 27300
atatgaaaag ccttttatct ttgggggaag tttgaagatg agactgtttc tggtgtgtac 27360
ttgctaaggt ttatgtcagt tcaagattat aagcccccca gggactatga ggtacttgcc 27420
tgttgtatga cagttcttag ctcacctgtg cgaccggcta gcatttcatt tttaaatttg 27480
tgtgtcaact tgtgtgtgat tcacatcctt atagtgttta gcagaatgta agttaaggca 27540
ggagcttcct cctgcctgtg tggtgatagg ggaggggggca ttcacatgtt tctcattgtc 27600
aggtgctttt gattgaggct gggggcaagt tttaaaacat gatatatgca ctgaaaagtg 27660
cacatgtacc aggtgcacct cttggtgaga gttaacgaag tgcacatgct catgtcactg 27720
tcatgtggac cagagcgagc aggcagcacc agaggttccc tccaggccca ggttccagaa 27780
ggggctgttg gctcttctca ttagcacgag acaagccctg gccggccact ttctcaaatg 27840
cttacgggcc ttattgcact tagctctccc agccactctc atcagcagat gctgttgctg 27900
ttcacatttt acaggtgagg aaactgagat gcggagaggt gaggtcatta gcccaaggtg 27960
ggtcagcggc atagtccagg ccgctgttgt ctgctgctcc tctgtgtgtg ccaaggggca 28020
gcggggaggt gggtgggaat cctgaccagg cgaccacctt tggagtagag gaactaaggc 28080
gcggctgtcc tgaggccaca cagtaggttg agcagttaca gtaactgctt agtcccagtg 28140
acctcgttac tgtcgcatat tggctactaa gtatcttttc ctctgttacc tgagggccag 28200
tgtagactgt agggagagcc tggagcctgc cactgctcat ttctggggag cactgtgcag 28260
ccggccagtc atgggcacaa gagacccagg gcgagggctg agtttaaggt gaaatcttgt 28320
ctatttggaa caacaaccca aaactgtgtt acagtgttaa ctcctcacct ccaggatttg 28380
gggttcctgc cgtgagtgag tgtgtgcaag agtagggcag gagagtgcca ggagtgattg 28440
tgggaaggag tctatgagat ggaaaggaag ctgcttccta aactgtgggt gtcagggagg 28500
catagccatt gagtgttggc ttcttccaaa gcagtttctg atgagttctt tgggaaagta 28560
tttctttctc tgccttctta agaacatact ggcctcaggg cttaccctgc ctggtggtcg 28620
cagtggtgtc caggtgactc tggccccact ggcatgtcct cacacgctga gtccttggtt 28680
ggttgccctc aagtgtagac attaaagccc agaataggtg tgtactgaat gcactgtccc 28740
tacgttgcct atcactggca tttgaacttt tcgttagaca ctgattgttt tggttaaagg 28800
aattcctttt tttaatcctt caaggctgaa ggaaacaaaa cattgccttt tcttctggaa 28860
gaattcagtt ttactggtgg ggtggagggt ggggcatgag tgtggtctgg acagttgctc 28920
aggcagattt tgaatgccat tcggtgacag ttcttgttgg tgagaatatt tctaaaatag 28980
ccttttattt gctgaatttt ttaggggaaa aattttttta gtaaagttgt cttaaagagt 29040
gaaaacccaa agtagagaaa caatatcagt ataacataca atttaaaaaa tggcttcgaa 29100
gttacattaa atgatttcaa aaattctgcc aaataaaagt ctggggccaa gcacctctct 29160
ccatcccagc acatagggtg ggcgtggcag agactaactc ctgttccctg ttggctccct 29220
cccctcacgt ctctttgatg cttggtcacc tctggtgctg atccagggct acaggggctg 29280
ggcagaatgt gggtcctgct gtgaggggct ggggcctggg agtcgtcctg ggttcaggga 29340
ctactgatgc tgacagtgtt ctctgacccc ctttcattac taagaaaaaa caccaaacct 29400
ctgtacagct ttggcagcat tttgatgcct ggctgtggag agtcctgcat gttaaagcag 29460
tttttaaaat gaaatcttta caggtaccaa taataaagct cacagatcag gagactgaag 29520
tgaaagttga catcagcttt aacatggaga cgggcgtccg ggcagcggag ttcatcaaga 29580
attacatgaa ggtactgtgc ttggtgaccc agcgcggcga gagtgcagga ctggagtgct 29640
tgtgcttggt ggcatcctac gatgtttaca gctgtcagct gcacacacaa gtctttcgta 29700
acacagacta cacttacatt atttctccta caatattatt tctagagata ctttgaaatt 29760
acatagctgt ttttaaaatt tgcttttcct gagtaaccat tttataaagt tgacaattat 29820
tttagagagc tttgttaaaa tgttctttct agttattaca gactttgctt ctagctcagt 29880
gtgcctcatt cgcaggtttt acccaggtgg aagttgataa atcatgaggt gccttaaata 29940
tactcacttt gggaggtctc agtgcctgag gatgggcaga gagacttggt tgagctgaca 30000
tgtttgggac tctgaccatg tgcctggtct taaacgggtg gtcatgacct cctgttacag 30060
tagaggccgt gcagtcctta gcaggggcag acgcacctcc gggtggtcgt gacctcctgt 30120
tgcagtagag gctgttgcaa tccttagcag gggcaaatcc acccctgcaa tctggtccca 30180

-continued tcttgttcca ttttcaaggg ccttgctctt caggttcccc cttccccctt gtcatctggt 30240
ctgagggagc atgtccaccc caagcgcaac acgaacagca gcagccaggc tttccctccc 30300
tcctgccatc tcctgccgct ctgccttcct tgccagcctc actctgctct cctgctccgg 30360
aggcccccac tgtcctcatg gcctgtgtag caagcacata aacactccag tgaacgcgct 30420
ggtctcttcc tgagttcctt tgtgcctgtg gactcgtcat ggtaggggtg cacccctgct 30480
gagtcgtaac ccagggagag ctccacagtc tcgattttca caagcccctc aggaaattaa 30540
ttcttagcgt cccccaacca aagtttgaga cttaatgact gagagccttc agatgggcaa 30600
gaggatcgag gaaactttcc tttctgtctt gtgtgatttg ctatgtgaaa tctctttgaa 30660
agtatggtaa ttactcagta aatctttttc ttttggaatt tacagaaata ttcattgctg 30720
ccttacttga ttttagtatt gaaacagttc cttctgcaga gggacctgaa tgaagttttt 30780
acaggtggaa ttagctcata cagcctaatt ttaatggcca ttagctttct acaggtatgt 30840
atgctttctt gagactgttt ctgttgagac atgtgtaaga gtagactctt ccaaccagtt 30900
gcctagtggg ttccagcagc ctttgctctc cttttactgt attgtttcaa tttggtagag 30960
gctgatttct gattcttaca atcaaaccct cttgattaat gcacctttct ggatgctcat 31020
tttgtactgg gtgtaactgt tggtgcaggg gtgcccgtct ggttctgtga gtccagtgca 31080
catcagtcca agctcaggga attctctgta ttcagaaatg tccatttcat ggtaaacaat 31140
aaacatttct tggtgcttgt ctgtgattta tattgaaaaa aatttgtctc agaataaagt 31200
tgagtaccac atatgagaaa aggatttaca agagagcttt ctcagactga tgaaacatca 31260
ttattttgtc ttaaattata tgtggtcctt attttgctga gtaacatgga aaatctatca 31320
atagaaaacc tacgtgtttt aaaaagtatt gttaaatgct gtgatgtatt gataaactgt 31380
aattatactt tttaaacata taaaatcatc tctaattgga acagtaatta ttccgtttat 31440
attttcttga gtgaagaatt ctgtccttta caaaatcttg cctatataat ttagccgcac 31500
ggctgtattt ctccagtgtt taccattaat ttggtctttg tgattgtgct gagattaccg 31560
aatctgtcca tgatttggta atgttctcac tgtcatgaat gctatgatag tagaatcact 31620
gggtaactac ctgtgatgat cgcagcttcc ttggtctgtc tctgccaaga tgctttaaaa 31680
gtagtgaaaa tggaattcca tgtctgtttt cttacagttc tagtcacact gtcctgtctt 31740
cactttcccc tctgagatgt ggcccttata tatagccttt cttccatagt ttttggacat 31800
tattttgaat taaacatggg cctctgttct ttactgatat actcctgact tgcactattt 31860
tcatggcctt gtagtaacaa cagctactta atactttgat catgcatgtg ccatgtgcca 31920
ggcctgggtc cagggcctcc tccacccccct cagggggtcc tttcagtgat cctgtgaccc 31980
cacaggaggc caccacagca tgagtgggat tcctgtgttc actgccacat ccctgtgcct 32040
tgtccagtgc ccagagcttg tcctgcctca gcggtgtgac tgtggcagca tctgagtttc 32100
ttgactaagt gaggggagga ggcccaccct ggcaccggcc aggctcttgg atatgtgatt 32160
ttggctaaaa gacaaggaat aaggaaggga ataaaggtca ggccagaatc ggaatcctcc 32220
tcttgtgtgg tggaaatatg cagagaactc cggaattctt ctgaacccta aaaacatttg 32280
tatgctttct agctgcagct cctcctggca ctctgtgtta taaatagttt caagcaccgt 32340
gcttctctga gggctttctc tcatgtgccc tcgtccatcc ctttcgagtt ggcactgtcc 32400
gatagaattc tgtgatggtg atggccactt ctgcatggtc cggcaagggg cagggcgcca 32460
catgtggcta ctgagtattg cagtgtggct ggtgagagca acaagctgga tttttaatta 32520

-continued

```
atttgtttta attcatttaa atagacatgt gggcaatgca ggtctggaca gctgagaatt  32580
atgaccctca ggaggtgtgg tggacagtgg tttacttccg aacaagccca gtgcctgctt  32640
ttgaagacga tatggcactg aactgagagt ggtgctcatc tgtgtgacaa gcaggatgga  32700
agcttgctat aaatattgtg atataatgct aatgaccttt acacagctaa aatcaatcct  32760
ttcacttttc cggttttatg tgatactgcc atactagtca gtctaacact gacccctgtt  32820
ggttgtgctt cagcataacg aaattaggat gacgagaatc tgaaattaca tctaccatcc  32880
aggtgactaa gttatgcaga atatagtcca acttatttgc ccatatttgg ttaatcagat  32940
atctgtgttt gcaggaagtt tgctgtatgg attaccaatt tcaaaaatca aactacacta  33000
aaattcagat gagtccgttg tgttcctttt gaacactcct cgttgaagag gctgctgttc  33060
aggcttcctc gtggtgctgg tgagtgagcg agtgccactc actggtattg ccttgaagag  33120
gctgctggac agcagacttc gtcgcgtgct attttcttta gaacatgcca tgaatccata  33180
caaattgtgg gtgcattgct tttacagttg catccaagaa ttgatgcccg gagagctgat  33240
gaaaaccttg gaatgcttct tgtagaattt tttgaactct atgggagaaa ttttaattac  33300
ttgaaaaccg gtattagaat caaagaagga ggtgcctata tcgccaaaga ggagatcatg  33360
aaagccatga ccagcgggta cagaccgtcg atgctgtgca ttgaggaccc cctgctgcca  33420
ggtaagggcg ccctgatctc cactgctgag agctgggcca gcctcgggga cgtgctggtg  33480
acagggcctg tgttggggct ctgagagccc cgggcagttc atttgctctt gatgcaggtt  33540
tctcttatac taaccagtta ataatcacac tttgagaaat ccttatttaa tgcttctaat  33600
taacttttgt ctttctaact gtttacattc tataataaag aagaattaag gaaaatcttt  33660
tctttttctg attattgaag tataacatat ccaccctaaa ccatttgttt ctctgaagta  33720
tgtaatatag aaaaaccatg gatgccataa tccccttttta tttggacatg tatttctcca  33780
ctttttccct atatggatat taatgtttat tattgttatc ttgttgaaca catcccacaa  33840
cgcaaacacg tttgtcactt ggcttttgac ttaacgctta cccttgaccc tttcctatgt  33900
gtgtaggttg tgttttgtcg tgaggattgc cgcattgaag agtctaaggc tgggctagag  33960
gtttcccggt tttattccca ttggcgtatt caggggtatt tatgtcctca ttcctttggt  34020
gacagtcttt taaaatcttt gccaatctga taaaaccatg tgttaacgct tttaaattta  34080
tatttcttta atgattagtg gggttaaaca cattgctatt tatgaattcc acaaattttg  34140
attgagcgtc tgttaggtga gataccattc ttactgttgg tgataaaatc gttggcggac  34200
gggtgacaga acaggtggtg gagagcccag ctccaggcgc gtgtccctgg gccttctcct  34260
ctgtgtggct ctgtgtgctg tccgcccggt tgctggctgc cctcctctgc tgtgtgcaag  34320
gcctgtgtgt gtcggggaag cctttcttgt cacacatgtc atactttttc caatttgttt  34380
tttgcatttg tattttttta ttcagctcct atacatttaa aaaaacacct cagatttaat  34440
ggttgttttt gttttatggc ttctgggatg tgagctttat ttatttccta aagatcgtct  34500
caaggaaaac acattggctg atgtgttttg ttgttgttta tagatggcat gatttgtgca  34560
ggctcttgag tggttttctt ggtagcacgg tatggcagtg tatcatccat ttttgtccgt  34620
tggatgagtc acattggaga cattggcatt gtcttcaagt gtctgctgaa atgtactcaa  34680
aaaacaaaga cccacataat cgttgagtta taatataaat ctagaaaaga taaaactcca  34740
gtacttagaa catatatcct ttaaaagaaa tccacactta acctgattgt gaagaatgag  34800
ttgtttgtag attaaaatta gaaacagtgc ttttcttatg aaaattaagc ttctcctgac  34860
tggcttcctt ggtgactgct gtgacagatt cctttgattt gctgtcccag ttttccacac  34920
```

-continued gtgagaattc acattccatt ctaaaggatt tacttcctgt aggttccatt agcgttgact 34980
gagttgtgat gcacttgggg tgagctgccc ttctacctgc cctgttgggg cactgtgagg 35040
cctcctgatt gtcagatcag cgatcacagt gggtcggtgc tgctggtctg cacaatggta 35100
gtctttggct tcctcatgtt tctgccacct ggagaggtgg ctttttgtgg gctgtcactc 35160
cgtctgtgaa tggcagccgc ctccgtgagg tgggccatga gcacaggggc actgatgatg 35220
cagaccagtc ctctcggcac tcacagactg tgccctgtgc atggtgattg acagggcctt 35280
tgccagtgcc aagtgccacc cgtgcccatt gtgttcgcct gtctgggctt tgctggtagg 35340
gtctggaaga gtttcagtgg tgagggcctg cttcagagtc acttgtatga gaagatccaa 35400
aacatgtgga cgatggtgtg catgtgggga gggtctgaca tagccttttt gctgcaggga 35460
atgacgttgg ccggagctcc tatggcgcca tgcaggtgaa gcaggtcttc gattatgcct 35520
acatagtgct cagccatgct gtgtcaccgc tggccaggtc ctatccaaac agagacgccg 35580
aaaggtaatg ggttgtgtgt ctgcgtctgg gctcagcgtg cctgtgggat ggtacttatc 35640
cctttcctgt gtcatttacc tccatgaaat ttatgaaggg atgttctgcc gtatttcagt 35700
agaatctaga tatgttggtg aaggaaggcc ttctaggaat atgggatggc tgtgtgggat 35760
tcatccatgg ttgagagttg aaaatttctt tcttggagat ttgacatttt cttcagggtc 35820
ttttgttttg gggaggtgat ttctggcttt taaaattcag tccctaccat cttctcttat 35880
gtacactcgt cccttgttct acattttggg gcatttttac agtcccaaaa tgtagtcaga 35940
agtatttact tctcacccag atcattctgt ggtagtggaa agggtggtat ttgaaggggt 36000
gggagatgag ataggaatgg gaaggaagag taacgtggtc gtcaagagtg gaattcgaaa 36060
cagtttgata gatctgttct gtggtggatg atggaataaa caggtttcga ggcctggctc 36120
agcagccgct gcaggtgctg gtggtgctgg agctctgtgt gttcctgagc cgctgtctgc 36180
tcggtgtttt caggcggagc tctgggcccc atgtagggca ctcgtctcgg taccgtctcc 36240
attctcgtcc gtgcagtggg aagtgaaatg tcagcactgt atgatcatcg tgggtgggaa 36300
ggccccgctc ccctacttgg agctgcattt cacagtggtc ttctgtaggt agatgtactg 36360
cgatcccagg gtatgcttga gctgaatcat taaaagtcag agatatttgt caacgtattt 36420
tagctccttt cctactgtcc ttcacctagc gagatgatct gttaggggta taaggtagct 36480
gttcgagagg ggttctcagc tccctgacac ctgttgtact ctgttgatct ccaacaatgt 36540
ccctttgcag tactttagga agaatcatca aagtaactca ggaggtgatt gactaccgga 36600
ggtggatcaa agagaagtgg ggcagcaaag cccacccgtc gccaggcatg ggtgagagat 36660
taattcattt gtgttcatcc taaccactgg ctggcatgtt catgcagaag tgtctctatt 36720
cctttgtggt aaattggtca aattaagaaa atagctagtt tttctgatga gcattaatta 36780
agaagacaat aagatctaga gcagcactgt ccagtagaag caatataatg catgccacac 36840
atagaatttc aaagtttcta ggctgtgtca aatgtgaaaa gaaacaggtg aaataatttt 36900
gatagatttt attccactca agtcaaaata ttaacatttc aacatgtaat caacataaaa 36960
ataattaaga tattttatag ctgtttcttg tactgtctga aatccggtgt gtatttattc 37020
gtacttatag tacatcctaa ttaggatgct aaattttcgt aaaaaatact tgatctatat 37080
ttagatttta gaaagttcac agttgaagat gatttgcata cccaagttat tacaaacatg 37140
tttaatgttt tccaacaact aattgaatgt aatttttaaa attaaattag gcaaaaccta 37200
atgttgggtt tgttagtcac attagcagcg ttcccggctc agcagagccc gtgactgatg 37260

-continued

```
ctgccggggc ggctccacgc cgcagttctc aggagttatt aaccaaggct ttttccctcc  37320
acagacagca ggatcaagat caaagagcga atagccacat gcaatgggga gcagacgcag  37380
aaccgagagc ccgagtctcc ctatggccag cgcttgactt tgtcgctgtc cagcccccag  37440
ctcctgtctt caggctcctc ggcctcttct gtgtcttcac tttctgggag tgacgttgta  37500
agtgccctcc cctcctccgt gtgtctgttg gacagtttgt gtctctggta aatgtccata  37560
gccgcgagct taaaatctcc cccttggttt tgctcaggtt ttgtttcctt gtatgtgtgt  37620
ggaggtgggt ggggggcagc cccgtgatgt gggcaccagg cttcctttcc cctgccgtga  37680
accttcagaa cctgtctgtg cgactcatgc ggctgtcgag ggcagtaatc ctctaaatgg  37740
ttgaactaca gtggacttcc ttgagtagtt tttaaaaatt tatttgaaga ttaaaaaaaa  37800
aattaaatcc aagtatctct tctgtatttc ctttaacatt ctttttcagt tgtgatgaaa  37860
ttacttgaag gaagcctggg taggtttggg ctgcctgttc agaagttaga cttaatttga  37920
ataacctttc atagccagcc tggatgcagg cgtttctttt catagcttta aggaagtagt  37980
agtgcacctt tgtggtacag ctgtcctttt tgttttttgt accgggttca aggattcaga  38040
cacaccgccc tgcacaacgc ccagtgttta ccagttcagt ctgcaagcgc cagctcctct  38100
catggccggc ttacccaccg ccttgccaat gcccagtggc aaacctcagc ccaccacttc  38160
cagaacactg atcatgacaa ccaacaatca ggtacgtggc cctctggcac ccttcccgct  38220
ggtggcccct gggaacagca tccgagctgt gatatgcact agaggagatt gatggtcctt  38280
tgaattagaa gagtaacttt ttgagtattt ggccattggt gtgttgttct aggaaatcct  38340
ctctttttttg tggtgttgag gtcccccatg tatagtttca gcagcgagga cactgtggtt  38400
cttgagtgct gccgtggctt ttcacggggg ccaggttgac tgccttcctg caagtttcct  38460
cactgcccca gcatgagact gctgtcgagg gtcatcttga gagagcgact cagtcacgac  38520
ccacttagct gggcgccaag ccgtgccaga cacttgtccc tacttcctct cagaatctca  38580
atgaaagttt taatgtgaac ttattagact tttttcatgt ttgaaattag gcataatttc  38640
taaggctttt tctgttggaa tatactgttt ttaaaattta gataaaatta gaaatctaaa  38700
ggataatttt ataaatacta aattttgtat ctacttgcga ttatacatca cttgaatatg  38760
tgtgggtata aaacccaaca tgttaattga cttaaaacca ttttctgaaa tgtggggtat  38820
aatttgagca taaagctatg taggtacatg caaaagtgtt ttgactcatt tcttggagtt  38880
ttgcactctg ctctggggaa gacattctca caggatccac cgtgattctg gcggagcttc  38940
tgggatgctg gctctgtaat gacccacaga gctgatgagc agagccatgg cccagccgga  39000
caccgtaacg tgtctaattg cagcataagt gtaaaattca ggggcaatta tttacactct  39060
taaaatgaat tataccacag ataaacttgg tcgccttttt atggtcatca cagtggccct  39120
gacgtcctgg ccatgtgtca caaaggtgtt tgttttaacc acccacaagc cttggggccc  39180
ttgagagccc agtgcggctg ctgagctaca gagccacact ctgcggctgc ttgtgtggtt  39240
cgagtgtgaa gtccagggac gctgagggtt tataggtttt tatctaagaa gactcttggc  39300
cacagtcaat ctccagaggt tgttggggta aatgcacggg atgccaagat gcaaccaggt  39360
cagtattgca agtctgagaa aaggggttct cgttagcgca cttctgctgc tgacagtaac  39420
gggtgatgct gacatagaag cagcctggga cctggacagc aggcaaggaa ggaactgcca  39480
gccgtcccac ggcctctcag gccaccagtt gggccagcct tgggctgtga cccctgagtt  39540
cagcgtgtga gtagggggtt caccacgggg gtgacggttg ttcttctgat gactctaatg  39600
tcttgatcgt ttgatcttca atgagtttca aactttatga cttggattac tgggcatact  39660
```

-continued ttatatgcca gttgctgttt tagaatacga agtatttcca attcaaagca caatattgtt 39720
aggtaatagt aaaacagact gctctatgga gcccacatgc aactgtgcca tttatcagct 39780
gccctttggt ggtgctgagc ttagaagccg gatggttttc ctctgattgc tttggtaccc 39840
atggccgtct ctcattttgt tcctagacca ggtttactat acctccaccg accctagggg 39900
ttgctcctgt tccttgcaga caagctggtg tagaaggaac tgcgtctttg aaagccgtcc 39960
accacatgtc ttccccggcc attccctcag cgtcccccaa cccgctctcg agccctcatc 40020
tgtatcataa ggtatagctc tgtcctggtg cattcaccta cctgttcaag ctgccatgtg 40080
agaggcggtg ctaaatgttt tctcctccag agagaattcc agagagatca tttgaaaacg 40140
gaatttgctt tgttgtcatt cagcctgttt gcttgtcttt ccaaacaaaa cttaaaaaag 40200
ttaaattatt ttaagatgta atatatagtt taattggttg ccacaaacat ctcttaattc 40260
ctctgttgaa ctgattagca taaaactgaa gtttgaaata aggctcaaaa tgaagacttt 40320
tcccatttac ataattcatt tatatgctaa ataccttggt tttcaagaag caaatgataa 40380
aaccaagagc agatcttgcc atgatgtccc gtgtatgctg ctgtcattcc cacgttgcct 40440
gatccccgcc tggggcagga gcaagcgtca gggctggcag agctgtgtgc tgggcctcag 40500
cagggccctg gcatgcgtgc ccttgtggct cctctcaagt ccagctgtgt gcatggagga 40560
aacaggtcac gttaagtctc tatattcttg aagtacctga atgattggga gagccatggc 40620
gaggatcttc caggtcagcc cccgtcgtgt gtgatgttcc ttgggctctg cggatgctcg 40680
gtgctttcat cggtgtccac acctctttat tccgctcctc ctttgcttgt ctaatcctat 40740
tttgccagta agttttttat tcttgaggct ttgttggccc tgtgttgtat gatgattgtt 40800
tttaggagtt aagtaataga acatttcctc ttggatttat ccatccccga tagacacatt 40860
cagggtgaaa gaacaacttc gcacaccggc ctcttctttg cattttggct ttgctttccc 40920
agtctcctcc tgctgttttt cttgctctga gactttcctg aagccggcgt gtgttccctc 40980
tcagtctgct tggccgcgac tttgcagtgc agggaatgtg ctttgggtgt agcccaagca 41040
caggctgctg catgctggga tcgacaggct gctgagggcg agagcgccag gtcctggcac 41100
gtgtgacttg cttggttctt tctagaaggt cacagctggg ggaagaacat gacagggacc 41160
ttcttacttc tgtttttttg gagacagaat ctcactccat cacccaggct ggagtgcagt 41220
ggtgtgatct cagctcactg caacctccgc ctcccgggtt caagcaattc ttgtgcctca 41280
gcttcttgag tagctggaat tacaggtgtg tgccaccaca cccagccaat ttttgtattt 41340
ttagtagaga cggggtttca ccatgttggt caggctggtc tcaagctcct gacctcaagt 41400
gacatgcctg cctcggcctc ccaaagtggt ggaattacag gtgcaagcca ttggcacctg 41460
gctagggacc ttcttatttc tatggataag tggaacaagt tagaagtgag gttctgctga 41520
atttgtgtgg tttgatcctg gtacatggtt cttgccttta gtcattcacg gaatgggaag 41580
aatgcttttc tctcagatgg aggagttggg aagtcccaga gggcaggtgt ccatccctgc 41640
tctctatgta acatcacgtc ggtgcttagt gtggtcactg cccgaggacg tgggcattgt 41700
gcctgctgtc tggctccaac actgctgtct ctctctttct ccagcagcac aacggcatga 41760
aactgtccat gaagggctct cacggccaca cccaaggcgg cggctacagc tctgtgggta 41820
gcggaggtgt gcggcccccct gtgggcaaca ggggacacca ccagtataac cgcaccggct 41880
ggaggaggaa aaaacacaca cacacacggg acagtctgcc cgtgagcctc agcagataat 41940
ggctcctggc tgcgtcagcc tcccccaccc ctctgcagac tgccccgcgg cctcggccac 42000

```
cggcagggga accgagacca gcaccccgca cgtcagccgg gctcgcggca cgcccgccgc  42060
tgatcactct gcatgtttct tcgtgtggtg gtcgcgtcca tcttcaagaa cagctcgttg  42120
tgctcatctg tgaagcctta ttaaacgtgg acgttgtttt ctgccttccc aggattcttc  42180
cttcagtgct gaggcaggtc gggctcagga actgcaggga cgtgaacatg cgcttgcggt  42240
ttgaggtagc cgtgtctgtt ccttcgcggt ttgctatttt catttcctgt tcgtcaaagc  42300
agcagaggag atcaaacccc gttcgtgtgt ctttcctcca cggataagct tgggaggtca  42360
ttgttttact gccctcacat tttgtttgaa atttcagaac tgtttttcta tgtaaatatt  42420
gaaaacttat gatttgtgca ataactcaga tattttttat ttaatttcct attttcacat  42480
aagttatatt taagggagga gggaattttt tttaaacaag cttaggtcct ttcccgagct  42540
gcattttcta agttgggtca tcgtgtcggc tggttgtctg acgagcatcg ttacaaacac  42600
catgatgagg ggtttggggt tttattttga tgtcttttct tttggtcgga agtgagtgaa  42660
ggagccaggt cgccctgaag gttttccaaa gggcttggct ccagagccac ctggcagact  42720
gcccgtggcc ctgctgtcgg gccccaggcc gttgtcctgc tctgaccaca gagttttaat  42780
gttttggttt tcacttcttt taaactggac aacaaatcca gcatttcaag tgccagaagt  42840
ataactttct aaggagagaa gggttgtcac attataaaat ctttaggaaa atgtgaactg  42900
gaaaacgctt cggtcagttt tagtgacata gcctgtgatg atgggtctgg tgactattat  42960
tgcggaccgt ggtacccagt tttaggaatg tggagaaagg aattctgttg attccgttga  43020
ggaatctgta gcgtatgcat tcgttctgtt aagagcaaat ctaggagaag tgcttcagct  43080
gcccagtgcg ccgtggggag tgttttaacg gatcgtgtcg caggagagca cagcccagcg  43140
ttggggccgg gaccgctggc gcccgacgtc ggaagcatac aggtatacta tgcaagtgta  43200
ttctgccaca acaaccactg tctttgttac cttttttga acaagaatat atccatcctg  43260
cctaaccctg agtttttgga gcaccacagt tgtcctggga gttggttgca tcttgtaggc  43320
catctgactt cctgttttta aaacgggggt ctggtcttgc taaacactac aggtaggttg  43380
gtctttgaag tccactagtg gagaatgtca agacaagata cttattacca tgacatctga  43440
tgcatgtgca gcagtgggga gttctagatt gatctctgaa tgtgatcgac gcccagcaag  43500
gacaagcttt aaaatgtctg cggtctgccc ttttgaagca ggactggctc actctgtcat  43560
tgggagctgt cagctgcgac tgcaggttct ctaggaggca ttccagaata gagtagcaca  43620
ctgtgtctgc agttctcgat gaccgaaagt tatcaaaaat atttaaaata tttaaattgt  43680
gaacctattg ataaagaata tttataaaaa ctgatctgta ggcctgtact aatctctacg  43740
cattagcaat attgactgta aacccacatt aaggaaacca ctacgggtct ggcagtgcgt  43800
gtcccgtggg gtgtgcattt taaaactcga ttcatagaca caggtaccat gttccatttc  43860
cgtcatggtg aagcaaatga attggcctgg ctaccactgt ggtcgcgtgc tacaggtttg  43920
acaaaaagat atcatgtttc gatttttttg tgtgtggaca acaatatgga agctaaaatt  43980
gacatatttt tatgtaaagt ttttctattc tttgattttt aataaacttt ggaaaccagt  44040
tt                                                                 44042
```

<210> SEQ ID NO 12
<211> LENGTH: 19
<212> TYPE: DNA
<213> ORGANISM: Artificial sequence
<220> FEATURE:
<223> OTHER INFORMATION: oligonucleotide motif

<400> SEQUENCE: 12
agggtagatg tgtttaact 19

<210> SEQ ID NO 13
<211> LENGTH: 17
<212> TYPE: DNA
<213> ORGANISM: Artificial sequence
<220> FEATURE:
<223> OTHER INFORMATION: oligonucleotide motif

<400> SEQUENCE: 13
cagcctaaac ttagtgg 17

<210> SEQ ID NO 14
<211> LENGTH: 20
<212> TYPE: DNA
<213> ORGANISM: Artificial sequence
<220> FEATURE:
<223> OTHER INFORMATION: oligonucleotide motif

<400> SEQUENCE: 14
aagccctcaa tgtaaaacac 20

<210> SEQ ID NO 15
<211> LENGTH: 19
<212> TYPE: DNA
<213> ORGANISM: Artificial sequence
<220> FEATURE:
<223> OTHER INFORMATION: oligonucleotide motif

<400> SEQUENCE: 15
aatagcaagt agaggagag 19

<210> SEQ ID NO 16
<211> LENGTH: 18
<212> TYPE: DNA
<213> ORGANISM: Artificial sequence
<220> FEATURE:
<223> OTHER INFORMATION: oligonucleotide motif

<400> SEQUENCE: 16
aaataaggat actggcga 18

<210> SEQ ID NO 17
<211> LENGTH: 20
<212> TYPE: DNA
<213> ORGANISM: Artificial sequence
<220> FEATURE:
<223> OTHER INFORMATION: oligonucleotide motif

<400> SEQUENCE: 17
gagggaacac ataataaaag 20

<210> SEQ ID NO 18
<211> LENGTH: 18
<212> TYPE: DNA
<213> ORGANISM: Artificial sequence
<220> FEATURE:
<223> OTHER INFORMATION: oligonucleotide motif

<400> SEQUENCE: 18
gtaatacctc tcacattc 18

<210> SEQ ID NO 19
<211> LENGTH: 19
<212> TYPE: DNA

<213> ORGANISM: Artificial sequence
<220> FEATURE:
<223> OTHER INFORMATION: oligonucleotide motif

<400> SEQUENCE: 19
agtaacacca atctcattg 19

<210> SEQ ID NO 20
<211> LENGTH: 19
<212> TYPE: DNA
<213> ORGANISM: Artificial sequence
<220> FEATURE:
<223> OTHER INFORMATION: oligonucleotide motif

<400> SEQUENCE: 20
gtgacagtat tcaatgatc 19

<210> SEQ ID NO 21
<211> LENGTH: 18
<212> TYPE: DNA
<213> ORGANISM: Artificial sequence
<220> FEATURE:
<223> OTHER INFORMATION: oligonucleotide motif

<400> SEQUENCE: 21
cagttccgta tcaccaac 18

<210> SEQ ID NO 22
<211> LENGTH: 20
<212> TYPE: DNA
<213> ORGANISM: Artificial sequence
<220> FEATURE:
<223> OTHER INFORMATION: oligonucleotide motif

<400> SEQUENCE: 22
aagtctaact caaagccatc 20

<210> SEQ ID NO 23
<211> LENGTH: 19
<212> TYPE: DNA
<213> ORGANISM: Artificial sequence
<220> FEATURE:
<223> OTHER INFORMATION: oligonucleotide motif

<400> SEQUENCE: 23
aggcttccat tttattgaa 19

<210> SEQ ID NO 24
<211> LENGTH: 18
<212> TYPE: DNA
<213> ORGANISM: Artificial sequence
<220> FEATURE:
<223> OTHER INFORMATION: oligonucleotide motif

<400> SEQUENCE: 24
ttttagaaaa cgaggcta 18

<210> SEQ ID NO 25
<211> LENGTH: 17
<212> TYPE: DNA
<213> ORGANISM: Artificial sequence
<220> FEATURE:
<223> OTHER INFORMATION: oligonucleotide motif

<400> SEQUENCE: 25
gtattcttat tcttgct 17

<210> SEQ ID NO 26
<211> LENGTH: 18
<212> TYPE: DNA
<213> ORGANISM: Artificial sequence
<220> FEATURE:
<223> OTHER INFORMATION: oligonucleotide motif

<400> SEQUENCE: 26
attattccca cagtaaga 18

<210> SEQ ID NO 27
<211> LENGTH: 19
<212> TYPE: DNA
<213> ORGANISM: Artificial sequence
<220> FEATURE:
<223> OTHER INFORMATION: oligonucleotide motif

<400> SEQUENCE: 27
aacaacaaac aggatgggc 19

<210> SEQ ID NO 28
<211> LENGTH: 19
<212> TYPE: DNA
<213> ORGANISM: Artificial sequence
<220> FEATURE:
<223> OTHER INFORMATION: oligonucleotide motif

<400> SEQUENCE: 28
atatccacaa tattctgat 19

<210> SEQ ID NO 29
<211> LENGTH: 20
<212> TYPE: DNA
<213> ORGANISM: Artificial sequence
<220> FEATURE:
<223> OTHER INFORMATION: oligonucleotide motif

<400> SEQUENCE: 29
aaagaaataa tgtcgtctgg 20

<210> SEQ ID NO 30
<211> LENGTH: 17
<212> TYPE: DNA
<213> ORGANISM: Artificial sequence
<220> FEATURE:
<223> OTHER INFORMATION: oligonucleotide motif

<400> SEQUENCE: 30
ccagagtaaa caaatcc 17

<210> SEQ ID NO 31
<211> LENGTH: 20
<212> TYPE: DNA
<213> ORGANISM: Artificial sequence
<220> FEATURE:
<223> OTHER INFORMATION: oligonucleotide motif

<400> SEQUENCE: 31
attcaacatt tttagtcacc 20

<210> SEQ ID NO 32
<211> LENGTH: 20
<212> TYPE: DNA
<213> ORGANISM: Artificial sequence
<220> FEATURE:

<223> OTHER INFORMATION: oligonucleotide motif

<400> SEQUENCE: 32
tttggtaatt cttttttag 20

<210> SEQ ID NO 33
<211> LENGTH: 20
<212> TYPE: DNA
<213> ORGANISM: Artificial sequence
<220> FEATURE:
<223> OTHER INFORMATION: oligonucleotide motif

<400> SEQUENCE: 33
caatgaggaa acaagagtca 20

<210> SEQ ID NO 34
<211> LENGTH: 20
<212> TYPE: DNA
<213> ORGANISM: Artificial sequence
<220> FEATURE:
<223> OTHER INFORMATION: oligonucleotide motif

<400> SEQUENCE: 34
ttcaaaataa tgtgggaggt 20

<210> SEQ ID NO 35
<211> LENGTH: 20
<212> TYPE: DNA
<213> ORGANISM: Artificial sequence
<220> FEATURE:
<223> OTHER INFORMATION: oligonucleotide motif

<400> SEQUENCE: 35
ggatatttga tacggcaaat 20

<210> SEQ ID NO 36
<211> LENGTH: 17
<212> TYPE: DNA
<213> ORGANISM: Artificial sequence
<220> FEATURE:
<223> OTHER INFORMATION: oligonucleotide motif

<400> SEQUENCE: 36
ctataagaag caaaccc 17

<210> SEQ ID NO 37
<211> LENGTH: 20
<212> TYPE: DNA
<213> ORGANISM: Artificial sequence
<220> FEATURE:
<223> OTHER INFORMATION: oligonucleotide motif

<400> SEQUENCE: 37
atataattca cgtttcactt 20

<210> SEQ ID NO 38
<211> LENGTH: 20
<212> TYPE: DNA
<213> ORGANISM: Artificial sequence
<220> FEATURE:
<223> OTHER INFORMATION: oligonucleotide motif

<400> SEQUENCE: 38
aatgattcac atgaaggtta 20

<210> SEQ ID NO 39
<211> LENGTH: 17
<212> TYPE: DNA
<213> ORGANISM: Artificial sequence
<220> FEATURE:
<223> OTHER INFORMATION: oligonucleotide motif

<400> SEQUENCE: 39
gttaggattt tgctatg 17

<210> SEQ ID NO 40
<211> LENGTH: 19
<212> TYPE: DNA
<213> ORGANISM: Artificial sequence
<220> FEATURE:
<223> OTHER INFORMATION: oligonucleotide motif

<400> SEQUENCE: 40
gtacaaatat caaccgtat 19

<210> SEQ ID NO 41
<211> LENGTH: 20
<212> TYPE: DNA
<213> ORGANISM: Artificial sequence
<220> FEATURE:
<223> OTHER INFORMATION: oligonucleotide motif

<400> SEQUENCE: 41
cacactattt caagatgcta 20

<210> SEQ ID NO 42
<211> LENGTH: 20
<212> TYPE: DNA
<213> ORGANISM: Artificial sequence
<220> FEATURE:
<223> OTHER INFORMATION: oligonucleotide motif

<400> SEQUENCE: 42
cacctataca atggagtatt 20

<210> SEQ ID NO 43
<211> LENGTH: 20
<212> TYPE: DNA
<213> ORGANISM: Artificial sequence
<220> FEATURE:
<223> OTHER INFORMATION: oligonucleotide motif

<400> SEQUENCE: 43
atcatacgtc attagagaac 20

<210> SEQ ID NO 44
<211> LENGTH: 19
<212> TYPE: DNA
<213> ORGANISM: Artificial sequence
<220> FEATURE:
<223> OTHER INFORMATION: oligonucleotide motif

<400> SEQUENCE: 44
cagaacagat actttgcca 19

<210> SEQ ID NO 45
<211> LENGTH: 19
<212> TYPE: DNA
<213> ORGANISM: Artificial sequence
<220> FEATURE:
<223> OTHER INFORMATION: oligonucleotide motif

<400> SEQUENCE: 45
aagaatggtt ggttaaggg 19

<210> SEQ ID NO 46
<211> LENGTH: 20
<212> TYPE: DNA
<213> ORGANISM: Artificial sequence
<220> FEATURE:
<223> OTHER INFORMATION: oligonucleotide motif

<400> SEQUENCE: 46
agaattggta aactggactg 20

<210> SEQ ID NO 47
<211> LENGTH: 17
<212> TYPE: DNA
<213> ORGANISM: Artificial sequence
<220> FEATURE:
<223> OTHER INFORMATION: oligonucleotide motif

<400> SEQUENCE: 47
agaattatat tggctgg 17

<210> SEQ ID NO 48
<211> LENGTH: 20
<212> TYPE: DNA
<213> ORGANISM: Artificial sequence
<220> FEATURE:
<223> OTHER INFORMATION: oligonucleotide motif

<400> SEQUENCE: 48
cctaaaccag acagaaaaga 20

<210> SEQ ID NO 49
<211> LENGTH: 19
<212> TYPE: DNA
<213> ORGANISM: Artificial sequence
<220> FEATURE:
<223> OTHER INFORMATION: oligonucleotide motif

<400> SEQUENCE: 49
accaattaga gcagaaatc 19

<210> SEQ ID NO 50
<211> LENGTH: 20
<212> TYPE: DNA
<213> ORGANISM: Artificial sequence
<220> FEATURE:
<223> OTHER INFORMATION: oligonucleotide motif

<400> SEQUENCE: 50
ttctaaataa cagatgggtc 20

<210> SEQ ID NO 51
<211> LENGTH: 20
<212> TYPE: DNA
<213> ORGANISM: Artificial sequence
<220> FEATURE:
<223> OTHER INFORMATION: oligonucleotide motif

<400> SEQUENCE: 51
tttataattt ttttccatct 20

<210> SEQ ID NO 52
<211> LENGTH: 20

<212> TYPE: DNA
<213> ORGANISM: Artificial sequence
<220> FEATURE:
<223> OTHER INFORMATION: oligonucleotide motif

<400> SEQUENCE: 52
gcaaatatca gattaacctc 20

<210> SEQ ID NO 53
<211> LENGTH: 20
<212> TYPE: DNA
<213> ORGANISM: Artificial sequence
<220> FEATURE:
<223> OTHER INFORMATION: oligonucleotide motif

<400> SEQUENCE: 53
aacggtatgg cagaagacaa 20

<210> SEQ ID NO 54
<211> LENGTH: 17
<212> TYPE: DNA
<213> ORGANISM: Artificial sequence
<220> FEATURE:
<223> OTHER INFORMATION: oligonucleotide motif

<400> SEQUENCE: 54
ttcaaccttt actgcat 17

<210> SEQ ID NO 55
<211> LENGTH: 20
<212> TYPE: DNA
<213> ORGANISM: Artificial sequence
<220> FEATURE:
<223> OTHER INFORMATION: oligonucleotide motif

<400> SEQUENCE: 55
actgataaag ggcatttcaa 20

<210> SEQ ID NO 56
<211> LENGTH: 17
<212> TYPE: DNA
<213> ORGANISM: Artificial sequence
<220> FEATURE:
<223> OTHER INFORMATION: oligonucleotide motif

<400> SEQUENCE: 56
cagtaggaat gtggctt 17

<210> SEQ ID NO 57
<211> LENGTH: 19
<212> TYPE: DNA
<213> ORGANISM: Artificial sequence
<220> FEATURE:
<223> OTHER INFORMATION: oligonucleotide motif

<400> SEQUENCE: 57
ttttatggca gggtttcac 19

<210> SEQ ID NO 58
<211> LENGTH: 17
<212> TYPE: DNA
<213> ORGANISM: Artificial sequence
<220> FEATURE:
<223> OTHER INFORMATION: oligonucleotide motif

<400> SEQUENCE: 58
tcactgttaa acctcac 17

<210> SEQ ID NO 59
<211> LENGTH: 20
<212> TYPE: DNA
<213> ORGANISM: Artificial sequence
<220> FEATURE:
<223> OTHER INFORMATION: oligonucleotide motif

<400> SEQUENCE: 59
caattttcta attcaatggt 20

<210> SEQ ID NO 60
<211> LENGTH: 19
<212> TYPE: DNA
<213> ORGANISM: Artificial sequence
<220> FEATURE:
<223> OTHER INFORMATION: oligonucleotide motif

<400> SEQUENCE: 60
aagatataat tcacccact 19

<210> SEQ ID NO 61
<211> LENGTH: 19
<212> TYPE: DNA
<213> ORGANISM: Artificial sequence
<220> FEATURE:
<223> OTHER INFORMATION: oligonucleotide motif

<400> SEQUENCE: 61
gccacataaa ggataaagt 19

<210> SEQ ID NO 62
<211> LENGTH: 19
<212> TYPE: DNA
<213> ORGANISM: Artificial sequence
<220> FEATURE:
<223> OTHER INFORMATION: oligonucleotide motif

<400> SEQUENCE: 62
cccattagaa gtaaggtga 19

<210> SEQ ID NO 63
<211> LENGTH: 19
<212> TYPE: DNA
<213> ORGANISM: Artificial sequence
<220> FEATURE:
<223> OTHER INFORMATION: oligonucleotide motif

<400> SEQUENCE: 63
atgtaaatta aaacttccc 19

<210> SEQ ID NO 64
<211> LENGTH: 20
<212> TYPE: DNA
<213> ORGANISM: Artificial sequence
<220> FEATURE:
<223> OTHER INFORMATION: oligonucleotide motif

<400> SEQUENCE: 64
tgagagcata aaagtacgga 20

<210> SEQ ID NO 65
<211> LENGTH: 18
<212> TYPE: DNA
<213> ORGANISM: Artificial sequence
<220> FEATURE:
<223> OTHER INFORMATION: oligonucleotide motif

<400> SEQUENCE: 65
ttcacaacag gtaaaggg 18

<210> SEQ ID NO 66
<211> LENGTH: 20
<212> TYPE: DNA
<213> ORGANISM: Artificial sequence
<220> FEATURE:
<223> OTHER INFORMATION: oligonucleotide motif

<400> SEQUENCE: 66
tgcattccta agtaacataa 20

<210> SEQ ID NO 67
<211> LENGTH: 20
<212> TYPE: DNA
<213> ORGANISM: Artificial sequence
<220> FEATURE:
<223> OTHER INFORMATION: oligonucleotide motif

<400> SEQUENCE: 67
agagaaaagt gatgagggaa 20

<210> SEQ ID NO 68
<211> LENGTH: 19
<212> TYPE: DNA
<213> ORGANISM: Artificial sequence
<220> FEATURE:
<223> OTHER INFORMATION: oligonucleotide motif

<400> SEQUENCE: 68
atacggatca ccagctaaa 19

<210> SEQ ID NO 69
<211> LENGTH: 19
<212> TYPE: DNA
<213> ORGANISM: Artificial sequence
<220> FEATURE:
<223> OTHER INFORMATION: oligonucleotide motif

<400> SEQUENCE: 69
catgttatgc acagaagat 19

<210> SEQ ID NO 70
<211> LENGTH: 20
<212> TYPE: DNA
<213> ORGANISM: Artificial sequence
<220> FEATURE:
<223> OTHER INFORMATION: oligonucleotide motif

<400> SEQUENCE: 70
cgctgaagaa ctaagtatta 20

<210> SEQ ID NO 71
<211> LENGTH: 19
<212> TYPE: DNA
<213> ORGANISM: Artificial sequence
<220> FEATURE:
<223> OTHER INFORMATION: oligonucleotide motif

<400> SEQUENCE: 71
caaacagatg gtggtgata 19

<210> SEQ ID NO 72
<211> LENGTH: 16
<212> TYPE: DNA
<213> ORGANISM: Artificial sequence
<220> FEATURE:
<223> OTHER INFORMATION: oligonucleotide motif

<400> SEQUENCE: 72
agtagccatt aggatg 16

<210> SEQ ID NO 73
<211> LENGTH: 19
<212> TYPE: DNA
<213> ORGANISM: Artificial sequence
<220> FEATURE:
<223> OTHER INFORMATION: oligonucleotide motif

<400> SEQUENCE: 73
atacacaggc tccataata 19

<210> SEQ ID NO 74
<211> LENGTH: 20
<212> TYPE: DNA
<213> ORGANISM: Artificial sequence
<220> FEATURE:
<223> OTHER INFORMATION: oligonucleotide motif

<400> SEQUENCE: 74
gatttttgta tagtccacaa 20

<210> SEQ ID NO 75
<211> LENGTH: 20
<212> TYPE: DNA
<213> ORGANISM: Artificial sequence
<220> FEATURE:
<223> OTHER INFORMATION: oligonucleotide motif

<400> SEQUENCE: 75
gcatctataa aaaagggaca 20

<210> SEQ ID NO 76
<211> LENGTH: 15
<212> TYPE: DNA
<213> ORGANISM: Artificial sequence
<220> FEATURE:
<223> OTHER INFORMATION: oligonucleotide motif

<400> SEQUENCE: 76
agtgcaagta tcgct 15

<210> SEQ ID NO 77
<211> LENGTH: 20
<212> TYPE: DNA
<213> ORGANISM: Artificial sequence
<220> FEATURE:
<223> OTHER INFORMATION: oligonucleotide motif

<400> SEQUENCE: 77
ccaaaagaat caagttcgta 20

<210> SEQ ID NO 78
<211> LENGTH: 19
<212> TYPE: DNA
<213> ORGANISM: Artificial sequence
<220> FEATURE:
<223> OTHER INFORMATION: oligonucleotide motif

<400> SEQUENCE: 78
cctcagacca aatttattt 19

<210> SEQ ID NO 79
<211> LENGTH: 20
<212> TYPE: DNA
<213> ORGANISM: Artificial sequence
<220> FEATURE:
<223> OTHER INFORMATION: oligonucleotide motif

<400> SEQUENCE: 79
ttcaacaagc atctattgta 20

<210> SEQ ID NO 80
<211> LENGTH: 18
<212> TYPE: DNA
<213> ORGANISM: Artificial sequence
<220> FEATURE:
<223> OTHER INFORMATION: oligonucleotide motif

<400> SEQUENCE: 80
caaaggttgt tgtactct 18

<210> SEQ ID NO 81
<211> LENGTH: 19
<212> TYPE: DNA
<213> ORGANISM: Artificial sequence
<220> FEATURE:
<223> OTHER INFORMATION: oligonucleotide motif

<400> SEQUENCE: 81
tcataaatct ttttccacg 19

<210> SEQ ID NO 82
<211> LENGTH: 20
<212> TYPE: DNA
<213> ORGANISM: Artificial sequence
<220> FEATURE:
<223> OTHER INFORMATION: oligonucleotide motif

<400> SEQUENCE: 82
cttgttacgg atttaatgtg 20

<210> SEQ ID NO 83
<211> LENGTH: 18
<212> TYPE: DNA
<213> ORGANISM: Artificial sequence
<220> FEATURE:
<223> OTHER INFORMATION: oligonucleotide motif

<400> SEQUENCE: 83
gctataaaaa tagaagcc 18

<210> SEQ ID NO 84
<211> LENGTH: 19
<212> TYPE: DNA
<213> ORGANISM: Artificial sequence
<220> FEATURE:
<223> OTHER INFORMATION: oligonucleotide motif

<400> SEQUENCE: 84
tccttagcaa actaaacat 19

<210> SEQ ID NO 85

<211> LENGTH: 20
<212> TYPE: DNA
<213> ORGANISM: Artificial sequence
<220> FEATURE:
<223> OTHER INFORMATION: oligonucleotide motif

<400> SEQUENCE: 85
agcaaaaggc aggtattcaa 20

<210> SEQ ID NO 86
<211> LENGTH: 20
<212> TYPE: DNA
<213> ORGANISM: Artificial sequence
<220> FEATURE:
<223> OTHER INFORMATION: oligonucleotide motif

<400> SEQUENCE: 86
gaatccattt acatattcac 20

<210> SEQ ID NO 87
<211> LENGTH: 19
<212> TYPE: DNA
<213> ORGANISM: Artificial sequence
<220> FEATURE:
<223> OTHER INFORMATION: oligonucleotide motif

<400> SEQUENCE: 87
tccagtatcc aaaacatac 19

<210> SEQ ID NO 88
<211> LENGTH: 19
<212> TYPE: DNA
<213> ORGANISM: Artificial sequence
<220> FEATURE:
<223> OTHER INFORMATION: oligonucleotide motif

<400> SEQUENCE: 88
agcttaaaga agaacggtt 19

<210> SEQ ID NO 89
<211> LENGTH: 17
<212> TYPE: DNA
<213> ORGANISM: Artificial sequence
<220> FEATURE:
<223> OTHER INFORMATION: oligonucleotide motif

<400> SEQUENCE: 89
cacaacgtgc ctacctt 17

<210> SEQ ID NO 90
<211> LENGTH: 19
<212> TYPE: DNA
<213> ORGANISM: Artificial sequence
<220> FEATURE:
<223> OTHER INFORMATION: oligonucleotide motif

<400> SEQUENCE: 90
ccagaatcca agaaaatgg 19

<210> SEQ ID NO 91
<211> LENGTH: 20
<212> TYPE: DNA
<213> ORGANISM: Artificial sequence
<220> FEATURE:
<223> OTHER INFORMATION: oligonucleotide motif

<400> SEQUENCE: 91
tcacctcgaa ctaaacaagt 20

<210> SEQ ID NO 92
<211> LENGTH: 18
<212> TYPE: DNA
<213> ORGANISM: Artificial sequence
<220> FEATURE:
<223> OTHER INFORMATION: oligonucleotide motif

<400> SEQUENCE: 92
gtatctttct gtactatt 18

<210> SEQ ID NO 93
<211> LENGTH: 19
<212> TYPE: DNA
<213> ORGANISM: Artificial sequence
<220> FEATURE:
<223> OTHER INFORMATION: oligonucleotide motif

<400> SEQUENCE: 93
gtcattctac taacaaacg 19

<210> SEQ ID NO 94
<211> LENGTH: 19
<212> TYPE: DNA
<213> ORGANISM: Artificial sequence
<220> FEATURE:
<223> OTHER INFORMATION: oligonucleotide motif

<400> SEQUENCE: 94
tggaaaagga agaaccatt 19

<210> SEQ ID NO 95
<211> LENGTH: 19
<212> TYPE: DNA
<213> ORGANISM: Artificial sequence
<220> FEATURE:
<223> OTHER INFORMATION: oligonucleotide motif

<400> SEQUENCE: 95
aatacaactc ttccgtgat 19

<210> SEQ ID NO 96
<211> LENGTH: 17
<212> TYPE: DNA
<213> ORGANISM: Artificial sequence
<220> FEATURE:
<223> OTHER INFORMATION: oligonucleotide motif

<400> SEQUENCE: 96
aataccctga cgagctg 17

<210> SEQ ID NO 97
<211> LENGTH: 20
<212> TYPE: DNA
<213> ORGANISM: Artificial sequence
<220> FEATURE:
<223> OTHER INFORMATION: oligonucleotide motif

<400> SEQUENCE: 97
tcataaaaca tgatccttgc 20

<210> SEQ ID NO 98
<211> LENGTH: 19
<212> TYPE: DNA

<213> ORGANISM: Artificial sequence
<220> FEATURE:
<223> OTHER INFORMATION: oligonucleotide motif

<400> SEQUENCE: 98
ctaaagcaga tccatagaa 19

<210> SEQ ID NO 99
<211> LENGTH: 20
<212> TYPE: DNA
<213> ORGANISM: Artificial sequence
<220> FEATURE:
<223> OTHER INFORMATION: oligonucleotide motif

<400> SEQUENCE: 99
agactataac ttttgctaca 20

<210> SEQ ID NO 100
<211> LENGTH: 20
<212> TYPE: DNA
<213> ORGANISM: Artificial sequence
<220> FEATURE:
<223> OTHER INFORMATION: oligonucleotide motif

<400> SEQUENCE: 100
agcaatgact tgaacatagt 20

<210> SEQ ID NO 101
<211> LENGTH: 19
<212> TYPE: DNA
<213> ORGANISM: Artificial sequence
<220> FEATURE:
<223> OTHER INFORMATION: oligonucleotide motif

<400> SEQUENCE: 101
ataaaacaag catacgggc 19

<210> SEQ ID NO 102
<211> LENGTH: 19
<212> TYPE: DNA
<213> ORGANISM: Artificial sequence
<220> FEATURE:
<223> OTHER INFORMATION: oligonucleotide motif

<400> SEQUENCE: 102
atgagatacc agcagatag 19

<210> SEQ ID NO 103
<211> LENGTH: 20
<212> TYPE: DNA
<213> ORGANISM: Artificial sequence
<220> FEATURE:
<223> OTHER INFORMATION: oligonucleotide motif

<400> SEQUENCE: 103
agaagaaatc ctgagtaatc 20

<210> SEQ ID NO 104
<211> LENGTH: 17
<212> TYPE: DNA
<213> ORGANISM: Artificial sequence
<220> FEATURE:
<223> OTHER INFORMATION: oligonucleotide motif

<400> SEQUENCE: 104
ccctaaaaag tgacgta 17

<210> SEQ ID NO 105
<211> LENGTH: 17
<212> TYPE: DNA
<213> ORGANISM: Artificial sequence
<220> FEATURE:
<223> OTHER INFORMATION: oligonucleotide motif

<400> SEQUENCE: 105
ttaagttaga tcacggc 17

<210> SEQ ID NO 106
<211> LENGTH: 17
<212> TYPE: DNA
<213> ORGANISM: Artificial sequence
<220> FEATURE:
<223> OTHER INFORMATION: oligonucleotide motif

<400> SEQUENCE: 106
gtggatacag aaagcca 17

<210> SEQ ID NO 107
<211> LENGTH: 16
<212> TYPE: DNA
<213> ORGANISM: Artificial sequence
<220> FEATURE:
<223> OTHER INFORMATION: oligonucleotide motif

<400> SEQUENCE: 107
gtatcggcag gagatt 16

<210> SEQ ID NO 108
<211> LENGTH: 20
<212> TYPE: DNA
<213> ORGANISM: Artificial sequence
<220> FEATURE:
<223> OTHER INFORMATION: oligonucleotide motif

<400> SEQUENCE: 108
taactaattg attccattgc 20

<210> SEQ ID NO 109
<211> LENGTH: 18
<212> TYPE: DNA
<213> ORGANISM: Artificial sequence
<220> FEATURE:
<223> OTHER INFORMATION: oligonucleotide motif

<400> SEQUENCE: 109
agaagaacgg aaattgcc 18

<210> SEQ ID NO 110
<211> LENGTH: 18
<212> TYPE: DNA
<213> ORGANISM: Artificial sequence
<220> FEATURE:
<223> OTHER INFORMATION: oligonucleotide motif

<400> SEQUENCE: 110
ataatgattt tcctatcc 18

<210> SEQ ID NO 111
<211> LENGTH: 18
<212> TYPE: DNA
<213> ORGANISM: Artificial sequence
<220> FEATURE:

<223> OTHER INFORMATION: oligonucleotide motif

<400> SEQUENCE: 111
atggttttgt ggagaagg 18

<210> SEQ ID NO 112
<211> LENGTH: 20
<212> TYPE: DNA
<213> ORGANISM: Artificial sequence
<220> FEATURE:
<223> OTHER INFORMATION: oligonucleotide motif

<400> SEQUENCE: 112
tgctgctgtg aaaagaaatg 20

<210> SEQ ID NO 113
<211> LENGTH: 19
<212> TYPE: DNA
<213> ORGANISM: Artificial sequence
<220> FEATURE:
<223> OTHER INFORMATION: oligonucleotide motif

<400> SEQUENCE: 113
gtgtccaatt ttttattat 19

<210> SEQ ID NO 114
<211> LENGTH: 20
<212> TYPE: DNA
<213> ORGANISM: Artificial sequence
<220> FEATURE:
<223> OTHER INFORMATION: oligonucleotide motif

<400> SEQUENCE: 114
gatggaatca actgtgtagt 20

<210> SEQ ID NO 115
<211> LENGTH: 19
<212> TYPE: DNA
<213> ORGANISM: Artificial sequence
<220> FEATURE:
<223> OTHER INFORMATION: oligonucleotide motif

<400> SEQUENCE: 115
gatggtgaca aattattct 19

<210> SEQ ID NO 116
<211> LENGTH: 17
<212> TYPE: DNA
<213> ORGANISM: Artificial sequence
<220> FEATURE:
<223> OTHER INFORMATION: oligonucleotide motif

<400> SEQUENCE: 116
tgcttttggg aatcttt 17

<210> SEQ ID NO 117
<211> LENGTH: 20
<212> TYPE: DNA
<213> ORGANISM: Artificial sequence
<220> FEATURE:
<223> OTHER INFORMATION: oligonucleotide motif

<400> SEQUENCE: 117
gatgtcctac aatgaacacg 20

<210> SEQ ID NO 118
<211> LENGTH: 19
<212> TYPE: DNA
<213> ORGANISM: Artificial sequence
<220> FEATURE:
<223> OTHER INFORMATION: oligonucleotide motif

<400> SEQUENCE: 118
gtacaaggac aaagtaacc 19

<210> SEQ ID NO 119
<211> LENGTH: 17
<212> TYPE: DNA
<213> ORGANISM: Artificial sequence
<220> FEATURE:
<223> OTHER INFORMATION: oligonucleotide motif

<400> SEQUENCE: 119
tgaaacgcct atctcta 17

<210> SEQ ID NO 120
<211> LENGTH: 20
<212> TYPE: DNA
<213> ORGANISM: Artificial sequence
<220> FEATURE:
<223> OTHER INFORMATION: oligonucleotide motif

<400> SEQUENCE: 120
atactattta tgcttatgga 20

<210> SEQ ID NO 121
<211> LENGTH: 20
<212> TYPE: DNA
<213> ORGANISM: Artificial sequence
<220> FEATURE:
<223> OTHER INFORMATION: oligonucleotide motif

<400> SEQUENCE: 121
ttgtaatcaa ggcaataagg 20

<210> SEQ ID NO 122
<211> LENGTH: 18
<212> TYPE: DNA
<213> ORGANISM: Artificial sequence
<220> FEATURE:
<223> OTHER INFORMATION: oligonucleotide motif

<400> SEQUENCE: 122
gaagtccaat aacgcaga 18

<210> SEQ ID NO 123
<211> LENGTH: 20
<212> TYPE: DNA
<213> ORGANISM: Artificial sequence
<220> FEATURE:
<223> OTHER INFORMATION: oligonucleotide motif

<400> SEQUENCE: 123
atatccaatc tctatatgtg 20

<210> SEQ ID NO 124
<211> LENGTH: 20
<212> TYPE: DNA
<213> ORGANISM: Artificial sequence
<220> FEATURE:
<223> OTHER INFORMATION: oligonucleotide motif

<400> SEQUENCE: 124
gccttacaca agactatatt 20

<210> SEQ ID NO 125
<211> LENGTH: 19
<212> TYPE: DNA
<213> ORGANISM: Artificial sequence
<220> FEATURE:
<223> OTHER INFORMATION: oligonucleotide motif

<400> SEQUENCE: 125
tgctgaattt tatgttaac 19

<210> SEQ ID NO 126
<211> LENGTH: 20
<212> TYPE: DNA
<213> ORGANISM: Artificial sequence
<220> FEATURE:
<223> OTHER INFORMATION: oligonucleotide motif

<400> SEQUENCE: 126
cacaagatga tgggtttaag 20

<210> SEQ ID NO 127
<211> LENGTH: 16
<212> TYPE: DNA
<213> ORGANISM: Artificial sequence
<220> FEATURE:
<223> OTHER INFORMATION: oligonucleotide motif

<400> SEQUENCE: 127
ttagtggttt gggtgc 16

<210> SEQ ID NO 128
<211> LENGTH: 19
<212> TYPE: DNA
<213> ORGANISM: Artificial sequence
<220> FEATURE:
<223> OTHER INFORMATION: oligonucleotide motif

<400> SEQUENCE: 128
agattgttac cttactgat 19

<210> SEQ ID NO 129
<211> LENGTH: 20
<212> TYPE: DNA
<213> ORGANISM: Artificial sequence
<220> FEATURE:
<223> OTHER INFORMATION: oligonucleotide motif

<400> SEQUENCE: 129
tattacaaat atcaatctcc 20

<210> SEQ ID NO 130
<211> LENGTH: 19
<212> TYPE: DNA
<213> ORGANISM: Artificial sequence
<220> FEATURE:
<223> OTHER INFORMATION: oligonucleotide motif

<400> SEQUENCE: 130
taccaaaagc atagagtgg 19

<210> SEQ ID NO 131
<211> LENGTH: 17

<212> TYPE: DNA
<213> ORGANISM: Artificial sequence
<220> FEATURE:
<223> OTHER INFORMATION: oligonucleotide motif

<400> SEQUENCE: 131
aattatcttc ccgctac 17

<210> SEQ ID NO 132
<211> LENGTH: 17
<212> TYPE: DNA
<213> ORGANISM: Artificial sequence
<220> FEATURE:
<223> OTHER INFORMATION: oligonucleotide motif

<400> SEQUENCE: 132
gttgggtgga ataggca 17

<210> SEQ ID NO 133
<211> LENGTH: 17
<212> TYPE: DNA
<213> ORGANISM: Artificial sequence
<220> FEATURE:
<223> OTHER INFORMATION: oligonucleotide motif

<400> SEQUENCE: 133
tcgatttccc gttccaa 17

<210> SEQ ID NO 134
<211> LENGTH: 20
<212> TYPE: DNA
<213> ORGANISM: Artificial sequence
<220> FEATURE:
<223> OTHER INFORMATION: oligonucleotide motif

<400> SEQUENCE: 134
acaacctaca cataaattgc 20

<210> SEQ ID NO 135
<211> LENGTH: 19
<212> TYPE: DNA
<213> ORGANISM: Artificial sequence
<220> FEATURE:
<223> OTHER INFORMATION: oligonucleotide motif

<400> SEQUENCE: 135
actataagaa ctcccaaca 19

<210> SEQ ID NO 136
<211> LENGTH: 19
<212> TYPE: DNA
<213> ORGANISM: Artificial sequence
<220> FEATURE:
<223> OTHER INFORMATION: oligonucleotide motif

<400> SEQUENCE: 136
gagaaaaaga gttacaagc 19

<210> SEQ ID NO 137
<211> LENGTH: 19
<212> TYPE: DNA
<213> ORGANISM: Artificial sequence
<220> FEATURE:
<223> OTHER INFORMATION: oligonucleotide motif

<400> SEQUENCE: 137

-continued

```
aactggaggg agagaagag                                                    19


<210> SEQ ID NO 138
<211> LENGTH: 20
<212> TYPE: DNA
<213> ORGANISM: Artificial sequence
<220> FEATURE:
<223> OTHER INFORMATION: oligonucleotide motif

<400> SEQUENCE: 138

tttctaagag cagaggtaca                                                   20


<210> SEQ ID NO 139
<211> LENGTH: 17
<212> TYPE: DNA
<213> ORGANISM: Artificial sequence
<220> FEATURE:
<223> OTHER INFORMATION: oligonucleotide motif

<400> SEQUENCE: 139

agaagtaaca agagcct                                                      17


<210> SEQ ID NO 140
<211> LENGTH: 18
<212> TYPE: DNA
<213> ORGANISM: Artificial sequence
<220> FEATURE:
<223> OTHER INFORMATION: oligonucleotide motif

<400> SEQUENCE: 140

agtatcaaac cagacctc                                                     18


<210> SEQ ID NO 141
<211> LENGTH: 17
<212> TYPE: DNA
<213> ORGANISM: Artificial sequence
<220> FEATURE:
<223> OTHER INFORMATION: oligonucleotide motif

<400> SEQUENCE: 141

ccacaaccga aagactt                                                      17


<210> SEQ ID NO 142
<211> LENGTH: 19
<212> TYPE: DNA
<213> ORGANISM: Artificial sequence
<220> FEATURE:
<223> OTHER INFORMATION: oligonucleotide motif

<400> SEQUENCE: 142

aatacacact gcattttca                                                    19


<210> SEQ ID NO 143
<211> LENGTH: 17
<212> TYPE: DNA
<213> ORGANISM: Artificial sequence
<220> FEATURE:
<223> OTHER INFORMATION: oligonucleotide motif

<400> SEQUENCE: 143

ccaggtagat agcacag                                                      17


<210> SEQ ID NO 144
<211> LENGTH: 20
<212> TYPE: DNA
<213> ORGANISM: Artificial sequence
```

<220> FEATURE:
<223> OTHER INFORMATION: oligonucleotide motif

<400> SEQUENCE: 144
ccatgacaaa gtaacaacag 20

<210> SEQ ID NO 145
<211> LENGTH: 19
<212> TYPE: DNA
<213> ORGANISM: Artificial sequence
<220> FEATURE:
<223> OTHER INFORMATION: oligonucleotide motif

<400> SEQUENCE: 145
cagaatttcc tttgagtta 19

<210> SEQ ID NO 146
<211> LENGTH: 20
<212> TYPE: DNA
<213> ORGANISM: Artificial sequence
<220> FEATURE:
<223> OTHER INFORMATION: oligonucleotide motif

<400> SEQUENCE: 146
ccttcgcaag aaagaattga 20

<210> SEQ ID NO 147
<211> LENGTH: 18
<212> TYPE: DNA
<213> ORGANISM: Artificial sequence
<220> FEATURE:
<223> OTHER INFORMATION: oligonucleotide motif

<400> SEQUENCE: 147
tcatacatac acgcttct 18

<210> SEQ ID NO 148
<211> LENGTH: 17
<212> TYPE: DNA
<213> ORGANISM: Artificial sequence
<220> FEATURE:
<223> OTHER INFORMATION: oligonucleotide motif

<400> SEQUENCE: 148
tgcgaaaaga ttggagg 17

<210> SEQ ID NO 149
<211> LENGTH: 20
<212> TYPE: DNA
<213> ORGANISM: Artificial sequence
<220> FEATURE:
<223> OTHER INFORMATION: oligonucleotide motif

<400> SEQUENCE: 149
cacaggacgc ttacatgaat 20

<210> SEQ ID NO 150
<211> LENGTH: 19
<212> TYPE: DNA
<213> ORGANISM: Artificial sequence
<220> FEATURE:
<223> OTHER INFORMATION: oligonucleotide motif

<400> SEQUENCE: 150
gctgtttttt tttcttaac 19

<210> SEQ ID NO 151
<211> LENGTH: 19
<212> TYPE: DNA
<213> ORGANISM: Artificial sequence
<220> FEATURE:
<223> OTHER INFORMATION: oligonucleotide motif

<400> SEQUENCE: 151
accataagtg agtgttctt 19

<210> SEQ ID NO 152
<211> LENGTH: 20
<212> TYPE: DNA
<213> ORGANISM: Artificial sequence
<220> FEATURE:
<223> OTHER INFORMATION: oligonucleotide motif

<400> SEQUENCE: 152
acacaagccc atagaaacag 20

<210> SEQ ID NO 153
<211> LENGTH: 17
<212> TYPE: DNA
<213> ORGANISM: Artificial sequence
<220> FEATURE:
<223> OTHER INFORMATION: oligonucleotide motif

<400> SEQUENCE: 153
cagtagtaac caccaag 17

<210> SEQ ID NO 154
<211> LENGTH: 19
<212> TYPE: DNA
<213> ORGANISM: Artificial sequence
<220> FEATURE:
<223> OTHER INFORMATION: oligonucleotide motif

<400> SEQUENCE: 154
cctgcaaact tttatttat 19

<210> SEQ ID NO 155
<211> LENGTH: 17
<212> TYPE: DNA
<213> ORGANISM: Artificial sequence
<220> FEATURE:
<223> OTHER INFORMATION: oligonucleotide motif

<400> SEQUENCE: 155
acttagtaat agcagca 17

<210> SEQ ID NO 156
<211> LENGTH: 19
<212> TYPE: DNA
<213> ORGANISM: Artificial sequence
<220> FEATURE:
<223> OTHER INFORMATION: oligonucleotide motif

<400> SEQUENCE: 156
atgaatactc cgaagactt 19

<210> SEQ ID NO 157
<211> LENGTH: 20
<212> TYPE: DNA
<213> ORGANISM: Artificial sequence
<220> FEATURE:
<223> OTHER INFORMATION: oligonucleotide motif

<400> SEQUENCE: 157
aaagaaaagg atcacaagcc 20

<210> SEQ ID NO 158
<211> LENGTH: 19
<212> TYPE: DNA
<213> ORGANISM: Artificial sequence
<220> FEATURE:
<223> OTHER INFORMATION: oligonucleotide motif

<400> SEQUENCE: 158
agacagaaat cacctaaca 19

<210> SEQ ID NO 159
<211> LENGTH: 20
<212> TYPE: DNA
<213> ORGANISM: Artificial sequence
<220> FEATURE:
<223> OTHER INFORMATION: oligonucleotide motif

<400> SEQUENCE: 159
tagaacagac attattcatc 20

<210> SEQ ID NO 160
<211> LENGTH: 18
<212> TYPE: DNA
<213> ORGANISM: Artificial sequence
<220> FEATURE:
<223> OTHER INFORMATION: oligonucleotide motif

<400> SEQUENCE: 160
agttacacgg agcagcac 18

<210> SEQ ID NO 161
<211> LENGTH: 20
<212> TYPE: DNA
<213> ORGANISM: Artificial sequence
<220> FEATURE:
<223> OTHER INFORMATION: oligonucleotide motif

<400> SEQUENCE: 161
cactatacac agaacactat 20

<210> SEQ ID NO 162
<211> LENGTH: 18
<212> TYPE: DNA
<213> ORGANISM: Artificial sequence
<220> FEATURE:
<223> OTHER INFORMATION: oligonucleotide motif

<400> SEQUENCE: 162
agctgtctaa atacatgg 18

<210> SEQ ID NO 163
<211> LENGTH: 20
<212> TYPE: DNA
<213> ORGANISM: Artificial sequence
<220> FEATURE:
<223> OTHER INFORMATION: oligonucleotide motif

<400> SEQUENCE: 163
atgaacctat tttatgcttc 20

<210> SEQ ID NO 164

<211> LENGTH: 18
<212> TYPE: DNA
<213> ORGANISM: Artificial sequence
<220> FEATURE:
<223> OTHER INFORMATION: oligonucleotide motif

<400> SEQUENCE: 164
accatcatta acctgcgt 18

<210> SEQ ID NO 165
<211> LENGTH: 18
<212> TYPE: DNA
<213> ORGANISM: Artificial sequence
<220> FEATURE:
<223> OTHER INFORMATION: oligonucleotide motif

<400> SEQUENCE: 165
agtaaagtgc ccagatgt 18

<210> SEQ ID NO 166
<211> LENGTH: 19
<212> TYPE: DNA
<213> ORGANISM: Artificial sequence
<220> FEATURE:
<223> OTHER INFORMATION: oligonucleotide motif

<400> SEQUENCE: 166
ttccctatga aatcctcaa 19

<210> SEQ ID NO 167
<211> LENGTH: 20
<212> TYPE: DNA
<213> ORGANISM: Artificial sequence
<220> FEATURE:
<223> OTHER INFORMATION: oligonucleotide motif

<400> SEQUENCE: 167
cactcttcat agaatgcaac 20

<210> SEQ ID NO 168
<211> LENGTH: 20
<212> TYPE: DNA
<213> ORGANISM: Artificial sequence
<220> FEATURE:
<223> OTHER INFORMATION: oligonucleotide motif

<400> SEQUENCE: 168
aatgcttaat ttttctctct 20

<210> SEQ ID NO 169
<211> LENGTH: 20
<212> TYPE: DNA
<213> ORGANISM: Artificial sequence
<220> FEATURE:
<223> OTHER INFORMATION: oligonucleotide motif

<400> SEQUENCE: 169
ttagagacga tgcctataac 20

<210> SEQ ID NO 170
<211> LENGTH: 19
<212> TYPE: DNA
<213> ORGANISM: Artificial sequence
<220> FEATURE:
<223> OTHER INFORMATION: oligonucleotide motif

<400> SEQUENCE: 170
tgaatagttc ccatagatt 19

<210> SEQ ID NO 171
<211> LENGTH: 19
<212> TYPE: DNA
<213> ORGANISM: Artificial sequence
<220> FEATURE:
<223> OTHER INFORMATION: oligonucleotide motif

<400> SEQUENCE: 171
cagcataatt gttttcttt 19

<210> SEQ ID NO 172
<211> LENGTH: 19
<212> TYPE: DNA
<213> ORGANISM: Artificial sequence
<220> FEATURE:
<223> OTHER INFORMATION: oligonucleotide motif

<400> SEQUENCE: 172
atgtcattat gttttagtt 19

<210> SEQ ID NO 173
<211> LENGTH: 18
<212> TYPE: DNA
<213> ORGANISM: Artificial sequence
<220> FEATURE:
<223> OTHER INFORMATION: oligonucleotide motif

<400> SEQUENCE: 173
cagcagtatc tcttagaa 18

<210> SEQ ID NO 174
<211> LENGTH: 16
<212> TYPE: DNA
<213> ORGANISM: Artificial sequence
<220> FEATURE:
<223> OTHER INFORMATION: oligonucleotide motif

<400> SEQUENCE: 174
cggtaagggt tcggtg 16

<210> SEQ ID NO 175
<211> LENGTH: 19
<212> TYPE: DNA
<213> ORGANISM: Artificial sequence
<220> FEATURE:
<223> OTHER INFORMATION: oligonucleotide motif

<400> SEQUENCE: 175
catgaaccac attaggaac 19

<210> SEQ ID NO 176
<211> LENGTH: 19
<212> TYPE: DNA
<213> ORGANISM: Artificial sequence
<220> FEATURE:
<223> OTHER INFORMATION: oligonucleotide motif

<400> SEQUENCE: 176
cattcaacac acacgacaa 19

<210> SEQ ID NO 177
<211> LENGTH: 19
<212> TYPE: DNA

<213> ORGANISM: Artificial sequence
<220> FEATURE:
<223> OTHER INFORMATION: oligonucleotide motif

<400> SEQUENCE: 177
aagtatccaa gactcaaga 19

<210> SEQ ID NO 178
<211> LENGTH: 16
<212> TYPE: DNA
<213> ORGANISM: Artificial sequence
<220> FEATURE:
<223> OTHER INFORMATION: oligonucleotide motif

<400> SEQUENCE: 178
ccacagaaac accgag 16

<210> SEQ ID NO 179
<211> LENGTH: 19
<212> TYPE: DNA
<213> ORGANISM: Artificial sequence
<220> FEATURE:
<223> OTHER INFORMATION: oligonucleotide motif

<400> SEQUENCE: 179
tggaaaaggg aagggaaga 19

<210> SEQ ID NO 180
<211> LENGTH: 17
<212> TYPE: DNA
<213> ORGANISM: Artificial sequence
<220> FEATURE:
<223> OTHER INFORMATION: oligonucleotide motif

<400> SEQUENCE: 180
agagagtccg aagcctg 17

<210> SEQ ID NO 181
<211> LENGTH: 18
<212> TYPE: DNA
<213> ORGANISM: Artificial sequence
<220> FEATURE:
<223> OTHER INFORMATION: oligonucleotide motif

<400> SEQUENCE: 181
atgggaaagg taacgagc 18

<210> SEQ ID NO 182
<211> LENGTH: 18
<212> TYPE: DNA
<213> ORGANISM: Artificial sequence
<220> FEATURE:
<223> OTHER INFORMATION: oligonucleotide motif

<400> SEQUENCE: 182
ctatcctaca agtccgaa 18

<210> SEQ ID NO 183
<211> LENGTH: 19
<212> TYPE: DNA
<213> ORGANISM: Artificial sequence
<220> FEATURE:
<223> OTHER INFORMATION: oligonucleotide motif

<400> SEQUENCE: 183
cattgctttt ataatccta 19

<210> SEQ ID NO 184
<211> LENGTH: 18
<212> TYPE: DNA
<213> ORGANISM: Artificial sequence
<220> FEATURE:
<223> OTHER INFORMATION: oligonucleotide motif

<400> SEQUENCE: 184
ctttttaagg acaggagg 18

<210> SEQ ID NO 185
<211> LENGTH: 20
<212> TYPE: DNA
<213> ORGANISM: Artificial sequence
<220> FEATURE:
<223> OTHER INFORMATION: oligonucleotide motif

<400> SEQUENCE: 185
gatgaaagat aagtgagcat 20

<210> SEQ ID NO 186
<211> LENGTH: 20
<212> TYPE: DNA
<213> ORGANISM: Artificial sequence
<220> FEATURE:
<223> OTHER INFORMATION: oligonucleotide motif

<400> SEQUENCE: 186
gaagcctgta ataattaagc 20

<210> SEQ ID NO 187
<211> LENGTH: 18
<212> TYPE: DNA
<213> ORGANISM: Artificial sequence
<220> FEATURE:
<223> OTHER INFORMATION: oligonucleotide motif

<400> SEQUENCE: 187
caccctagta aagcaaac 18

<210> SEQ ID NO 188
<211> LENGTH: 18
<212> TYPE: DNA
<213> ORGANISM: Artificial sequence
<220> FEATURE:
<223> OTHER INFORMATION: oligonucleotide motif

<400> SEQUENCE: 188
gcaaatgtaa gccttttt 18

<210> SEQ ID NO 189
<211> LENGTH: 17
<212> TYPE: DNA
<213> ORGANISM: Artificial sequence
<220> FEATURE:
<223> OTHER INFORMATION: oligonucleotide motif

<400> SEQUENCE: 189
acctgacagc taccgac 17

<210> SEQ ID NO 190
<211> LENGTH: 17
<212> TYPE: DNA
<213> ORGANISM: Artificial sequence
<220> FEATURE:

<223> OTHER INFORMATION: oligonucleotide motif

<400> SEQUENCE: 190
aagagtgggt tgtaagc 17

<210> SEQ ID NO 191
<211> LENGTH: 20
<212> TYPE: DNA
<213> ORGANISM: Artificial sequence
<220> FEATURE:
<223> OTHER INFORMATION: oligonucleotide motif

<400> SEQUENCE: 191
tagtgaaaat atttggagtt 20

<210> SEQ ID NO 192
<211> LENGTH: 18
<212> TYPE: DNA
<213> ORGANISM: Artificial sequence
<220> FEATURE:
<223> OTHER INFORMATION: oligonucleotide motif

<400> SEQUENCE: 192
tttcagcacc ttaaaccc 18

<210> SEQ ID NO 193
<211> LENGTH: 20
<212> TYPE: DNA
<213> ORGANISM: Artificial sequence
<220> FEATURE:
<223> OTHER INFORMATION: oligonucleotide motif

<400> SEQUENCE: 193
ttaagggaaa ggaaacgtca 20

<210> SEQ ID NO 194
<211> LENGTH: 20
<212> TYPE: DNA
<213> ORGANISM: Artificial sequence
<220> FEATURE:
<223> OTHER INFORMATION: oligonucleotide motif

<400> SEQUENCE: 194
gtaggtaaag ggcaaaggaa 20

<210> SEQ ID NO 195
<211> LENGTH: 18
<212> TYPE: DNA
<213> ORGANISM: Artificial sequence
<220> FEATURE:
<223> OTHER INFORMATION: oligonucleotide motif

<400> SEQUENCE: 195
gtgaattaaa gccaaagc 18

<210> SEQ ID NO 196
<211> LENGTH: 19
<212> TYPE: DNA
<213> ORGANISM: Artificial sequence
<220> FEATURE:
<223> OTHER INFORMATION: oligonucleotide motif

<400> SEQUENCE: 196
tgtttttgta ttttagtat 19

<210> SEQ ID NO 197
<211> LENGTH: 20
<212> TYPE: DNA
<213> ORGANISM: Artificial sequence
<220> FEATURE:
<223> OTHER INFORMATION: oligonucleotide motif

<400> SEQUENCE: 197
gaggtttttt ttagtgaatt 20

<210> SEQ ID NO 198
<211> LENGTH: 17
<212> TYPE: DNA
<213> ORGANISM: Artificial sequence
<220> FEATURE:
<223> OTHER INFORMATION: oligonucleotide motif

<400> SEQUENCE: 198
gaggagctaa acggaca 17

<210> SEQ ID NO 199
<211> LENGTH: 20
<212> TYPE: DNA
<213> ORGANISM: Artificial sequence
<220> FEATURE:
<223> OTHER INFORMATION: oligonucleotide motif

<400> SEQUENCE: 199
gtttagtctt atgttctcac 20

<210> SEQ ID NO 200
<211> LENGTH: 19
<212> TYPE: DNA
<213> ORGANISM: Artificial sequence
<220> FEATURE:
<223> OTHER INFORMATION: oligonucleotide motif

<400> SEQUENCE: 200
caaatactga atatgcccg 19

<210> SEQ ID NO 201
<211> LENGTH: 18
<212> TYPE: DNA
<213> ORGANISM: Artificial sequence
<220> FEATURE:
<223> OTHER INFORMATION: oligonucleotide motif

<400> SEQUENCE: 201
accatttaaa tcgccaac 18

<210> SEQ ID NO 202
<211> LENGTH: 20
<212> TYPE: DNA
<213> ORGANISM: Artificial sequence
<220> FEATURE:
<223> OTHER INFORMATION: oligonucleotide motif

<400> SEQUENCE: 202
cagtaagagt agcccaacaa 20

<210> SEQ ID NO 203
<211> LENGTH: 20
<212> TYPE: DNA
<213> ORGANISM: Artificial sequence
<220> FEATURE:
<223> OTHER INFORMATION: oligonucleotide motif

<400> SEQUENCE: 203
taacggcaac atcaaatagc 20

<210> SEQ ID NO 204
<211> LENGTH: 18
<212> TYPE: DNA
<213> ORGANISM: Artificial sequence
<220> FEATURE:
<223> OTHER INFORMATION: oligonucleotide motif

<400> SEQUENCE: 204
actgagcacc aactacac 18

<210> SEQ ID NO 205
<211> LENGTH: 20
<212> TYPE: DNA
<213> ORGANISM: Artificial sequence
<220> FEATURE:
<223> OTHER INFORMATION: oligonucleotide motif

<400> SEQUENCE: 205
cctaatttta tgtatcacat 20

<210> SEQ ID NO 206
<211> LENGTH: 20
<212> TYPE: DNA
<213> ORGANISM: Artificial sequence
<220> FEATURE:
<223> OTHER INFORMATION: oligonucleotide motif

<400> SEQUENCE: 206
ctaggaatta taacaaatca 20

<210> SEQ ID NO 207
<211> LENGTH: 20
<212> TYPE: DNA
<213> ORGANISM: Artificial sequence
<220> FEATURE:
<223> OTHER INFORMATION: oligonucleotide motif

<400> SEQUENCE: 207
actccaaaga acatactcac 20

<210> SEQ ID NO 208
<211> LENGTH: 20
<212> TYPE: DNA
<213> ORGANISM: Artificial sequence
<220> FEATURE:
<223> OTHER INFORMATION: oligonucleotide motif

<400> SEQUENCE: 208
taagagaaac aatcacacca 20

<210> SEQ ID NO 209
<211> LENGTH: 19
<212> TYPE: DNA
<213> ORGANISM: Artificial sequence
<220> FEATURE:
<223> OTHER INFORMATION: oligonucleotide motif

<400> SEQUENCE: 209
tgtcctaaaa tatcagcag 19

<210> SEQ ID NO 210
<211> LENGTH: 19

<212> TYPE: DNA
<213> ORGANISM: Artificial sequence
<220> FEATURE:
<223> OTHER INFORMATION: oligonucleotide motif

<400> SEQUENCE: 210
cttttaatga gacagtgca 19

<210> SEQ ID NO 211
<211> LENGTH: 20
<212> TYPE: DNA
<213> ORGANISM: Artificial sequence
<220> FEATURE:
<223> OTHER INFORMATION: oligonucleotide motif

<400> SEQUENCE: 211
ttgtagcata agatggaaag 20

<210> SEQ ID NO 212
<211> LENGTH: 20
<212> TYPE: DNA
<213> ORGANISM: Artificial sequence
<220> FEATURE:
<223> OTHER INFORMATION: oligonucleotide motif

<400> SEQUENCE: 212
aaactgtagc caataactgt 20

<210> SEQ ID NO 213
<211> LENGTH: 20
<212> TYPE: DNA
<213> ORGANISM: Artificial sequence
<220> FEATURE:
<223> OTHER INFORMATION: oligonucleotide motif

<400> SEQUENCE: 213
attcatccta acacaagtag 20

<210> SEQ ID NO 214
<211> LENGTH: 19
<212> TYPE: DNA
<213> ORGANISM: Artificial sequence
<220> FEATURE:
<223> OTHER INFORMATION: oligonucleotide motif

<400> SEQUENCE: 214
cacgaaagga acagctaag 19

<210> SEQ ID NO 215
<211> LENGTH: 16
<212> TYPE: DNA
<213> ORGANISM: Artificial sequence
<220> FEATURE:
<223> OTHER INFORMATION: oligonucleotide motif

<400> SEQUENCE: 215
acaacaggca agtacc 16

<210> SEQ ID NO 216
<211> LENGTH: 18
<212> TYPE: DNA
<213> ORGANISM: Artificial sequence
<220> FEATURE:
<223> OTHER INFORMATION: oligonucleotide motif

<400> SEQUENCE: 216
gctaaacact ataaggat 18

<210> SEQ ID NO 217
<211> LENGTH: 18
<212> TYPE: DNA
<213> ORGANISM: Artificial sequence
<220> FEATURE:
<223> OTHER INFORMATION: oligonucleotide motif

<400> SEQUENCE: 217
cccgtaagca tttgagaa 18

<210> SEQ ID NO 218
<211> LENGTH: 20
<212> TYPE: DNA
<213> ORGANISM: Artificial sequence
<220> FEATURE:
<223> OTHER INFORMATION: oligonucleotide motif

<400> SEQUENCE: 218
agccaatatg cgacagtaac 20

<210> SEQ ID NO 219
<211> LENGTH: 20
<212> TYPE: DNA
<213> ORGANISM: Artificial sequence
<220> FEATURE:
<223> OTHER INFORMATION: oligonucleotide motif

<400> SEQUENCE: 219
taaccaaaac aatcagtgtc 20

<210> SEQ ID NO 220
<211> LENGTH: 18
<212> TYPE: DNA
<213> ORGANISM: Artificial sequence
<220> FEATURE:
<223> OTHER INFORMATION: oligonucleotide motif

<400> SEQUENCE: 220
aacagggaac aggagtta 18

<210> SEQ ID NO 221
<211> LENGTH: 17
<212> TYPE: DNA
<213> ORGANISM: Artificial sequence
<220> FEATURE:
<223> OTHER INFORMATION: oligonucleotide motif

<400> SEQUENCE: 221
atttatcaac ttccacc 17

<210> SEQ ID NO 222
<211> LENGTH: 17
<212> TYPE: DNA
<213> ORGANISM: Artificial sequence
<220> FEATURE:
<223> OTHER INFORMATION: oligonucleotide motif

<400> SEQUENCE: 222
cgtttaagac caggcac 17

<210> SEQ ID NO 223
<211> LENGTH: 20
<212> TYPE: DNA
<213> ORGANISM: Artificial sequence -continued
<220> FEATURE:
<223> OTHER INFORMATION: oligonucleotide motif

<400> SEQUENCE: 223
acaaaggaac tcaggaagag 20

<210> SEQ ID NO 224
<211> LENGTH: 17
<212> TYPE: DNA
<213> ORGANISM: Artificial sequence
<220> FEATURE:
<223> OTHER INFORMATION: oligonucleotide motif

<400> SEQUENCE: 224
tcacagacaa gcaccaa 17

<210> SEQ ID NO 225
<211> LENGTH: 20
<212> TYPE: DNA
<213> ORGANISM: Artificial sequence
<220> FEATURE:
<223> OTHER INFORMATION: oligonucleotide motif

<400> SEQUENCE: 225
tactttttaa aacacgtagg 20

<210> SEQ ID NO 226
<211> LENGTH: 19
<212> TYPE: DNA
<213> ORGANISM: Artificial sequence
<220> FEATURE:
<223> OTHER INFORMATION: oligonucleotide motif

<400> SEQUENCE: 226
gcacaatcac aaagaccaa 19

<210> SEQ ID NO 227
<211> LENGTH: 18
<212> TYPE: DNA
<213> ORGANISM: Artificial sequence
<220> FEATURE:
<223> OTHER INFORMATION: oligonucleotide motif

<400> SEQUENCE: 227
tcagtaaaga acagaggc 18

<210> SEQ ID NO 228
<211> LENGTH: 19
<212> TYPE: DNA
<213> ORGANISM: Artificial sequence
<220> FEATURE:
<223> OTHER INFORMATION: oligonucleotide motif

<400> SEQUENCE: 228
catatttcca ccacacaag 19

<210> SEQ ID NO 229
<211> LENGTH: 16
<212> TYPE: DNA
<213> ORGANISM: Artificial sequence
<220> FEATURE:
<223> OTHER INFORMATION: oligonucleotide motif

<400> SEQUENCE: 229
agtaaaccac tgtcca 16

<210> SEQ ID NO 230
<211> LENGTH: 17
<212> TYPE: DNA
<213> ORGANISM: Artificial sequence
<220> FEATURE:
<223> OTHER INFORMATION: oligonucleotide motif

<400> SEQUENCE: 230
tcctctttgg cgatata 17

<210> SEQ ID NO 231
<211> LENGTH: 19
<212> TYPE: DNA
<213> ORGANISM: Artificial sequence
<220> FEATURE:
<223> OTHER INFORMATION: oligonucleotide motif

<400> SEQUENCE: 231
cataaatacc cctgaatac 19

<210> SEQ ID NO 232
<211> LENGTH: 17
<212> TYPE: DNA
<213> ORGANISM: Artificial sequence
<220> FEATURE:
<223> OTHER INFORMATION: oligonucleotide motif

<400> SEQUENCE: 232
cgattttatc accaaca 17

<210> SEQ ID NO 233
<211> LENGTH: 20
<212> TYPE: DNA
<213> ORGANISM: Artificial sequence
<220> FEATURE:
<223> OTHER INFORMATION: oligonucleotide motif

<400> SEQUENCE: 233
acaatcaggt taagtgtgga 20

<210> SEQ ID NO 234
<211> LENGTH: 17
<212> TYPE: DNA
<213> ORGANISM: Artificial sequence
<220> FEATURE:
<223> OTHER INFORMATION: oligonucleotide motif

<400> SEQUENCE: 234
gaagccaaag actacca 17

<210> SEQ ID NO 235
<211> LENGTH: 20
<212> TYPE: DNA
<213> ORGANISM: Artificial sequence
<220> FEATURE:
<223> OTHER INFORMATION: oligonucleotide motif

<400> SEQUENCE: 235
tggtagggac tgaattttaa 20

<210> SEQ ID NO 236
<211> LENGTH: 15
<212> TYPE: DNA
<213> ORGANISM: Artificial sequence
<220> FEATURE:
<223> OTHER INFORMATION: oligonucleotide motif

<400> SEQUENCE: 236
cggtagtcaa tcacc 15

<210> SEQ ID NO 237
<211> LENGTH: 20
<212> TYPE: DNA
<213> ORGANISM: Artificial sequence
<220> FEATURE:
<223> OTHER INFORMATION: oligonucleotide motif

<400> SEQUENCE: 237
ctatcaaaat tatttcacct 20

<210> SEQ ID NO 238
<211> LENGTH: 20
<212> TYPE: DNA
<213> ORGANISM: Artificial sequence
<220> FEATURE:
<223> OTHER INFORMATION: oligonucleotide motif

<400> SEQUENCE: 238
acgaaaattt agcatcctaa 20

<210> SEQ ID NO 239
<211> LENGTH: 15
<212> TYPE: DNA
<213> ORGANISM: Artificial sequence
<220> FEATURE:
<223> OTHER INFORMATION: oligonucleotide motif

<400> SEQUENCE: 239
tggtaaacac tgggc 15

<210> SEQ ID NO 240
<211> LENGTH: 17
<212> TYPE: DNA
<213> ORGANISM: Artificial sequence
<220> FEATURE:
<223> OTHER INFORMATION: oligonucleotide motif

<400> SEQUENCE: 240
gattgttggt tgtcatg 17

<210> SEQ ID NO 241
<211> LENGTH: 19
<212> TYPE: DNA
<213> ORGANISM: Artificial sequence
<220> FEATURE:
<223> OTHER INFORMATION: oligonucleotide motif

<400> SEQUENCE: 241
aattataccc cacatttca 19

<210> SEQ ID NO 242
<211> LENGTH: 19
<212> TYPE: DNA
<213> ORGANISM: Artificial sequence
<220> FEATURE:
<223> OTHER INFORMATION: oligonucleotide motif

<400> SEQUENCE: 242
tgcaattaga cacgttacg 19

<210> SEQ ID NO 243

<211> LENGTH: 17
<212> TYPE: DNA
<213> ORGANISM: Artificial sequence
<220> FEATURE:
<223> OTHER INFORMATION: oligonucleotide motif

<400> SEQUENCE: 243
ggcaaccaat taaacta 17

<210> SEQ ID NO 244
<211> LENGTH: 17
<212> TYPE: DNA
<213> ORGANISM: Artificial sequence
<220> FEATURE:
<223> OTHER INFORMATION: oligonucleotide motif

<400> SEQUENCE: 244
cagttttatg ctaatca 17

<210> SEQ ID NO 245
<211> LENGTH: 20
<212> TYPE: DNA
<213> ORGANISM: Artificial sequence
<220> FEATURE:
<223> OTHER INFORMATION: oligonucleotide motif

<400> SEQUENCE: 245
gcaaaggagg agcggaataa 20

<210> SEQ ID NO 246
<211> LENGTH: 20
<212> TYPE: DNA
<213> ORGANISM: Artificial sequence
<220> FEATURE:
<223> OTHER INFORMATION: oligonucleotide motif

<400> SEQUENCE: 246
aaacagaagt aagaaggtcc 20

<210> SEQ ID NO 247
<211> LENGTH: 18
<212> TYPE: DNA
<213> ORGANISM: Artificial sequence
<220> FEATURE:
<223> OTHER INFORMATION: oligonucleotide motif

<400> SEQUENCE: 247
tccacttatc catagaaa 18

<210> SEQ ID NO 248
<211> LENGTH: 19
<212> TYPE: DNA
<213> ORGANISM: Artificial sequence
<220> FEATURE:
<223> OTHER INFORMATION: oligonucleotide motif

<400> SEQUENCE: 248
gctttgacga acaggaaat 19

<210> SEQ ID NO 249
<211> LENGTH: 20
<212> TYPE: DNA
<213> ORGANISM: Artificial sequence
<220> FEATURE:
<223> OTHER INFORMATION: oligonucleotide motif

<400> SEQUENCE: 249
ttccgaccaa aagaaaagac 20

<210> SEQ ID NO 250
<211> LENGTH: 18
<212> TYPE: DNA
<213> ORGANISM: Artificial sequence
<220> FEATURE:
<223> OTHER INFORMATION: oligonucleotide motif

<400> SEQUENCE: 250
gcgacacgat ccgttaaa 18

<210> SEQ ID NO 251
<211> LENGTH: 15
<212> TYPE: DNA
<213> ORGANISM: Artificial sequence
<220> FEATURE:
<223> OTHER INFORMATION: oligonucleotide motif

<400> SEQUENCE: 251
ccccgtttta aaaac 15

<210> SEQ ID NO 252
<211> LENGTH: 19
<212> TYPE: RNA
<213> ORGANISM: artificial
<220> FEATURE:
<223> OTHER INFORMATION: Human PAPD5 target RNA

<400> SEQUENCE: 252
caucaaugcu uuauaucga 19

<210> SEQ ID NO 253
<211> LENGTH: 19
<212> TYPE: RNA
<213> ORGANISM: artificial
<220> FEATURE:
<223> OTHER INFORMATION: Human PAPD5 target RNA

<400> SEQUENCE: 253
ggacgacacu ucaauuauu 19

<210> SEQ ID NO 254
<211> LENGTH: 19
<212> TYPE: RNA
<213> ORGANISM: artificial
<220> FEATURE:
<223> OTHER INFORMATION: Human PAPD5 RNA target sequence

<400> SEQUENCE: 254
gauaaaggau ggugguuca 19

<210> SEQ ID NO 255
<211> LENGTH: 19
<212> TYPE: RNA
<213> ORGANISM: artificial
<220> FEATURE:
<223> OTHER INFORMATION: human PAPD5 Target mRNA sequence

<400> SEQUENCE: 255
gaauagaccu gagccuuca 19

<210> SEQ ID NO 256
<211> LENGTH: 19
<212> TYPE: RNA

<213> ORGANISM: artificial
<220> FEATURE:
<223> OTHER INFORMATION: human PAPD7 target mRNA sequence

<400> SEQUENCE: 256
ggagugacgu ugauucaga 19

<210> SEQ ID NO 257
<211> LENGTH: 19
<212> TYPE: RNA
<213> ORGANISM: artificial
<220> FEATURE:
<223> OTHER INFORMATION: human PAPD7 target mRNA sequence

<400> SEQUENCE: 257
cggaguucau caagaauua 19

<210> SEQ ID NO 258
<211> LENGTH: 19
<212> TYPE: RNA
<213> ORGANISM: artificial
<220> FEATURE:
<223> OTHER INFORMATION: human PAPD7 target RNA sequence

<400> SEQUENCE: 258
cggaguucau caagaauua 19

<210> SEQ ID NO 259
<211> LENGTH: 19
<212> TYPE: RNA
<213> ORGANISM: artificial
<220> FEATURE:
<223> OTHER INFORMATION: human PAPD7 target mRNA sequence

<400> SEQUENCE: 259
gcgaauagcc acaugcaau 19

<210> SEQ ID NO 260
<211> LENGTH: 58
<212> TYPE: DNA
<213> ORGANISM: artificial
<220> FEATURE:
<223> OTHER INFORMATION: shRNA

<400> SEQUENCE: 260
ccgggccaca tatagagatt ggatactcga gtatccaatc tctatatgtg gctttttg 58

<210> SEQ ID NO 261
<211> LENGTH: 58
<212> TYPE: DNA
<213> ORGANISM: artificial
<220> FEATURE:
<223> OTHER INFORMATION: shRNA

<400> SEQUENCE: 261
ccggccaaca aatctcagca tggatctcga gatccatgct gagatttgtt ggtttttg 58

<210> SEQ ID NO 262
<211> LENGTH: 58
<212> TYPE: DNA
<213> ORGANISM: artificial
<220> FEATURE:
<223> OTHER INFORMATION: shRNA

<400> SEQUENCE: 262
ccggcgcctg taatcccagc actttctcga gaaagtgctg ggattacagg cgtttttg 58

-continued

```
<210> SEQ ID NO 263
<211> LENGTH: 58
<212> TYPE: DNA
<213> ORGANISM: artificial
<220> FEATURE:
<223> OTHER INFORMATION: shRNA

<400> SEQUENCE: 263

ccgggcctgt aatcccagca ctttactcga gtaaagtgct gggattacag gctttttg       58


<210> SEQ ID NO 264
<211> LENGTH: 58
<212> TYPE: DNA
<213> ORGANISM: artificial
<220> FEATURE:
<223> OTHER INFORMATION: shRNA

<400> SEQUENCE: 264

ccggcgatgt tggaaggagt tcatactcga gtatgaactc cttccaacat cgtttttg       58


<210> SEQ ID NO 265
<211> LENGTH: 19
<212> TYPE: DNA
<213> ORGANISM: artificial
<220> FEATURE:
<223> OTHER INFORMATION: Primer

<400> SEQUENCE: 265

ctgtgccttg ggtggcttt                                                  19


<210> SEQ ID NO 266
<211> LENGTH: 24
<212> TYPE: DNA
<213> ORGANISM: Artificial
<220> FEATURE:
<223> OTHER INFORMATION: primer

<400> SEQUENCE: 266

aaggaaagaa gtcagaaggc aaaa                                            24


<210> SEQ ID NO 267
<211> LENGTH: 25
<212> TYPE: DNA
<213> ORGANISM: artificial
<220> FEATURE:
<223> OTHER INFORMATION: probe

<400> SEQUENCE: 267

ttctttataa gggtcgatgt ccatg                                           25
```